(12) United States Patent
Lee et al.

(10) Patent No.: US 7,906,228 B2
(45) Date of Patent: Mar. 15, 2011

(54) COMPOUNDS FOR ELECTRONIC MATERIAL AND ORGANIC ELECTRONIC DEVICE USING THE SAME

(75) Inventors: Mi Ae Lee, Seoul (KR); Young Jun Cho, Seoul (KR); Hyuck Joo Kwon, Seoul (KR); Bong Ok Kim, Seoul (KR); Sung Min Kim, Seoul (KR); Seung Soo Yoon, Seoul (KR)

(73) Assignee: Gracel Display Inc., Seoul (KR)

( * ) Notice: Subject to any disclaimer, the term of this patent is extended or adjusted under 35 U.S.C. 154(b) by 112 days.

(21) Appl. No.: 12/386,429

(22) Filed: Apr. 17, 2009

(65) Prior Publication Data

US 2009/0288707 A1  Nov. 26, 2009

(30) Foreign Application Priority Data

Apr. 17, 2008  (KR) ...................... 10-2008-0035573

(51) Int. Cl.
  *H05B 33/14* (2006.01)
(52) U.S. Cl. ...................... 428/690; 548/529; 313/504; 313/506; 136/257; 257/102; 257/103; 257/E51.049
(58) Field of Classification Search .......... 257/E51.049, 257/102, 103; 428/690; 313/504, 506; 136/257; 548/529
See application file for complete search history.

(56) References Cited

U.S. PATENT DOCUMENTS

| 5,061,569 | A | 10/1991 | VanSlyke et al. |
| 5,077,142 | A | 12/1991 | Sakon et al. |
| 5,759,444 | A | 6/1998 | Enokida et al. |
| 5,858,563 | A | 1/1999 | Sano et al. |
| 5,935,712 | A | 8/1999 | Tan et al. |
| 5,989,737 | A | 11/1999 | Xie et al. |
| 6,203,933 | B1 | 3/2001 | Nakaya et al. |
| 6,465,115 | B2 | 10/2002 | Shi et al. |
| 6,515,182 | B2 | 2/2003 | Hosokawa et al. |
| 6,534,199 | B1 | 3/2003 | Hosokawa et al. |
| 6,713,192 | B2 | 3/2004 | Fukuoka et al. |
| 6,951,693 | B2 | 10/2005 | Hosokawa et al. |

(Continued)

FOREIGN PATENT DOCUMENTS

EP  1 167 488  4/2007

(Continued)

OTHER PUBLICATIONS

STN Structure Search Report (Sep. 22, 2010).*

(Continued)

*Primary Examiner* — David Wu
*Assistant Examiner* — Vu A Nguyen
(74) *Attorney, Agent, or Firm* — Edwin Oh

(57) ABSTRACT

The present invention relates to novel compounds for electronic material, and organic electroluminescent devices or organic solar cells comprising the same. Specifically, the compounds for electronic material according to the invention are characterized in that they are represented by Chemical Formula (1):

Chemical Formula 1

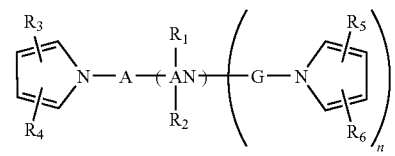

Since the compounds for electronic material, when being applied to an organic electroluminescent device, show good luminous efficiency and excellent life property of material, OLED's having very good operation life can be manufactured therefrom.

9 Claims, 1 Drawing Sheet

U.S. PATENT DOCUMENTS

| | | |
|---|---|---|
| 7,252,894 B2 | 8/2007 | Yu et al. |
| 2004/0161633 A1 | 8/2004 | Seo et al. |
| 2005/0064233 A1 | 3/2005 | Matsuura et al. |
| 2005/0211958 A1 | 9/2005 | Conley et al. |
| 2006/0033421 A1 | 2/2006 | Matsuura et al. |
| 2006/0043858 A1 | 3/2006 | Ikeda et al. |
| 2006/0046097 A1 | 3/2006 | Kim et al. |
| 2006/0110622 A1 | 5/2006 | Uchida et al. |
| 2006/0204783 A1 | 9/2006 | Conley et al. |
| 2006/0269782 A1 | 11/2006 | Liao et al. |
| 2007/0087222 A1 | 4/2007 | Kim et al. |
| 2007/0092759 A1 | 4/2007 | Begley et al. |
| 2007/0152568 A1 | 7/2007 | Lai et al. |

FOREIGN PATENT DOCUMENTS

| | | |
|---|---|---|
| JP | 1996-012600 | 1/1996 |
| JP | 2001-052870 | 2/2001 |
| JP | 2004-059535 | 2/2004 |
| JP | 2004-091334 | 3/2004 |
| JP | 2004-095850 | 3/2004 |
| JP | 2006 248900 | 9/2006 |
| WO | WO 2006/070897 | 7/2006 |
| WO | WO 2007/105917 | 9/2007 |

OTHER PUBLICATIONS

European Search Report corresponds with Europe Application No. 09 15 5931.

* cited by examiner

COMPOUNDS FOR ELECTRONIC MATERIAL AND ORGANIC ELECTRONIC DEVICE USING THE SAME

FIELD OF THE INVENTION

The present invention relates to novel compounds for electronic material, and organic electroluminescent devices comprising the same. Specifically, the invention relates to novel compounds for electronic material having blue electroluminescence and electron transport property with high triplet energy, and organic electroluminescent devices comprising the same as blue electroluminescent material, electron transport material or phosphorescent host material.

BACKGROUND OF THE INVENTION

Among display devices, electroluminescence devices (EL devices) are self-luminescent display devices showing the advantage of wide angle of view, excellent contrast and rapid response rate. Eastman Kodak developed in 1987 an organic EL device which employs a low molecular weight aromatic diamine and an aluminum complex as material for forming an EL layer, for the first time [Appl. Phys. Lett. 51, 913, 1987].

The most important factor to determine luminous efficiency, lifetime or the like in an organic EL device is electroluminescent material. Several properties required for such electroluminescent materials include that the material should have high fluorescent quantum yield in solid state and high mobility of electrons and holes, is not easily decomposed during vapor-deposition in vacuo, and forms uniform and stable thin film.

Organic electroluminescent materials can be generally classified into high-molecular materials and low-molecular materials. The low-molecular materials include metal complexes and thoroughly organic electroluminescent materials which do not contain metal, from the aspect of molecular structure. Such electroluminescent materials include chelate complexes such as tris(8-quinolinolato)aluminum complexes, coumarin derivatives, tetraphenylbutadiene derivatives, bis(styrylarylene) derivatives, oxadiazole derivatives. From those materials, it is reported that light emission of visible region from blue to red can be obtained; and realization of full-colored display devices is expected thereby.

In order to realize a full-colored OLED display, three EL materials (red, green and blue) are employed, and development of those EL materials having high efficiency and long life is a significant subject to enhance the features of the overall organic electroluminescence. EL materials can be functionally classified into host materials and dopant materials. It is generally known that a device structure having the most excellent EL properties can be fabricated with an EL layer prepared by doping a dopant to a host. Recently, development of organic EL devices with high efficiency and long life comes to the fore as an urgent subject, and particularly urgent is development of a material with far better EL properties as compared to conventional EL materials as considering EL properties required for medium to large sized OLED panels.

In the meanwhile, for conventional blue materials, a number of materials have been developed and commercialized since the development of diphenylvinyl-biphenyl (DPVBi) (Compound a) by Idemitsu-Kosan. In addition to the blue material system from Idemitsu-Kosan, dinaphthylanthracene (DNA) (Compound b), tetra(t-butyl)perylene (Compound c) system or the like have been known. However, extensive research and development should be performed with respect to these materials. The distryl compound system of Idemitsu-Kosan, which is known to have highest efficiency up to now, has 6 μm/W of power efficiency and beneficial device lifetime of more than 30,000 hr. However, when it is applied to a full-colored display, the lifetime is merely several thousand hours, owing to decrease of color purity over operation time. In case of blue electroluminescence, it becomes advantageous from the aspect of the luminous efficiency, if the electroluminescent wavelength is shifted a little toward longer wavelength. However, it is not easy to apply the material to a display of high quality because of unsatisfactory color purity in blue. Furthermore, the research and development of such materials are urgent because of the problems in color purity, efficiency and thermal stability.

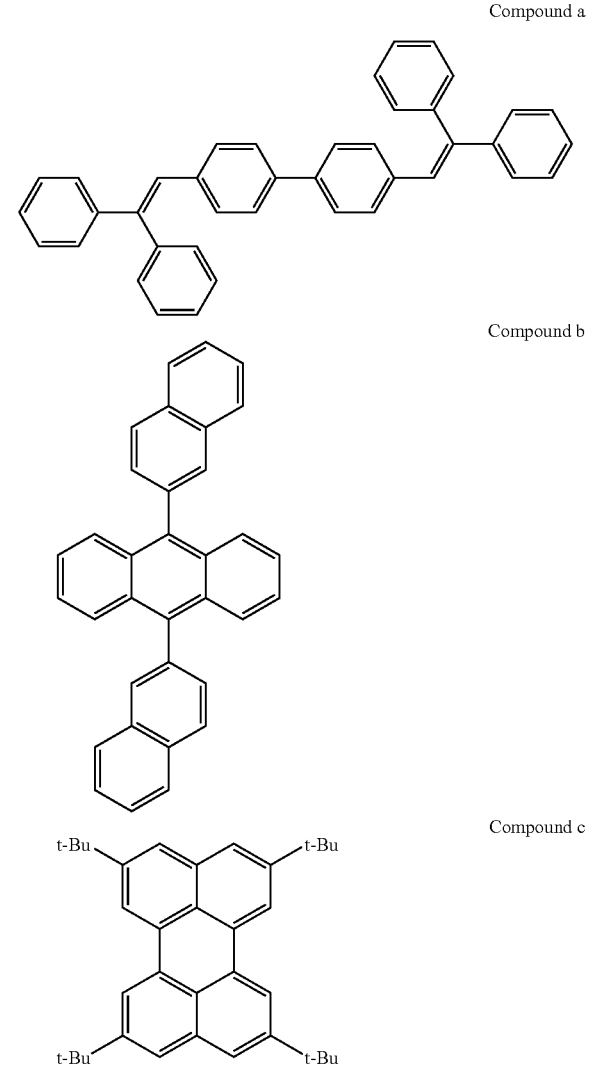

Compound a

Compound b

Compound c

In the meanwhile, according to a patent application of Mitsui Chemicals (Japan) (U.S. Pat. No. 7,166,240), the compounds shown below have the absorption spectra at 390 to 430 nm, with luminous efficiency of 4.6 cd/A. However, embodiment of pure blue color is impossible with the symmetrical structure of the Patent Publication, and the material, which cannot provide pure blue luminescence, is inadequate to be practically applied to a full-colored display.

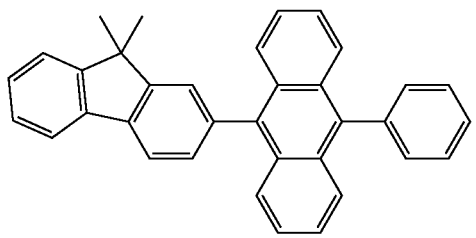

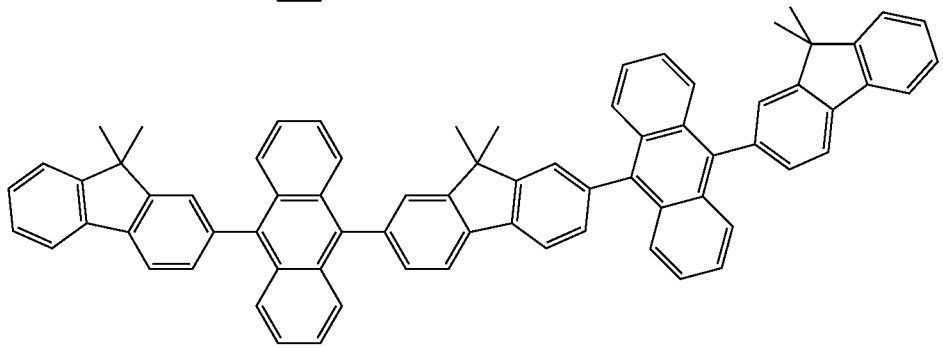

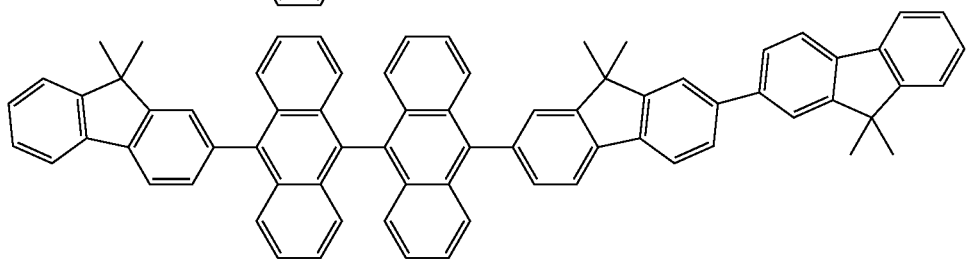

Representatives for conventional electron transport material include aluminum complexes such as tris(8-hydroxyquinoline)aluminum (III) (Alq), which has been used prior to the multilayer thin film OLED's disclosed by Kodak in 1987; and beryllium complexes such as bis(10-hydroxybenzo-[h]quinolinato)beryllium (Bebq), which was reported in the middle of 1990's in Japan [T. Sato et al., *J. Mater. Chem.* 10 (2000) 1151]. However, the limitation of the materials has come to the fore as OLED's have been practically used since 2002. Thereafter, many electron transport materials of high performance have been investigated and reported to approach their practical use.

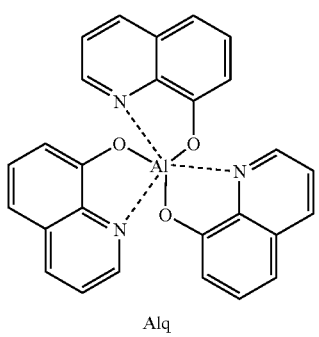

Alq

-continued

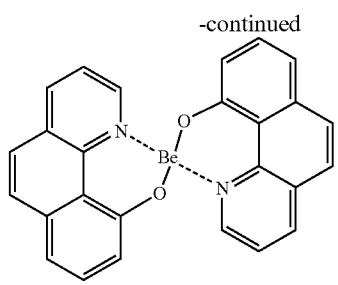

Bebq

In the meanwhile, non-metal complex electron transport materials of good features which have been reported up to the present include spiro-PBD [N. Johansson et al., *Adv. Mater.* 10 (1998) 1136], PyPySPyPy [M. Uchida et al., *Chem. Mater.* 13 (2001) 2680] and TPBI [Y.-T. Tao et al., *Appl. Phys. Lett.* 77 (2000) 1575] of Kodak. However, there remain various needs for improvement in terms of electroluminescent properties and lifetime.

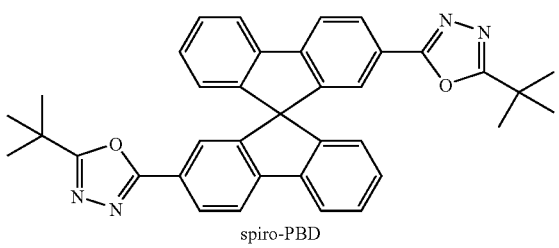

spiro-PBD

-continued

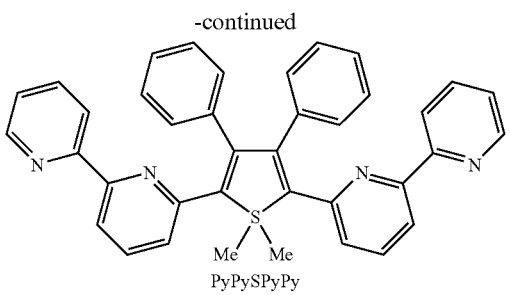
PyPySPyPy

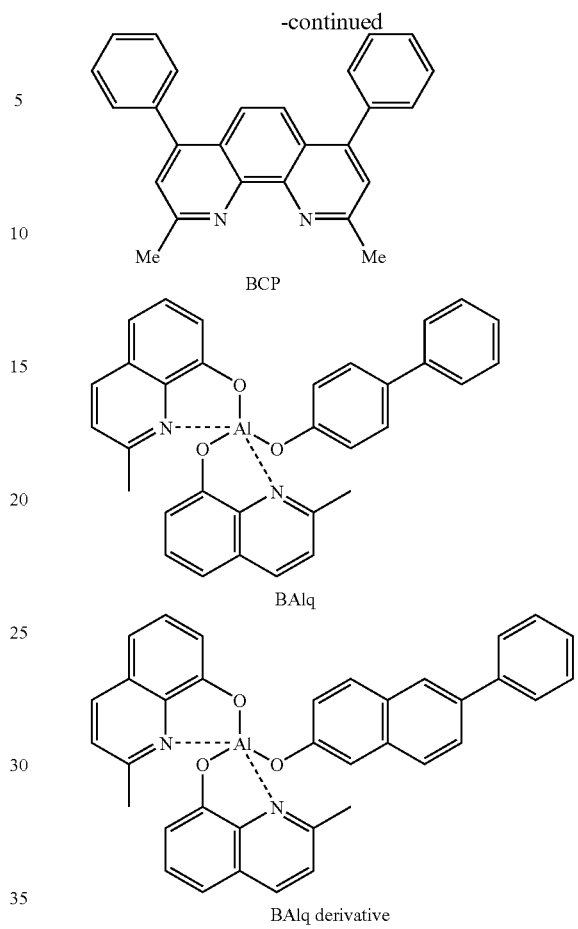
BCP

BAlq

BAlq derivative

Particularly noticeable is that conventional electron transport materials have only slightly improved operation voltage as compared to what was reported, or show the problem of considerable reduction of device operation lifetime. In addition, the materials exhibit adverse effects such as deviation in device lifetime for each color and deterioration of thermal stability. Up to the present, those adverse effects are in the way to achieve the objects such as reasonable power consumption and increased luminance, which have been the issues in manufacturing large-sized OLED panels.

As a host material for phosphorescent light emitting material, 4,4'-N,N'-dicarbazole-biphenyl (CBP) has been most widely known up to the present, and OLED's having high efficiency to which a hole blocking layer (such as BCP and BAlq) had been applied have been developed. Pioneer (Japan) or the like reported OLED's of high performances which were developed by using bis(2-methyl-8-quinolinato)(p-phenylphenolato)aluminum (III) (BAlq) derivatives as the host.

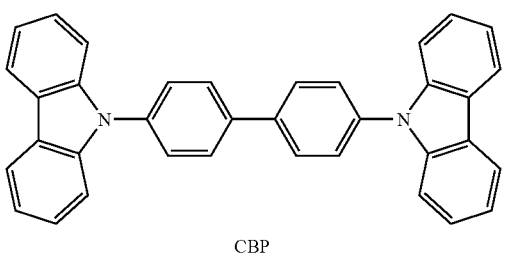
CBP

Though the conventional materials are advantageous in view of light emitting property, they have low glass transition temperature and very poor thermal stability, so that the materials tend to be changed during high temperature vapor-deposition in vacuo. In an organic electroluminescent device (OLED), it is defined that power efficiency=(π/voltage)×current efficiency. Thus, the power efficiency is inversely proportional to the voltage, and the power efficiency should be higher in order to obtain lower power consumption of an OLED. In practice, an OLED employing phosphorescent electroluminescent (EL) material shows significantly higher current efficiency (cd/A) than an OLED employing fluorescent EL material. However, in case that a conventional material such as BAlq and CBP as host material of the phosphorescent EL material is employed, no significant advantage can be obtained in terms of power efficiency (lm/w) because of higher operating voltage as compared to an OLED employing a fluorescent material.

Furthermore, there was no satisfactory result in view of life of an OLED, so that development of host material providing better stability and higher performance is still required.

SUMMARY OF THE INVENTION

The object of the present invention is to provide novel compounds for electronic material with improved luminous efficiency, power consumption and device life, as overcoming the disadvantage of conventional blue electroluminescent materials, electron transport materials and phosphorescent host materials as described above.

Another object of the invention is to provide organic electroluminescent devices with high efficiency and long life, which comprise said novel compounds for electronic material.

Still another object of the invention is to provide organic solar cells comprising said novel compounds for electronic material.

The present invention relates to compounds for electronic material represented by Chemical Formula (1), and organic electronic device comprising the same. Since the compounds for electronic material according to the invention show good luminous efficiency and excellent color purity and life property of material, OLED's having very good operation life can be manufactured therefrom.

The compounds for electronic material according to the invention, when being employed as host or electron transport layer of a phosphor in an organic electroluminescent device, lower the operation voltage to noticeably decrease the power consumption.

Chemical Formula 1

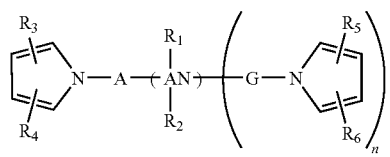

In Chemical Formula (1),

AN is an anthracene ring;

A and G independently represent a chemical bond, or they are selected from (C6-C60)arylene, (C3-C60)heteroarylene, 5- or 6-membered heterocycloalkylene containing one or more heteroatom(s) selected from N, O and S, (C3-C60)cycloalkylene, (C2-C60)alkenylene, (C2-C60)alkynylene, (C1-C60)alkylenoxy, (C6-C60)arylenoxy and (C6-C60)arylenethio;

$R_1$ through $R_6$ independently represent hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri (C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; or each of $R_1$ through $R_6$ may be linked to an adjacent substituent via (C3-C60)alkylene or (C3-C60)alkenylene with or without a fused ring to form an alicyclic ring, or a monocyclic or polycyclic aromatic ring; which may be represented by one of Compounds (A) to (C);

Compound (A)

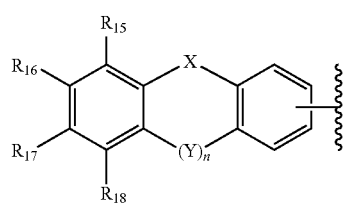

Compound (B)

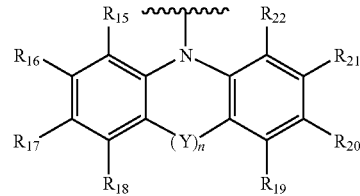

Compound (C)

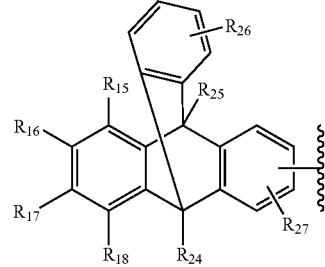

wherein, $R_1$ through $R_{27}$ are independently selected from hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl;

X and Y are independently selected from $CR_{28}R_{29}$, $NR_{30}$, S, O, $SiR_{30}R_{31}$, $PR_{32}$, CO, $BR_{33}$, $InR_{34}$, Se, $GeR_{35}R_{36}$, $SnR_{37}R_{38}$, $GaR_{39}$ and $R_{40}C=CR_{41}$; wherein $R_{28}$ through $R_{41}$ represent hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl, or each of $R_1$, through $R_6$ may be linked to an adjacent substituent via (C3-C60)alkylene or (C3-C60)alkenylene with or without a fused ring to form an alicyclic ring, or a monocyclic or polycyclic aromatic ring; n is an integer from 0 to 4; and the arylene, heteroarylene, heterocycloalkylene, cycloalkylene, alkenylene, alkynylene, alkylenoxy, arylenoxy, arylenethio of A and G; and the alkyl, alkenyl, alkynyl, cycloalkyl, heterocycloalkyl, aryl, heteroaryl, arylsilyl, alkylsilyl, alkylamino and arylamino group of $R_1$ through $R_6$, and $R_{15}$ through $R_{41}$ may be further substituted by halogen, (C1-C60)alkyl with or without halogen substituent(s), (C6-C60)aryl, (C3-C60)heteroaryl with or without (C6-C60)aryl substituent, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; or an alicyclic ring, or a monocyclic or polycyclic aromatic ring formed by linkage via (C3-C60)alkylene or (C3-C60)alkenylene with or without a fused ring.

DETAILED DESCRIPTION OF THE INVENTION

Figure 1:
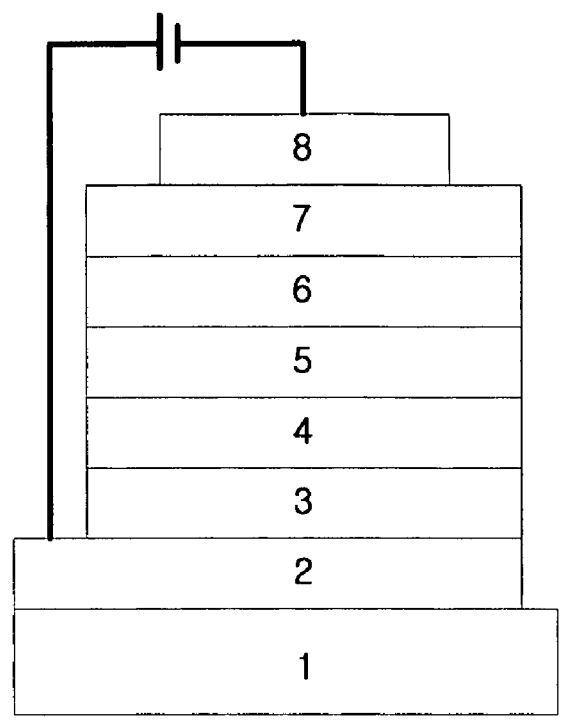
FIG. 1 is a cross-sectional view of an organic light emitting diode (OLED).

Referring now to the Drawings, FIG. 1 illustrates a cross-sectional view of an OLED of the present invention comprising a Glass 1, Transparent electrode 2, Hole injecting layer 3, Hole transport layer 4, Electroluminescent layer 5, Electron transport layer 6, Electron injecting layer 7 and Al cathode 8.

The term "alkyl", "alkoxy" and other substituents containing "alkyl" moiety described herein include both linear and branched species.

The term "aryl" described herein means an organic radical derived from aromatic hydrocarbon via elimination of one hydrogen atom. Each ring suitably comprises a monocyclic or fused ring system containing from 4 to 7, preferably from 5 to 6 cyclic atoms. Specific examples include phenyl, naphthyl, biphenyl, anthryl, phenylnaphthyl, tetrahydronaphthyl, indenyl, fluorenyl, phenanthryl, triphenylenyl, pyrenyl, perylenyl, chrysenyl, naphthacenyl and fluoranthenyl, but they are not restricted thereto.

The term "heteroaryl" described herein means an aryl group containing from 1 to 4 heteroatom(s) selected from N, O and S for the aromatic cyclic backbone atoms, and carbon atom(s) for remaining aromatic cyclic backbone atoms. The heteroaryl may be 5- or 6-membered monocyclic heteroaryl or a polycyclic heteroaryl which is fused with one or more benzene ring(s), and may be partially saturated. The heteroaryl groups include bivalent aryl group of which the heteroatom in the ring is oxidized or quarternized to form an N-oxide or a quaternary salt. Specific examples include monocyclic heteroaryl groups such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; and polycyclic heteroaryl groups such as benzofuranyl, benzothiophenyl, isobenzofuranyl, benzimidazolyl, benzothiazolyl, benzisothiazolyl, benzisoxazolyl, benzoxazolyl, isoindolyl, indolyl, indazolyl, benzothiadiazolyl, quinolyl, isoquinolyl, cinnolinyl, quinazolinyl, quinolizinyl, quinoxalinyl, carbazolyl, phenanthridinyl and benzodioxolyl; and corresponding N-oxides (for example, pyridyl N-oxide, quinolyl N-oxide) or quaternary salt thereof, but they are not restricted thereto.

The compounds of Chemical Formula (1) may be selected from those represented by one of Chemical Formulas (2) to (19):

Chemical Formula 2

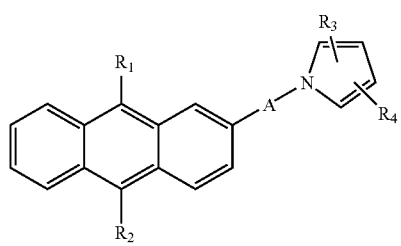

-continued

Chemical Formula 3

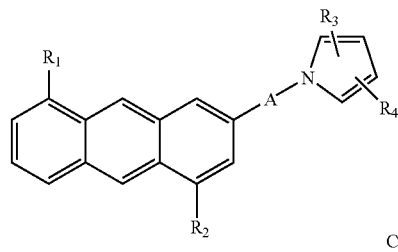

Chemical Formula 4

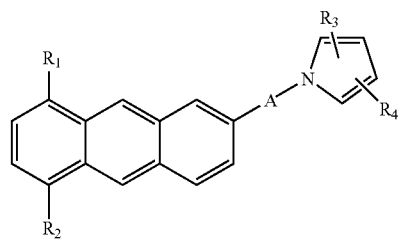

Chemical Formula 5

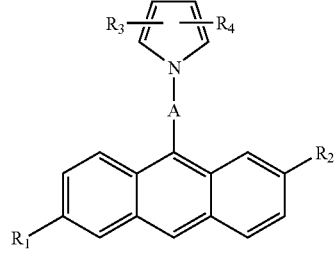

Chemical Formula 6

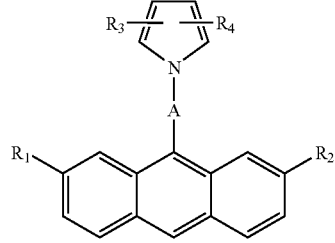

Chemical Formula 7

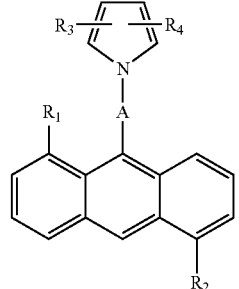

Chemical Formula 8

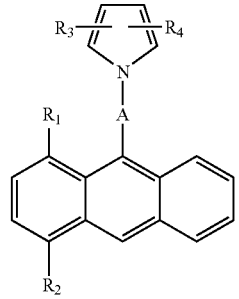

-continued
Chemical Formula 9
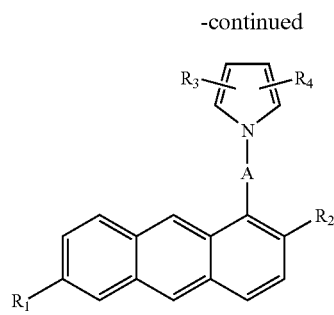
Chemical Formula 10
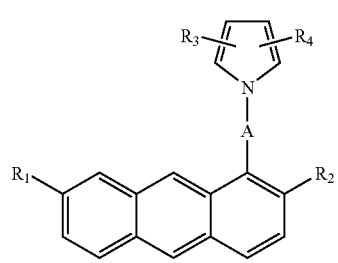
Chemical Formula 11
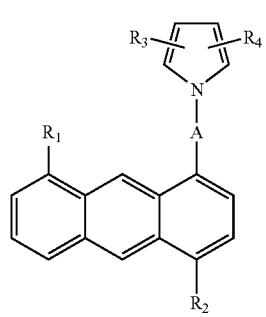
Chemical Formula 12
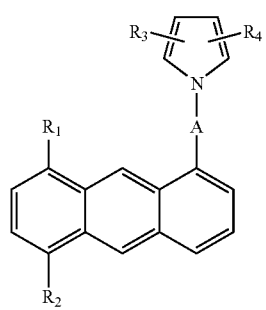
Chemical Formula 13
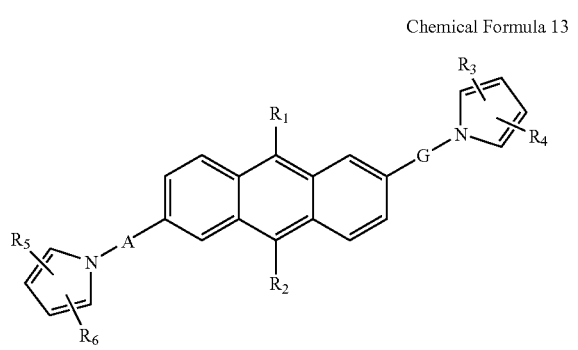
-continued
Chemical Formula 14
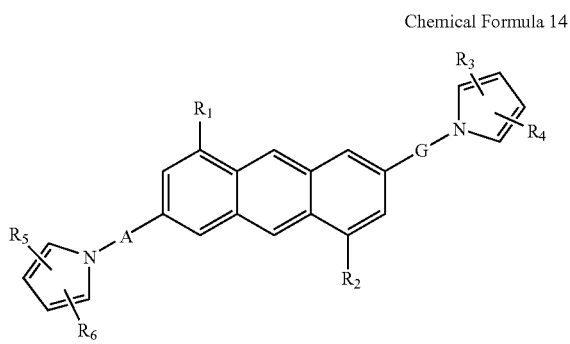
Chemical Formula 15
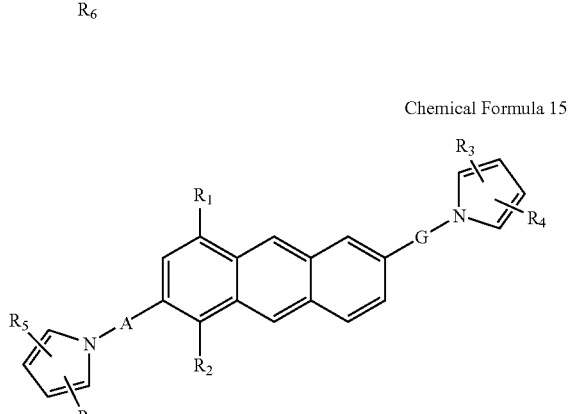
Chemical Formula 16
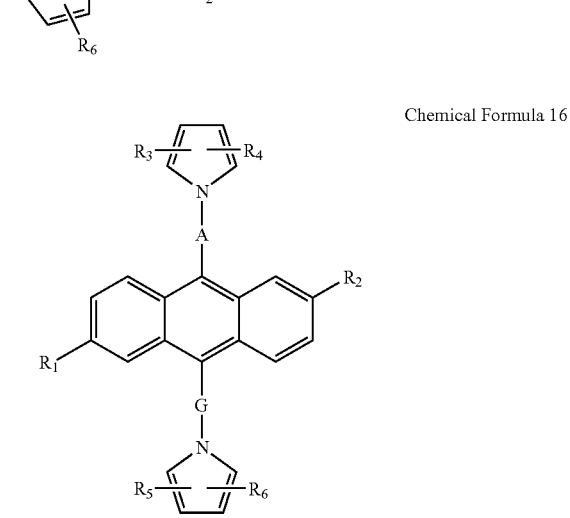
Chemical Formula 17
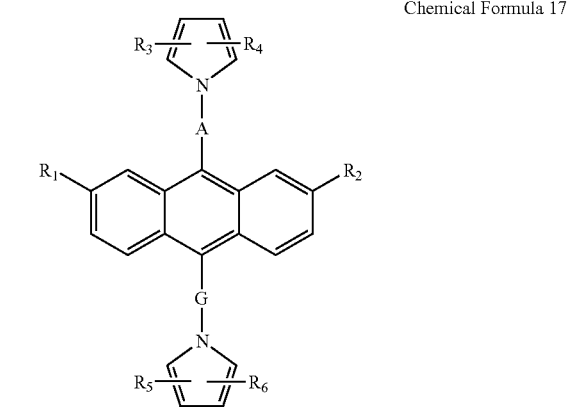

Chemical Formula 18
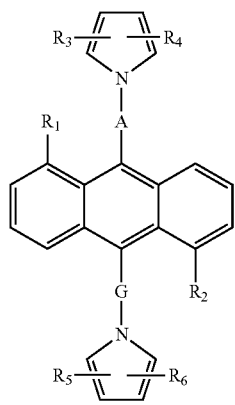
Chemical Formula 19
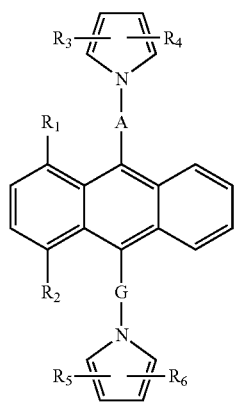
wherein, A, G and $R_1$ through $R_6$ are defined as in Chemical Formula (1).
In Chemical Formulas (1) through (19), A and G represent a chemical bond, or are selected from the following structures, but not restricted thereto:
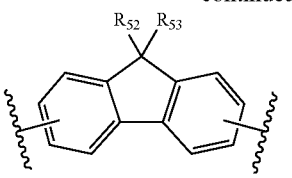
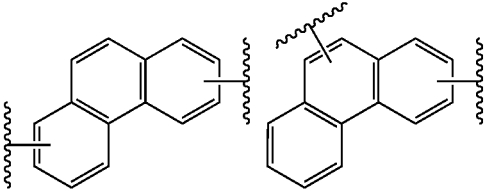
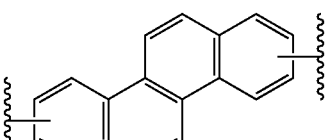
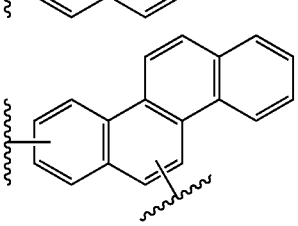
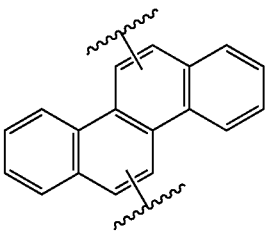
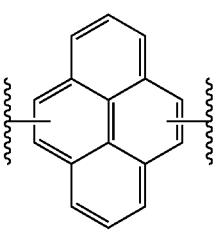
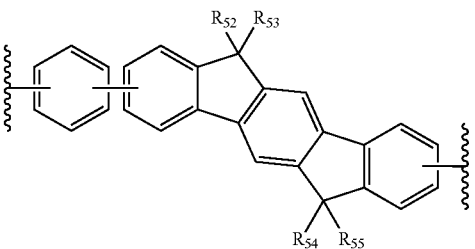

-continued
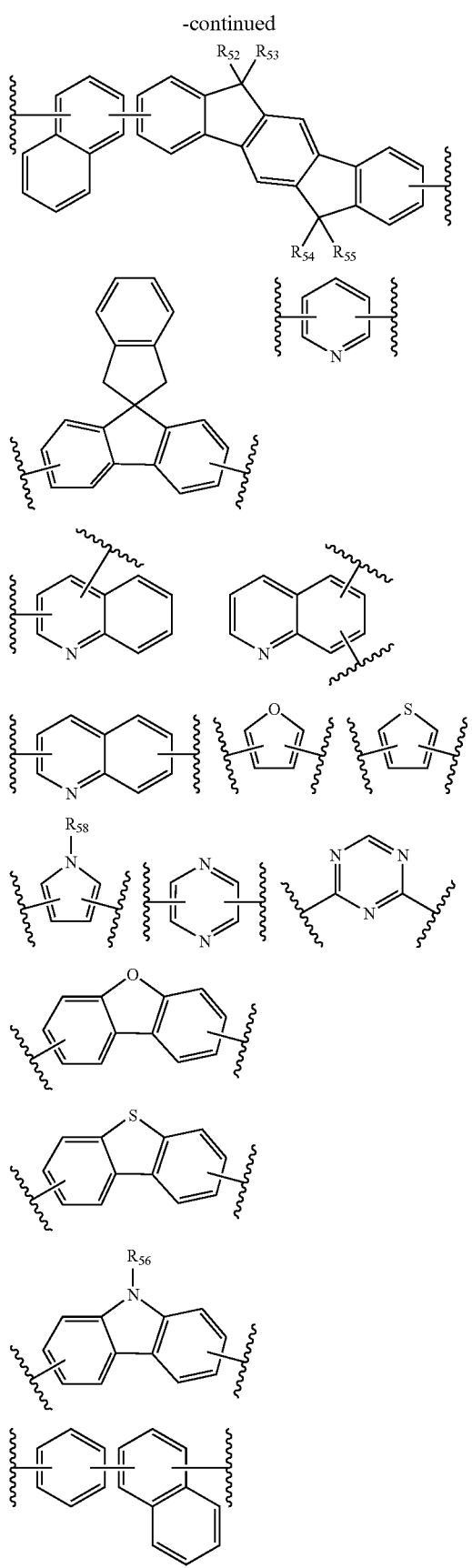
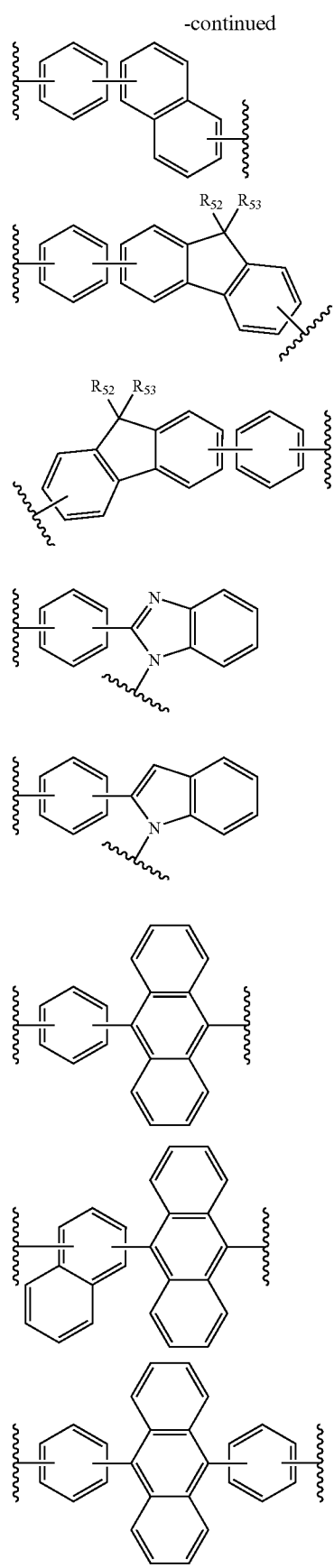

-continued

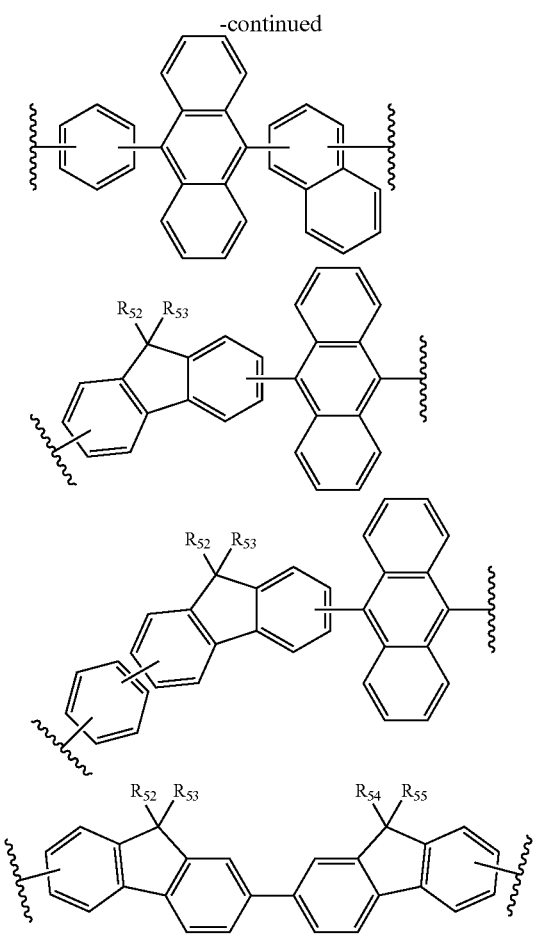

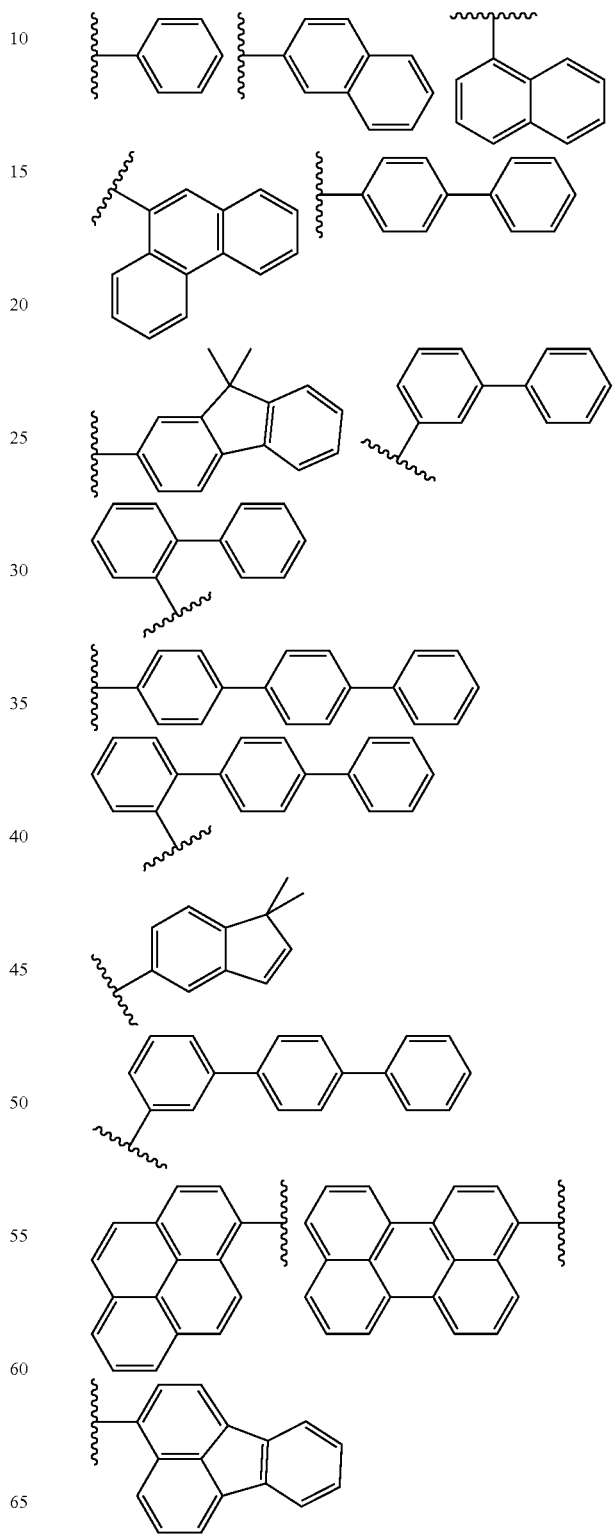

wherein, $R_{51}$ represents halogen, (C1-C60)alkyl, (C6-C60)aryl, (C4-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl;

$R_{52}$ through $R_{56}$ independently represent halogen, (C1-C60)alkyl, (C6-C60)aryl, (C4-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl; or each of $R_{52}$ through $R_{56}$ may be linked to an adjacent substituent via (C3-C60)alkylene or (C3-C60)alkenylene with or without a fused ring to form an alicyclic ring, or a monocyclic or polycyclic aromatic ring.

In Chemical Formulas (1) to (19), $R_1$ through $R_6$ are independently selected from hydrogen, methyl, ethyl, n-propyl, i-propyl, n-butyl, i-butyl, t-butyl, n-pentyl, i-pentyl, n-hexyl, n-heptyl, n-octyl, 2-ethylhexyl, n-nonyl, decyl, dodecyl, hexadecyl, trifluoromethyl, perfluoroethyl, trifluorethyl, perfluoropropyl, perfluorobutyl, methoxy, ethoxy, butoxy, hexyloxy, cyclopentyl, cyclohexyl, cycloheptyl, cyclooctyl, fluoro, cyano, trimethylsilyl, triethylsilyl, tripropylsilyl, tri(t-butyl)silyl, t-butyldimethylsilyl, dimethylphenylsilyl, triphenylsilyl and the following structures, but not restricted thereto.

-continued
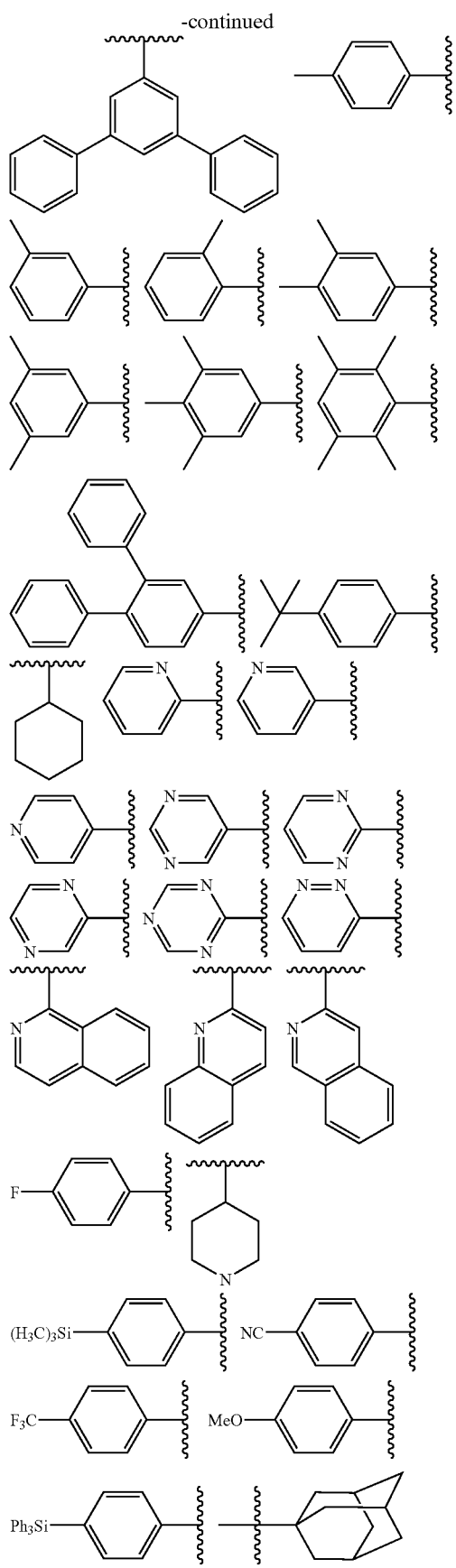
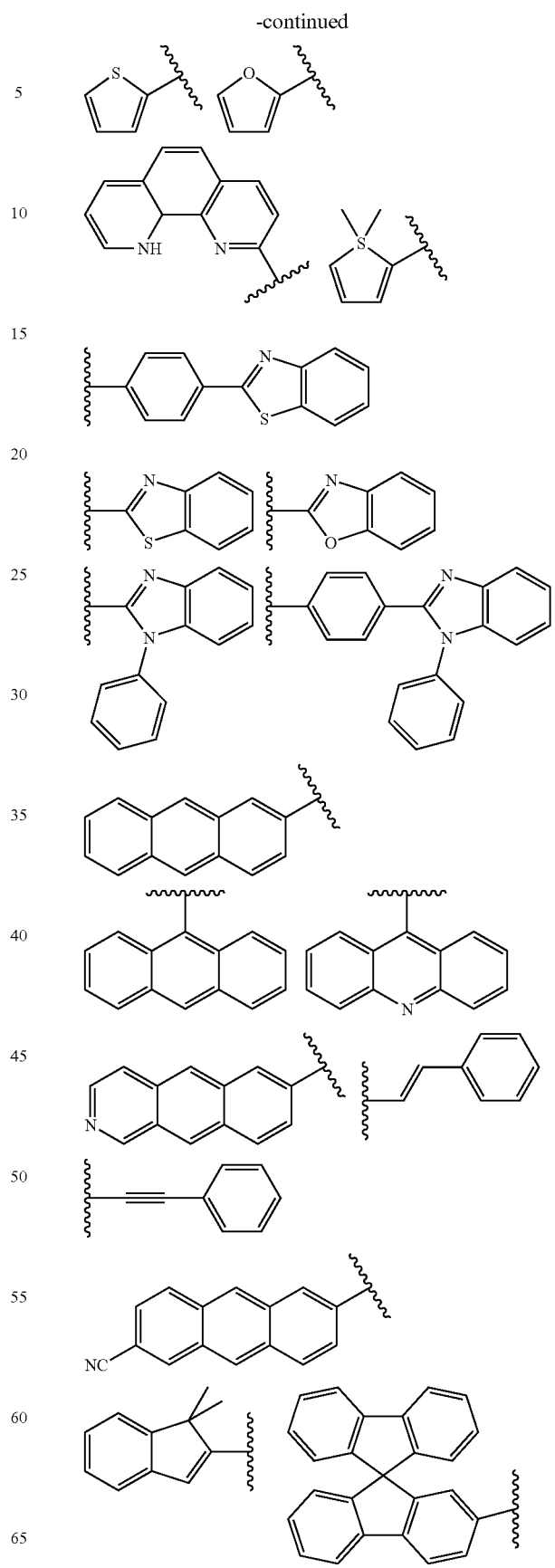

-continued
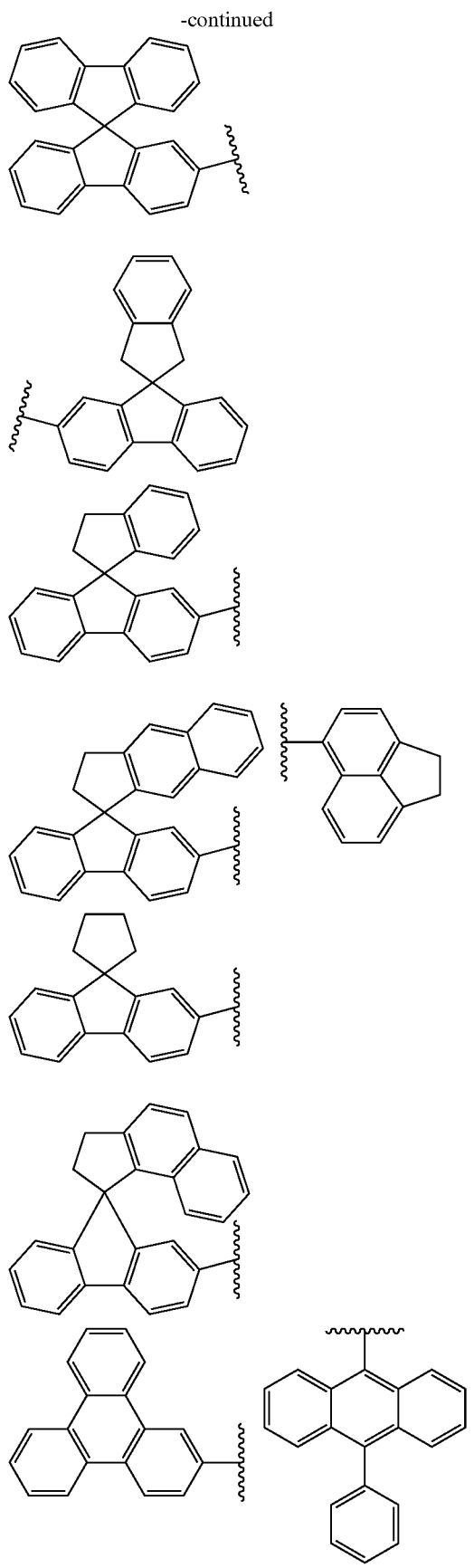
-continued
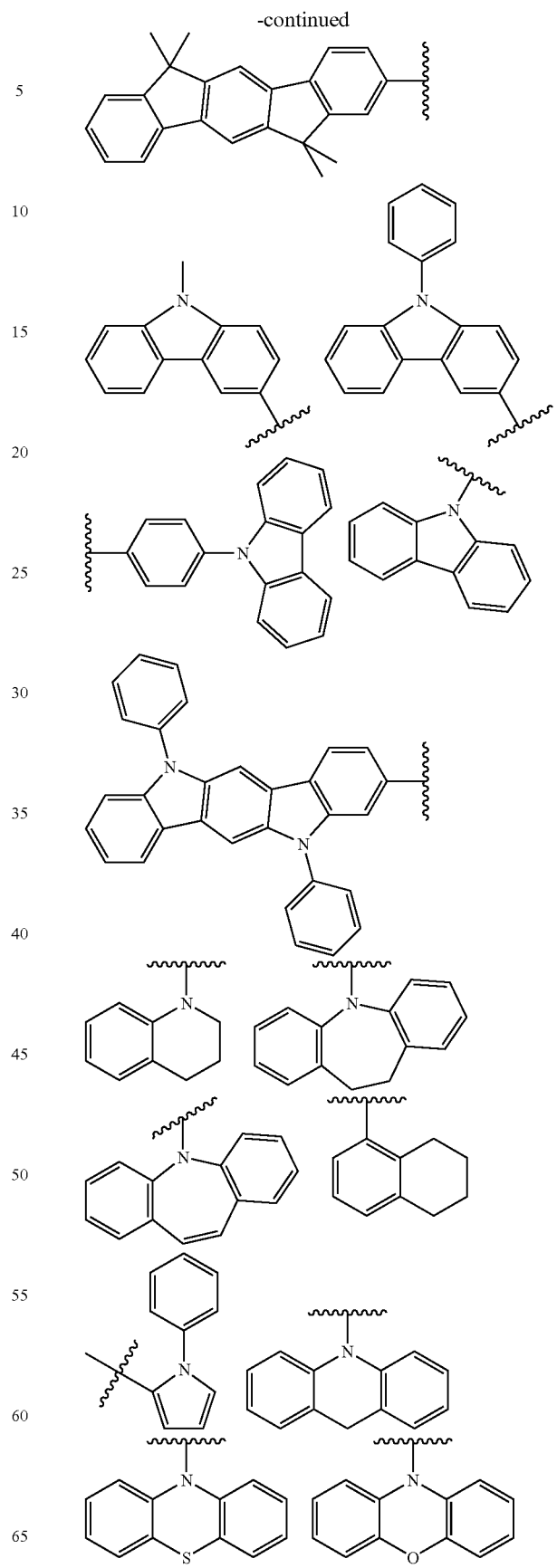

-continued
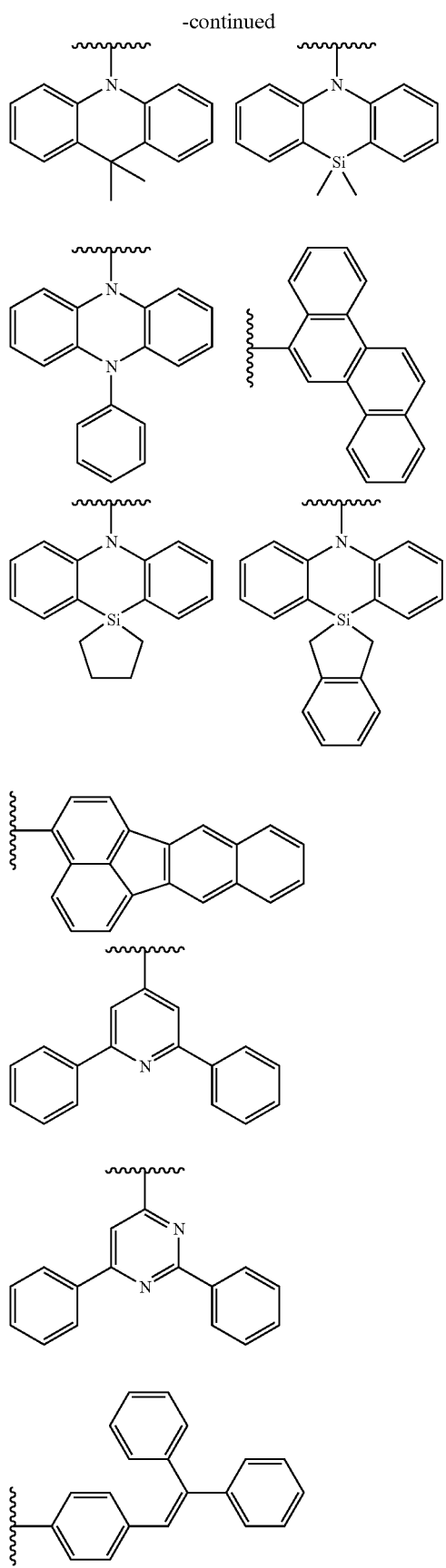
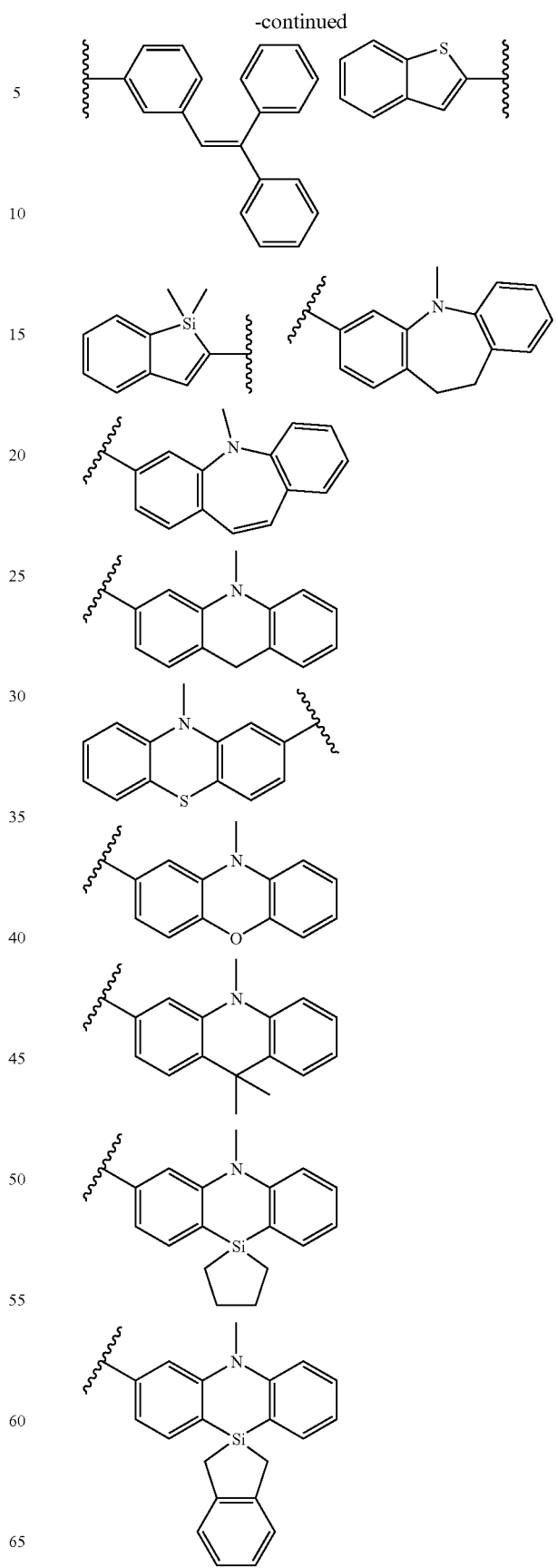

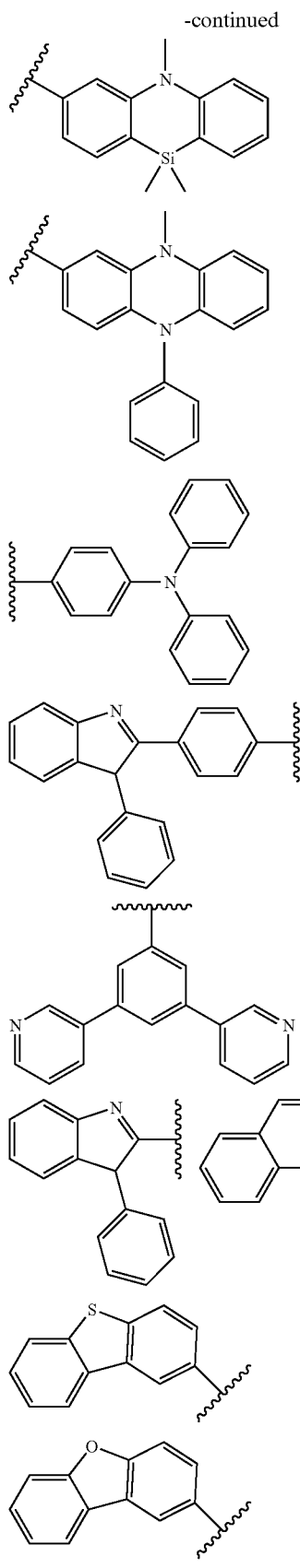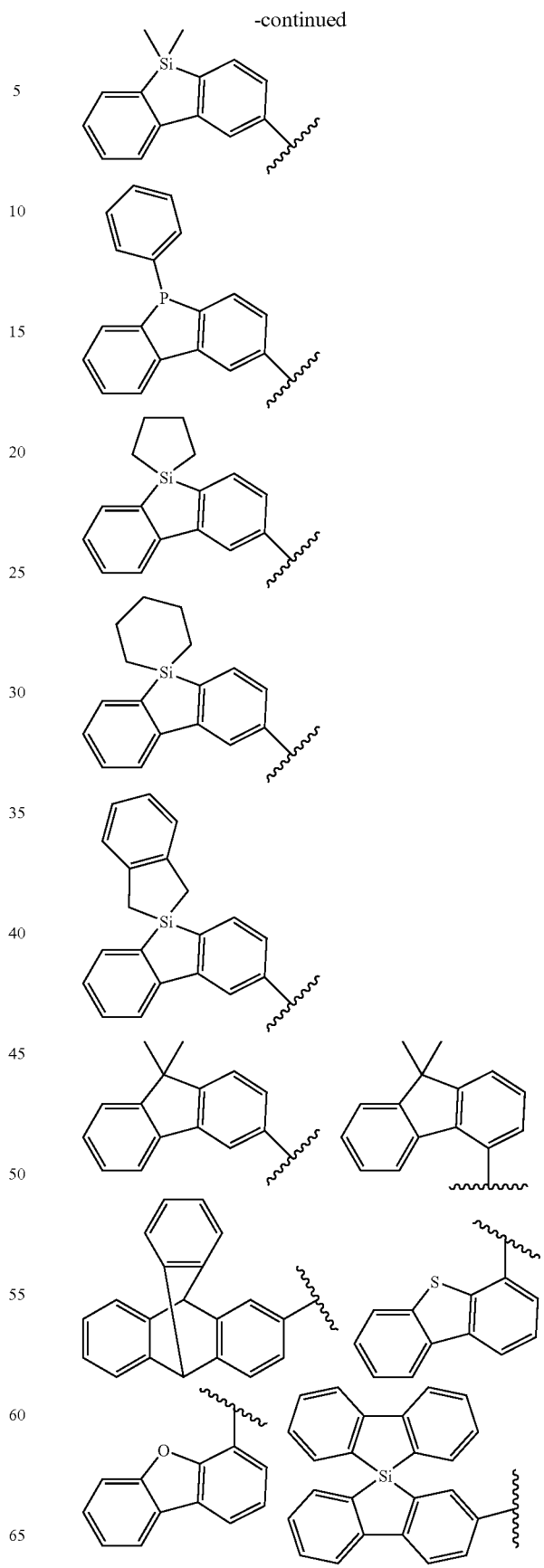

-continued
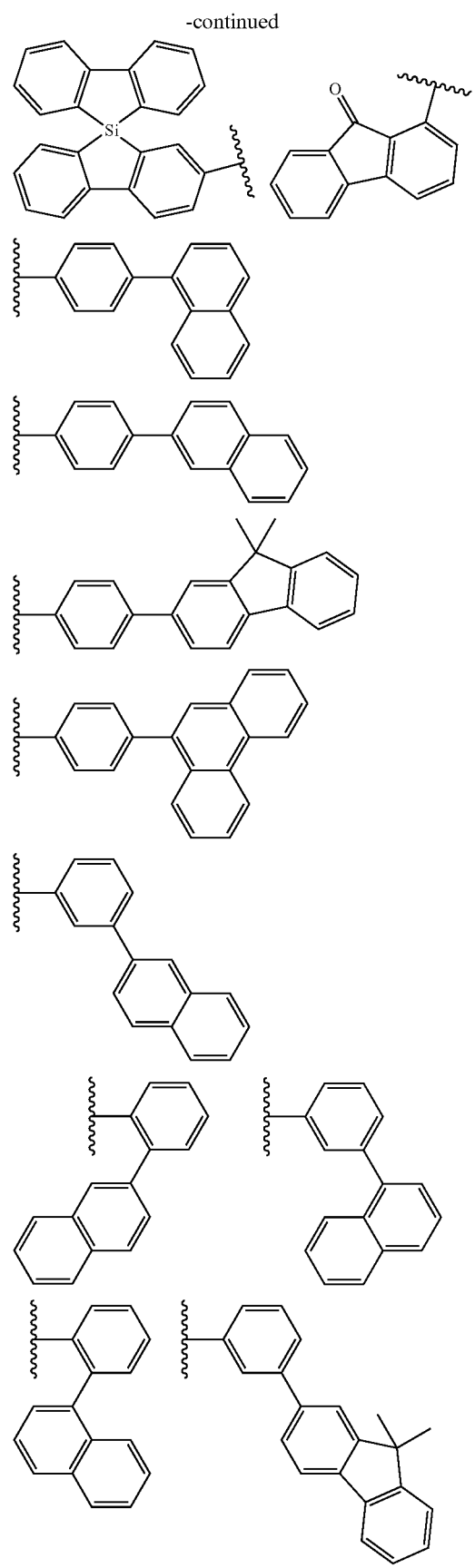
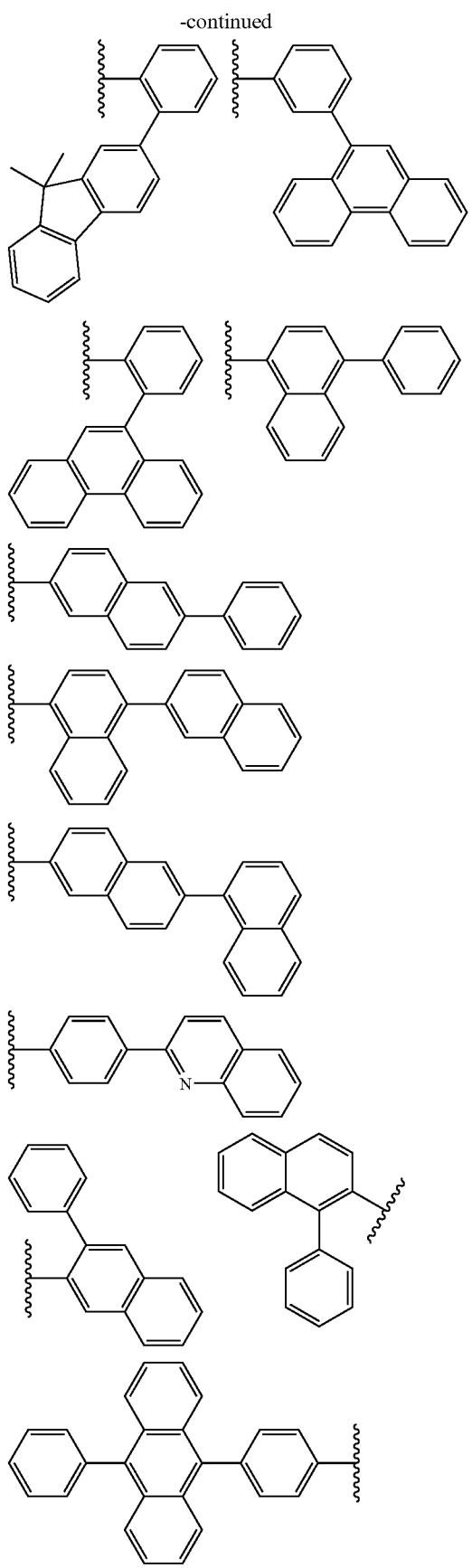

-continued
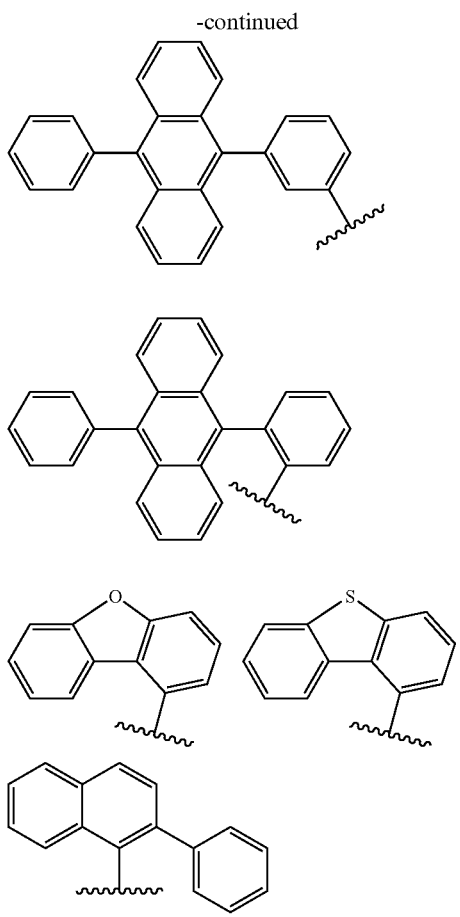
The compounds for electronic material according to the present invention can be more specifically exemplified by the following compounds, but are not restricted thereto.
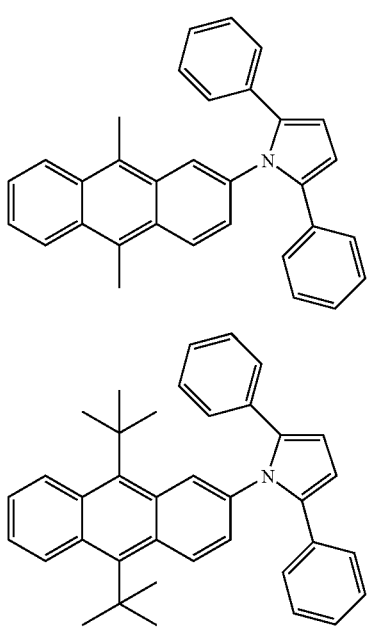
-continued
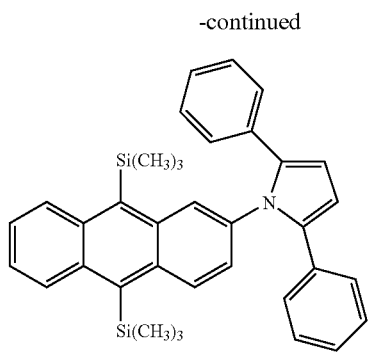
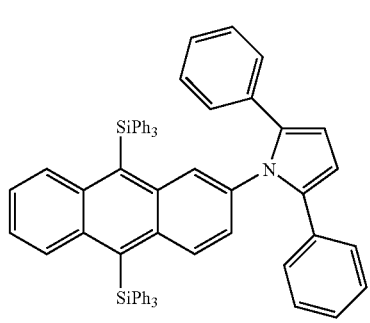
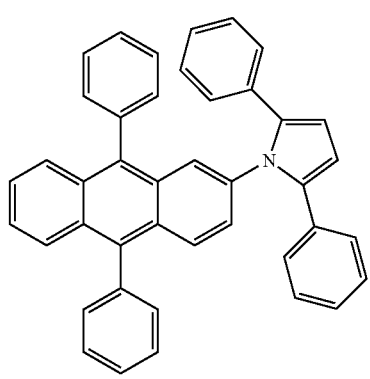
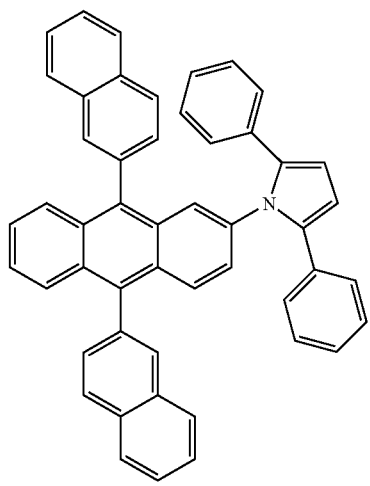

-continued
7
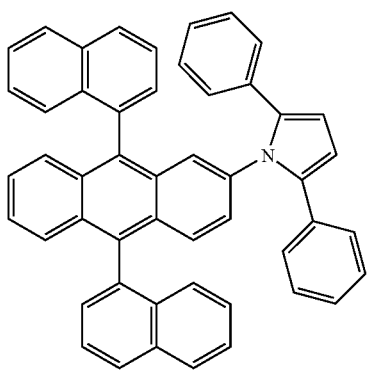
8
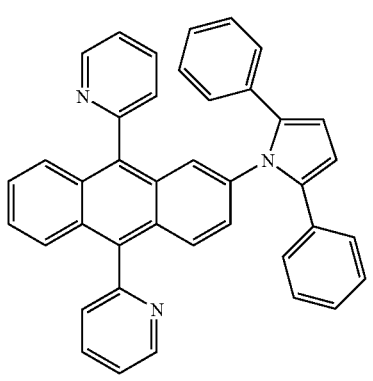
9
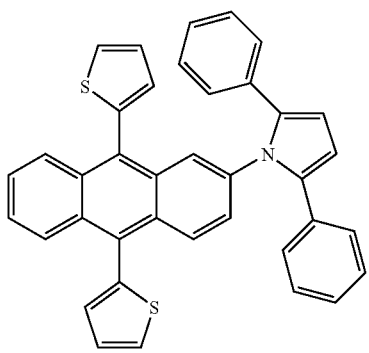
10
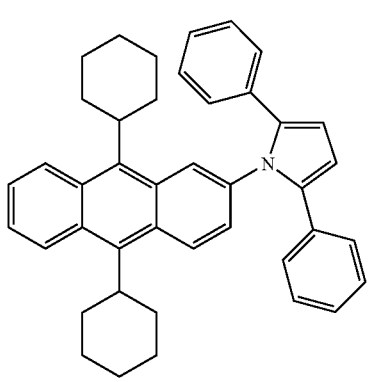
-continued
11
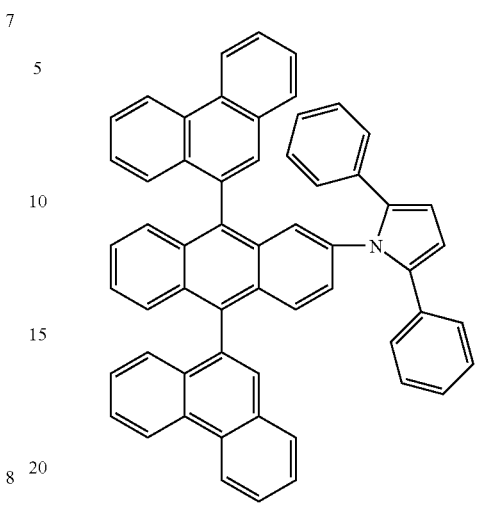
12
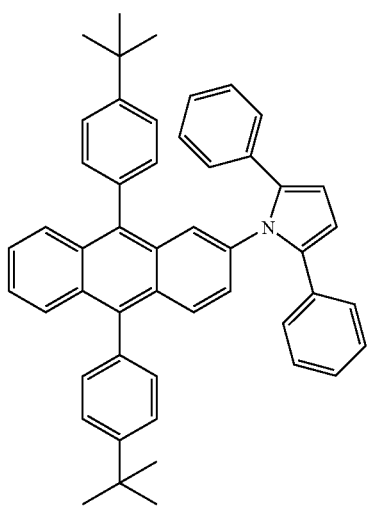
13
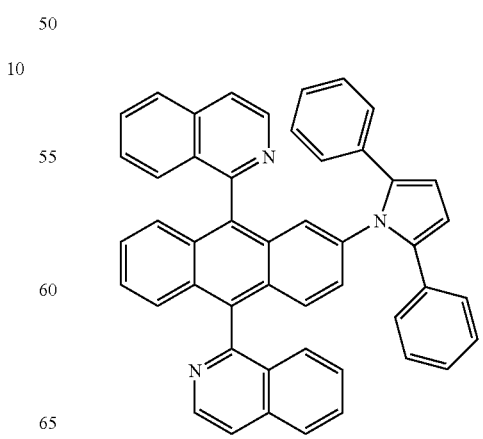

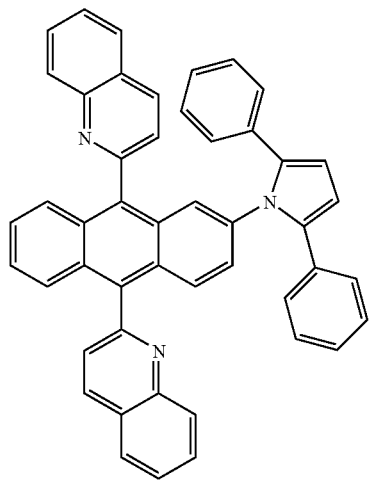
14
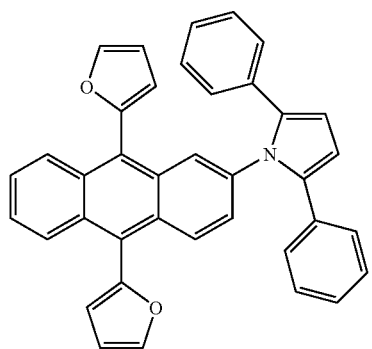
15
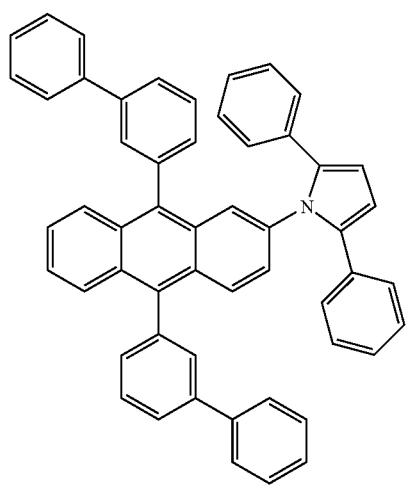
16
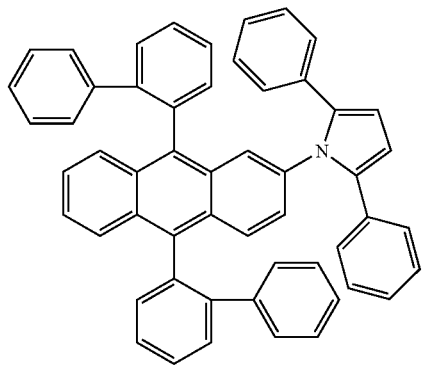
17

-continued
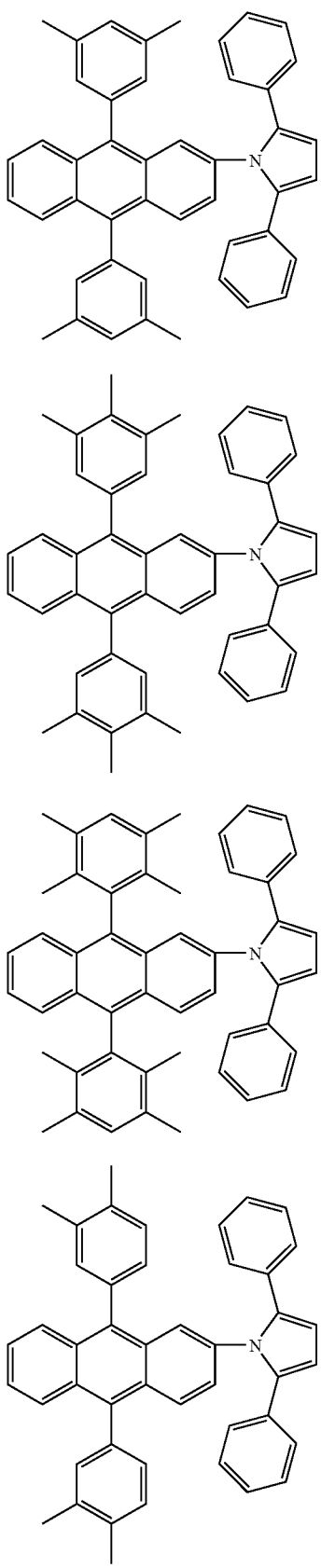
-continued
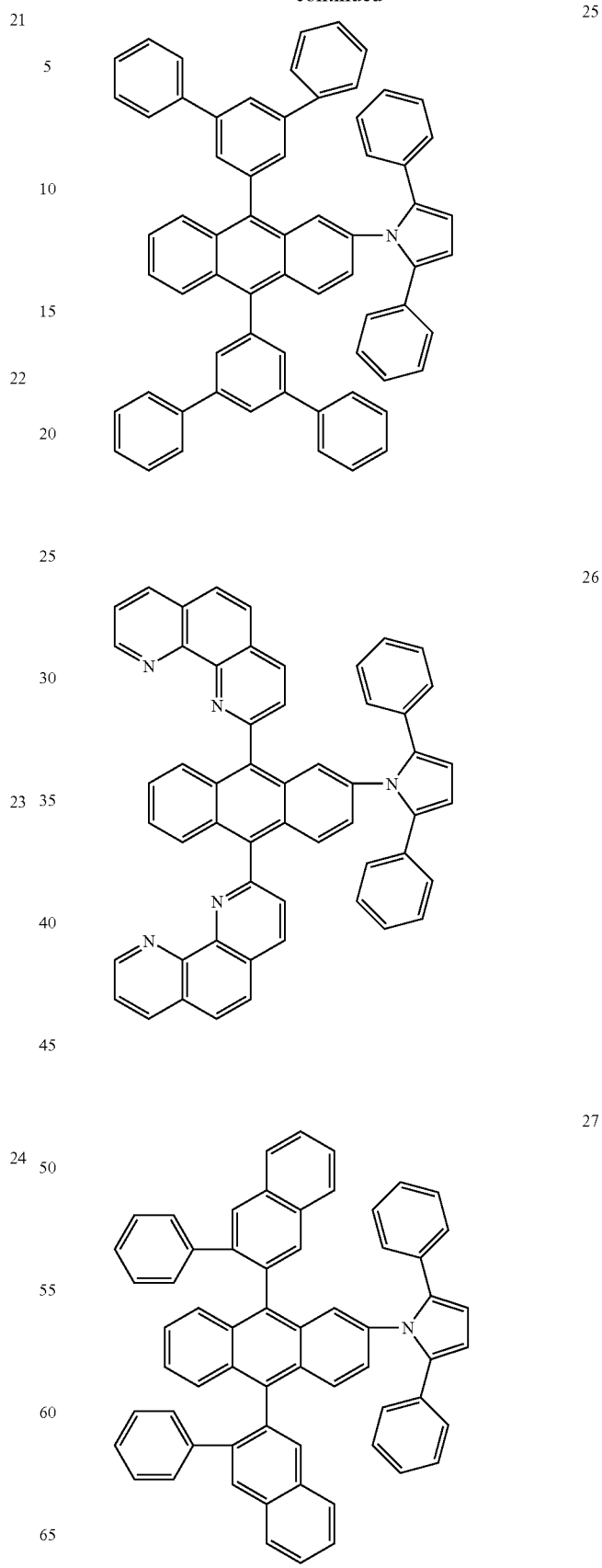

28
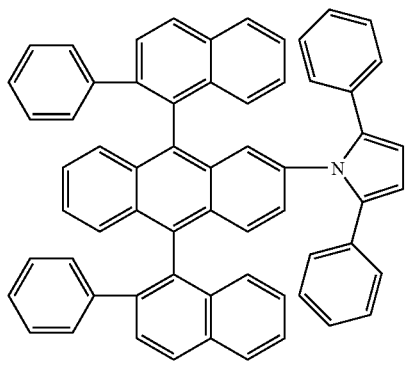
29
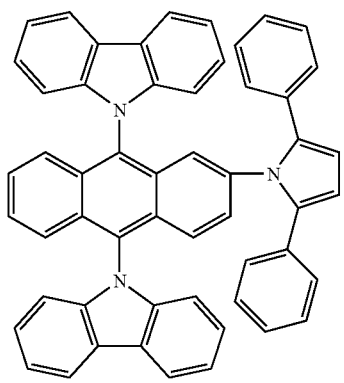
30
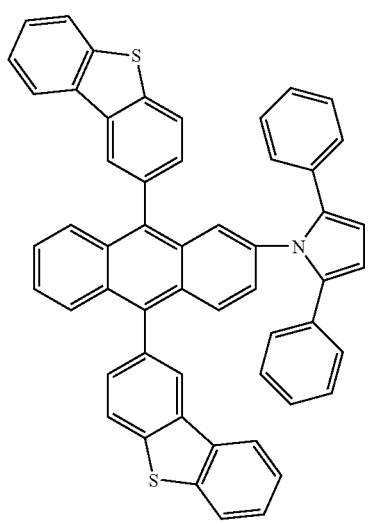
31
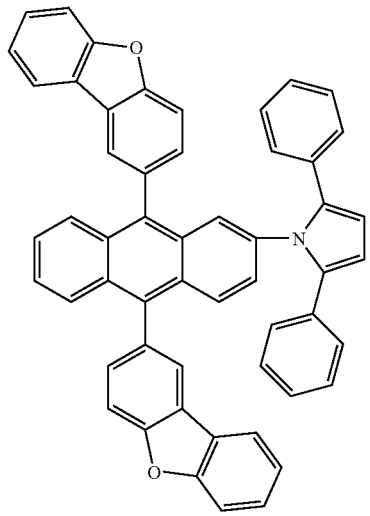
32
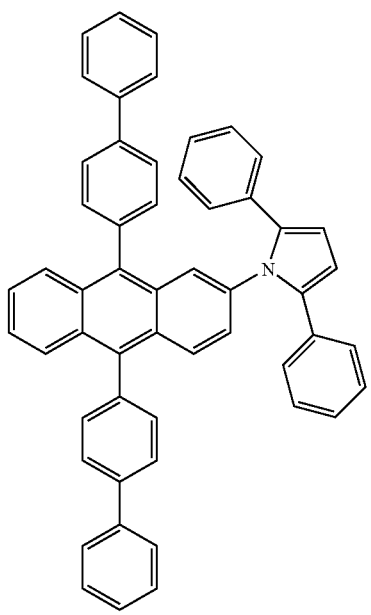
33

-continued
34
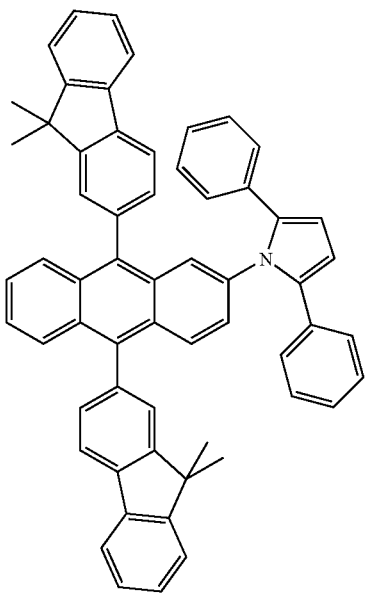
36
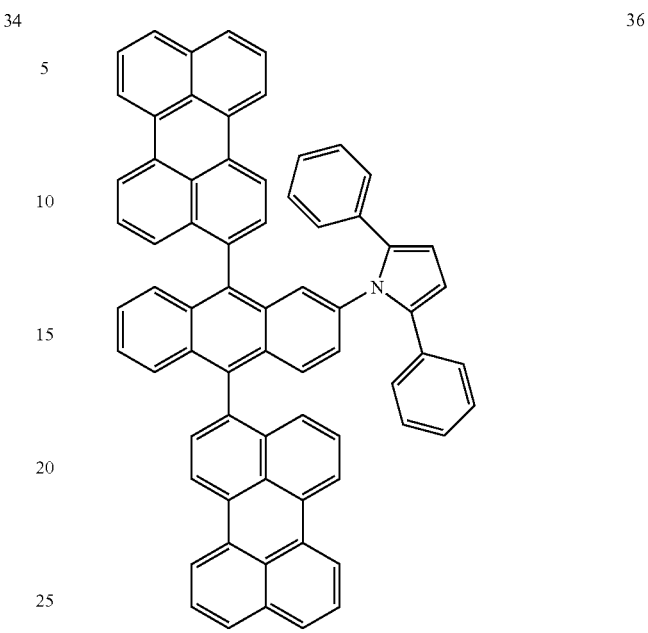
37
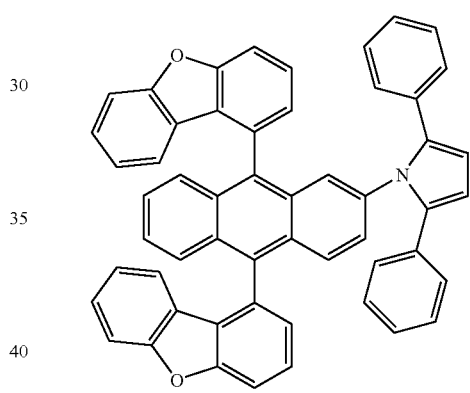
35
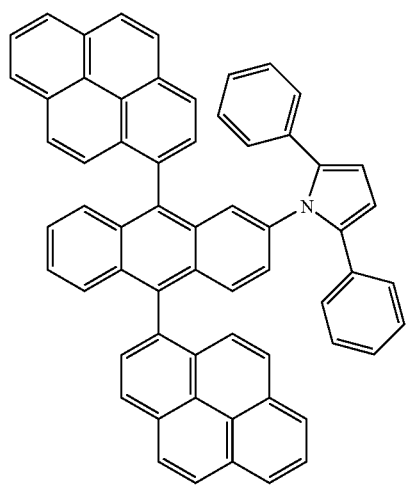
38
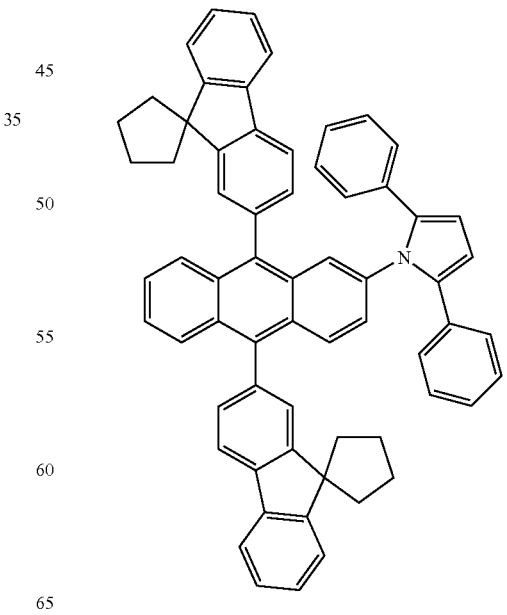

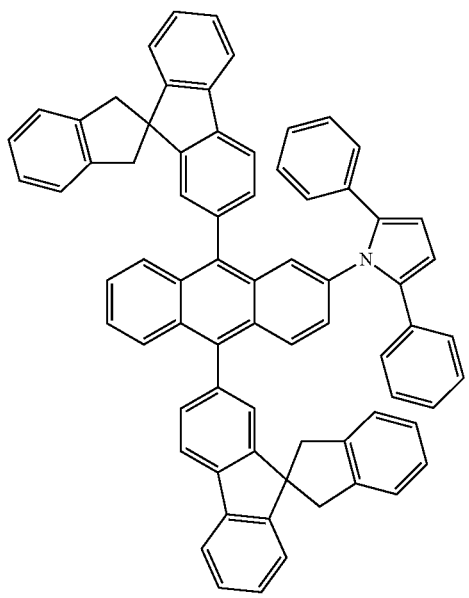
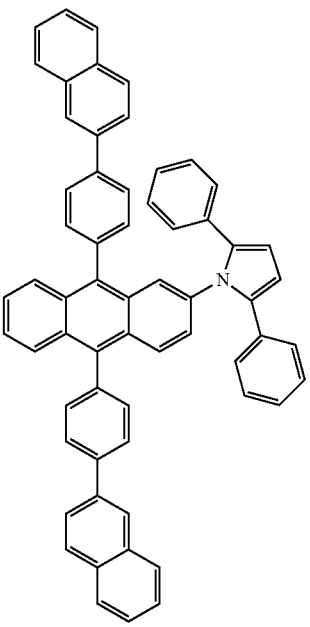
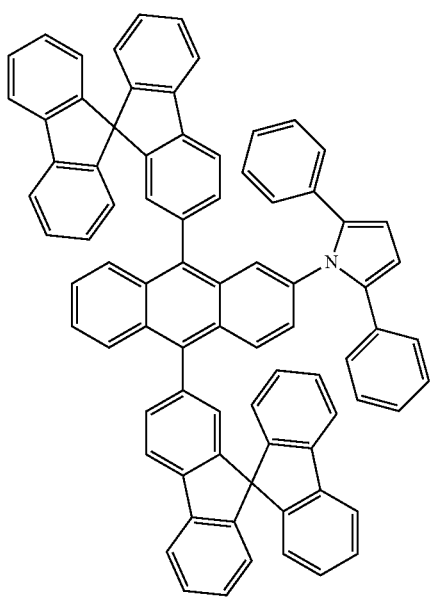
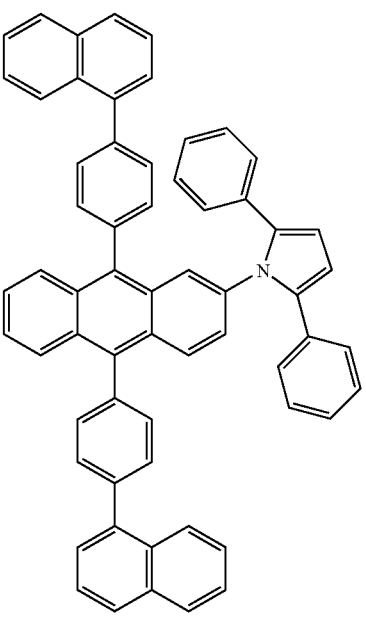

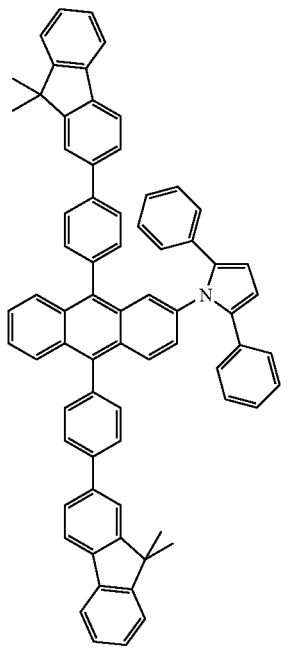
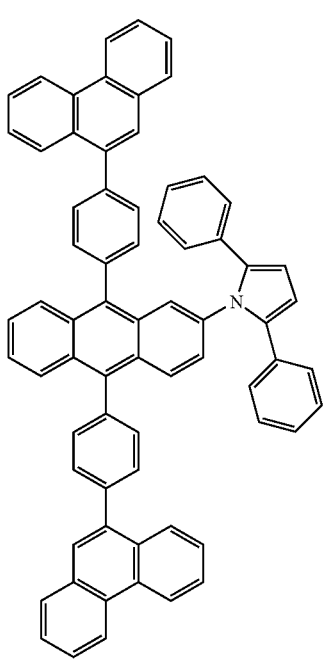
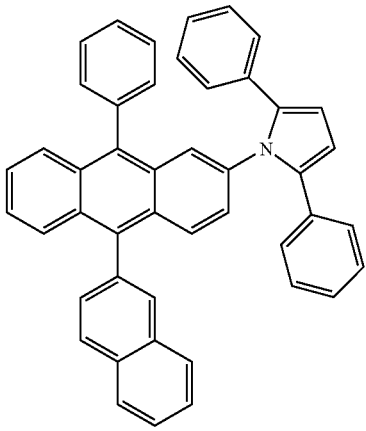
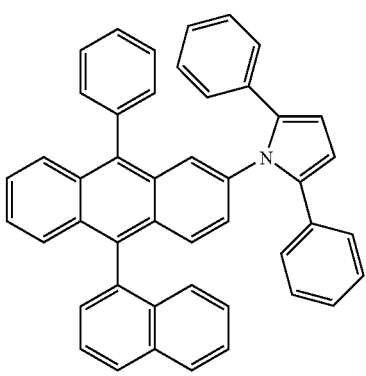
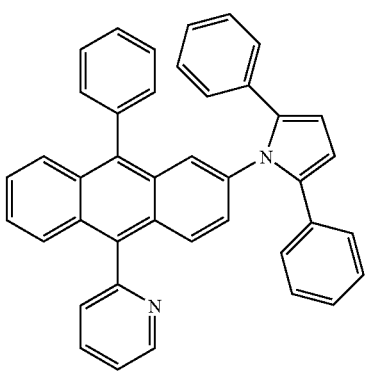
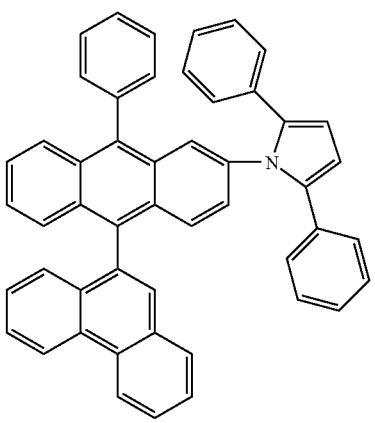

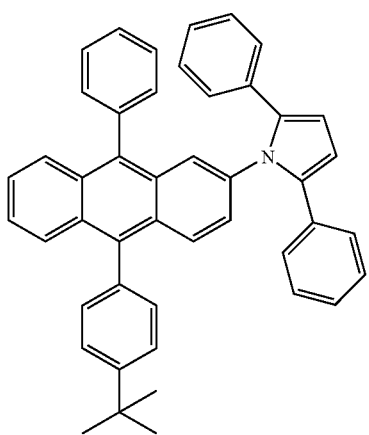
49
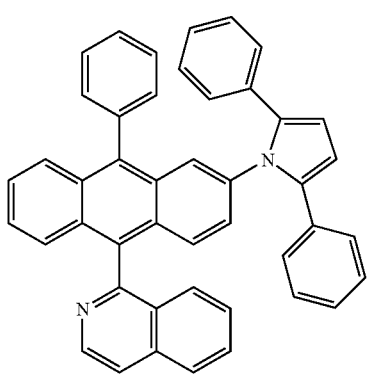
50
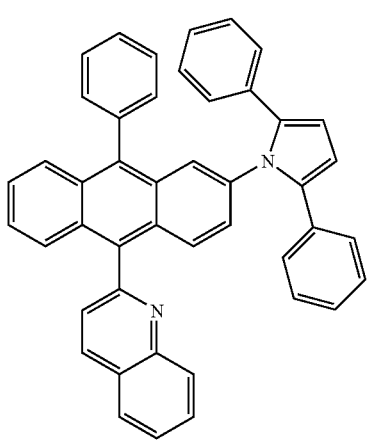
51
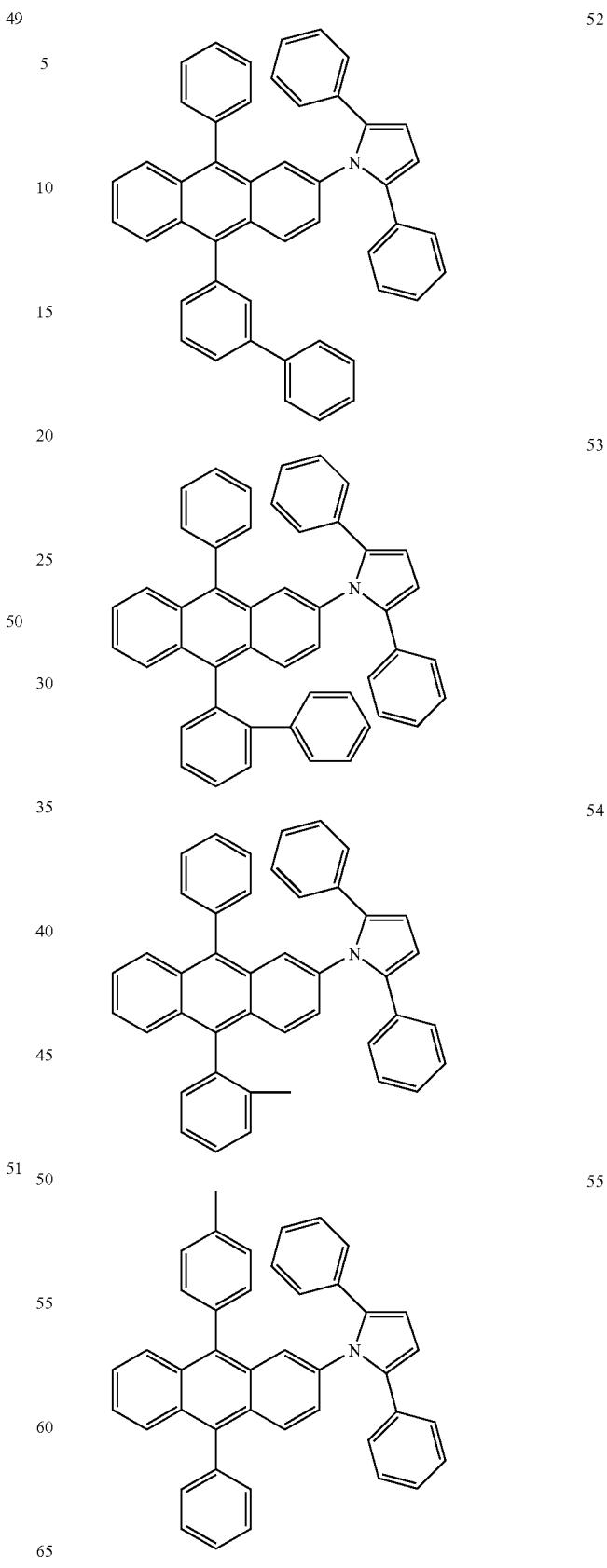
52
53
54
55

-continued
56
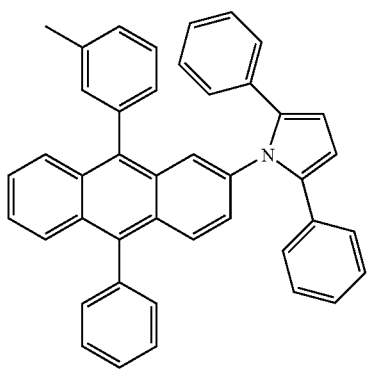
57
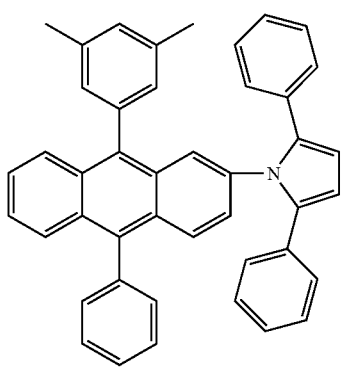
58
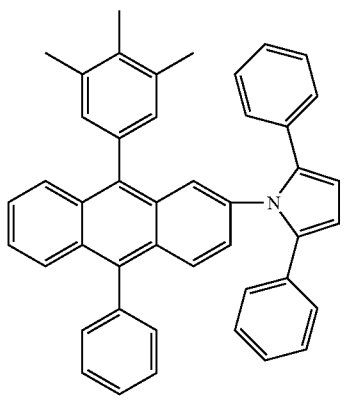
59
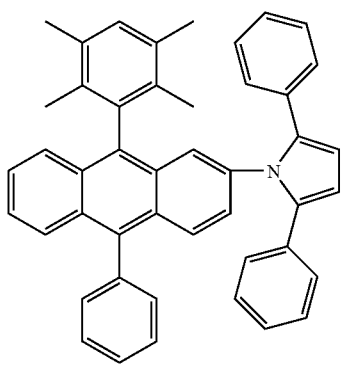
-continued
60
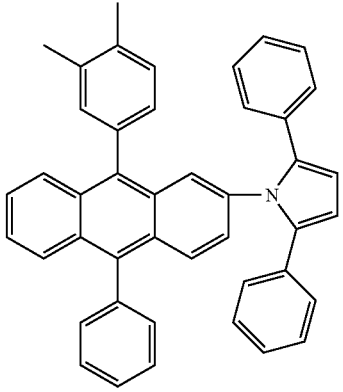
61
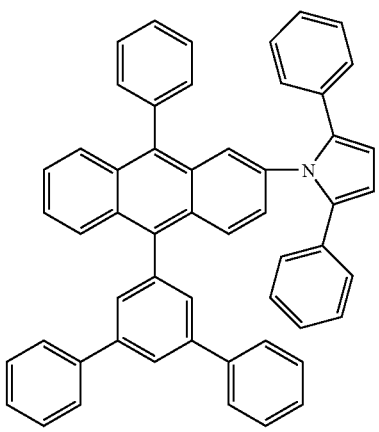
62
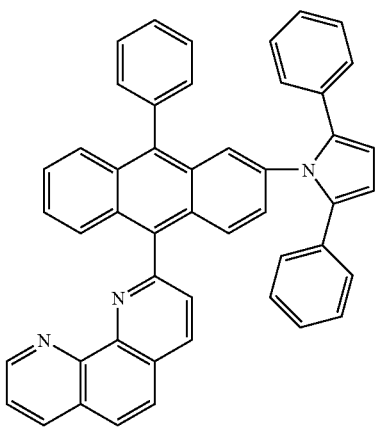

-continued
63
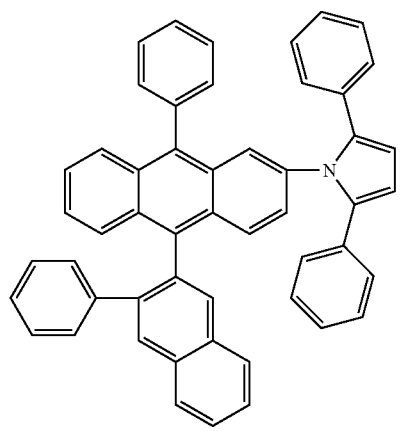
64
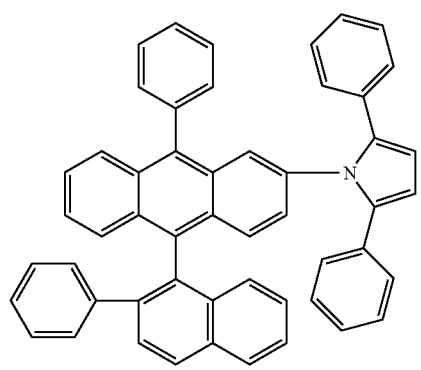
65
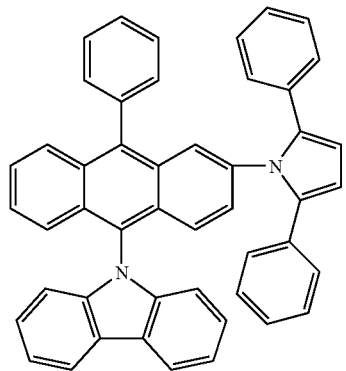
66
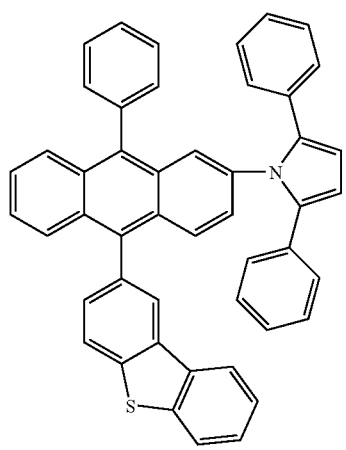
-continued
67
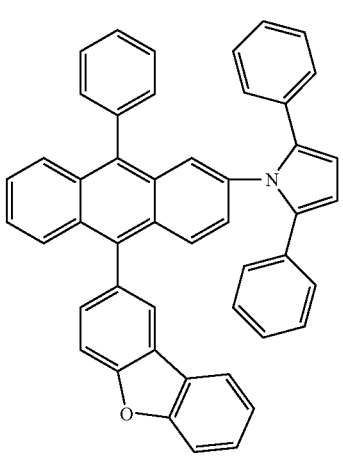
68
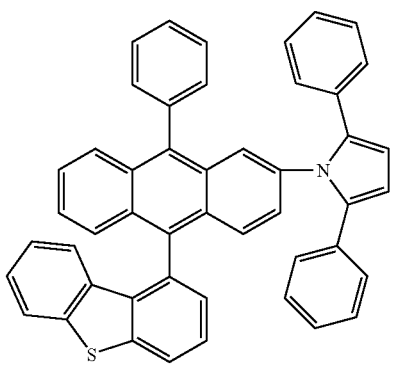
69
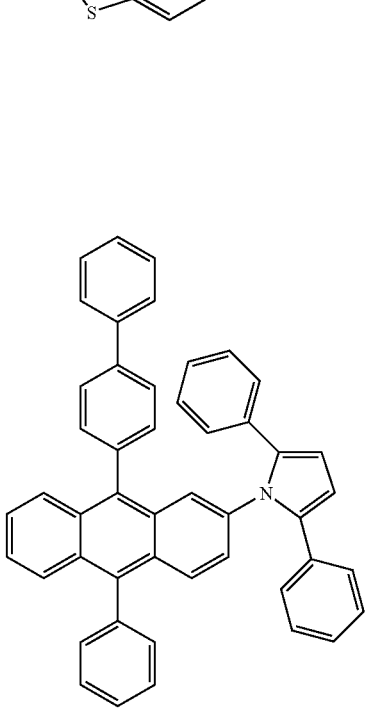

-continued
51
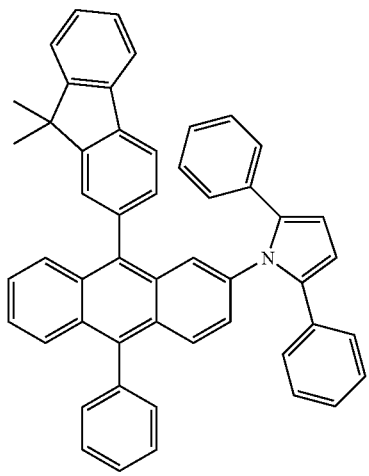
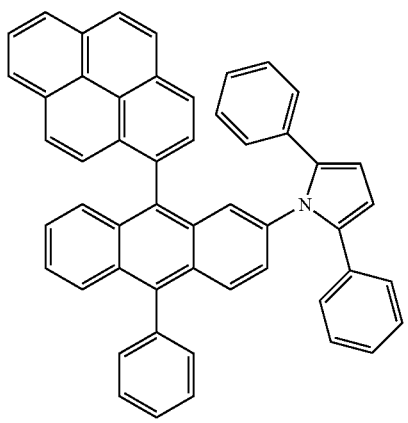
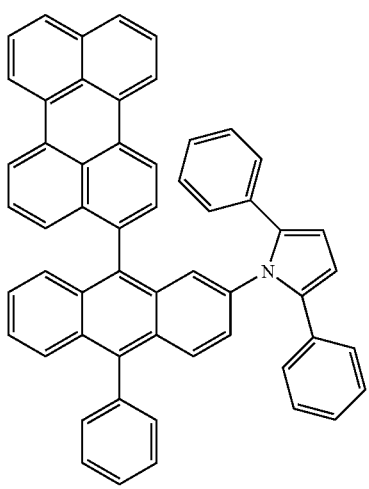
52
-continued
70
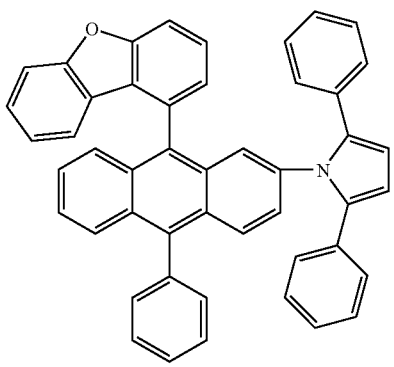
71
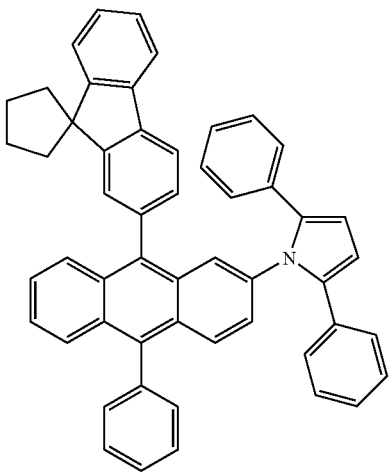
72
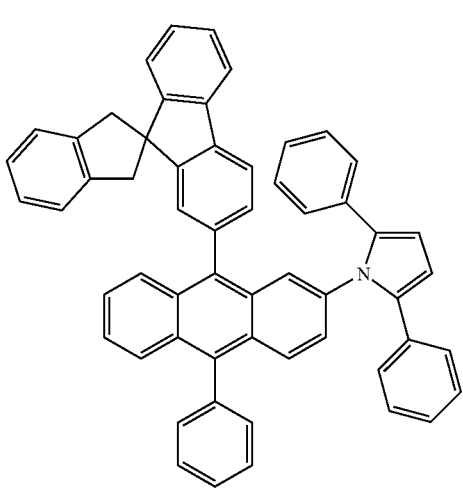
73
74
75

76
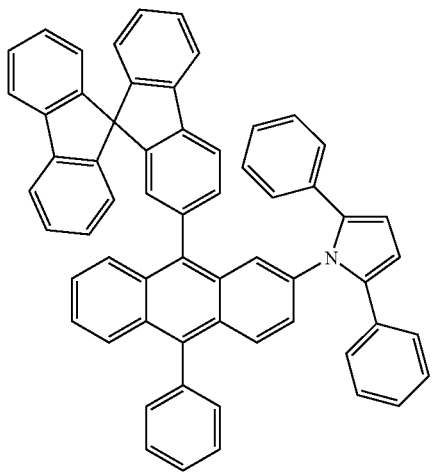
79
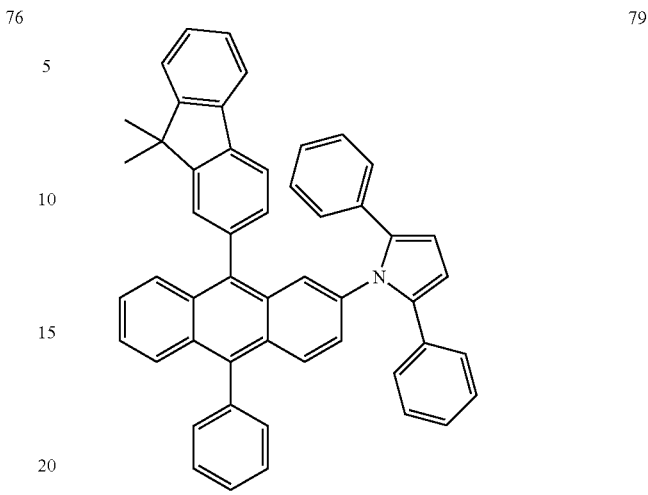
77
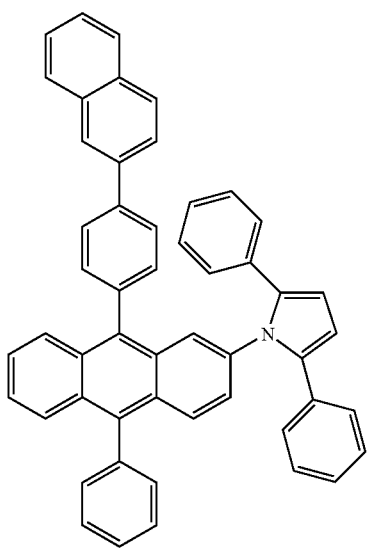
80
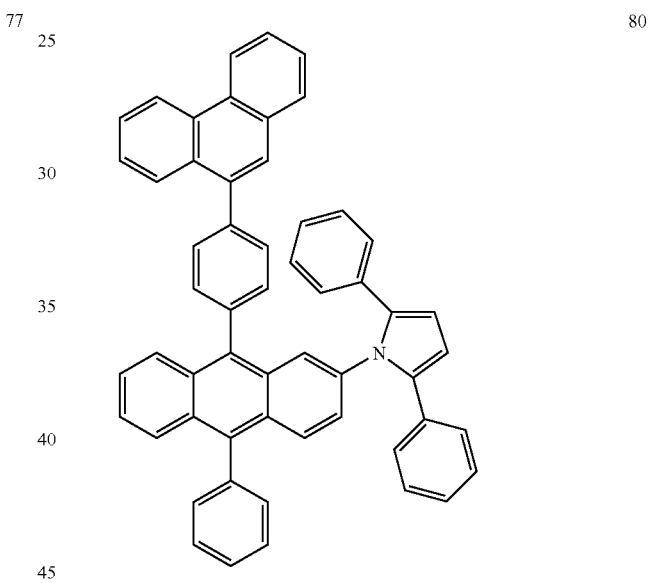
78
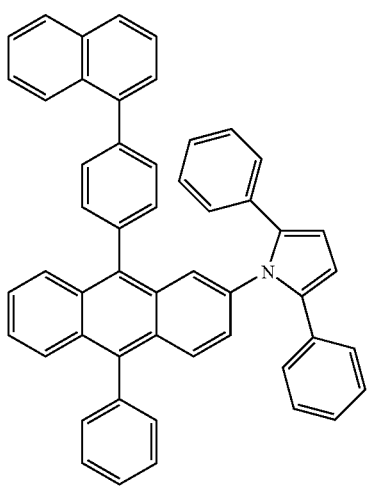
81
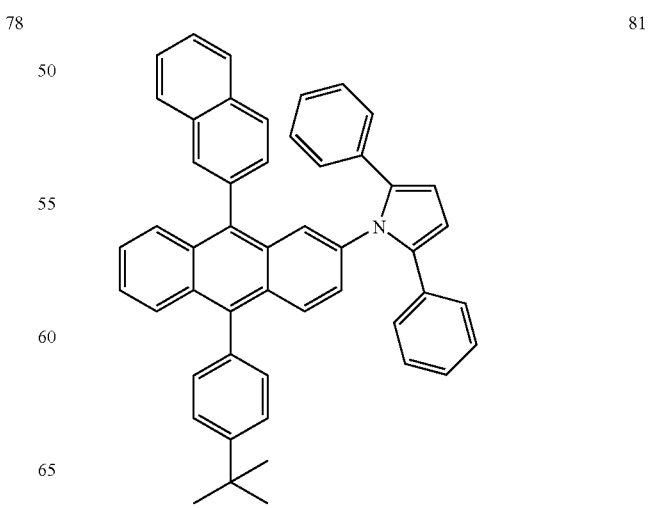

82
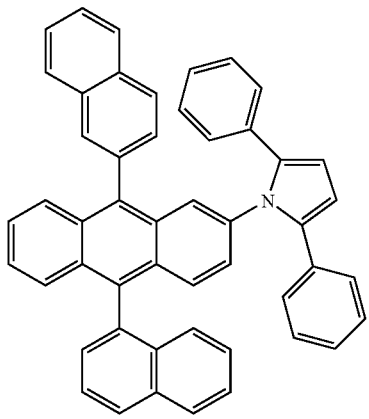
83
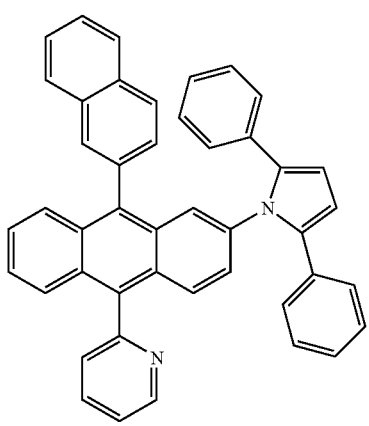
84
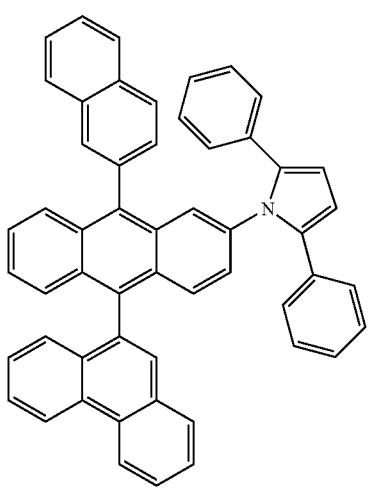
85
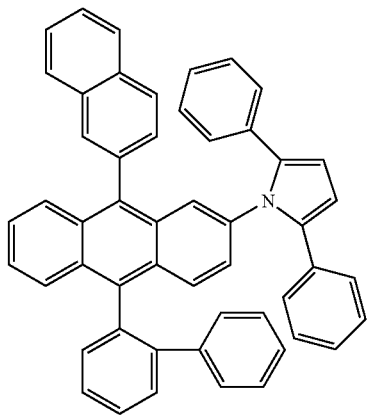
86
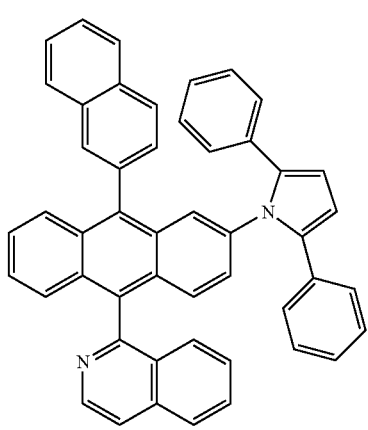
87
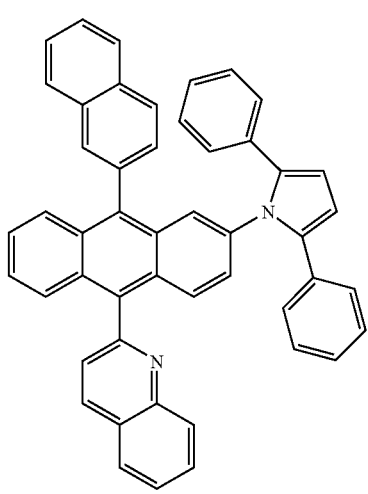

88
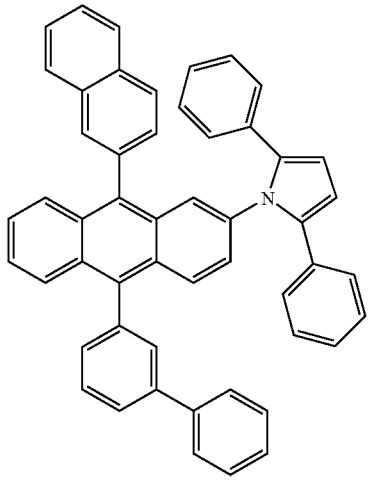
89
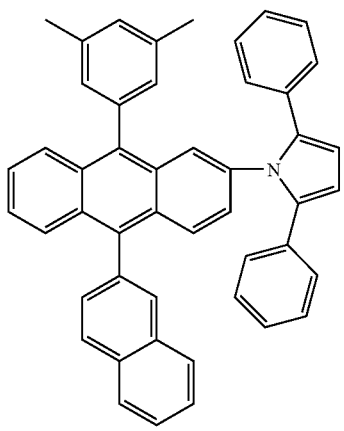
90
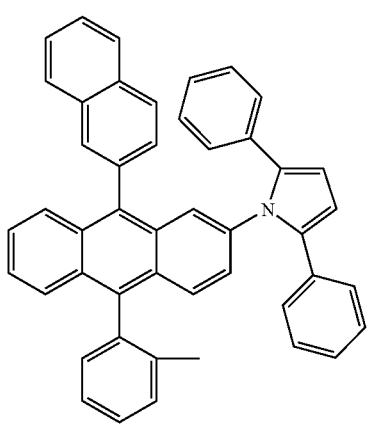
91
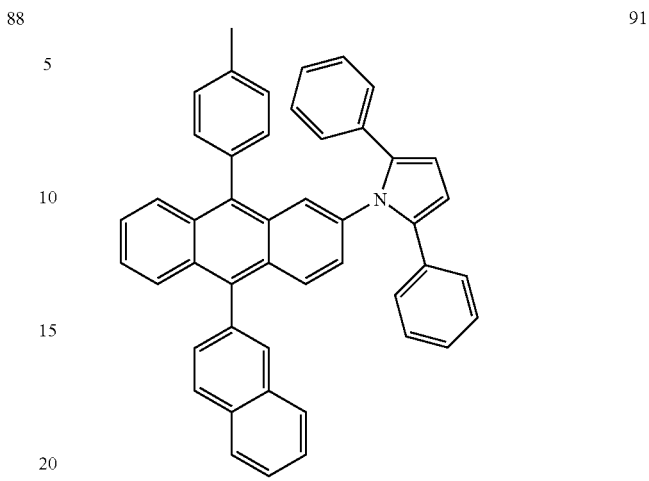
92
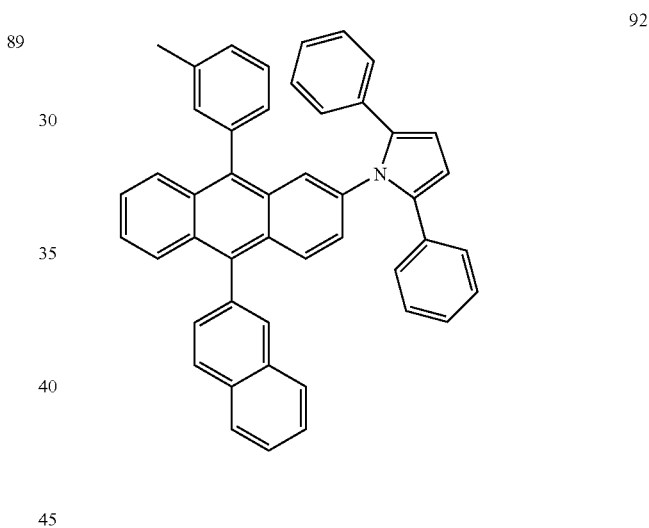
93
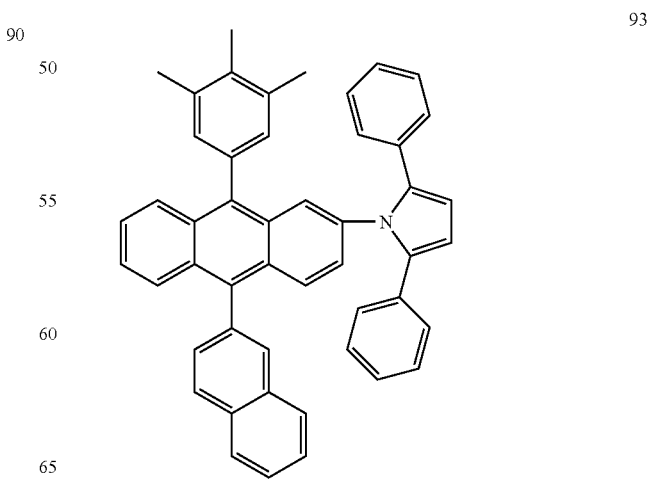

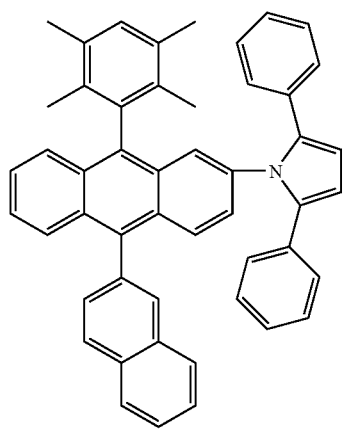
94
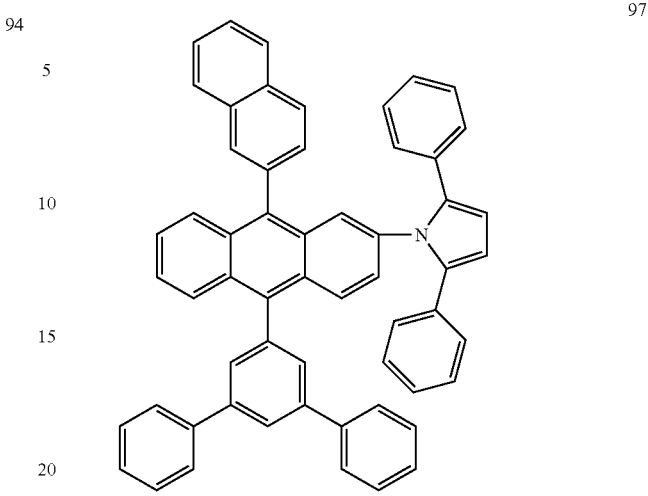
97
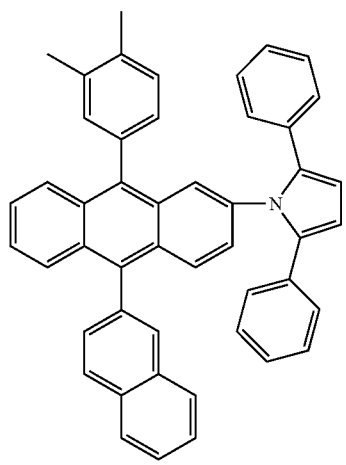
95
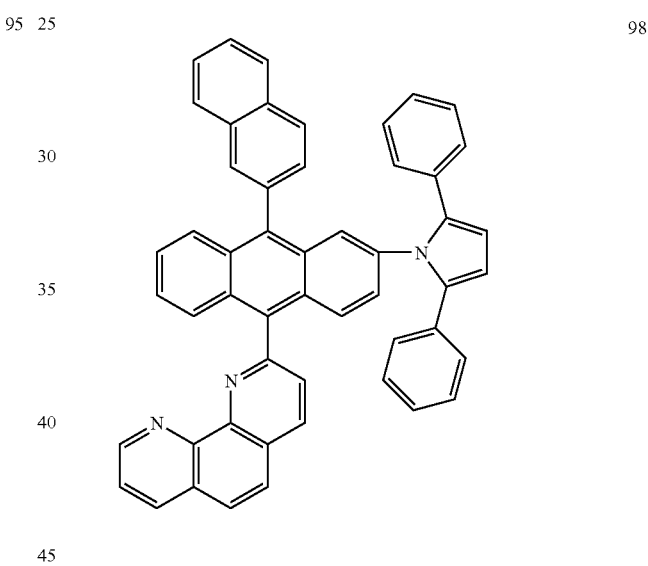
98
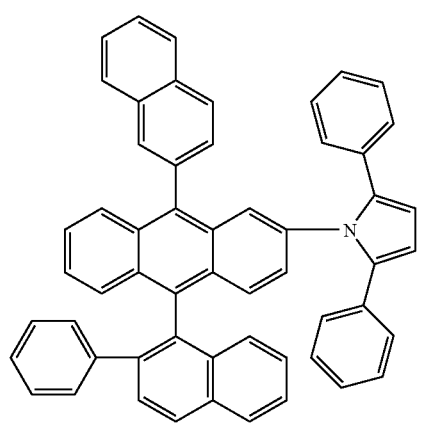
96
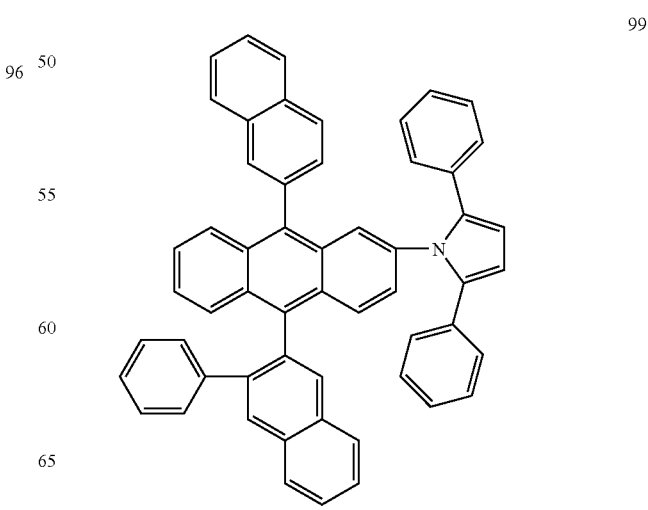
99

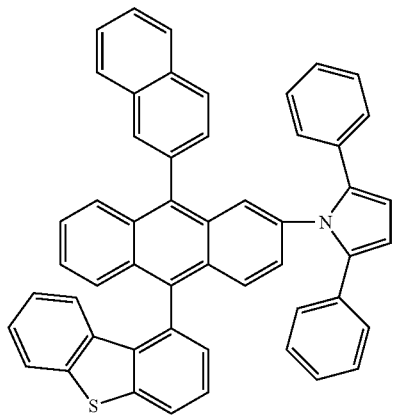
100
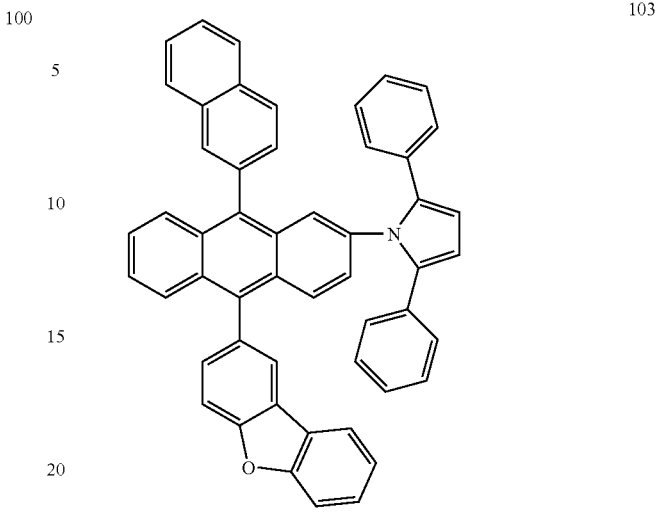
103
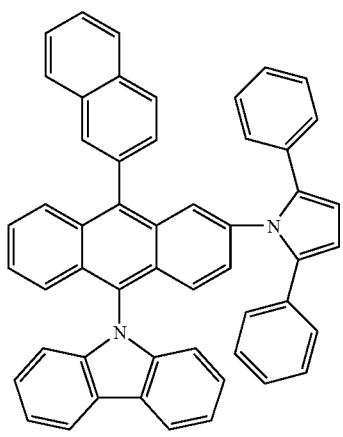
101
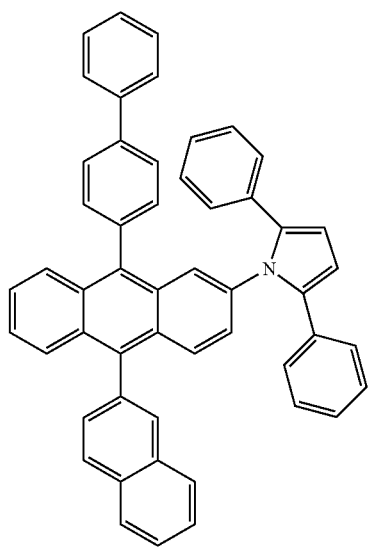
104
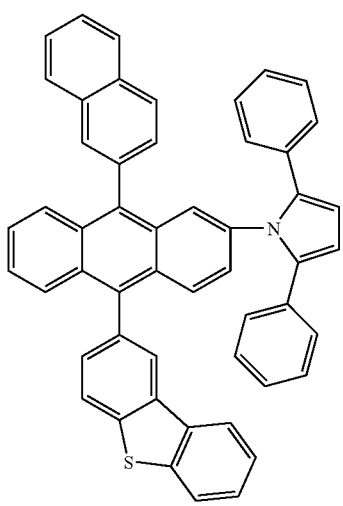
102
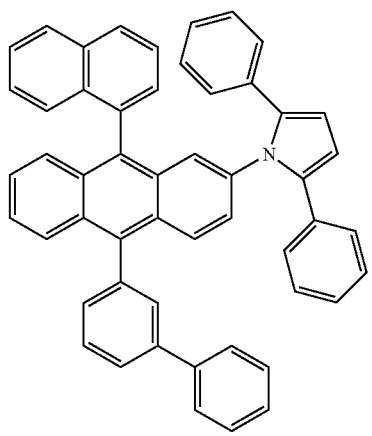
105

106
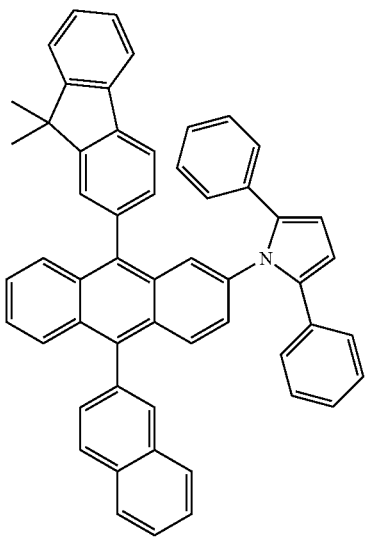
107
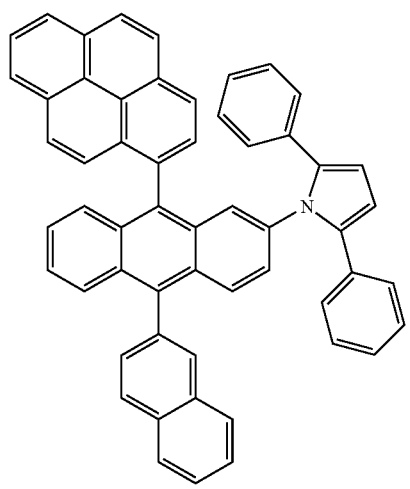
108
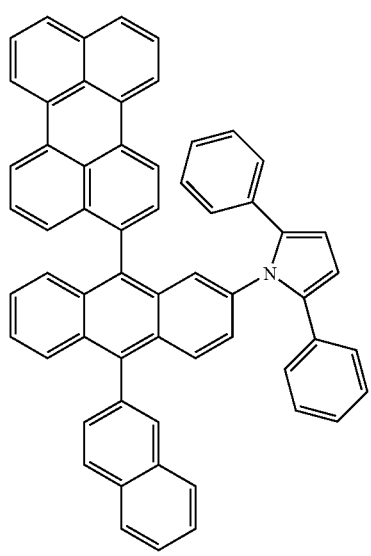
109
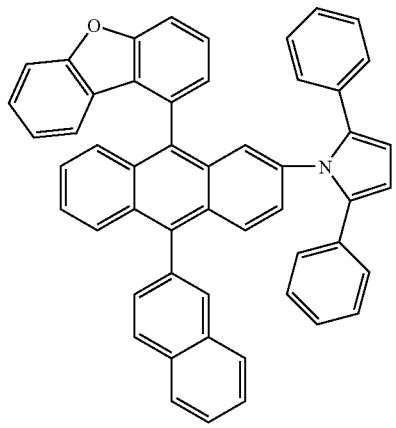
110
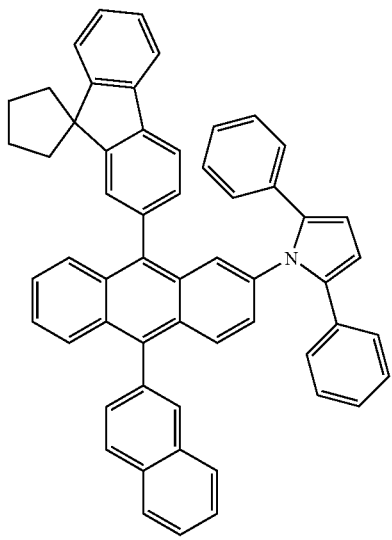
111
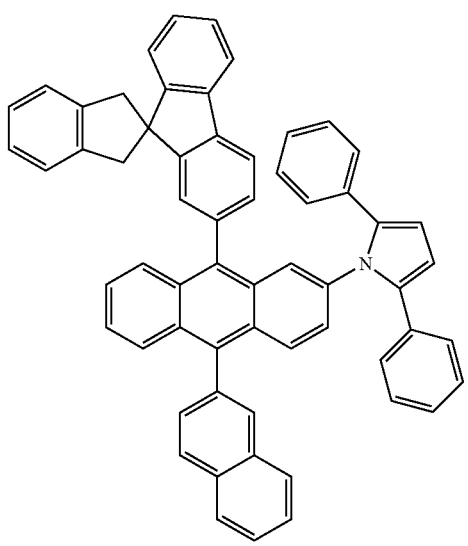

112 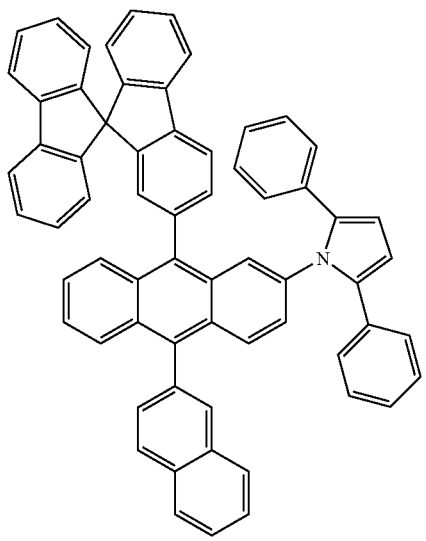
114 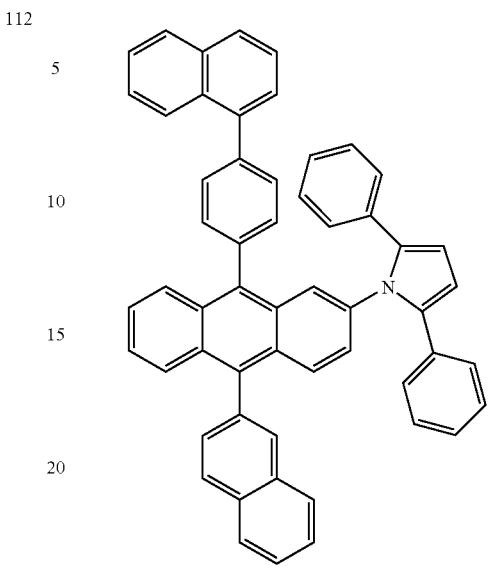
113 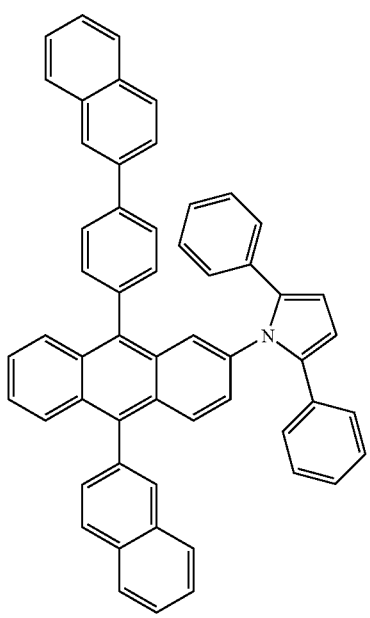
115 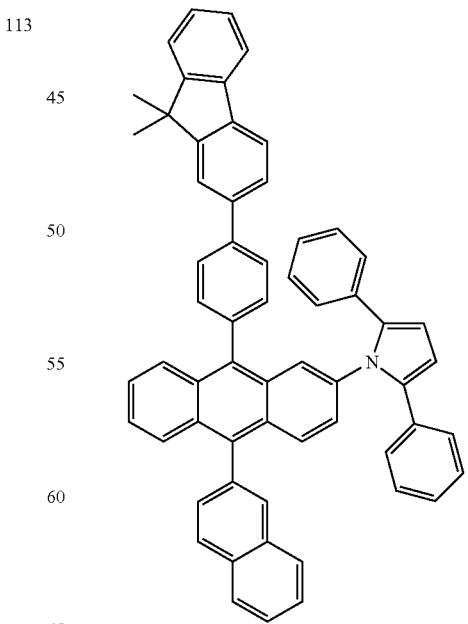

-continued
116
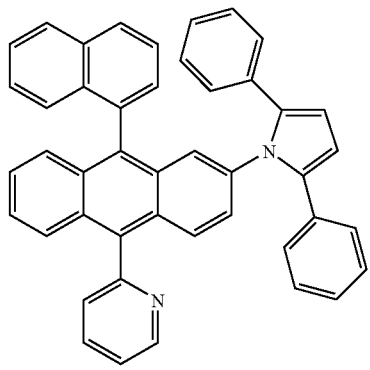
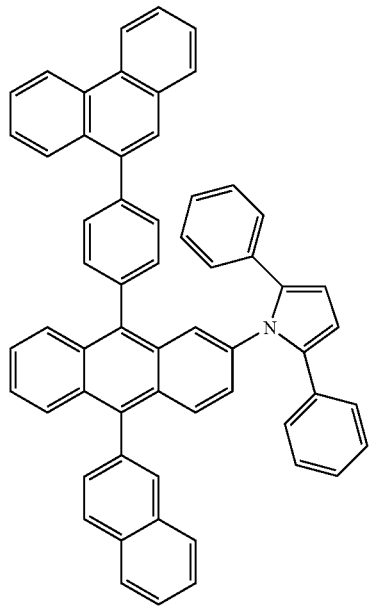
119
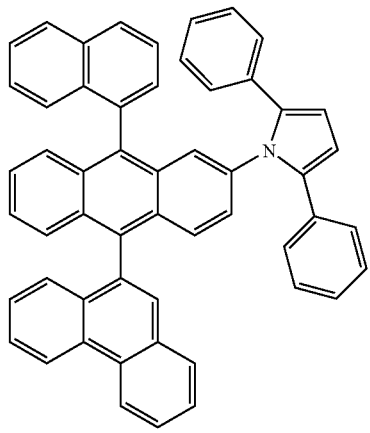
117
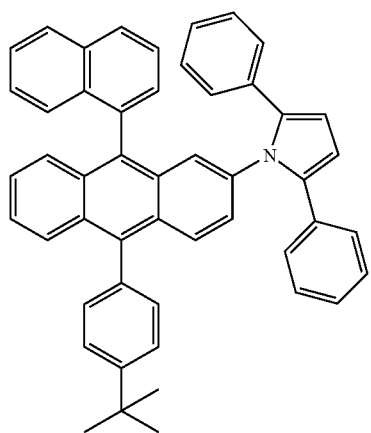
120
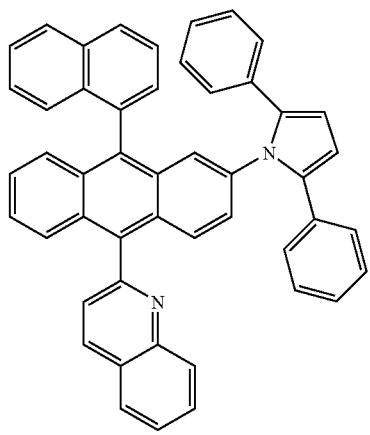
121
118
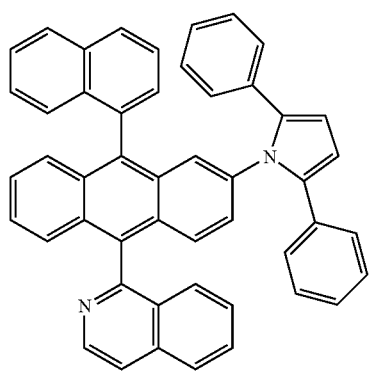
122
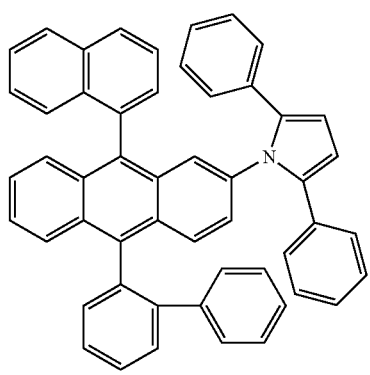

-continued
123
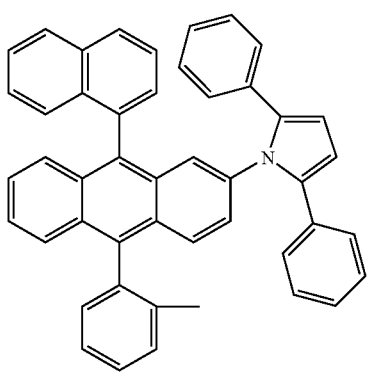
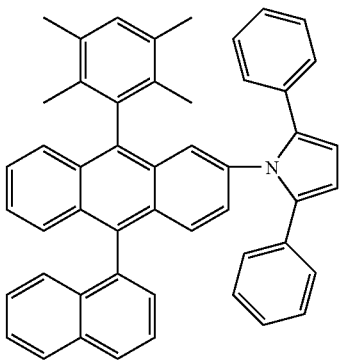 127
124
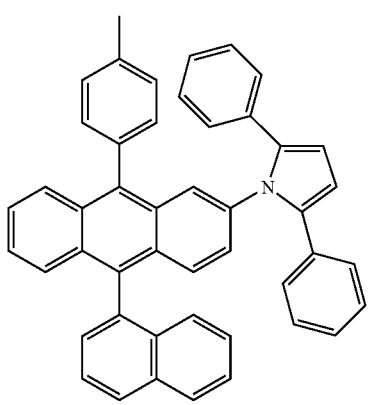
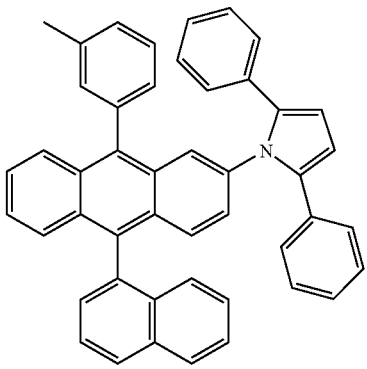 128
125
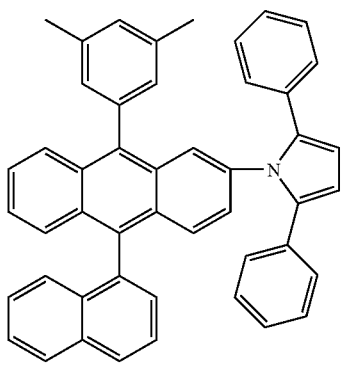
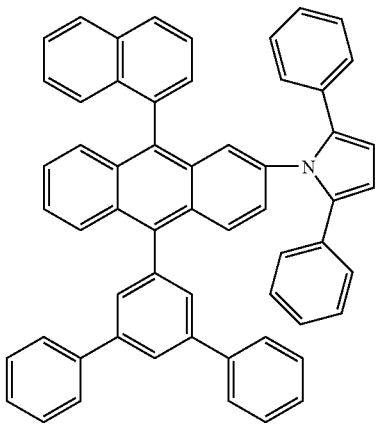 129
126
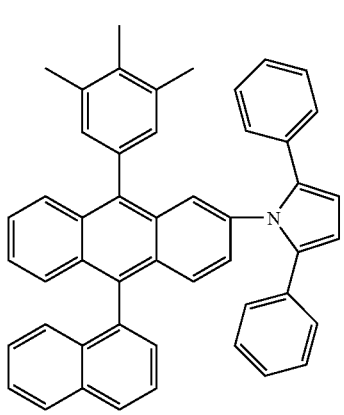
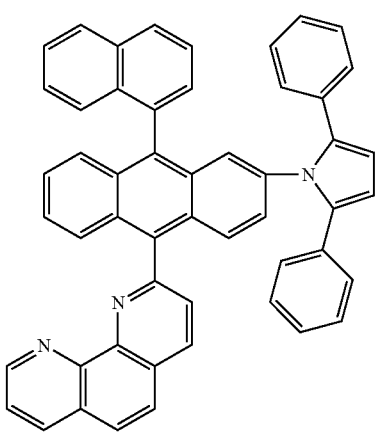 130

-continued
131 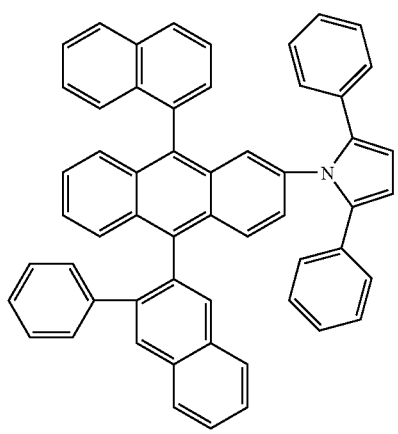
132 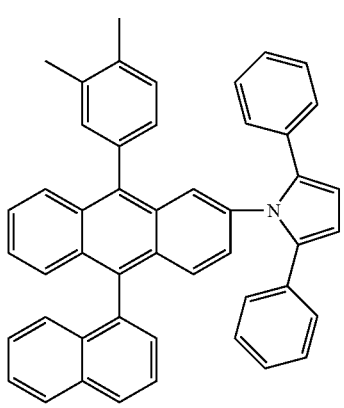
133 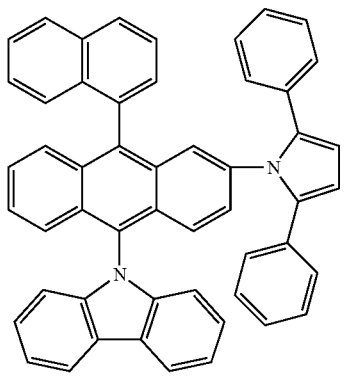
134 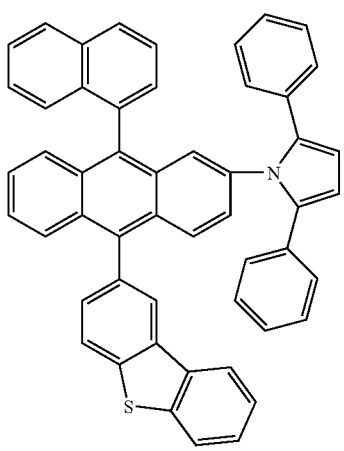
-continued
135 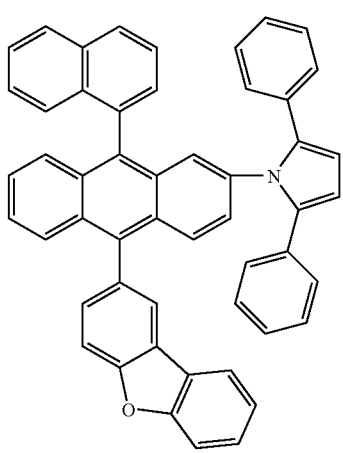
136 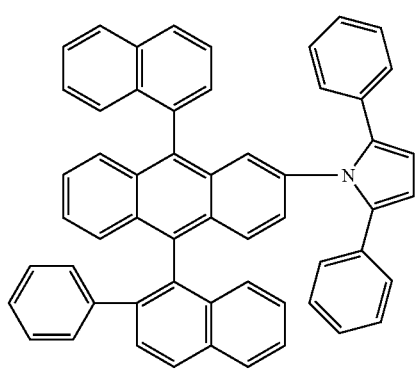
137 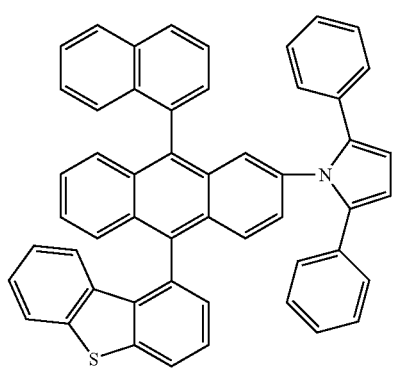

-continued
138
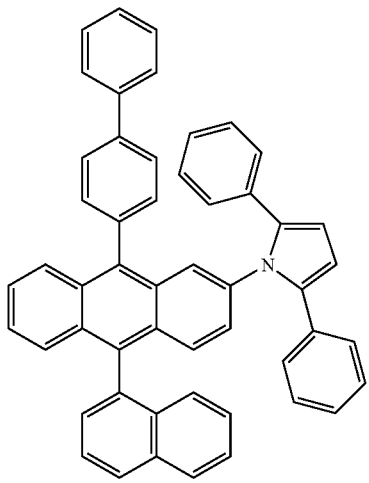
139
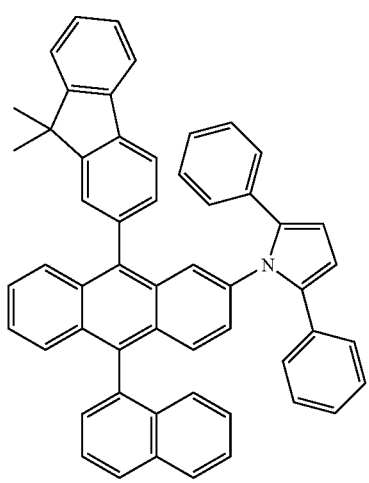
140
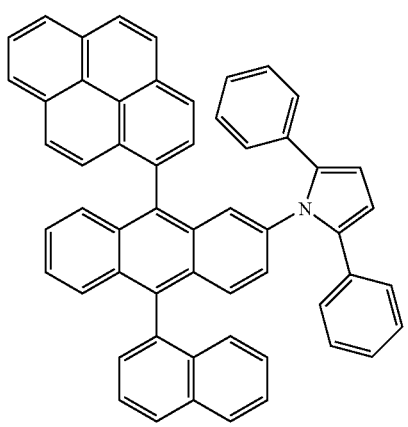
-continued
141
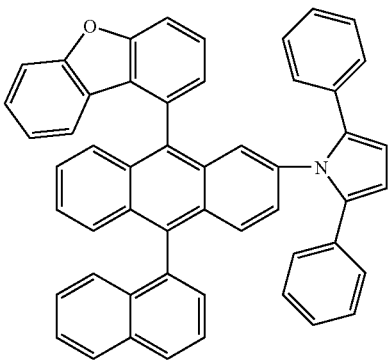
142
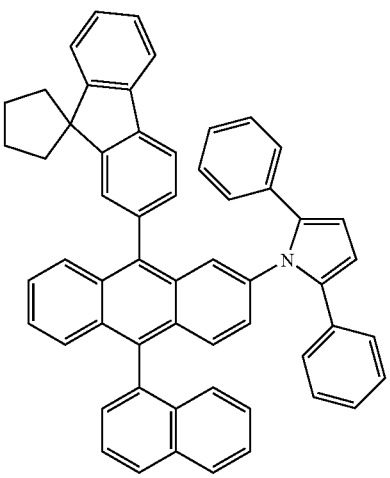
143
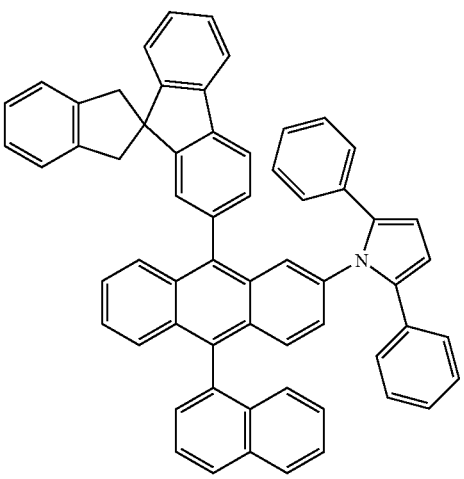

144
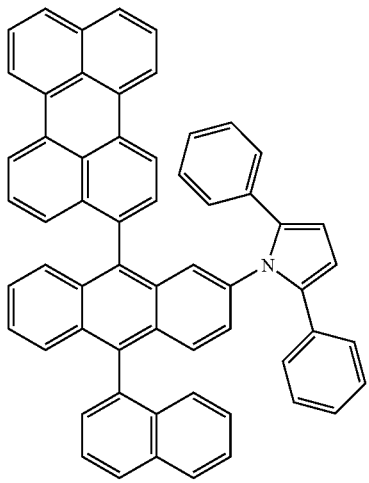
145
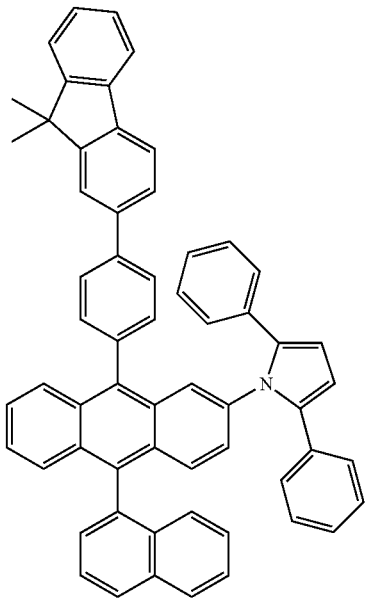
147
146
148
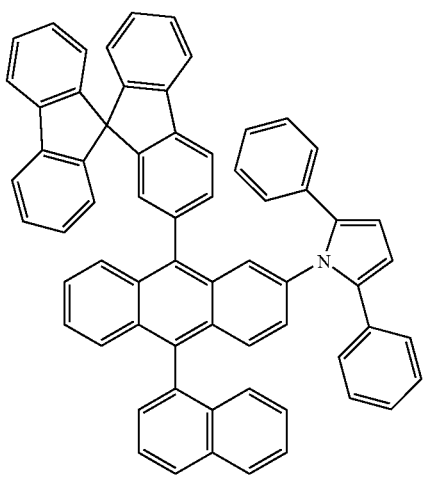
149
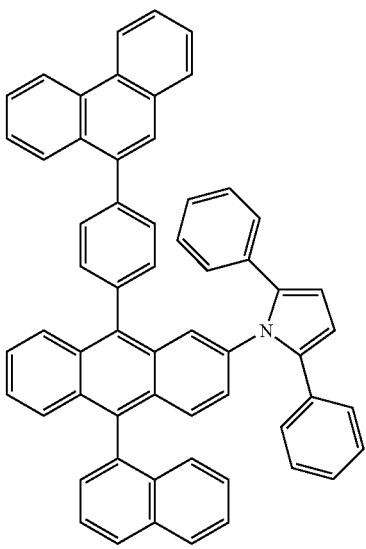

-continued
150
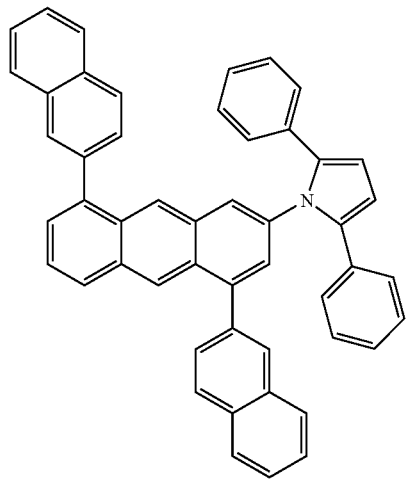
151
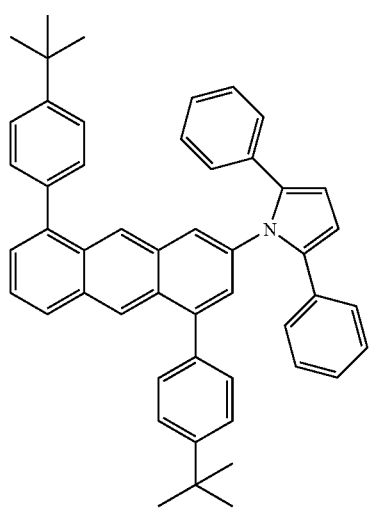
152
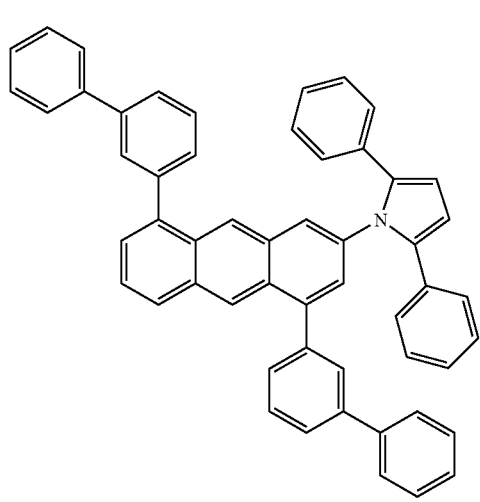
-continued
153
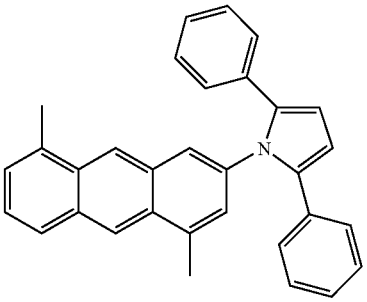
154
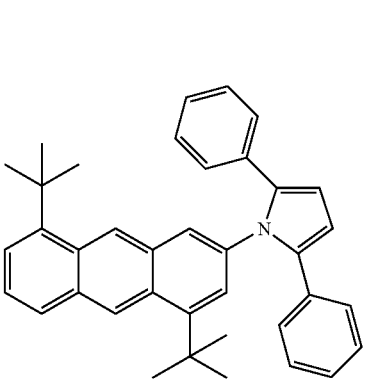
155
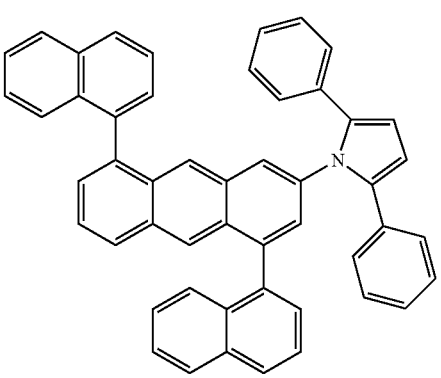
156

-continued
157 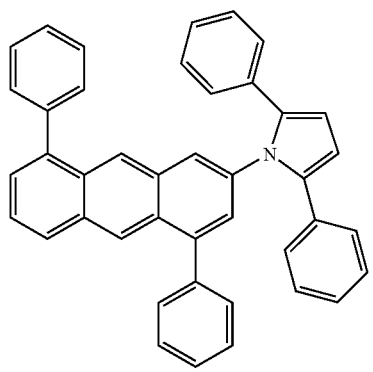
158 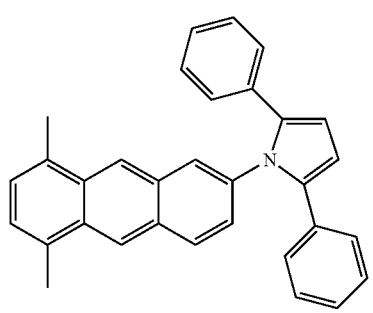
159 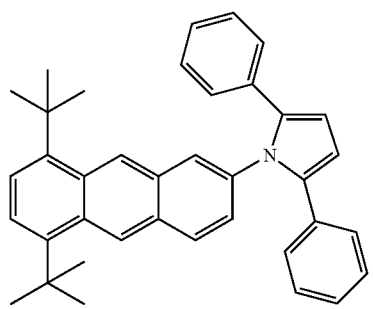
160 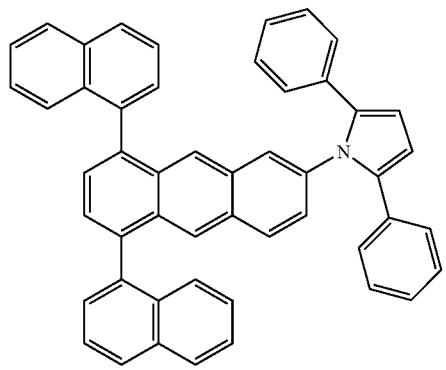
-continued
161 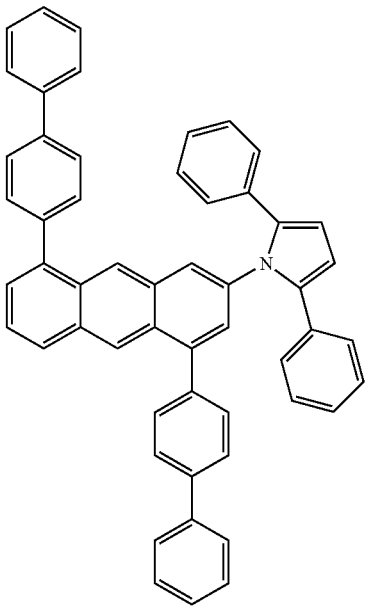
162 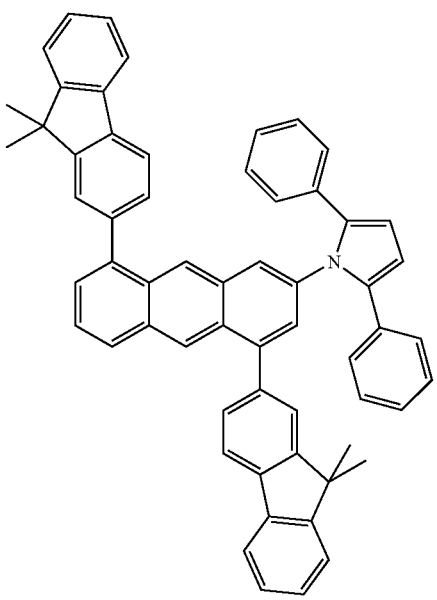

-continued
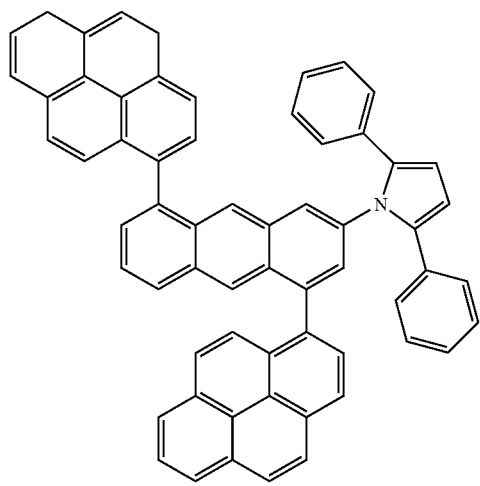
163
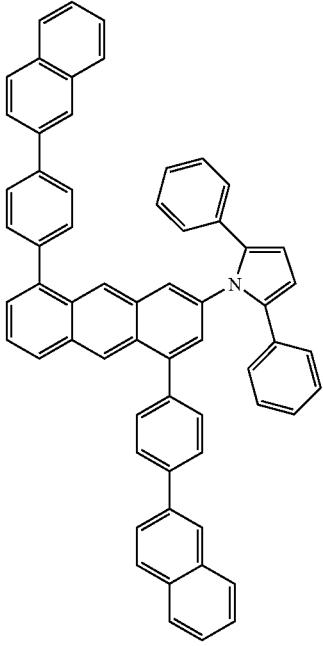
165
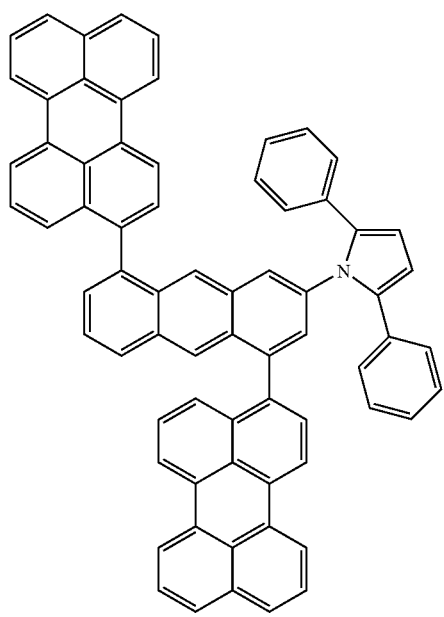
164
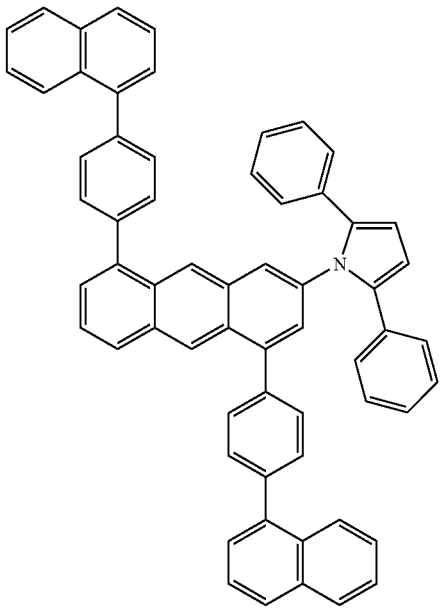
166

-continued
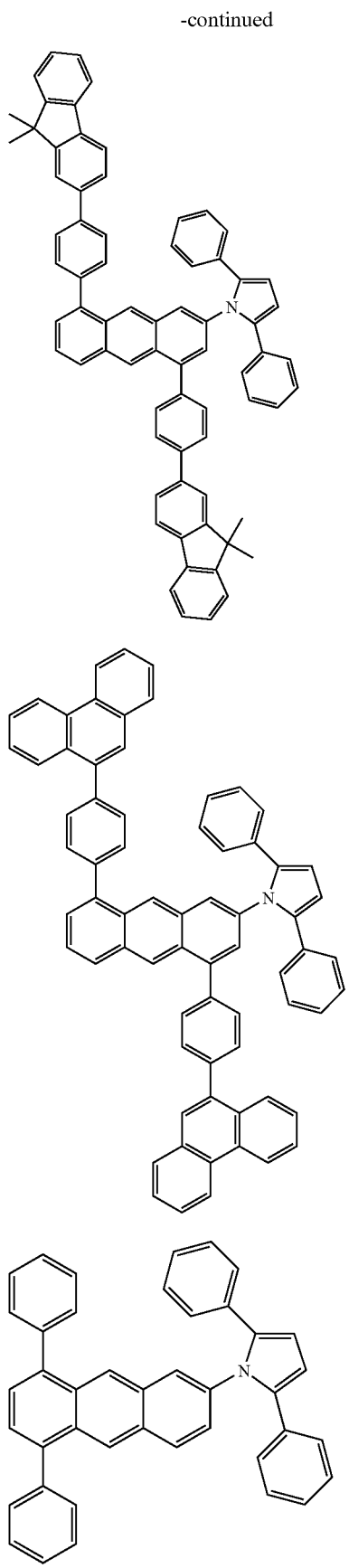
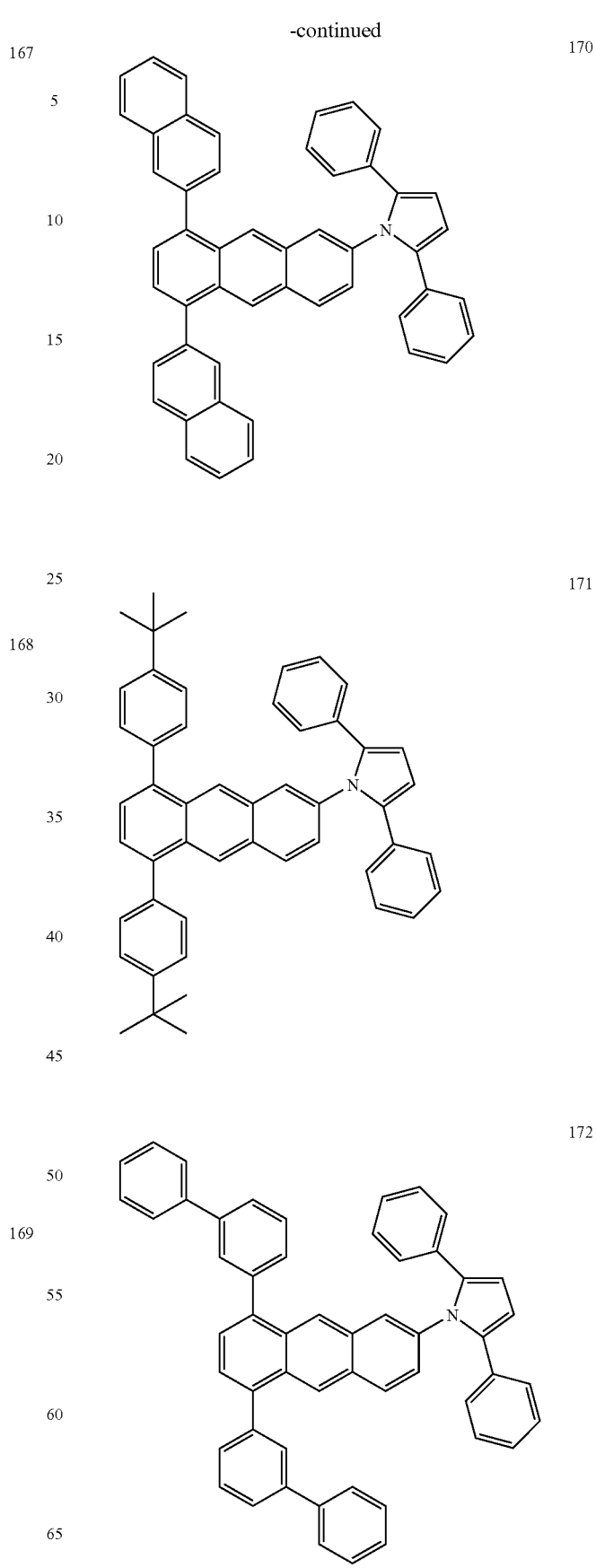

173
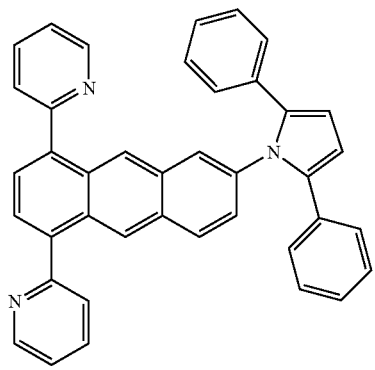
174
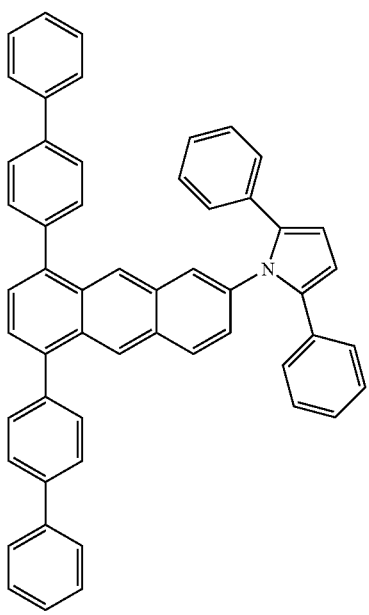
175
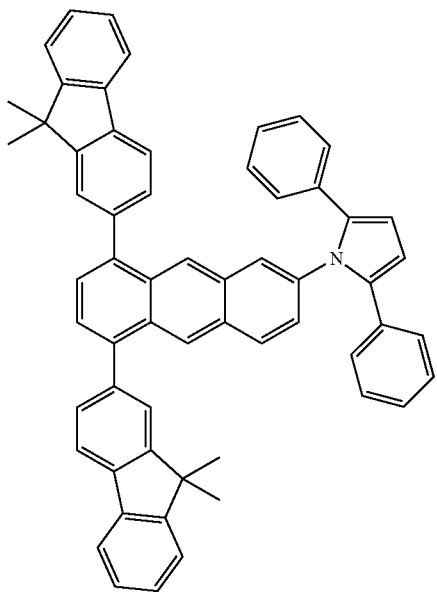
176
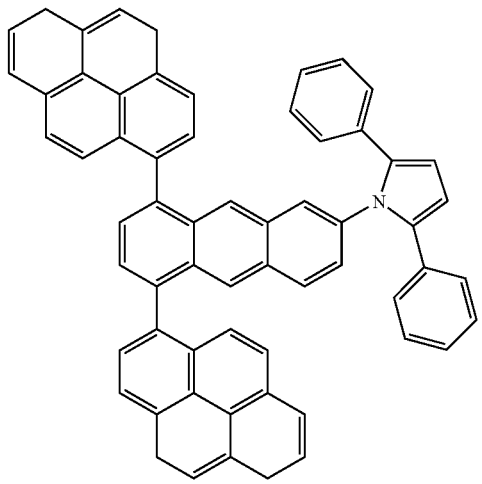
177
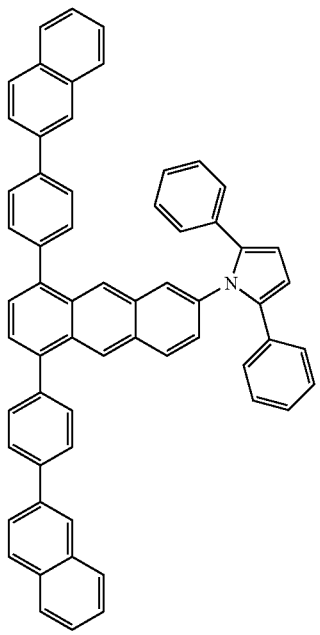

-continued
178
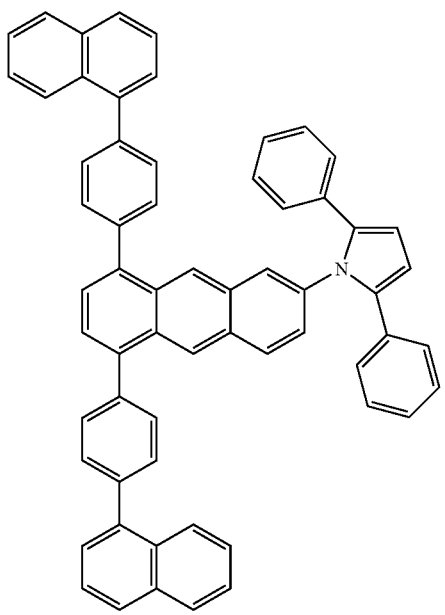
179
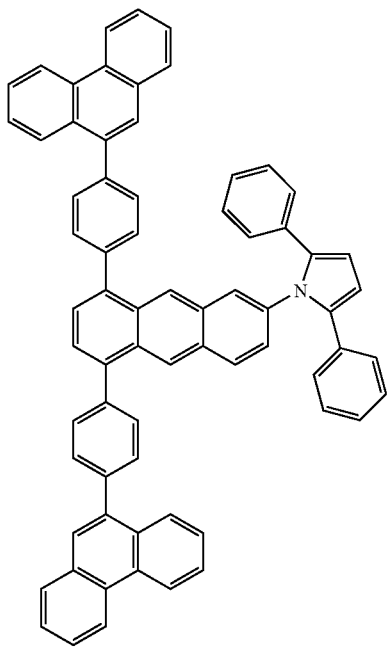
-continued
180
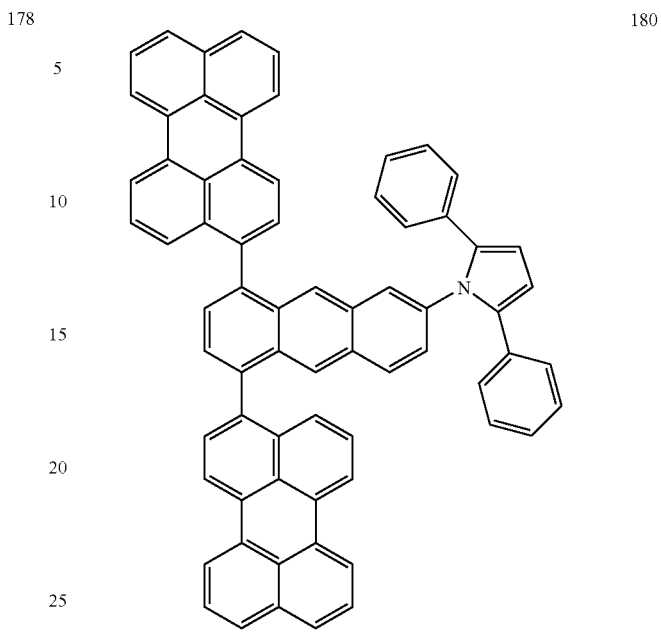
181
182
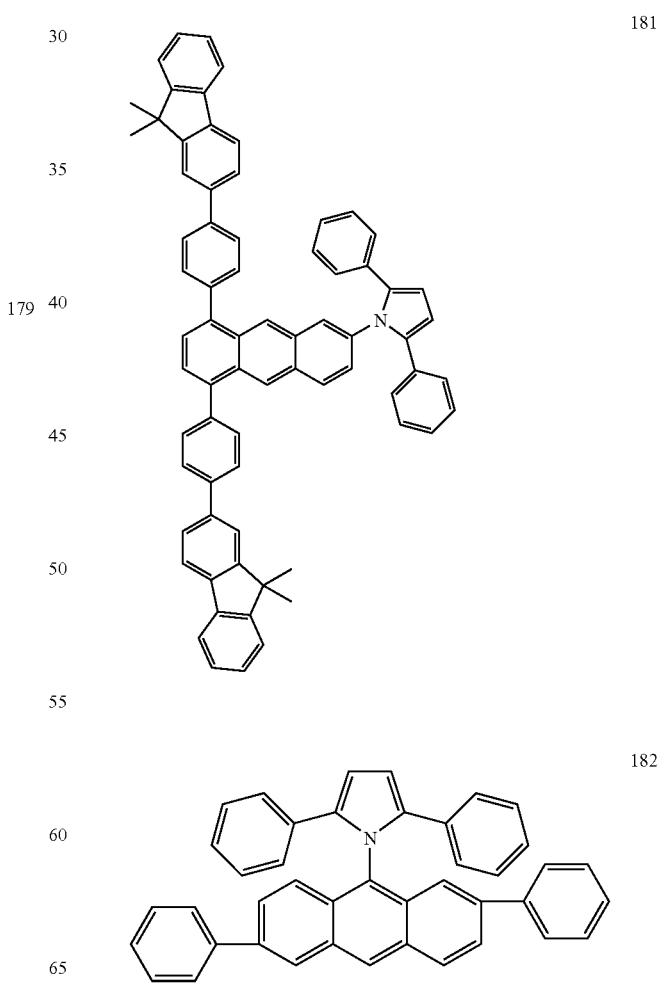

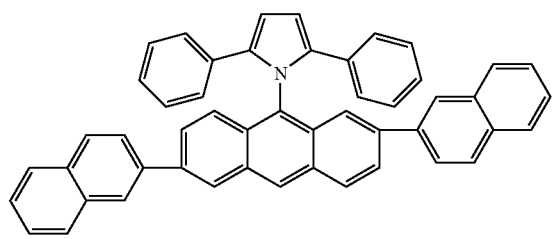
183
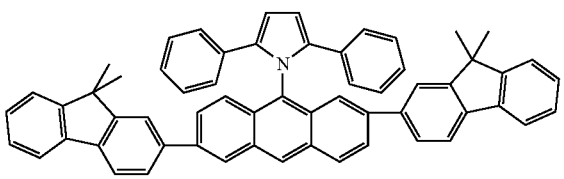
189
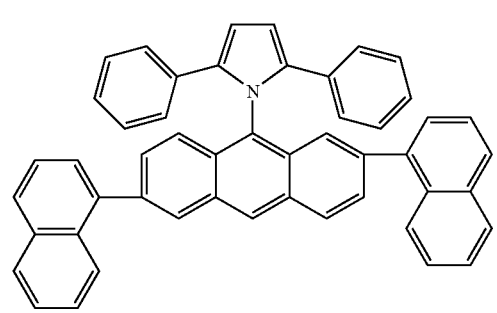
184
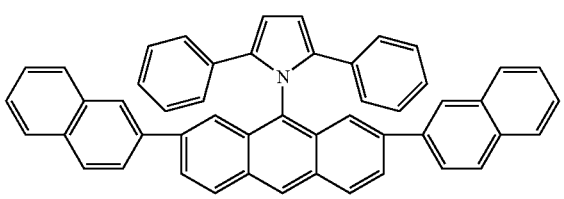
190
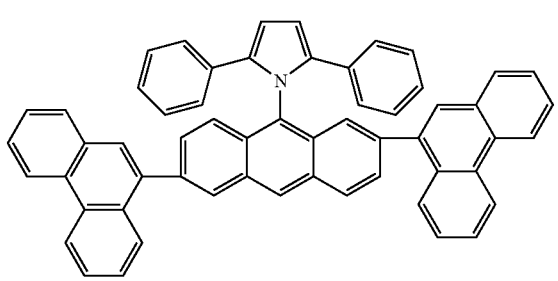
185
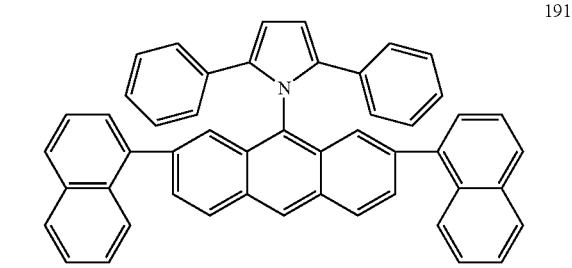
191
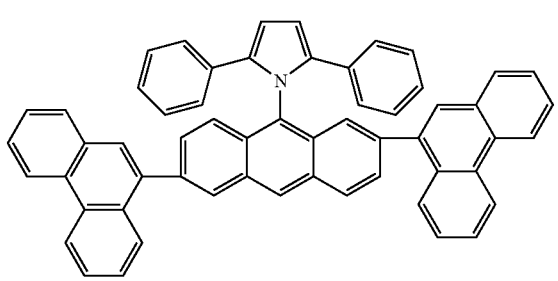
186
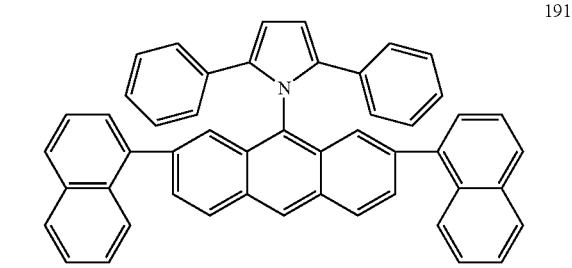
192
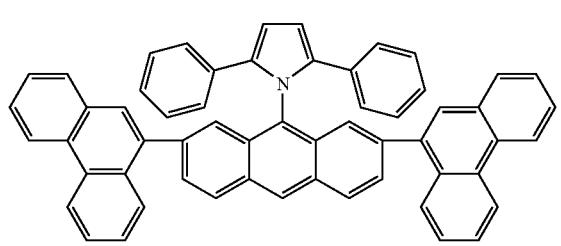
187
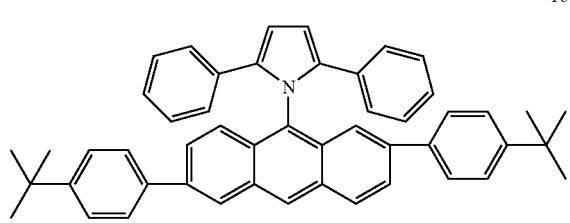
193
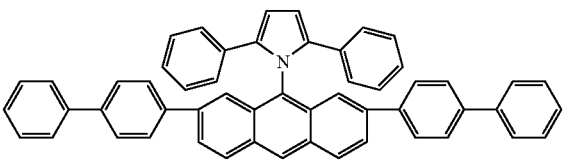
188
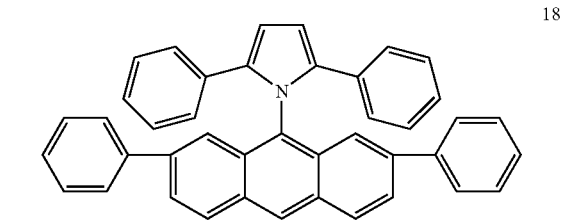
194
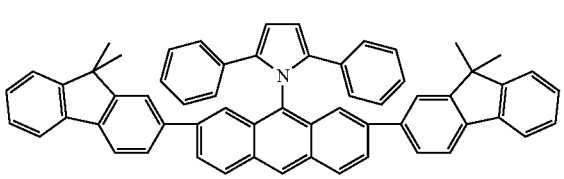
195
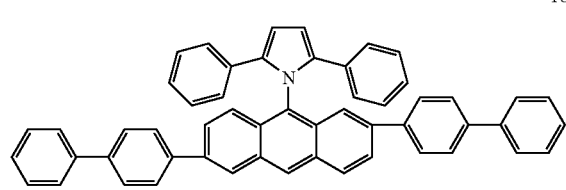
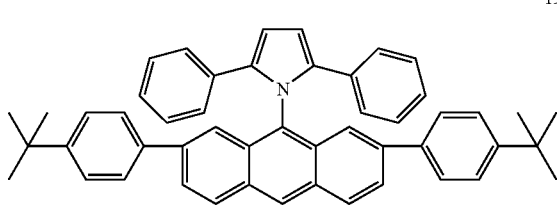

196
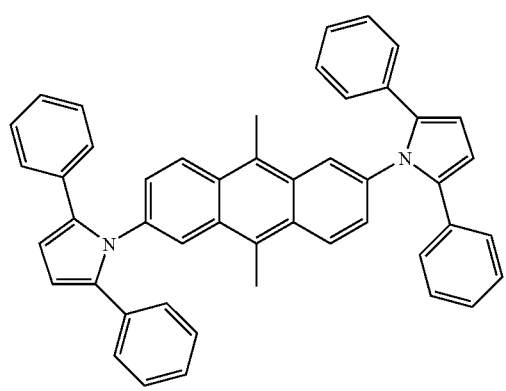
197
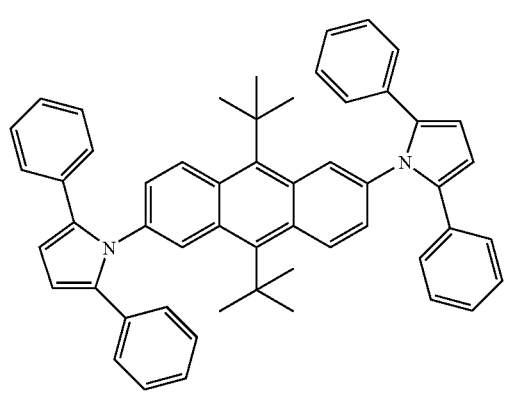
198
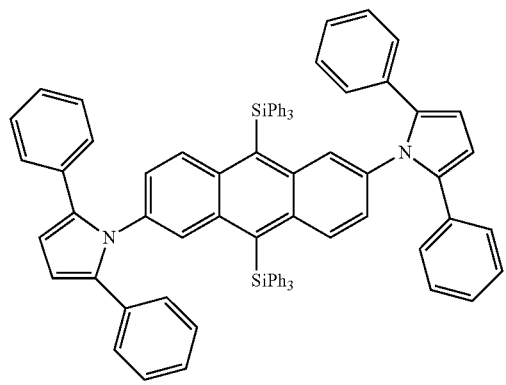
199
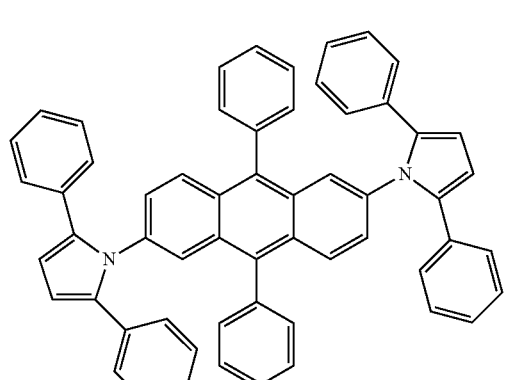
200
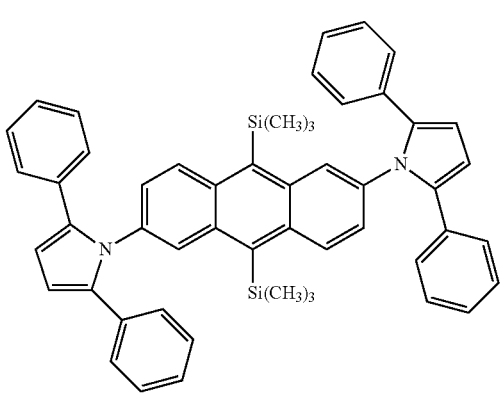
201
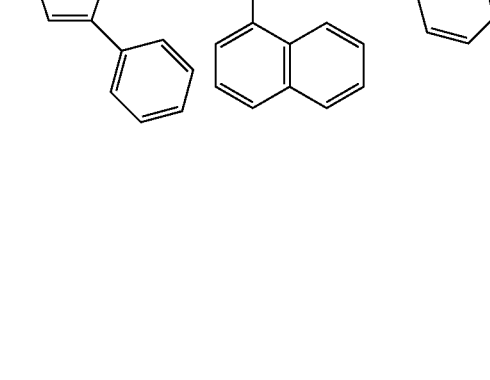
202
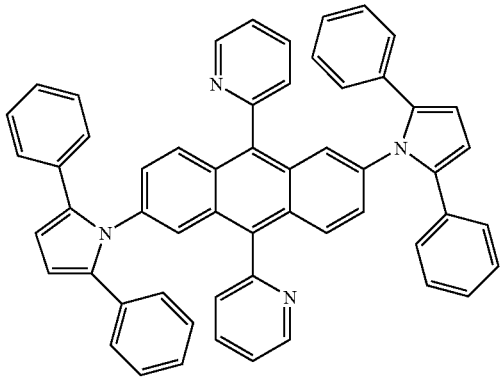

-continued
203
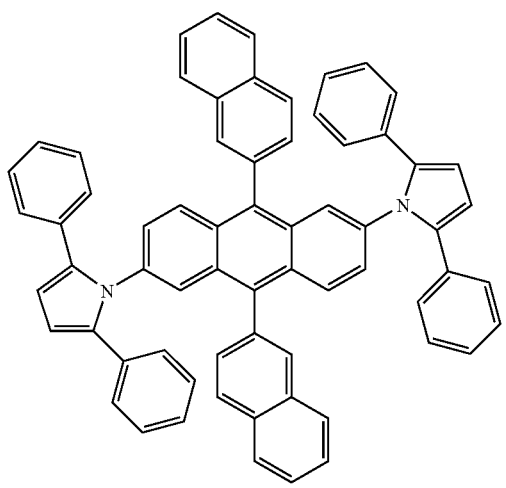
204
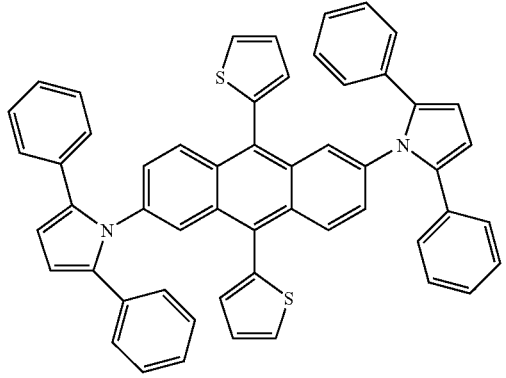
205
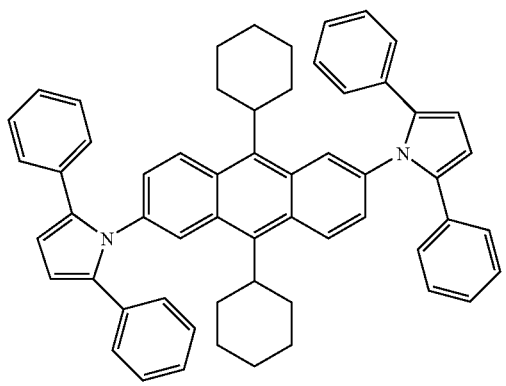
-continued
206
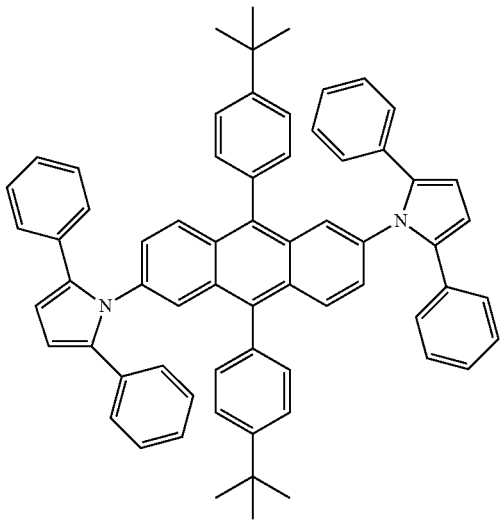
207
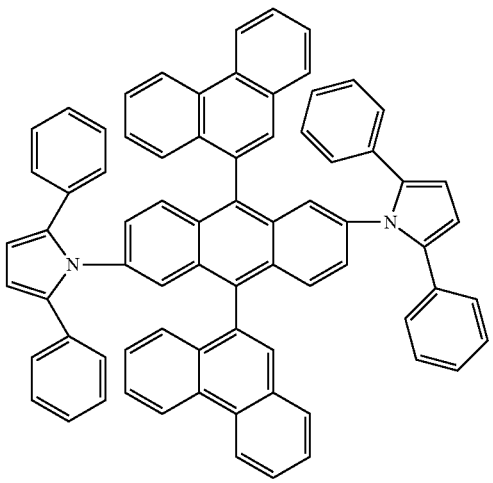
208
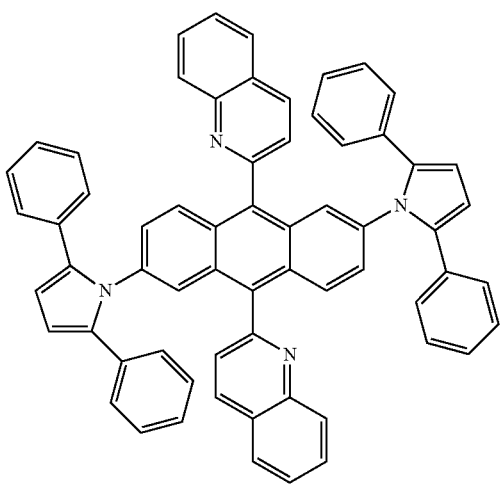

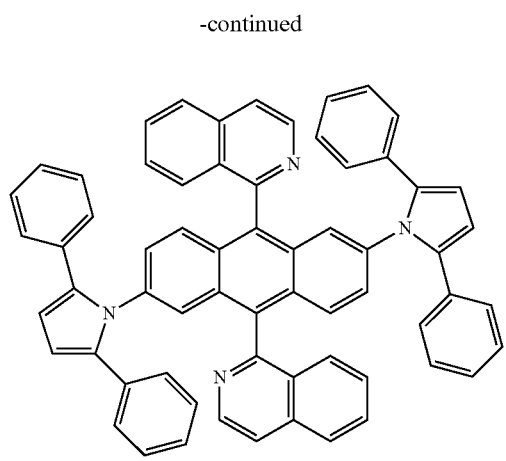
209
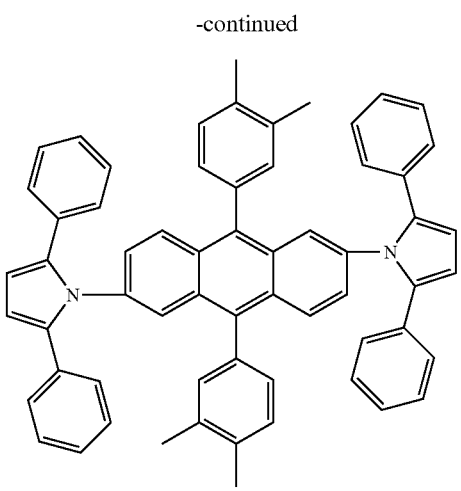
212
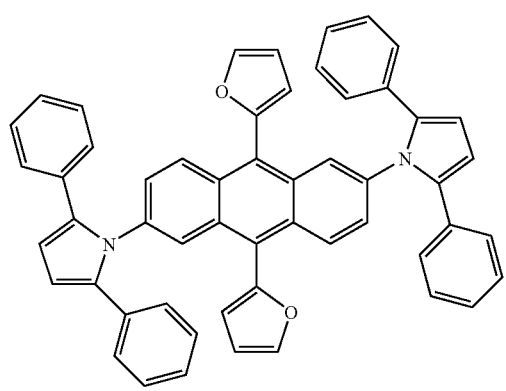
210
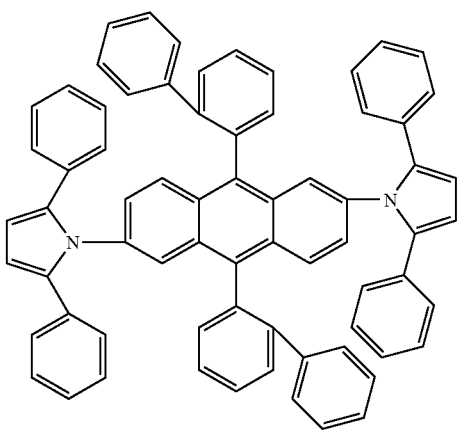
213
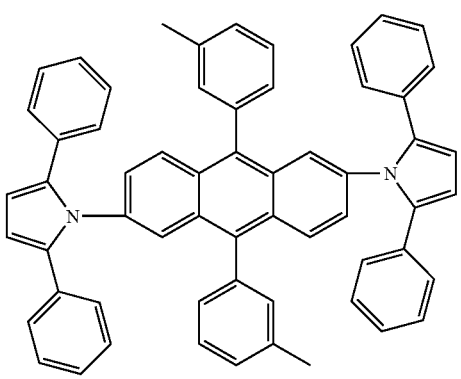
214
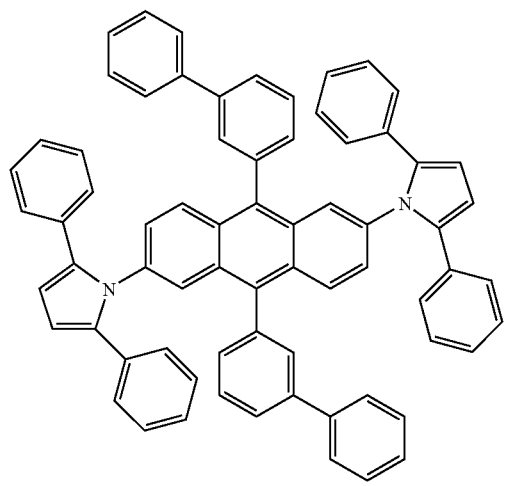
211
215

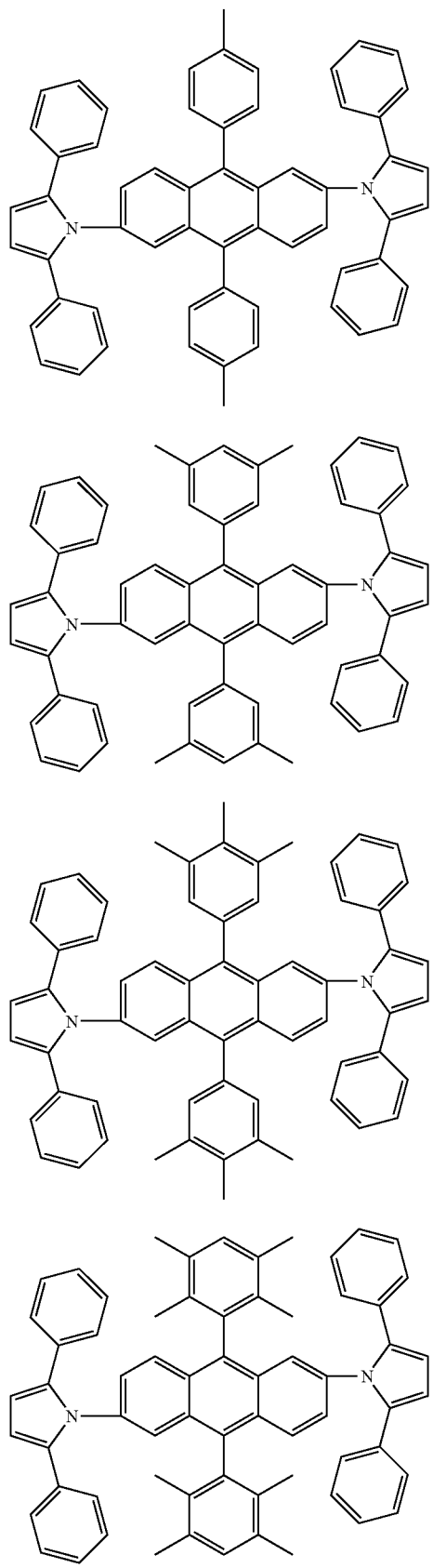
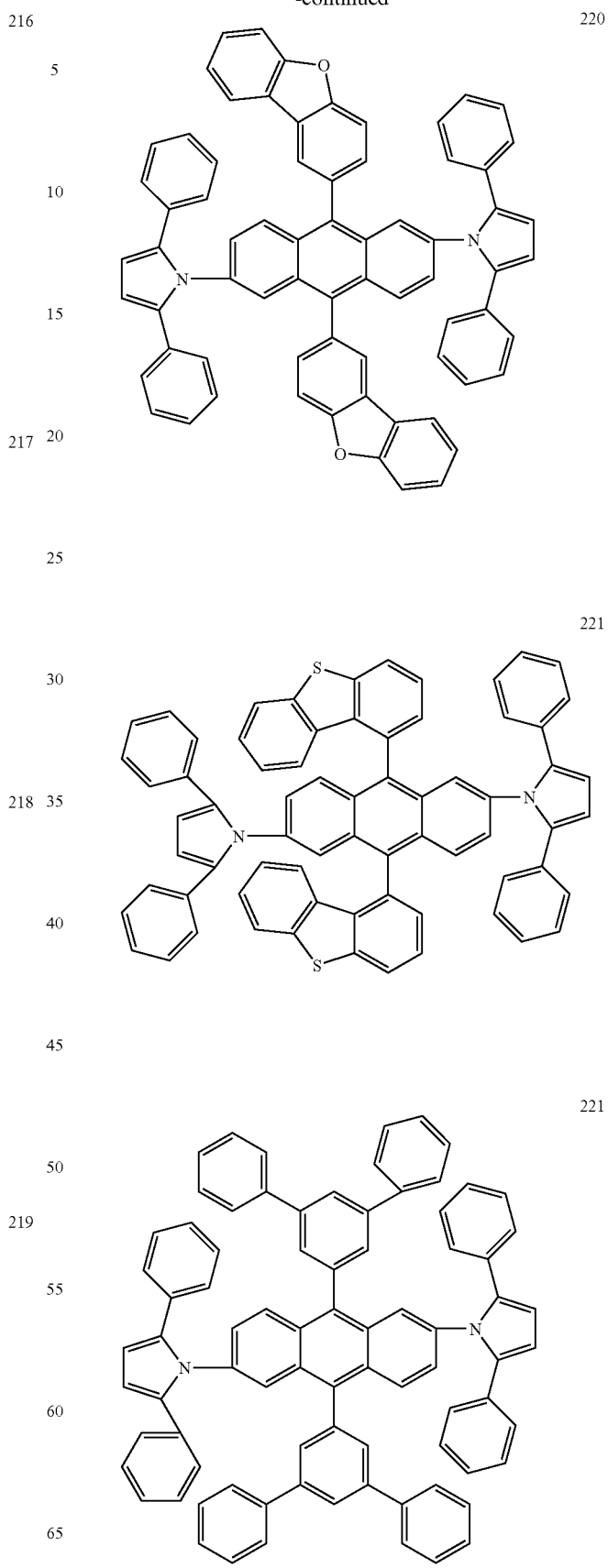

-continued
222
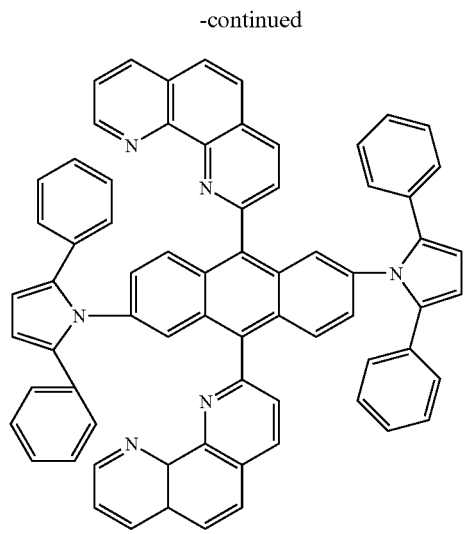
223
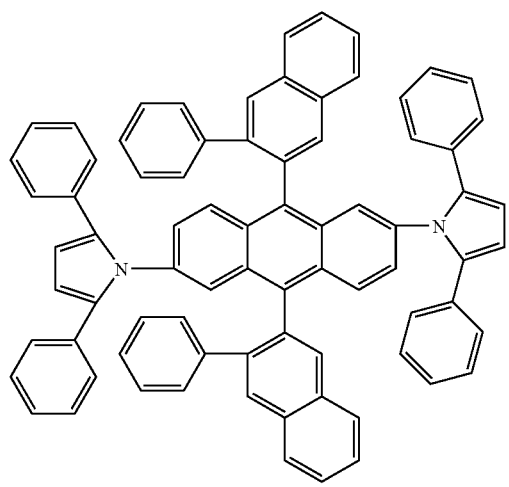
224
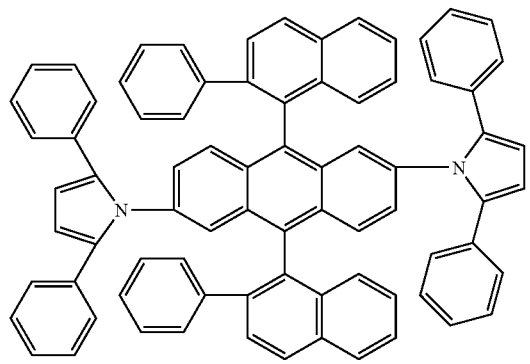
-continued
225
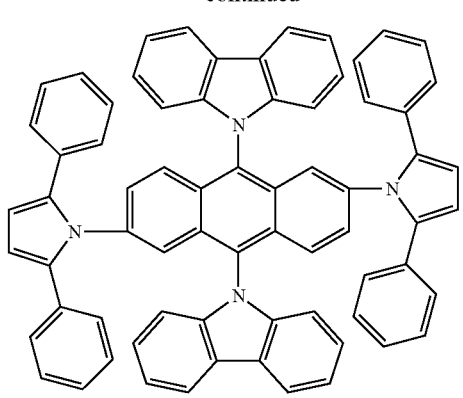
226
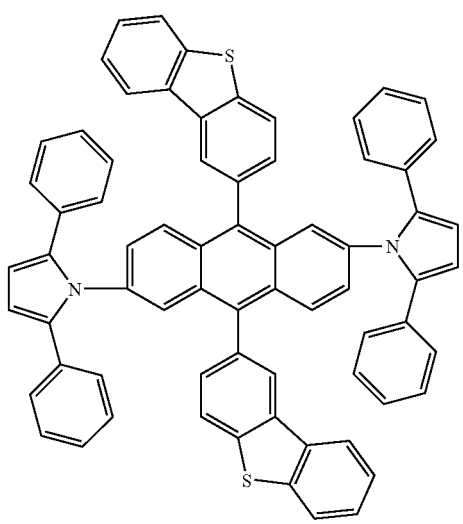
227
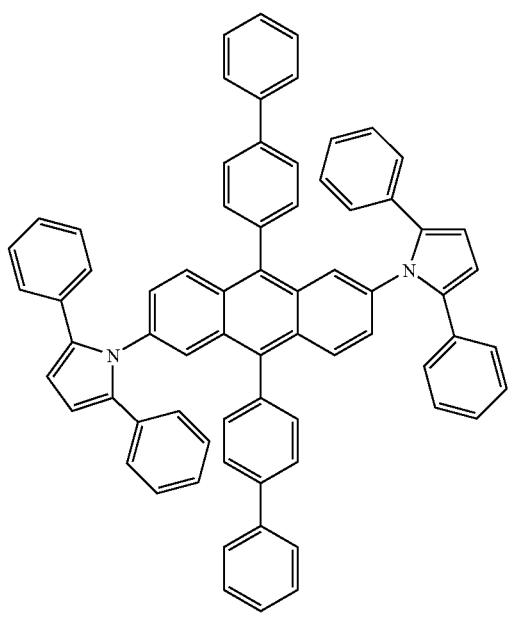

228
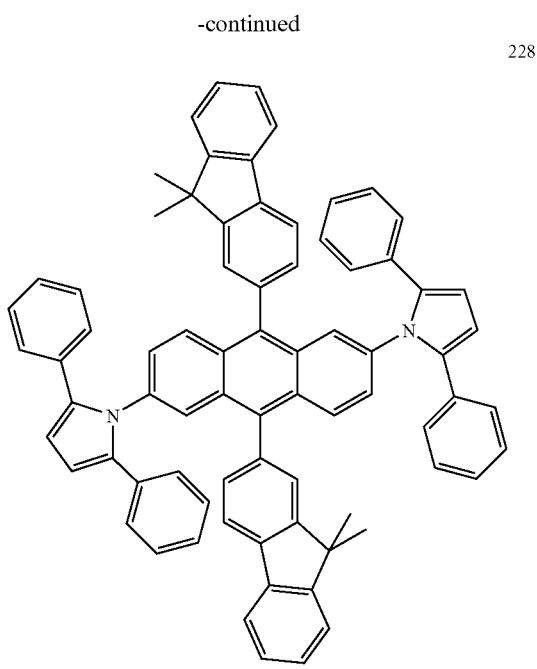
229
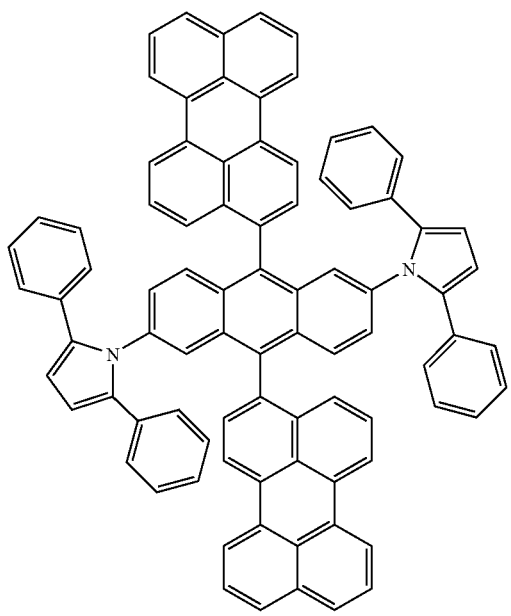
230
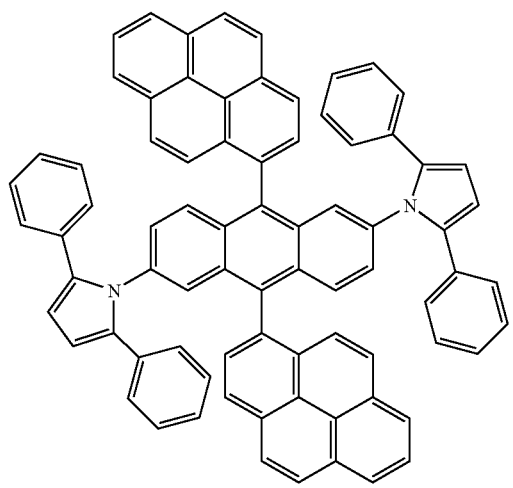
231
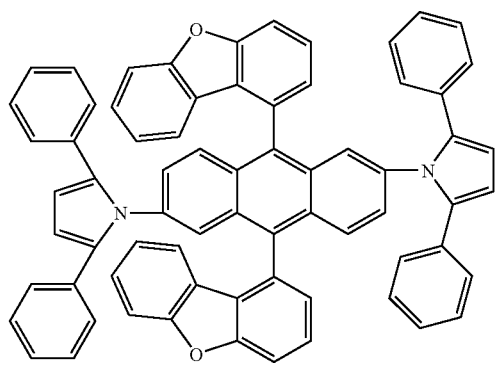
232
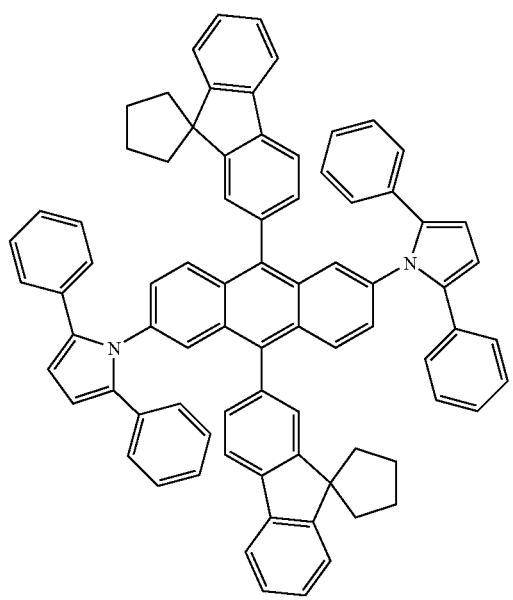

103
-continued
233
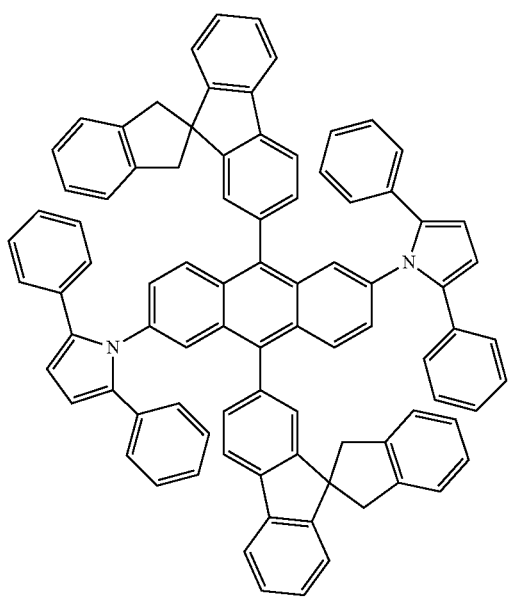
234
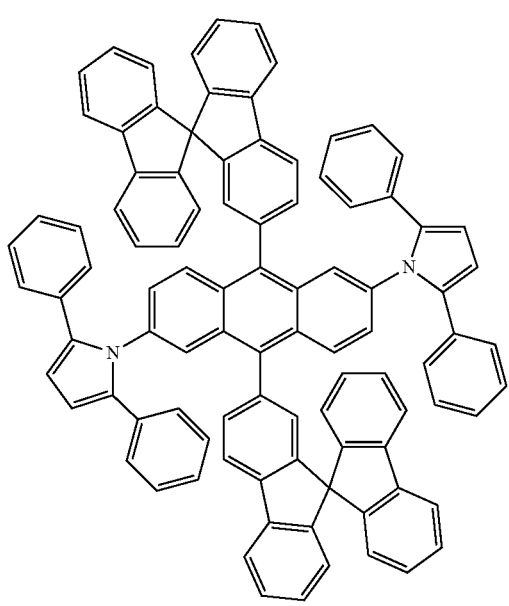
104
-continued
235
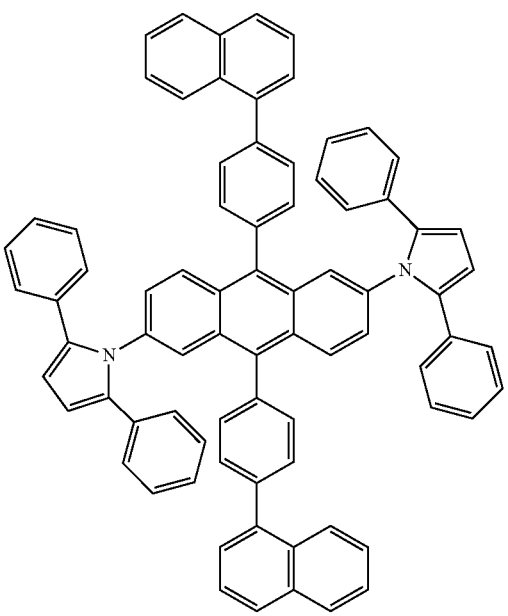
236
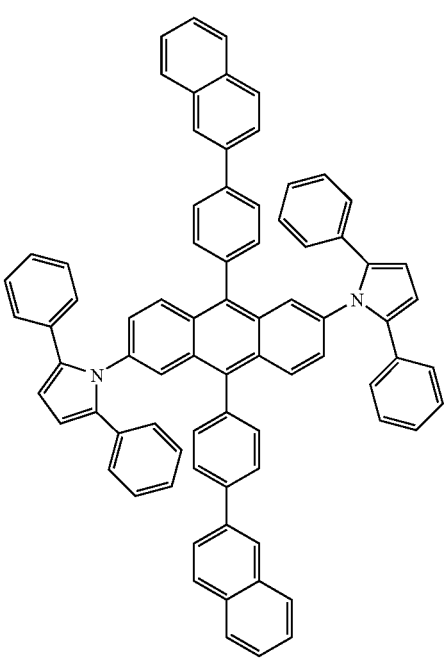

-continued
237
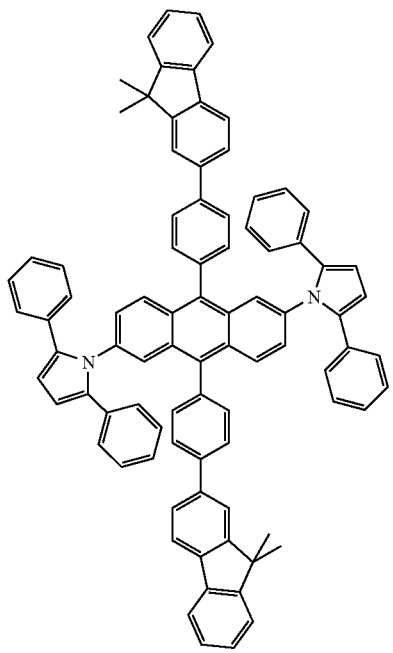
239
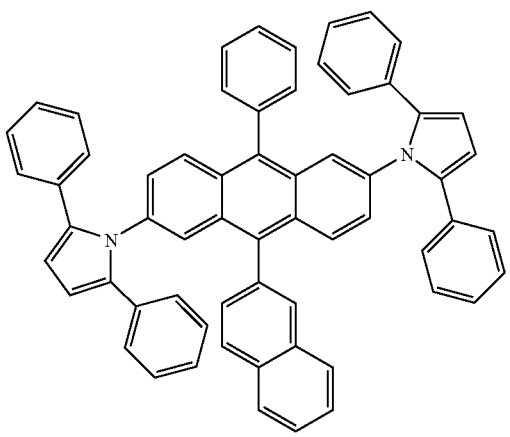
240
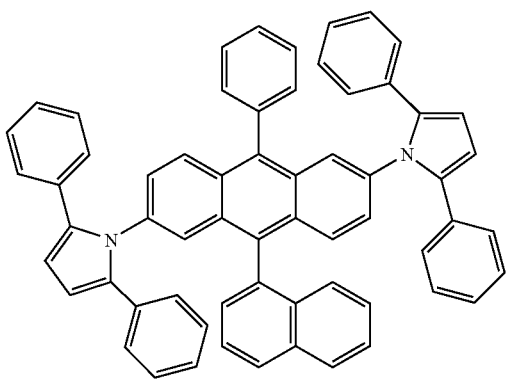
238
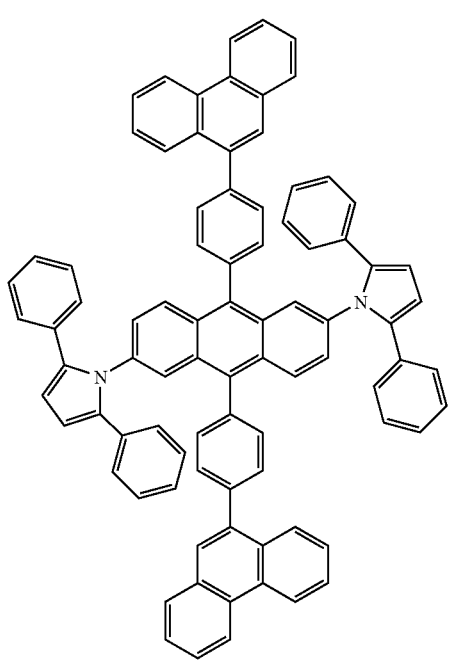
241
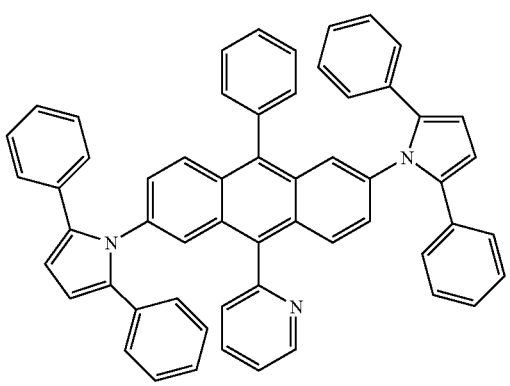

-continued
242
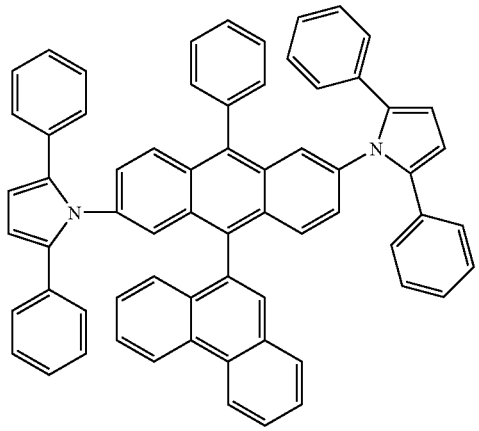
243
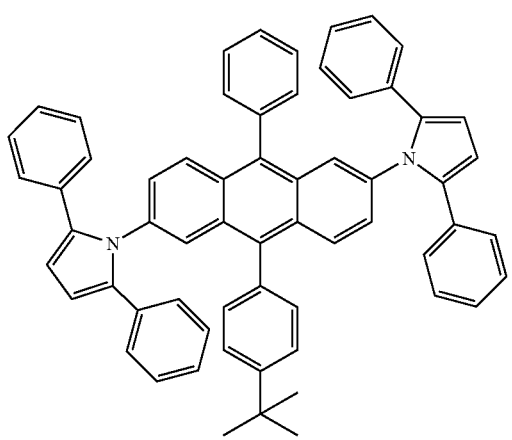
244
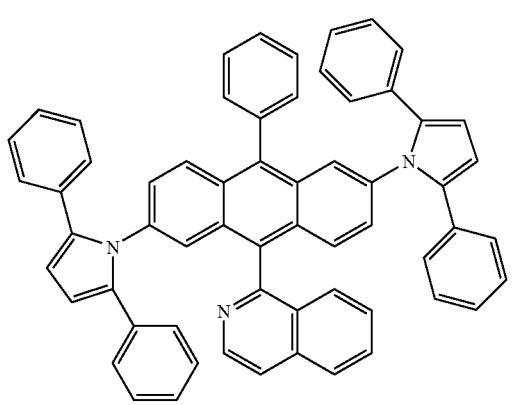
-continued
245
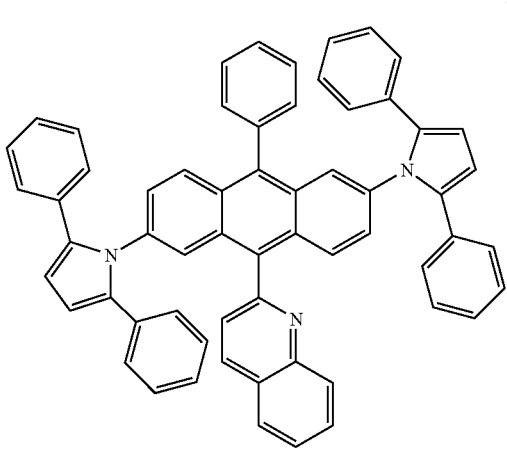
246
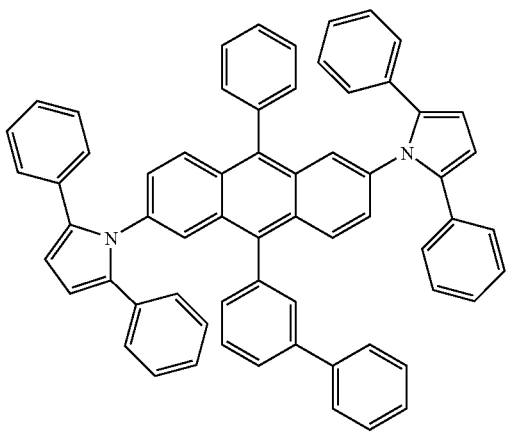
247
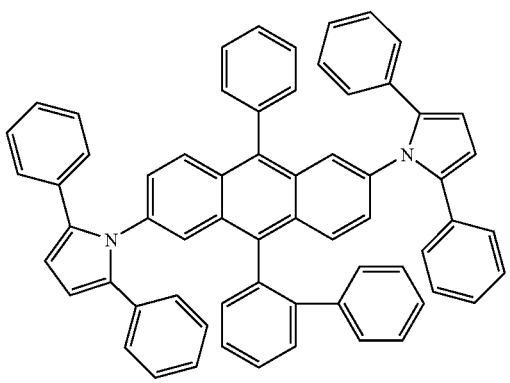

248
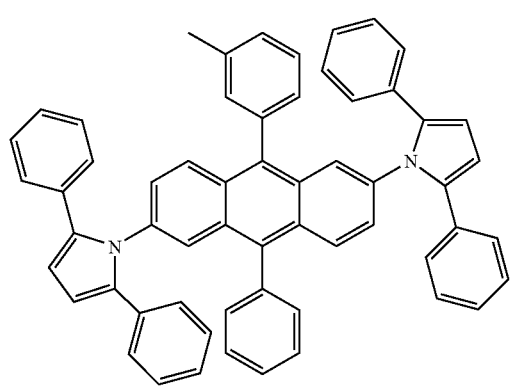
249
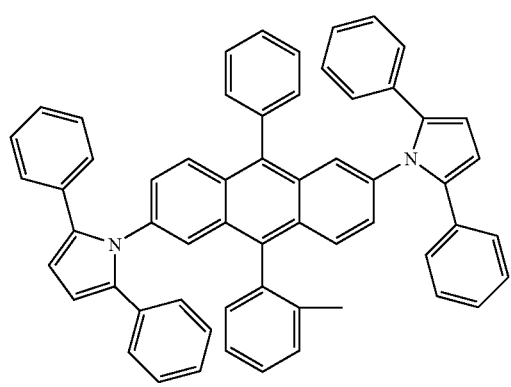
250
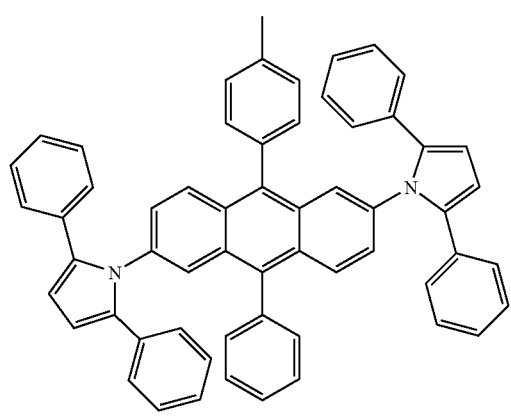
251
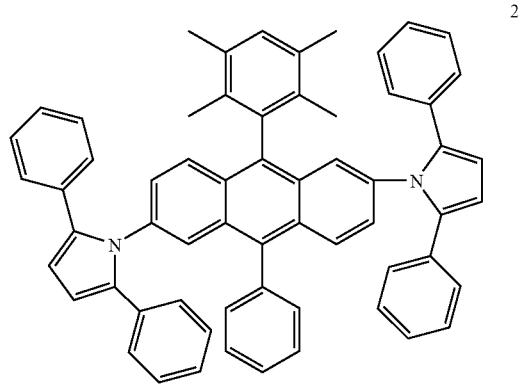
252
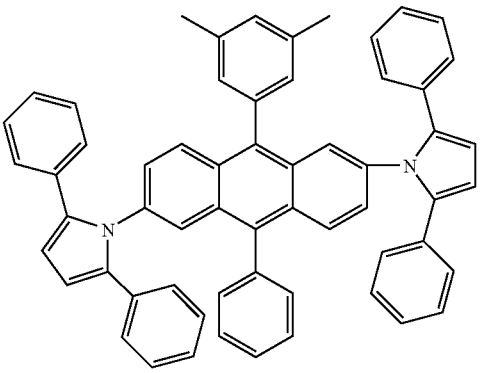
253
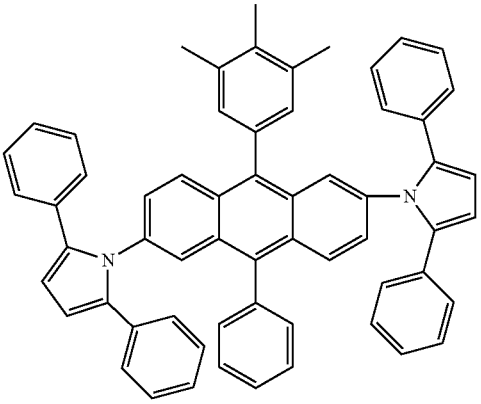
254
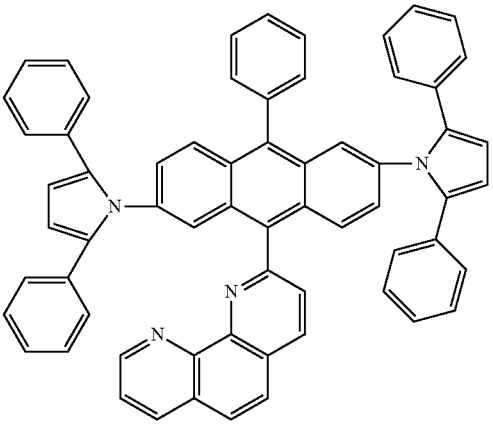
255
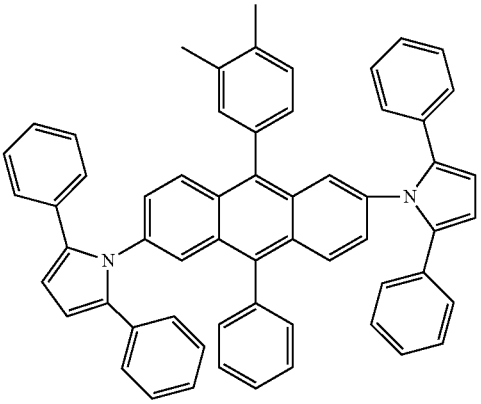

-continued
256
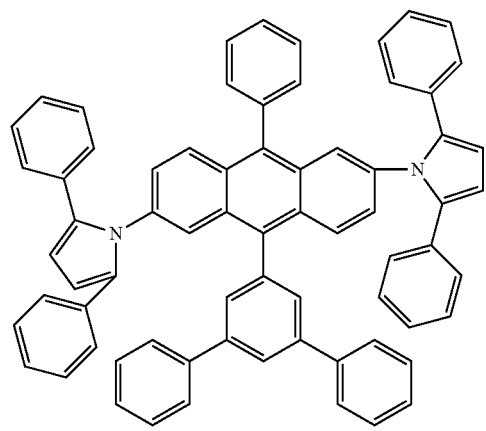
257
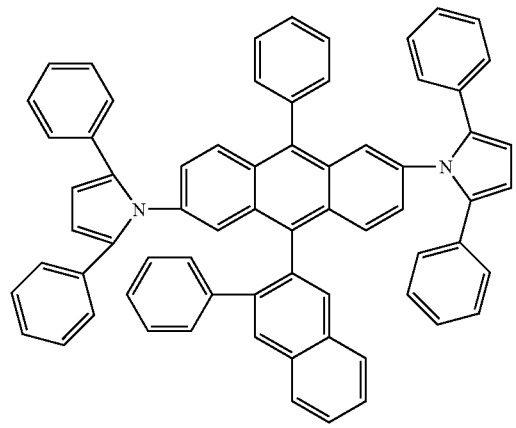
258
259
-continued
260
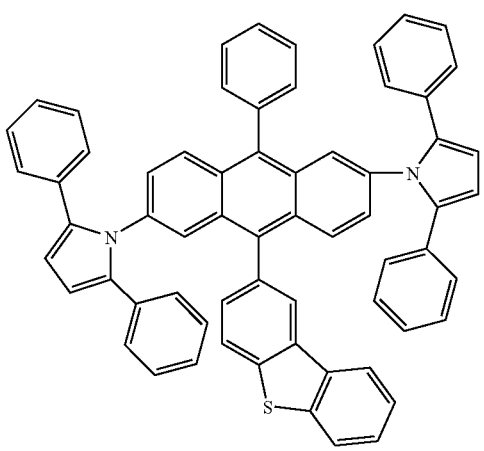
261
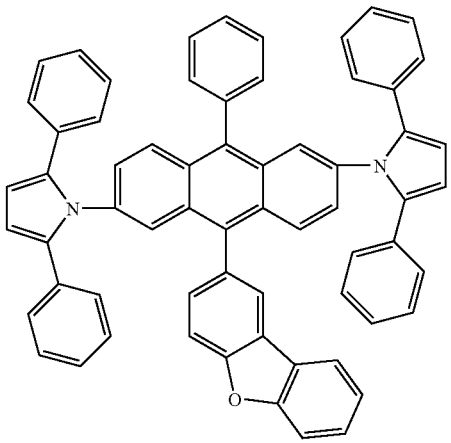
262
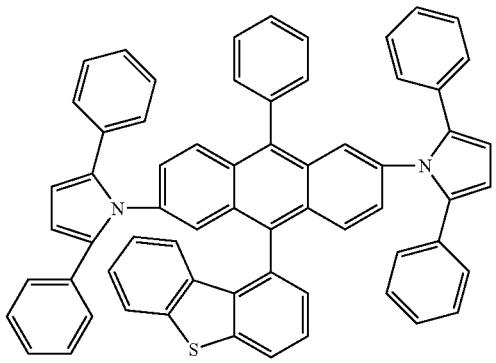

-continued
263
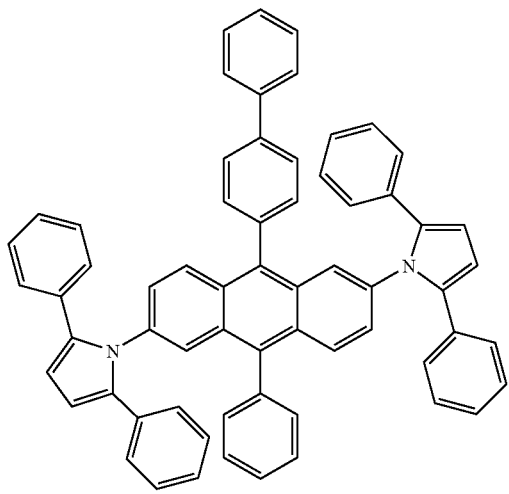
264
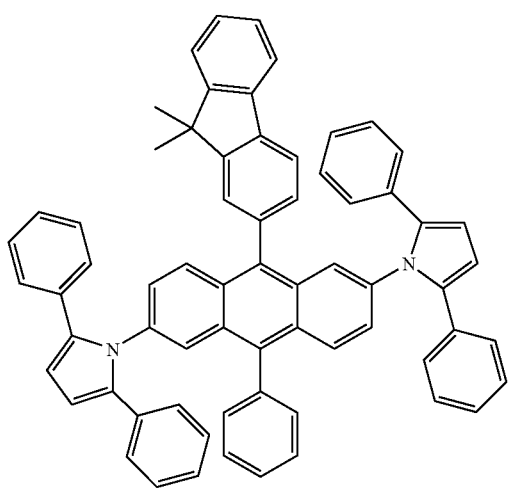
265
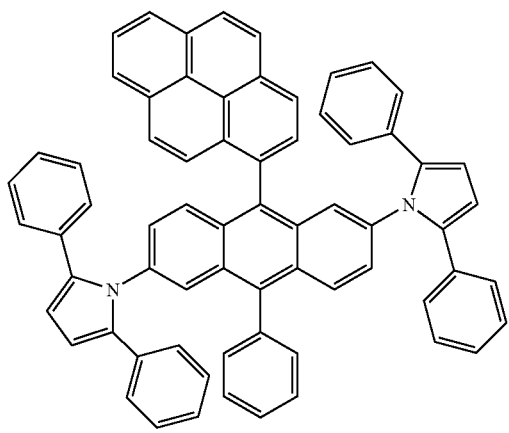
-continued
266
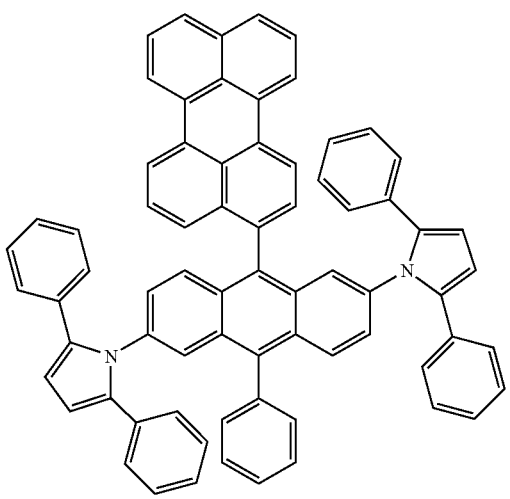
267
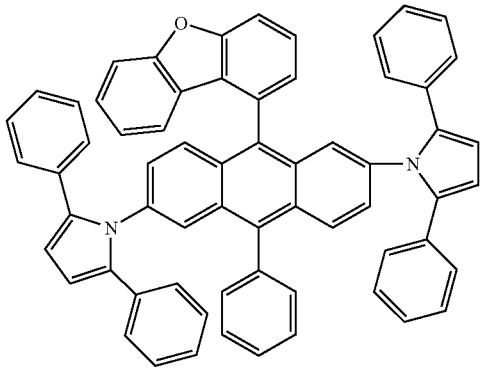
268
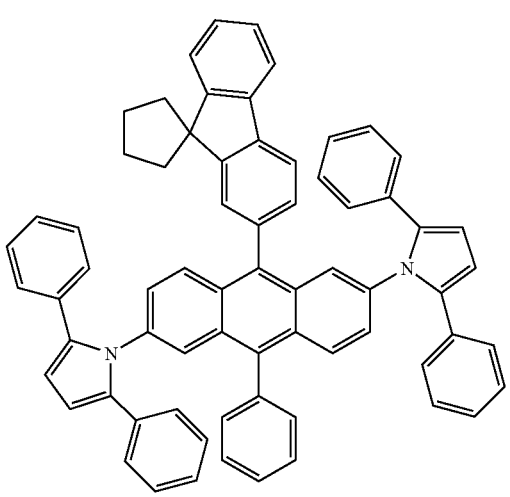

-continued
269
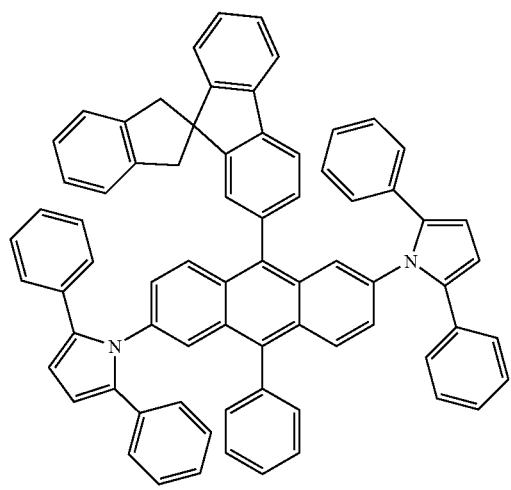
270
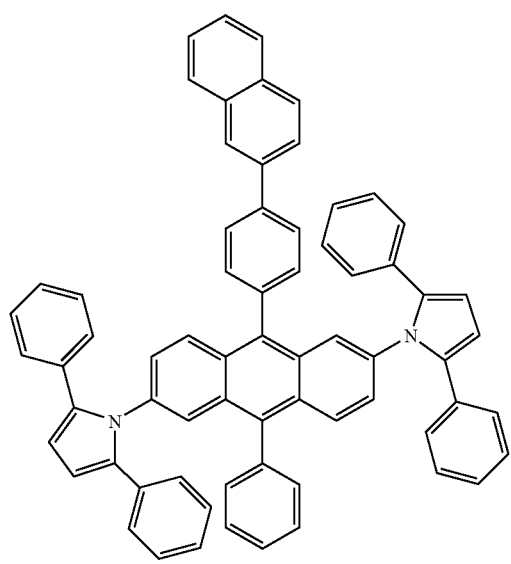
-continued
272
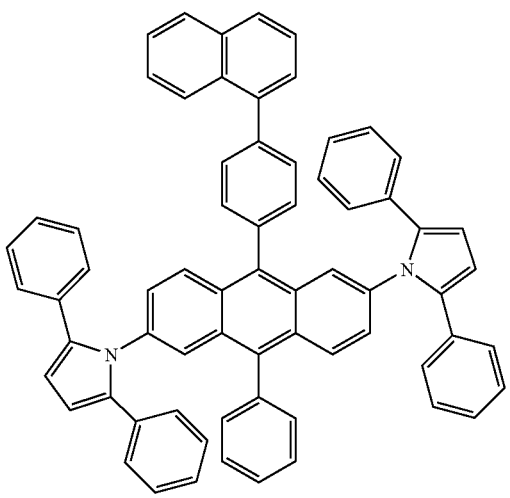
273
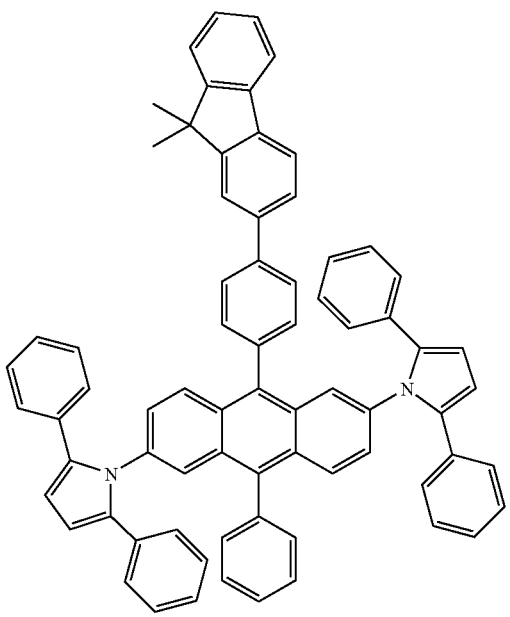

274
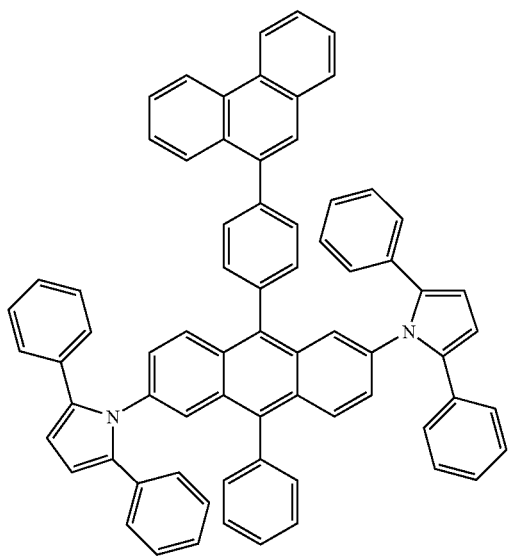
275
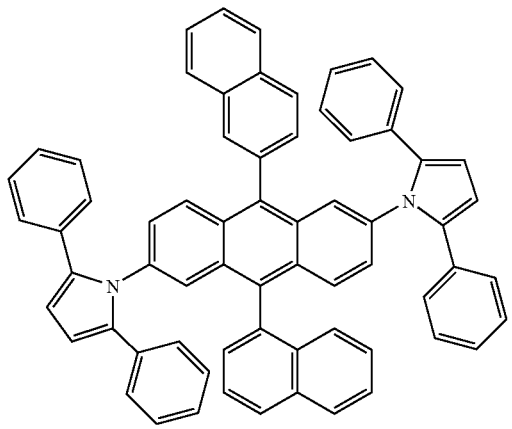
276
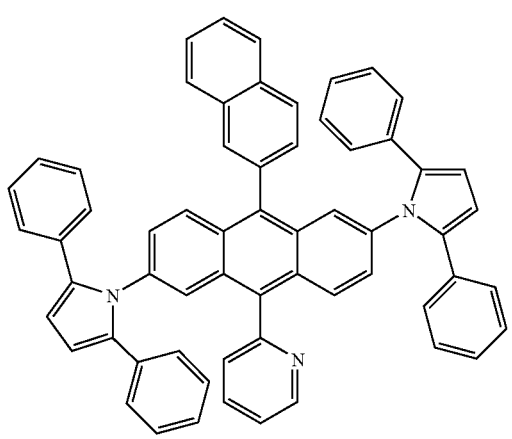
277
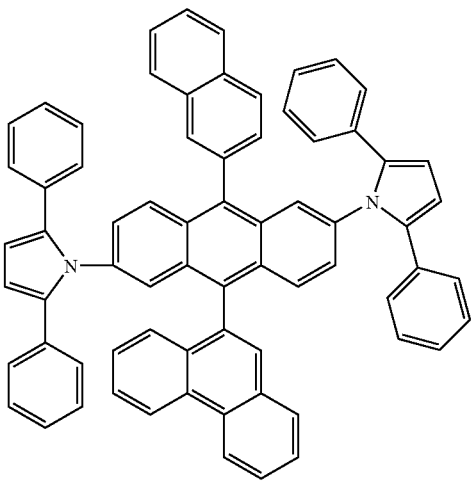
278
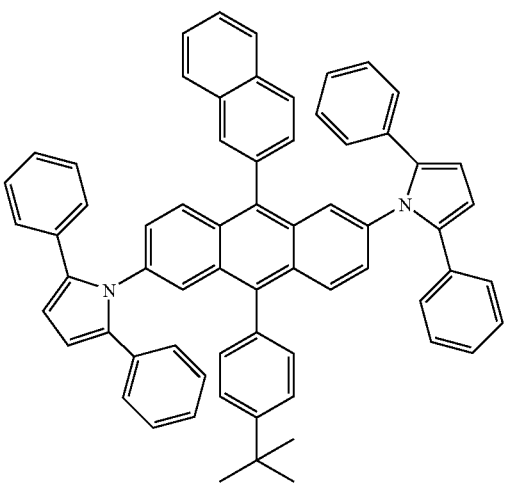
279
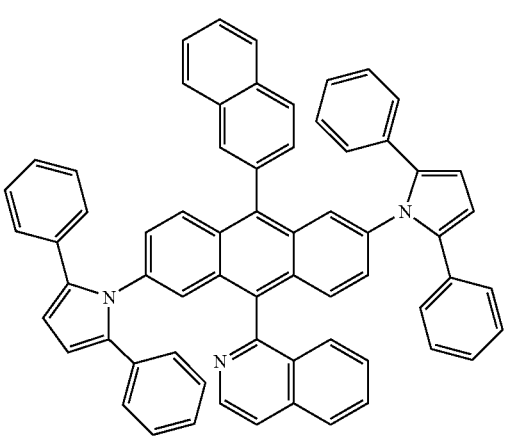

-continued
280
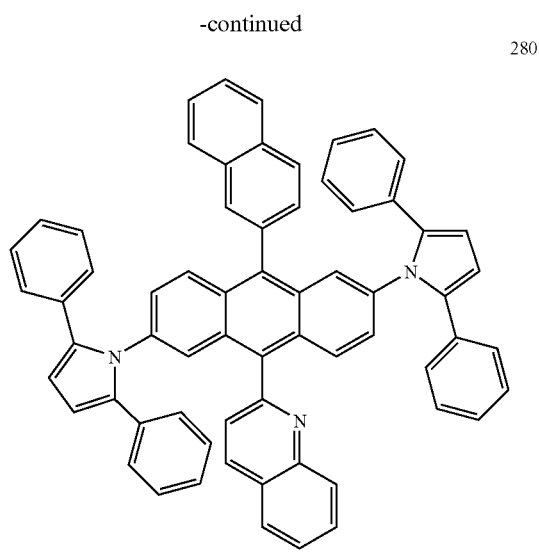
281
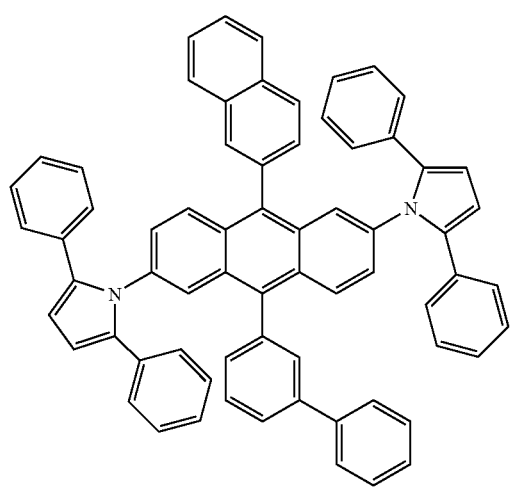
282
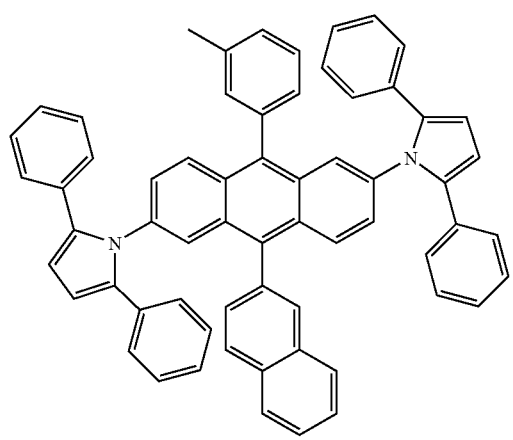
-continued
283
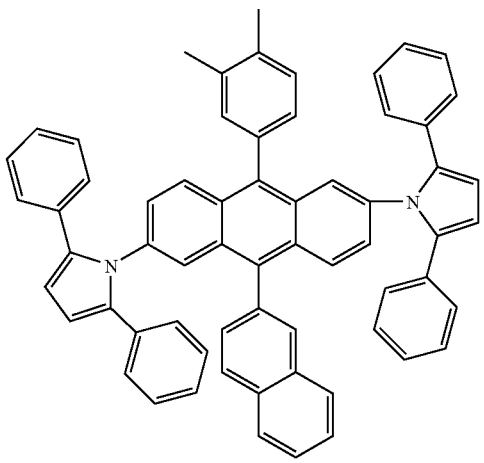
284
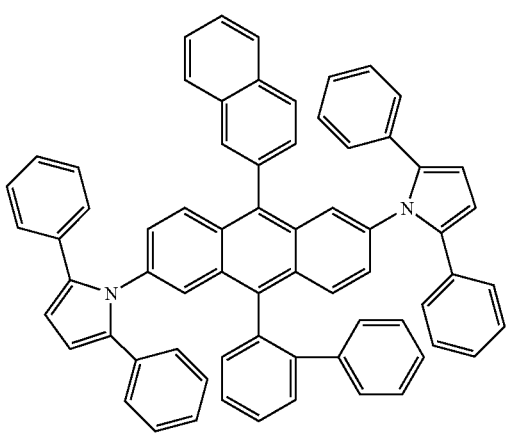
285
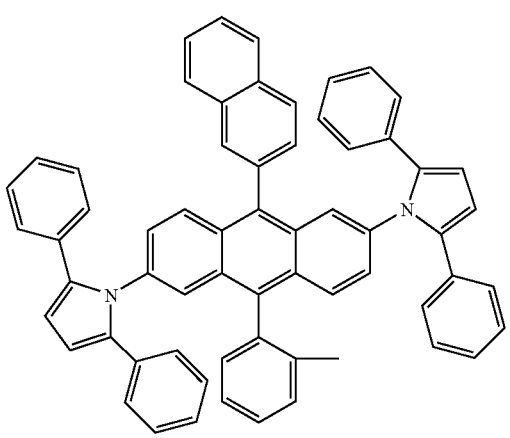

-continued
286
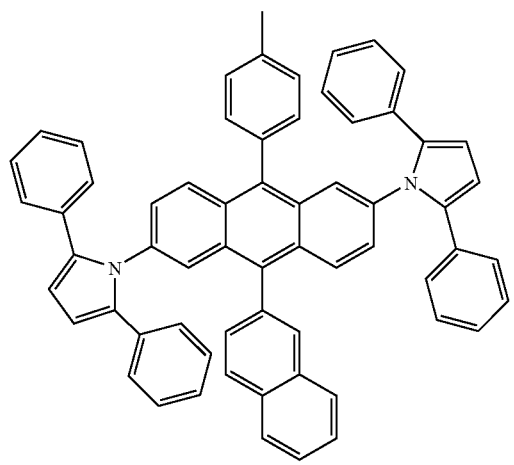
287
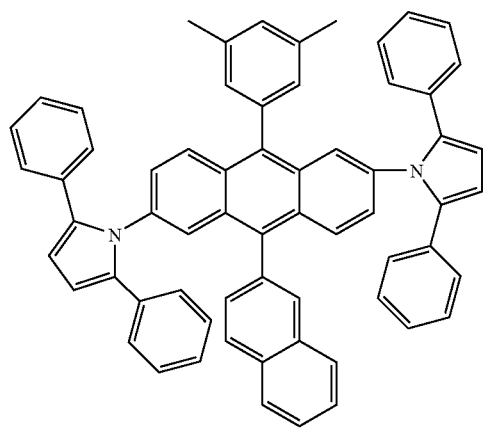
288
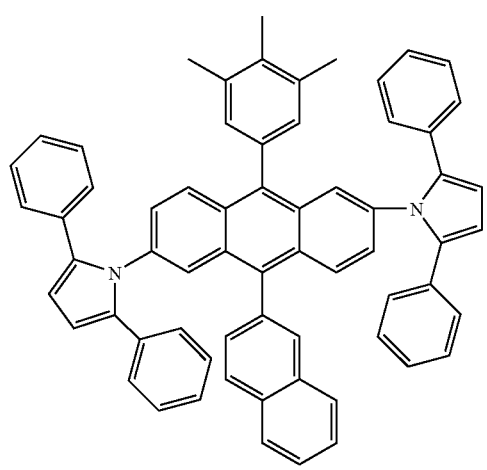
-continued
289
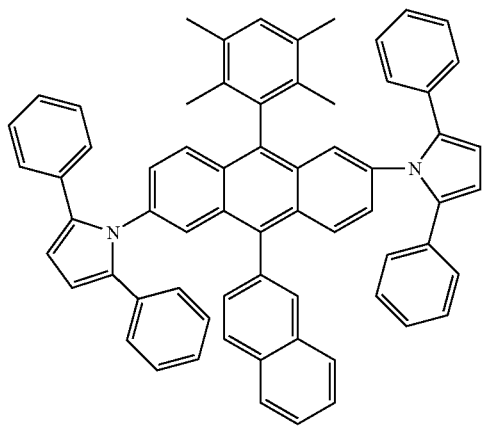
290
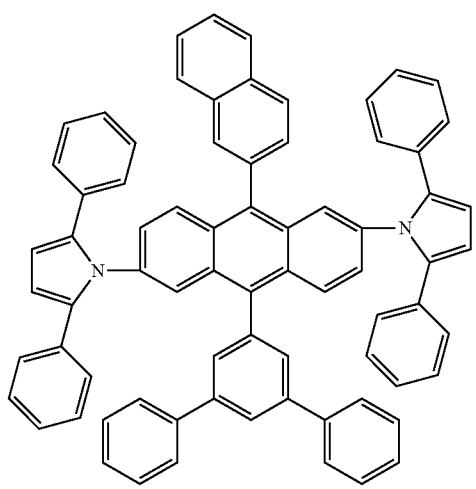
291
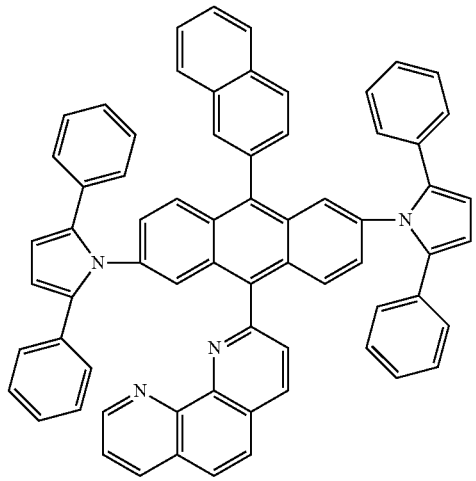

292
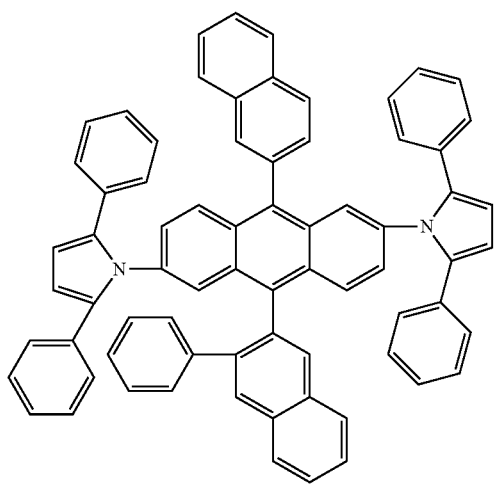
293
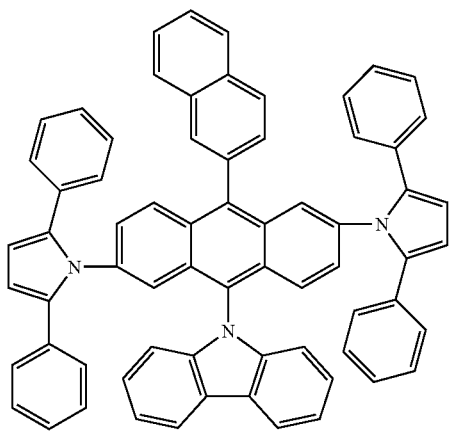
294
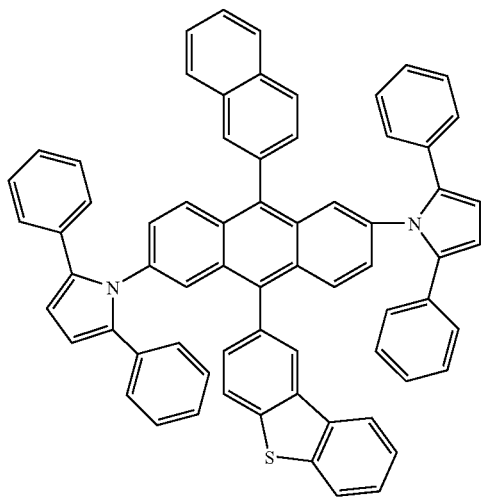
295
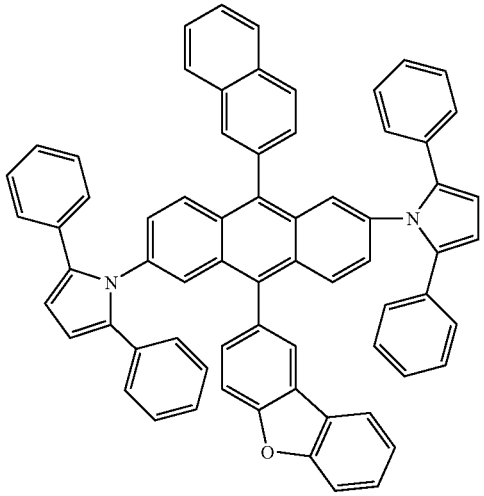
297
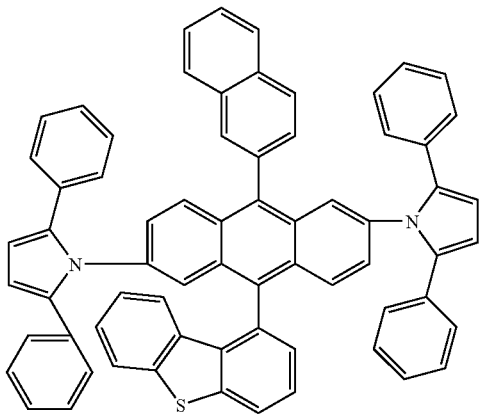
298
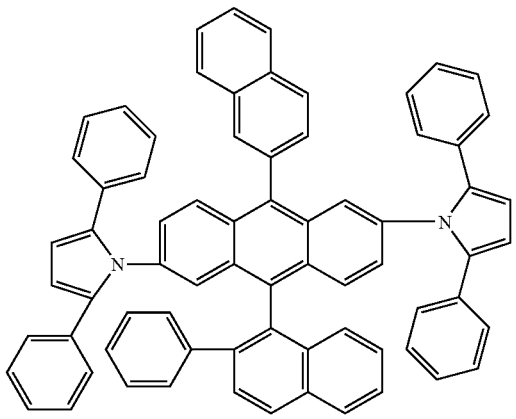

-continued
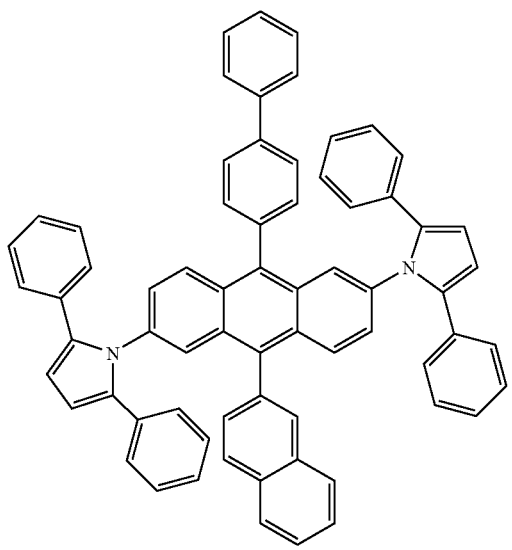
299
300
301
-continued
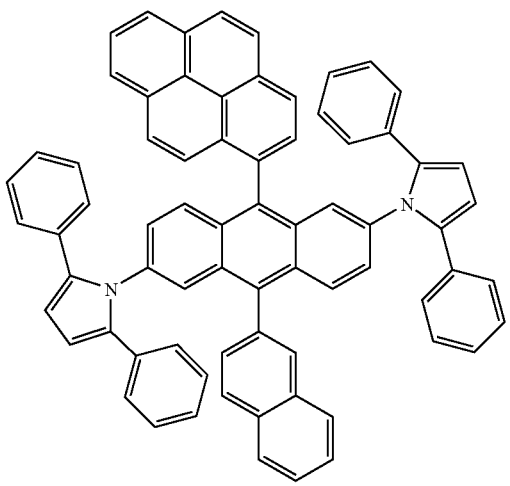
302
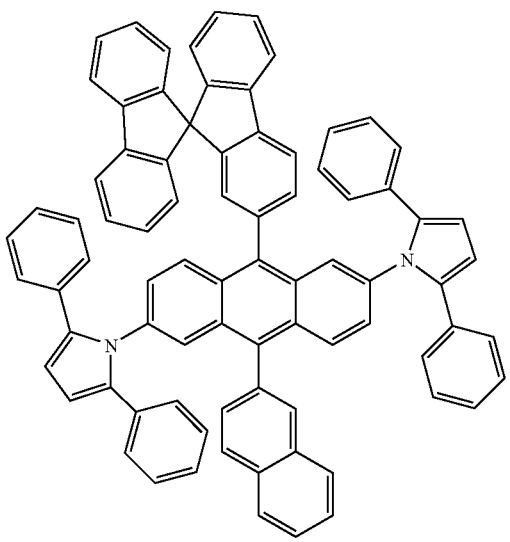
303
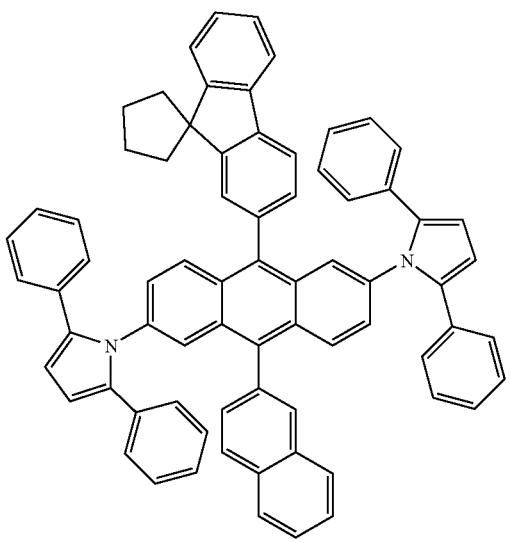
304

127
-continued
305
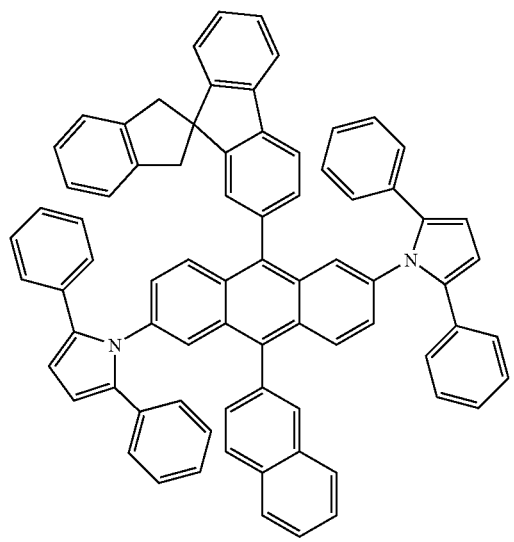
306
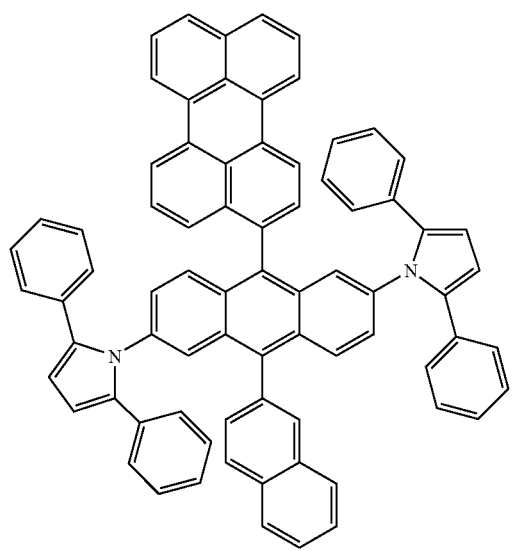
128
-continued
307
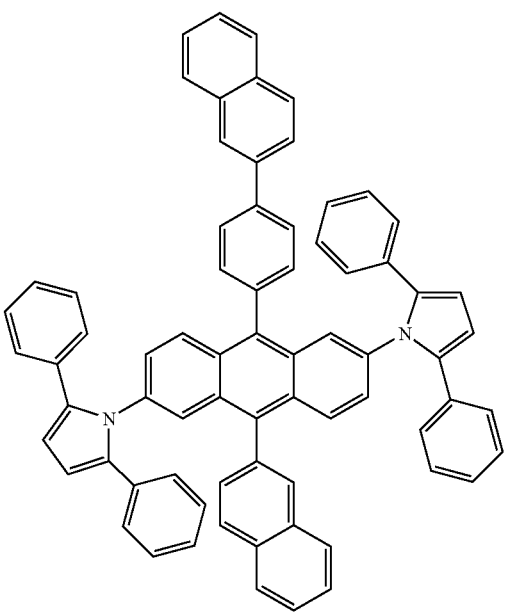
308
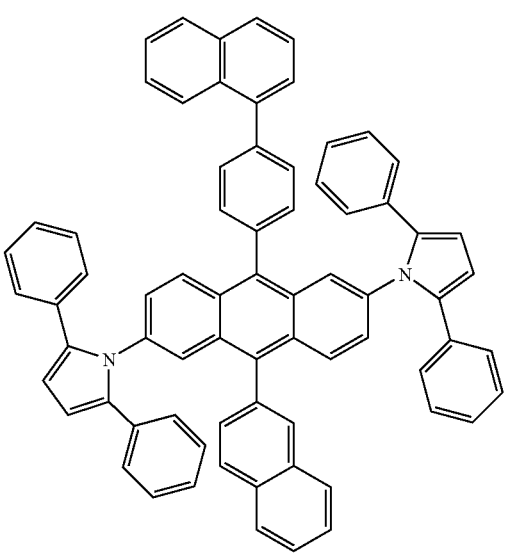

309
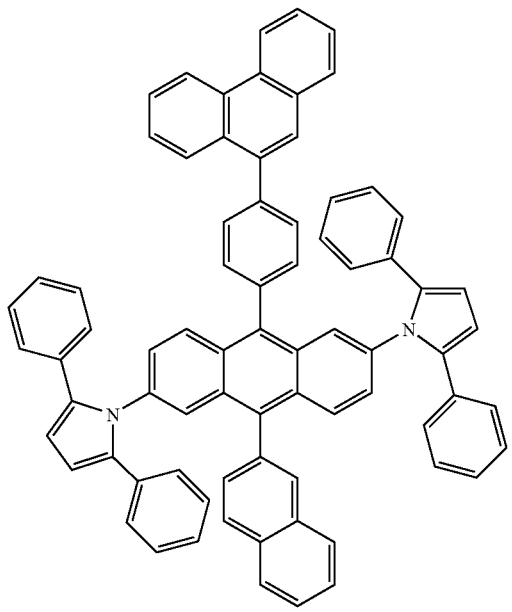
310
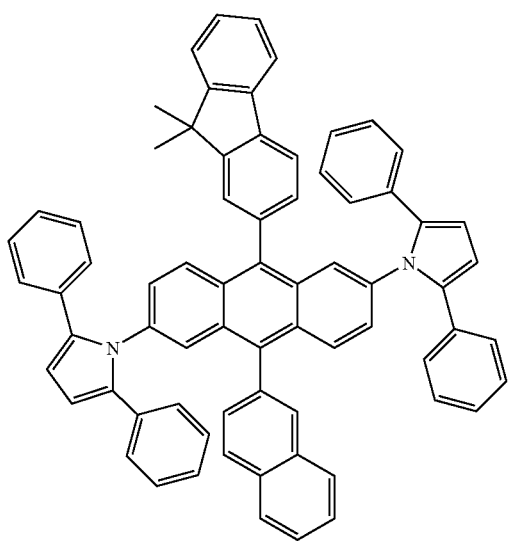
311
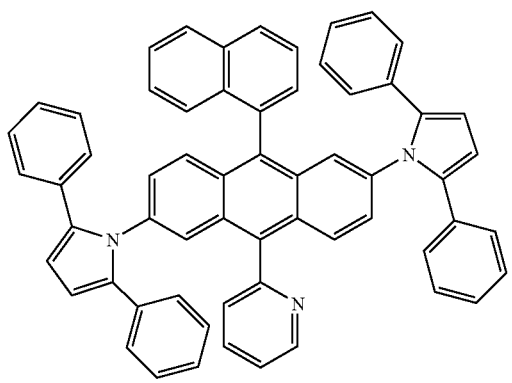
312
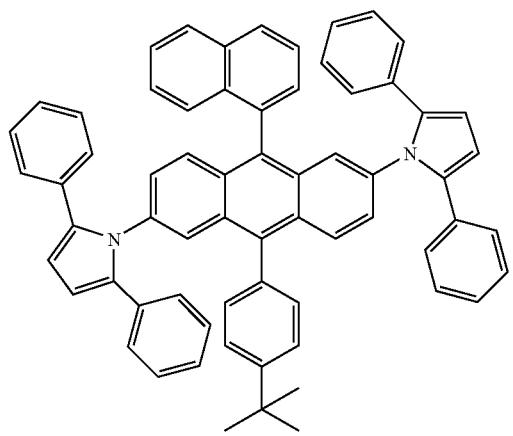
313
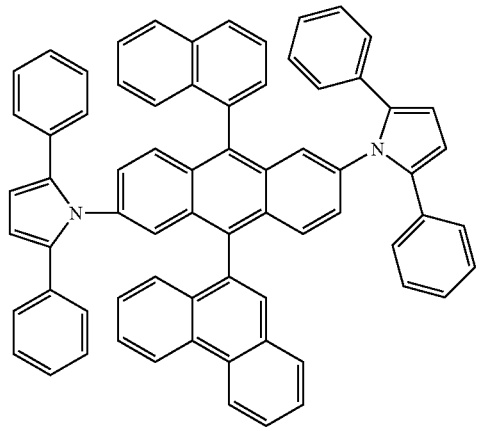
314
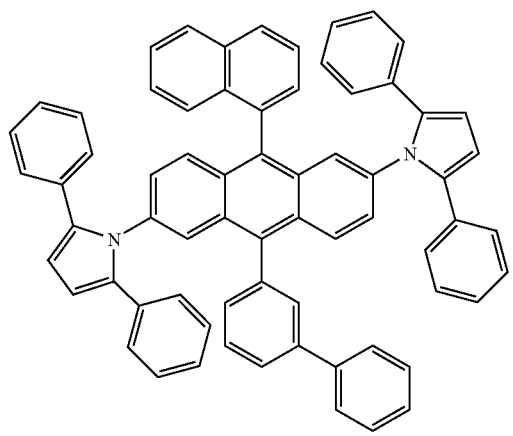

-continued
315
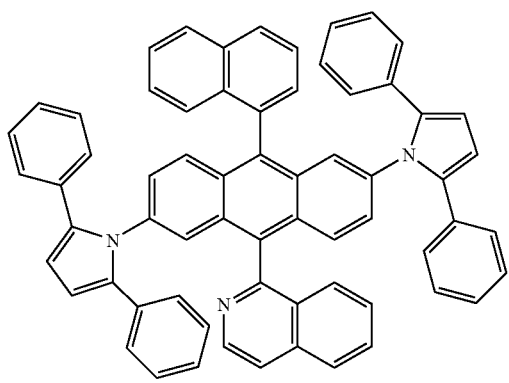
316
317
318
-continued
319
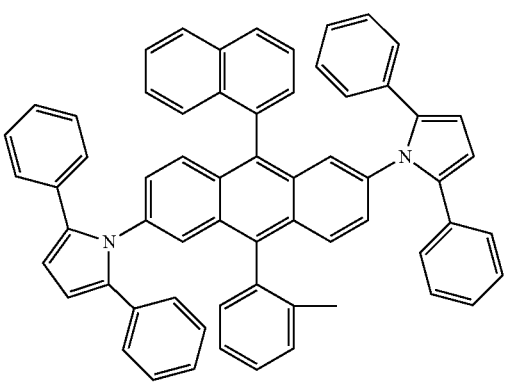
320
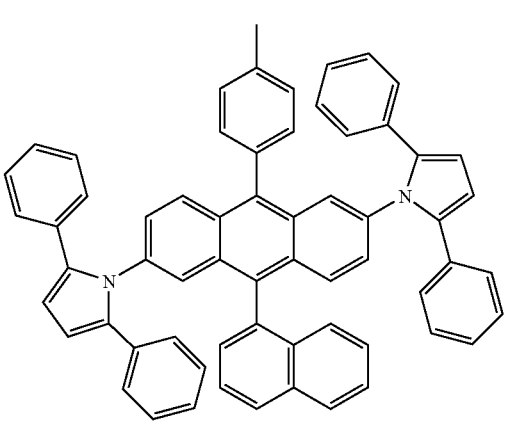
321
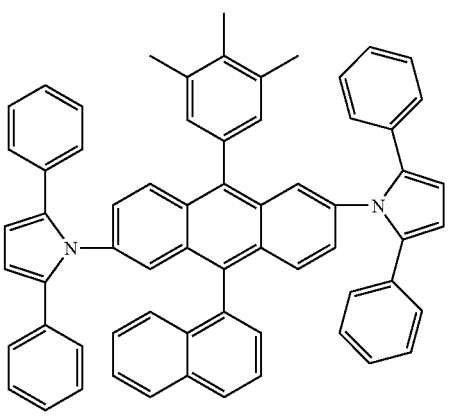
322
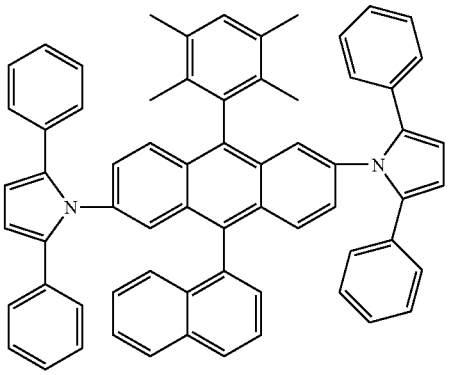

-continued
323
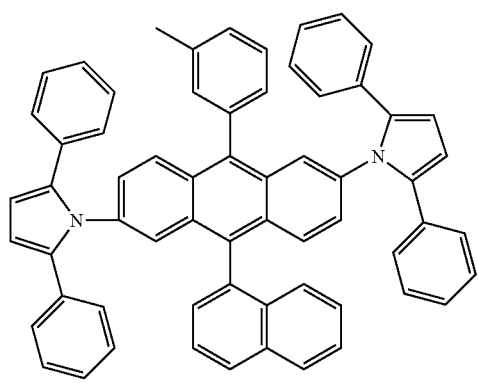
324
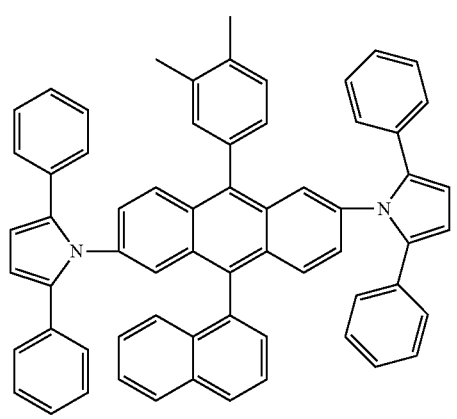
325
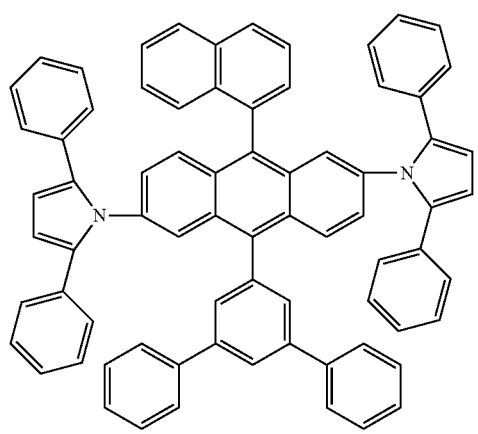
-continued
326
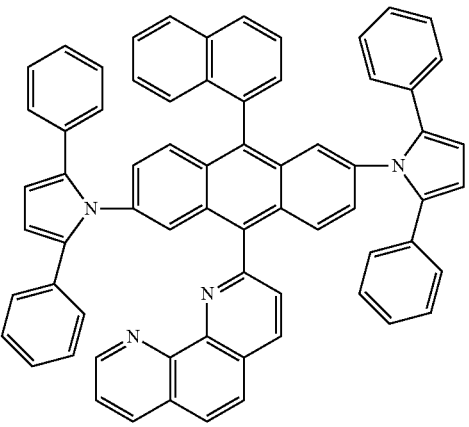
327
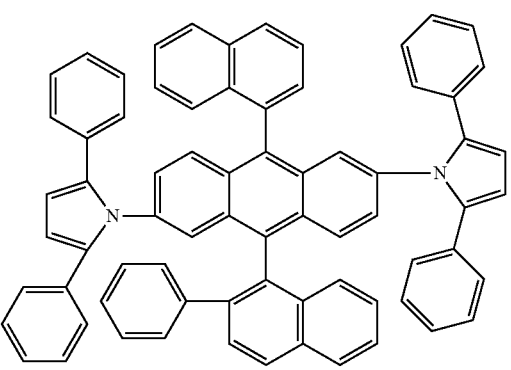
328
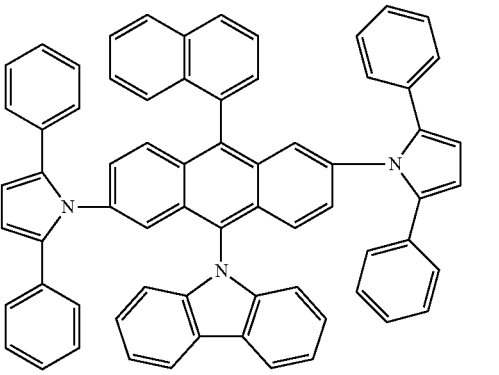
329
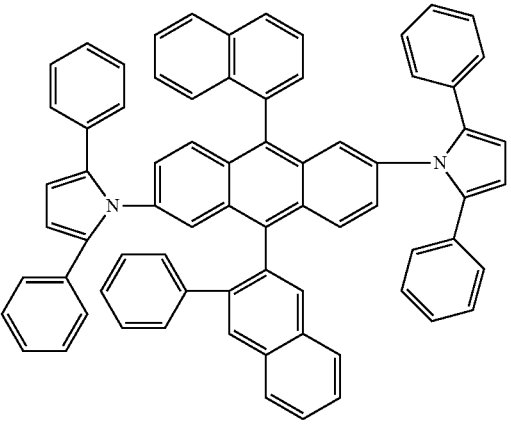

135
-continued
330
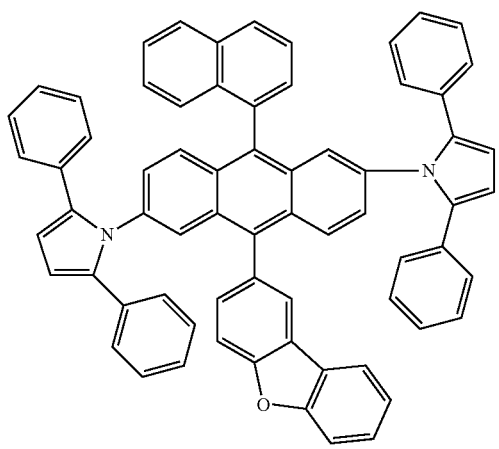
331
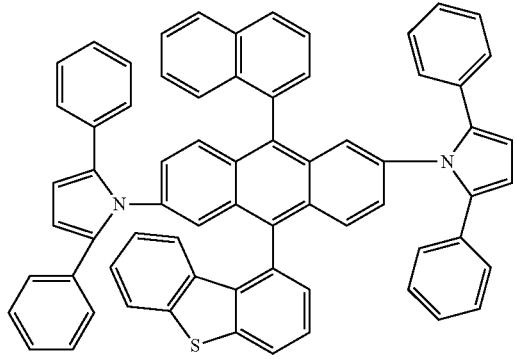
332
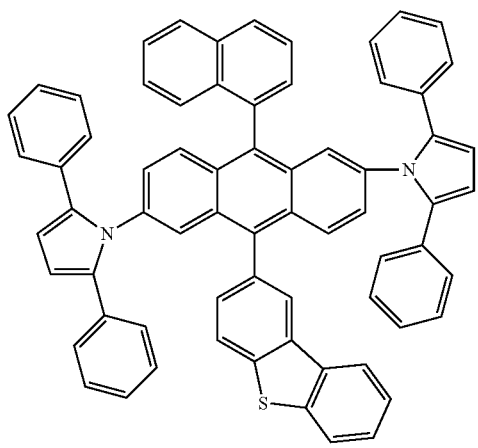
136
-continued
333
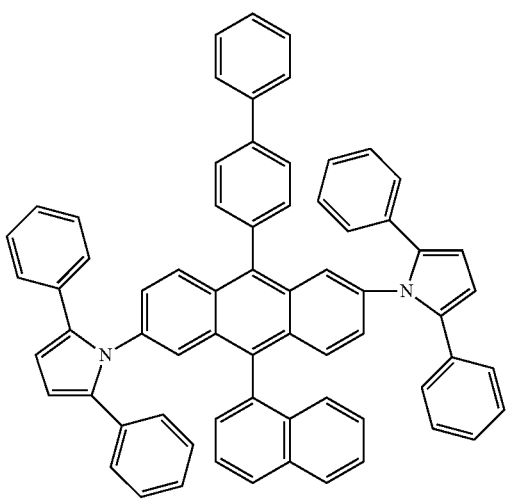
334
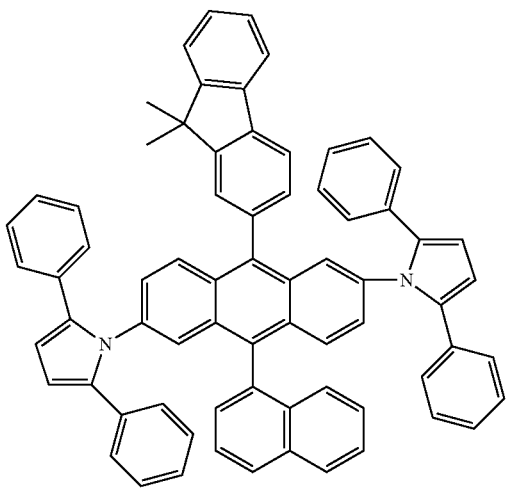
335
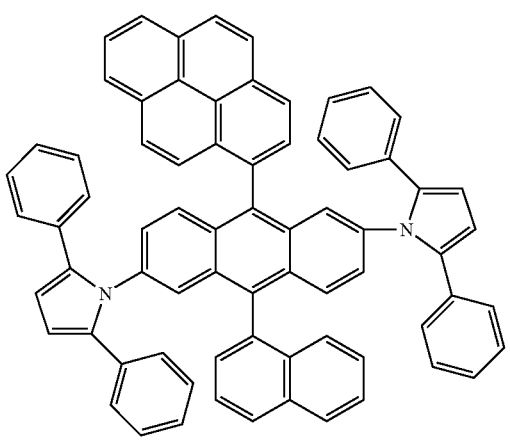

-continued
336
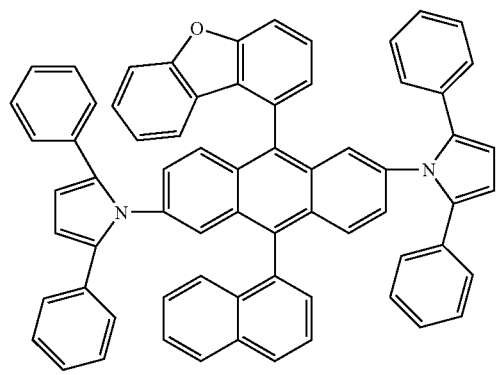
337
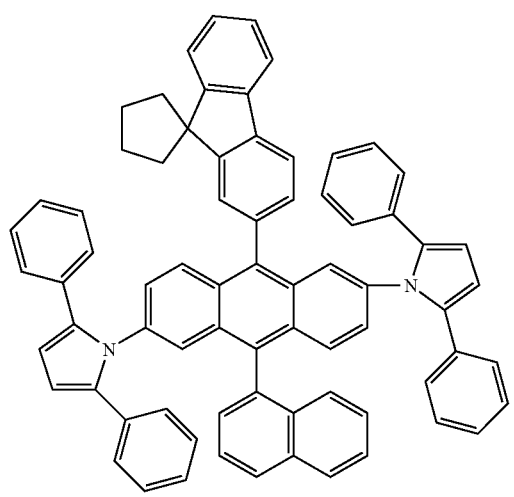
338
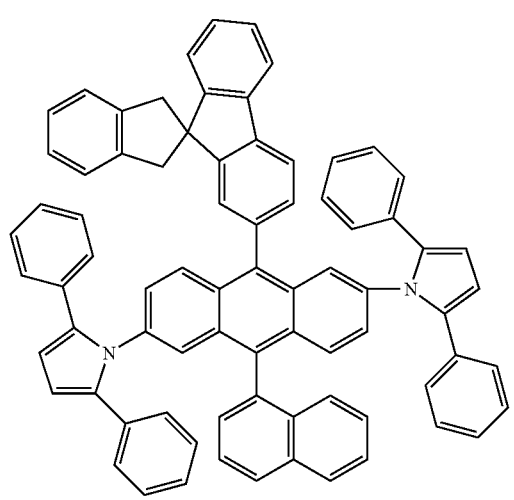
-continued
339
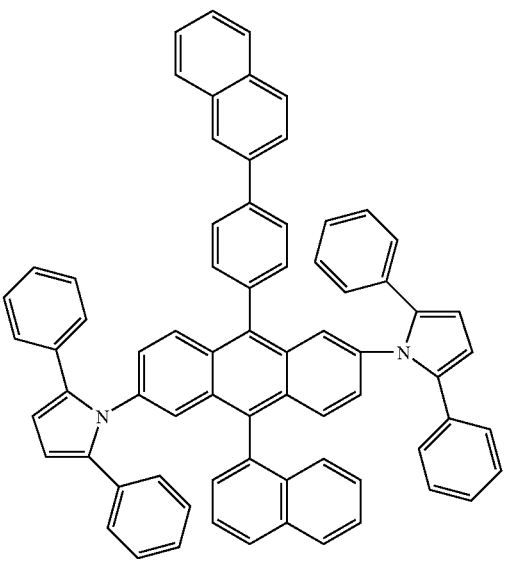
340
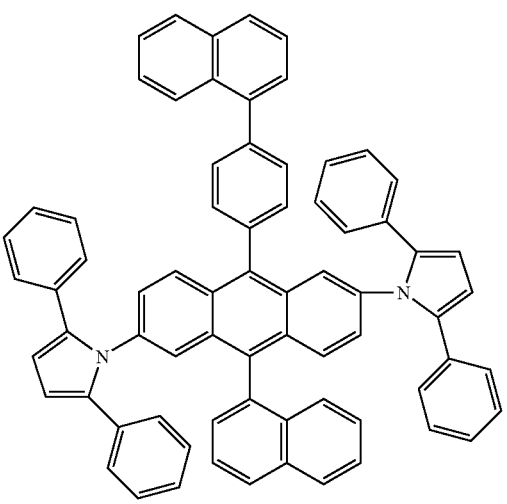

-continued
341
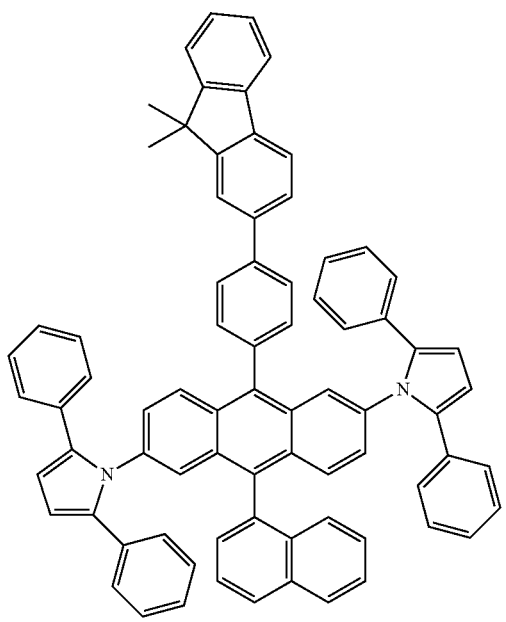
342
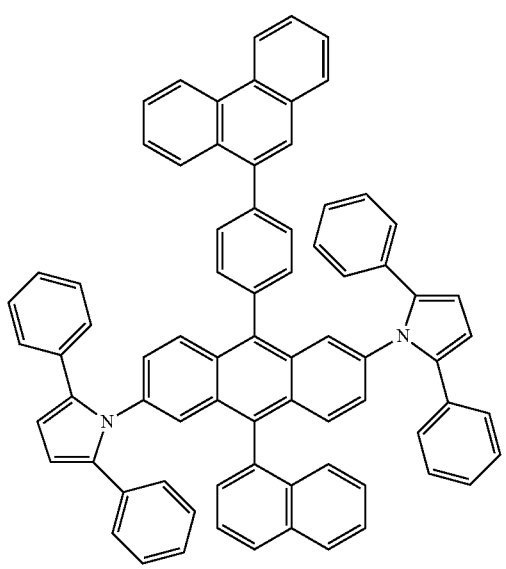
-continued
343
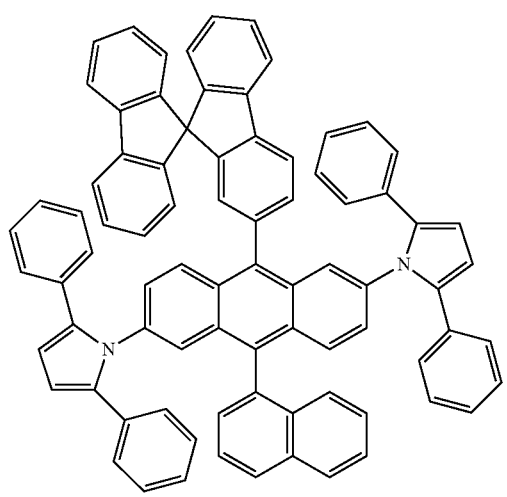
344
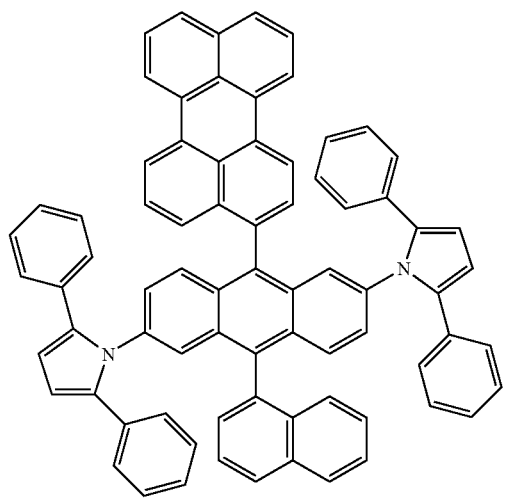
345
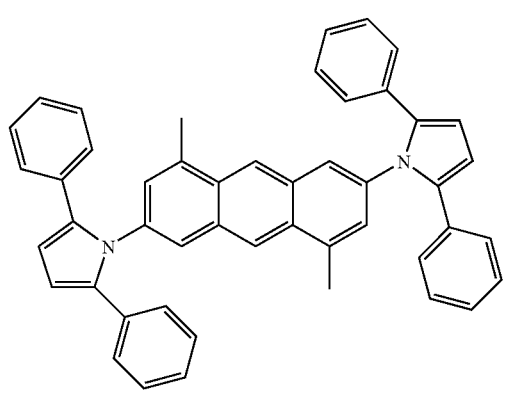

-continued
346
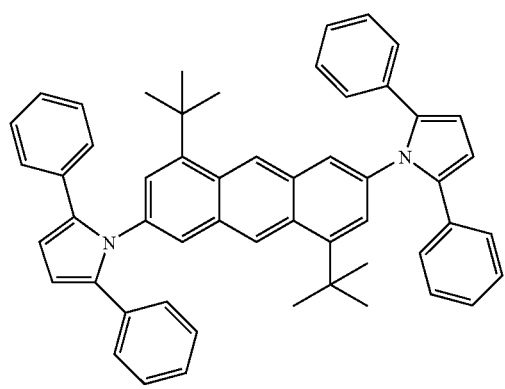
347
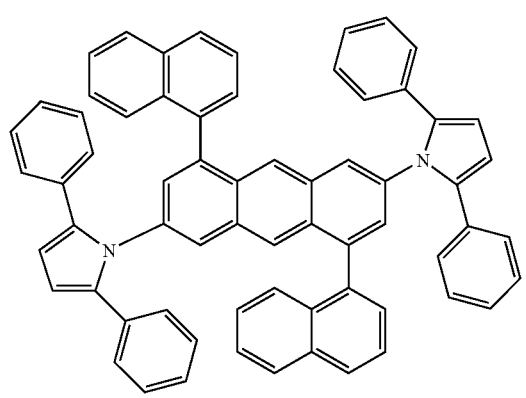
348
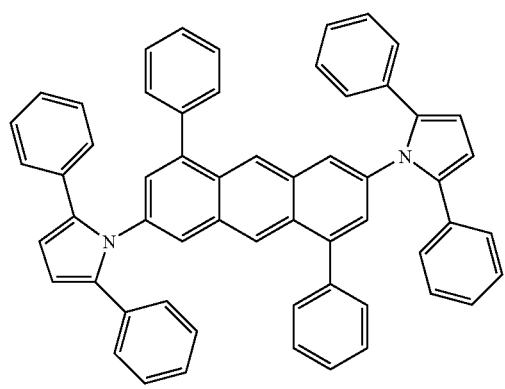
-continued
349
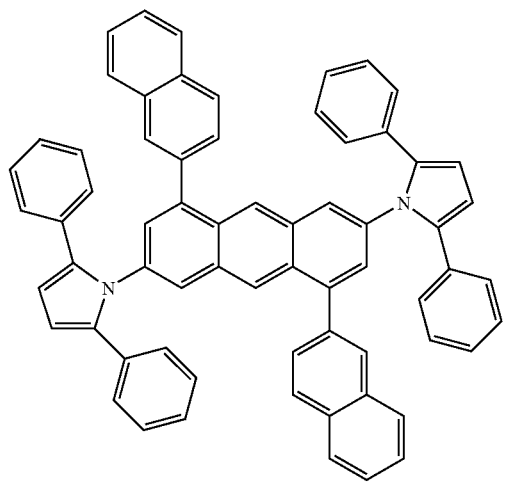
350
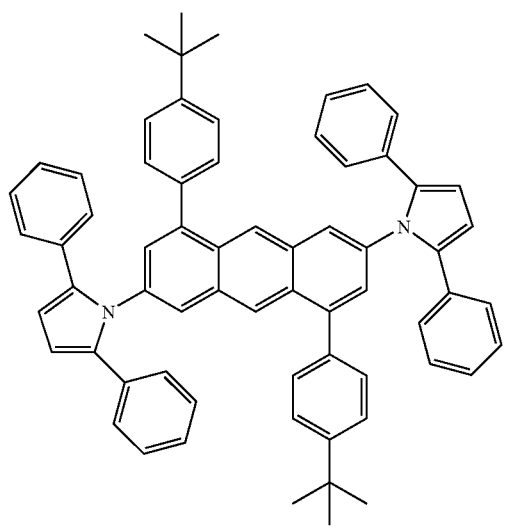
351
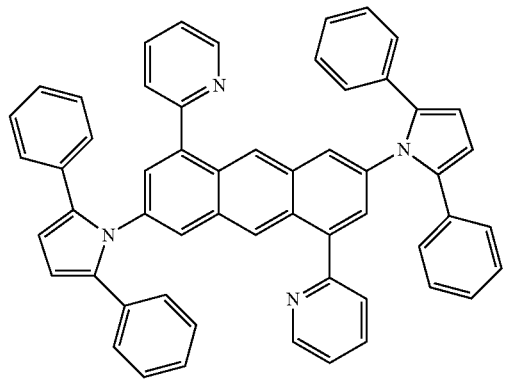

352
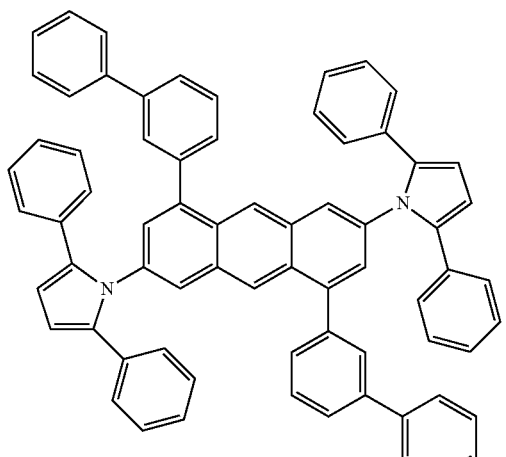
353
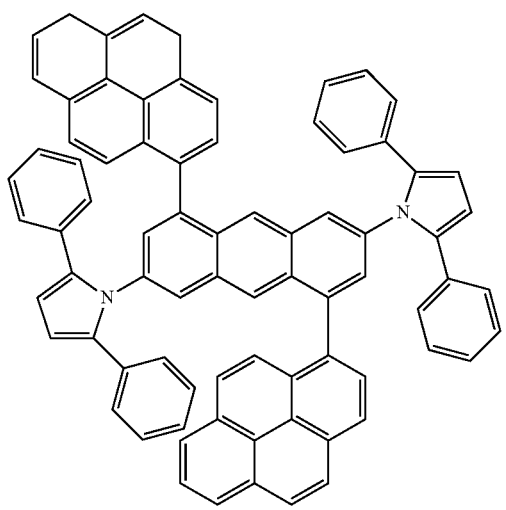
354
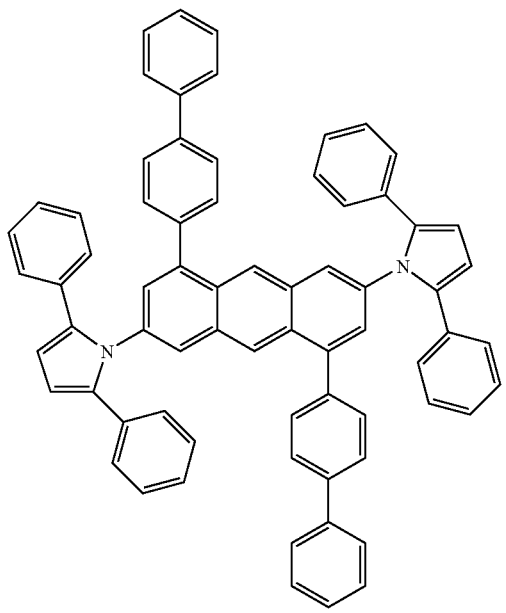
355
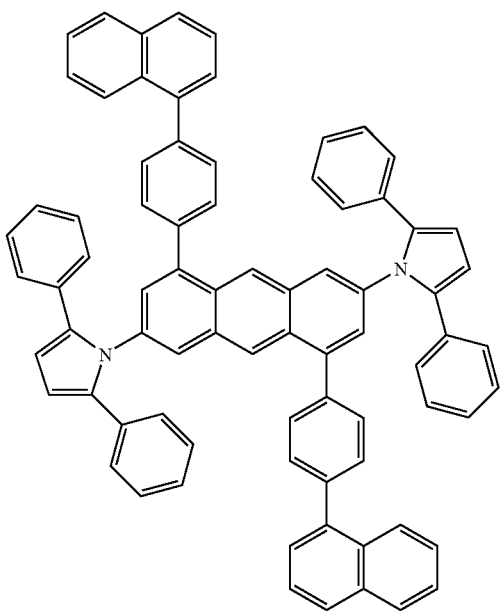
356
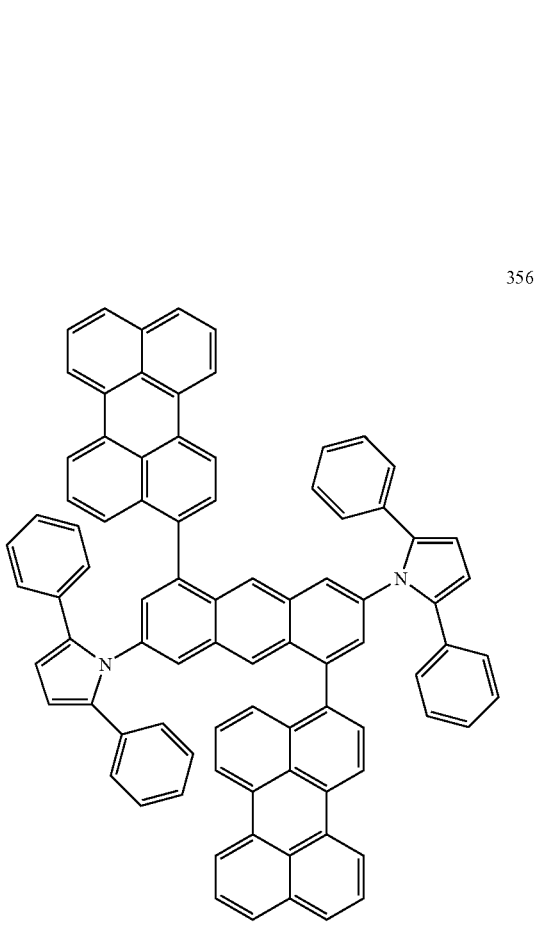

-continued
357
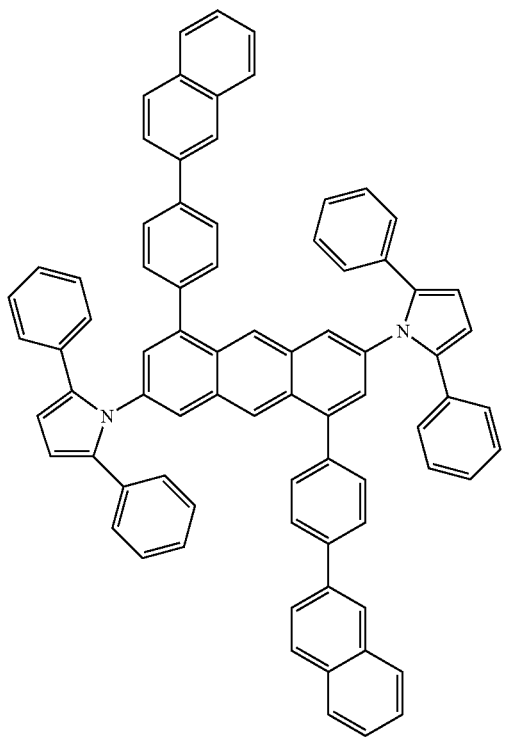
358
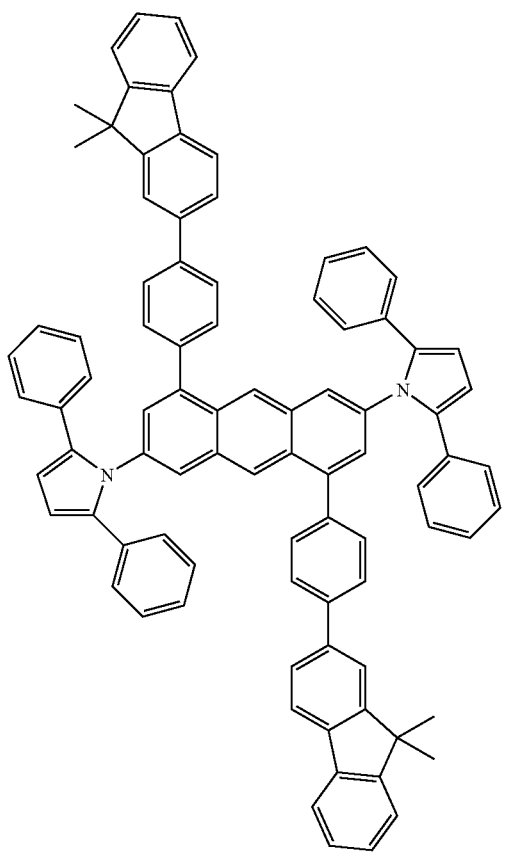
-continued
359
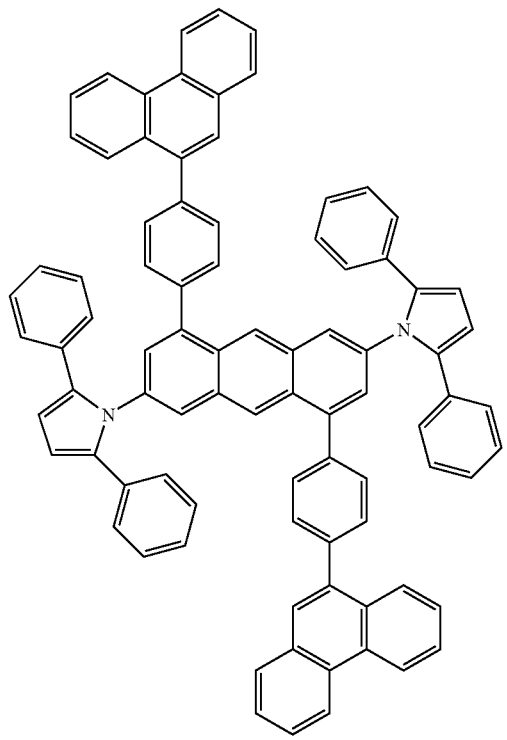
360
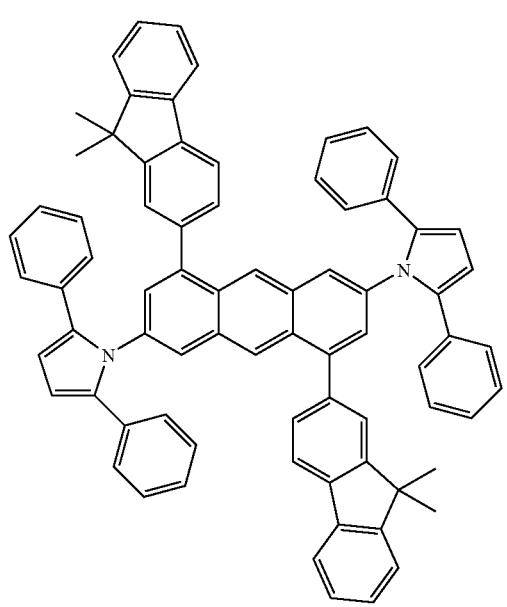

361
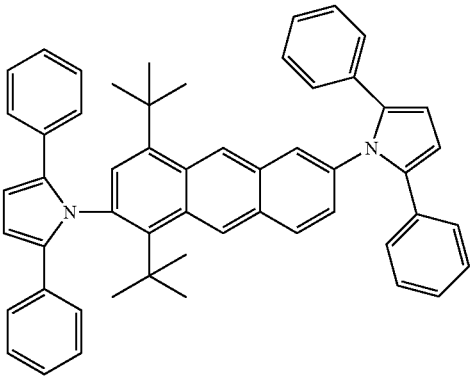
364
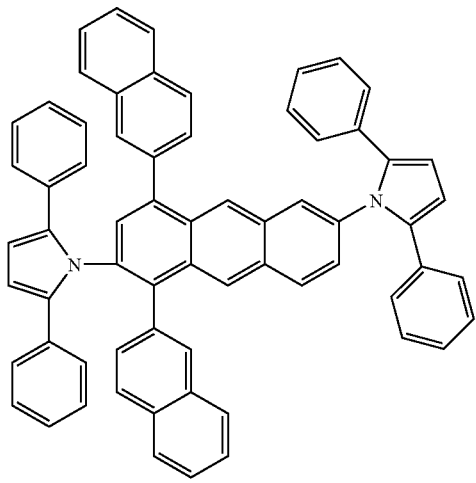
365
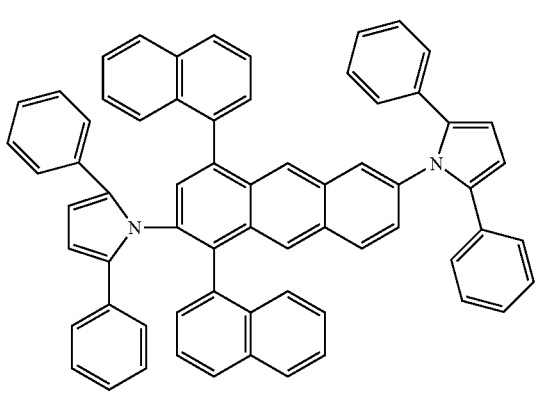
362
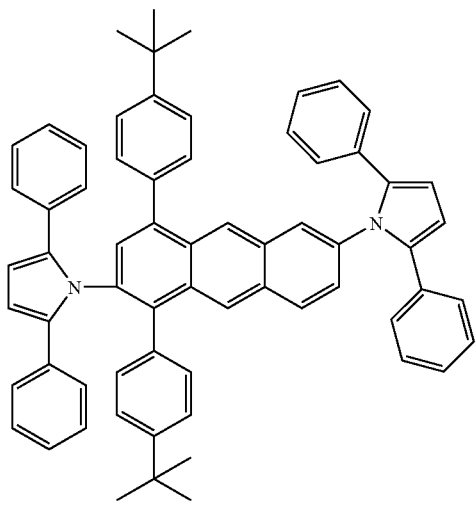
366
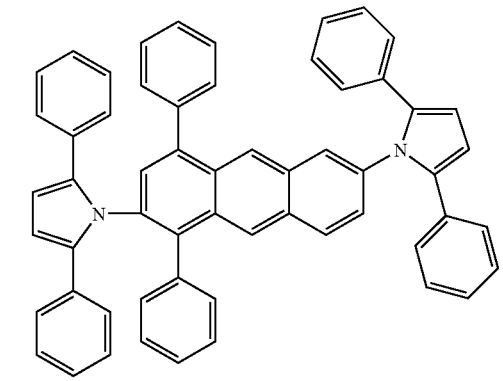
363
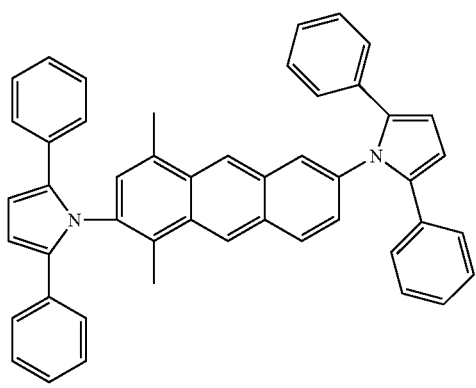
367
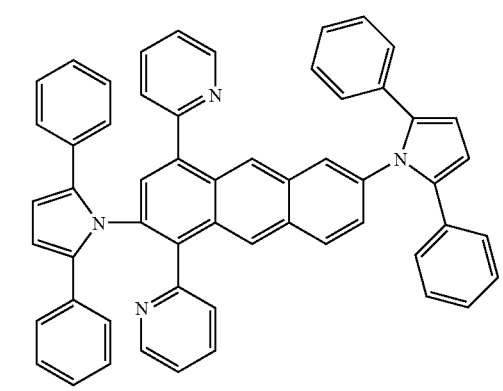

-continued
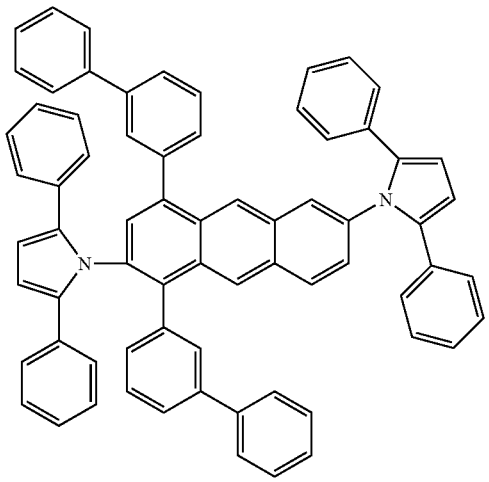
368
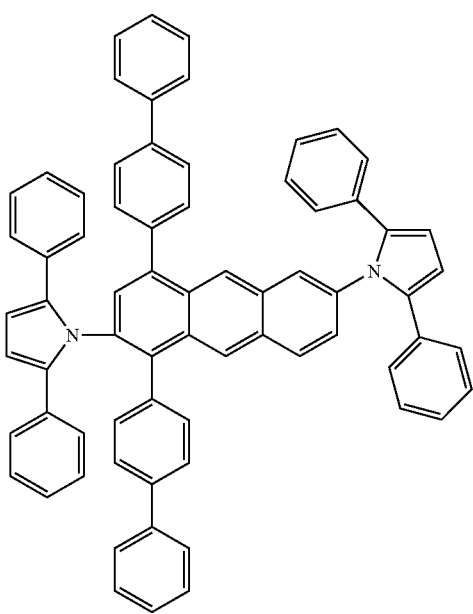
369
-continued
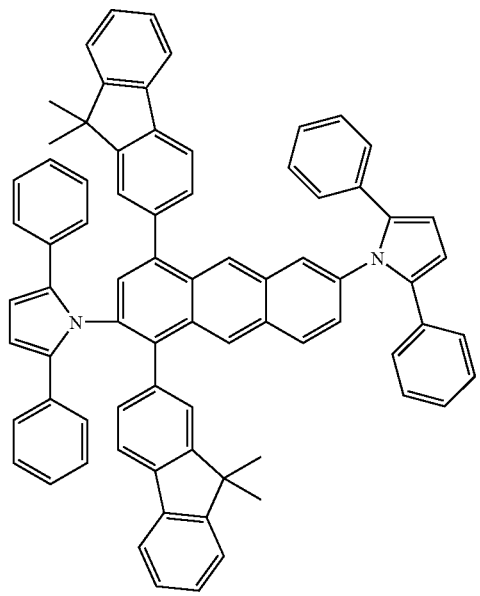
370
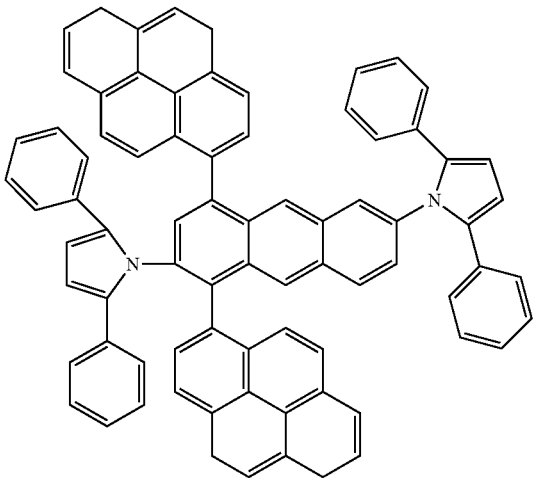
371

-continued
151
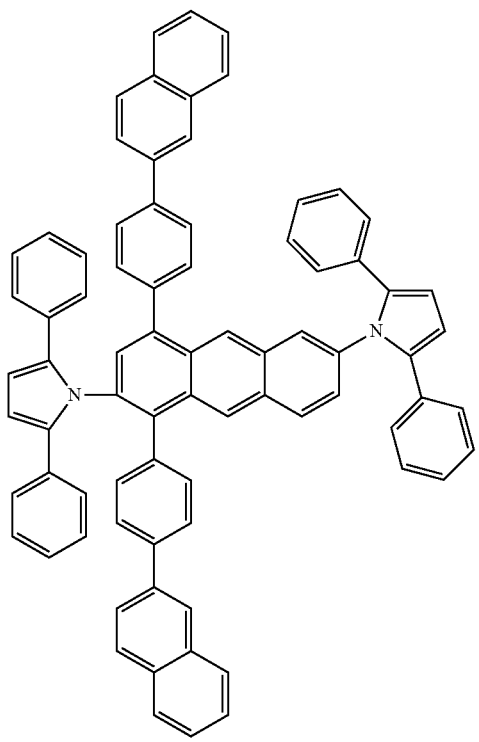
372
373
152
-continued
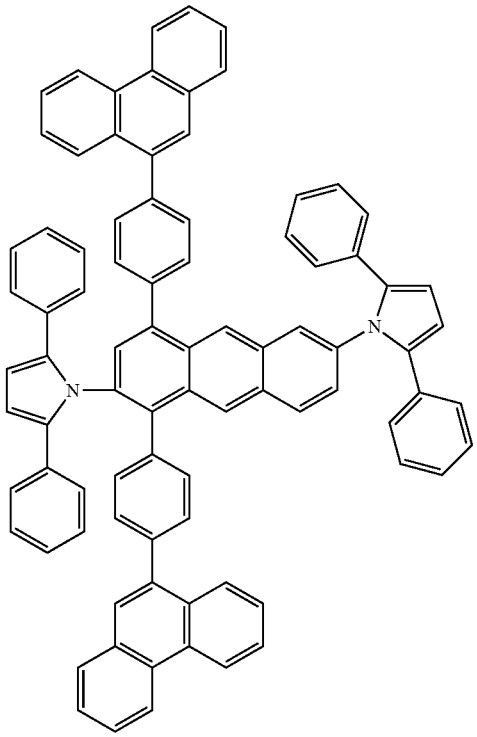
374
375
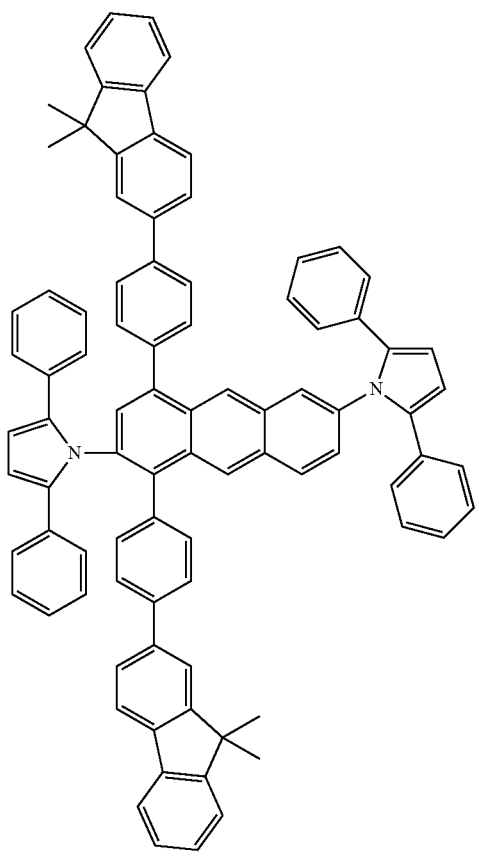
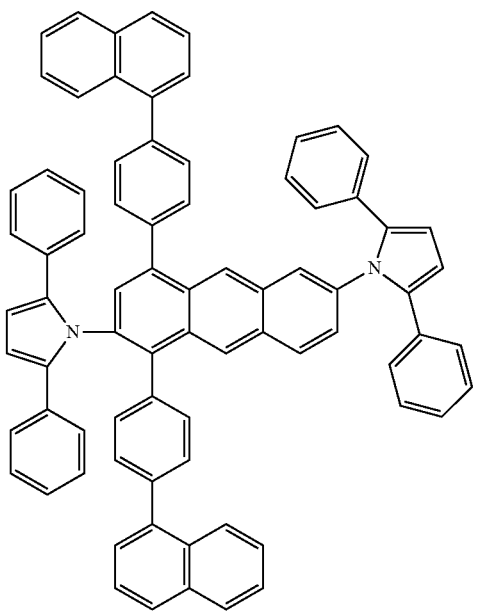

-continued
376
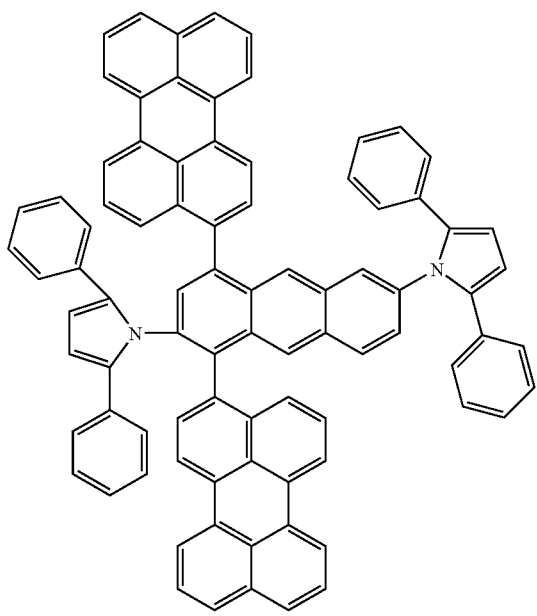
377
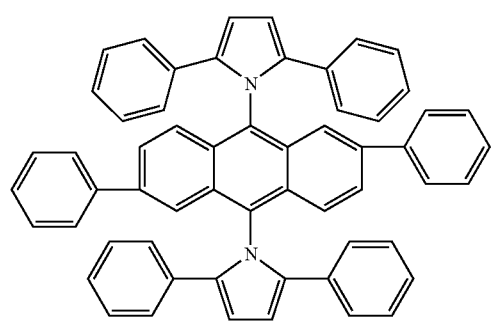
378
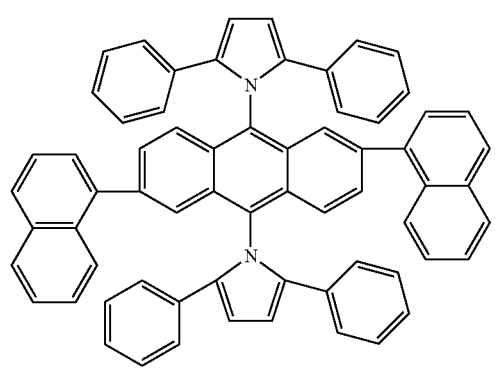
379
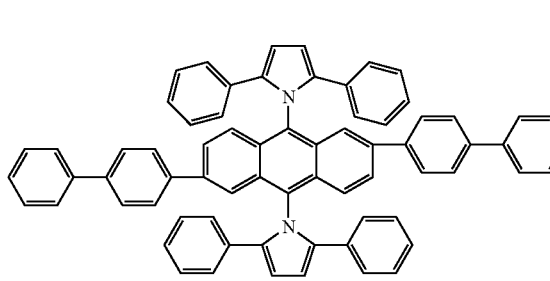
-continued
380
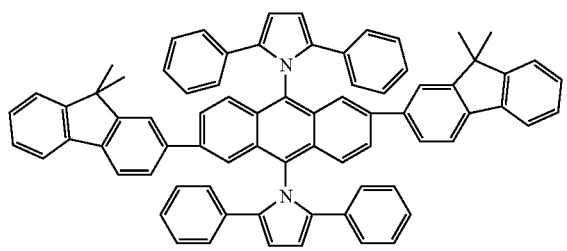
381
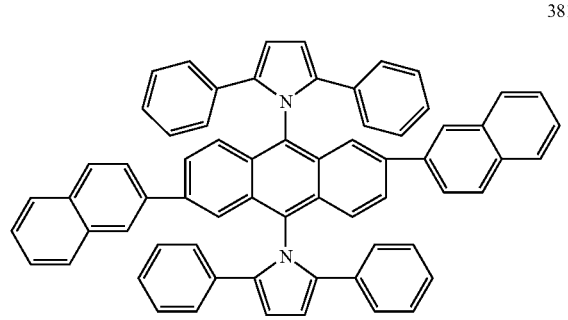
382
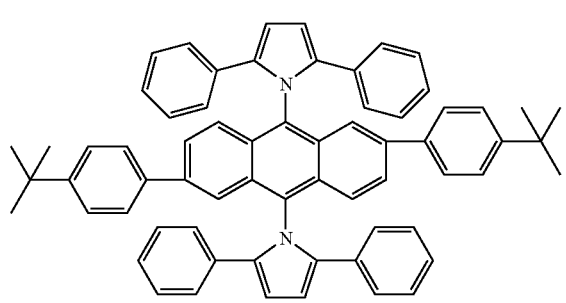
383
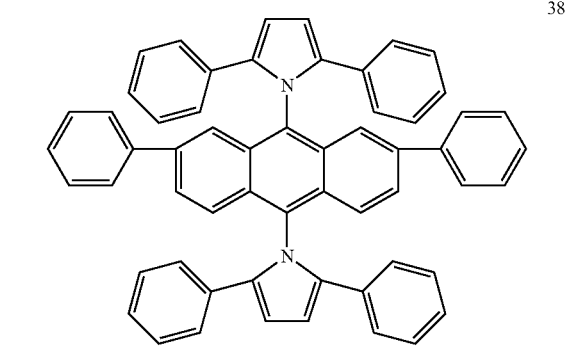
384
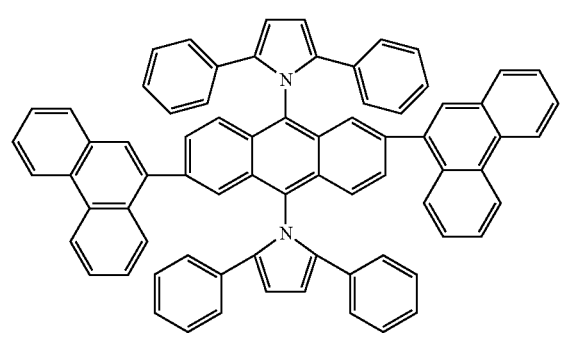

385

386

387

388

389

390

391

392

393

157 158
-continued
-continued
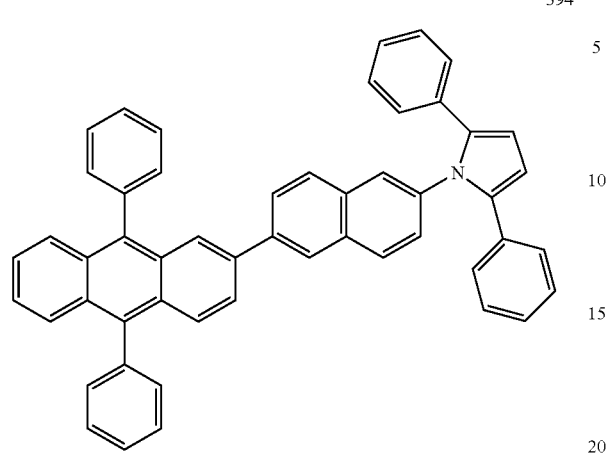
394
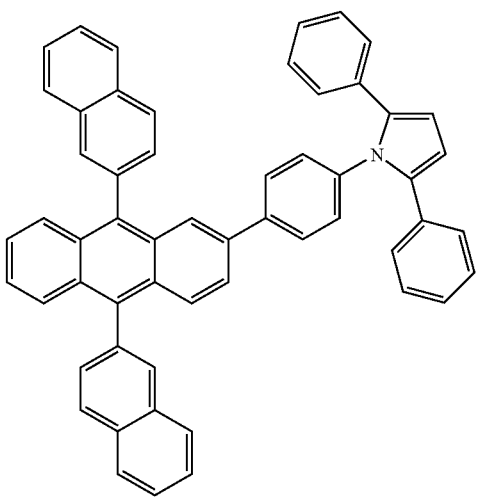
397
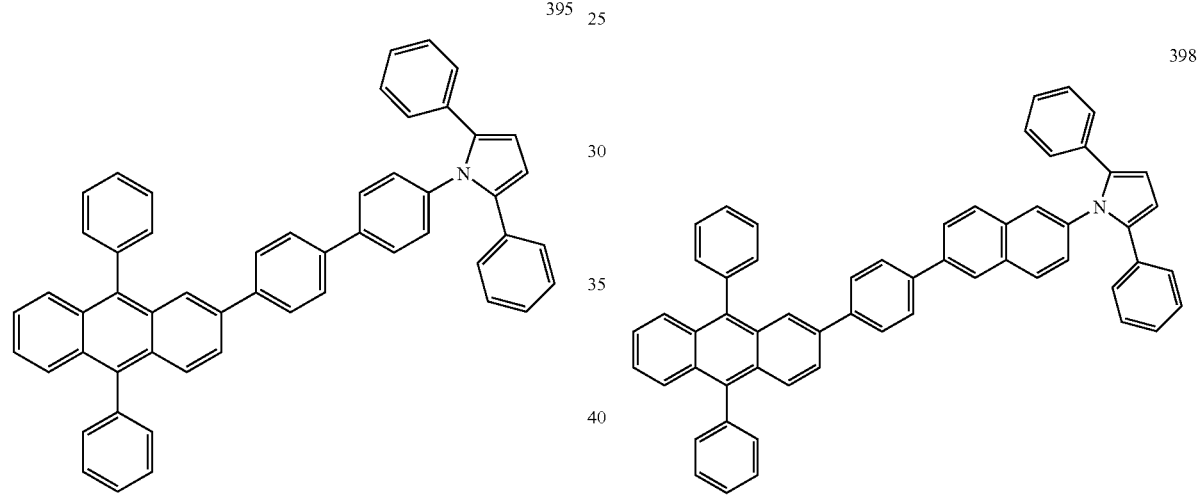
395
398
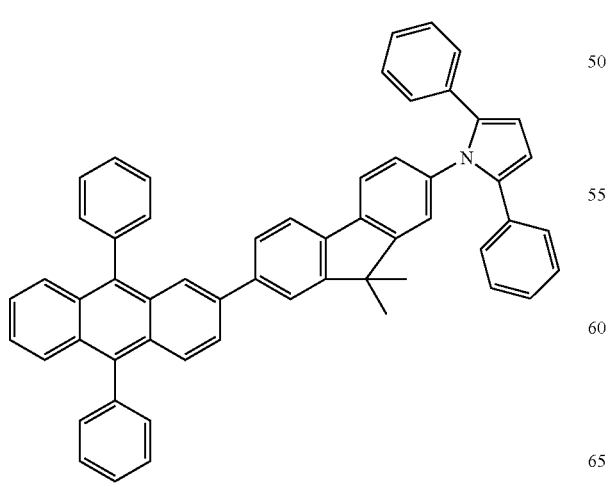
396
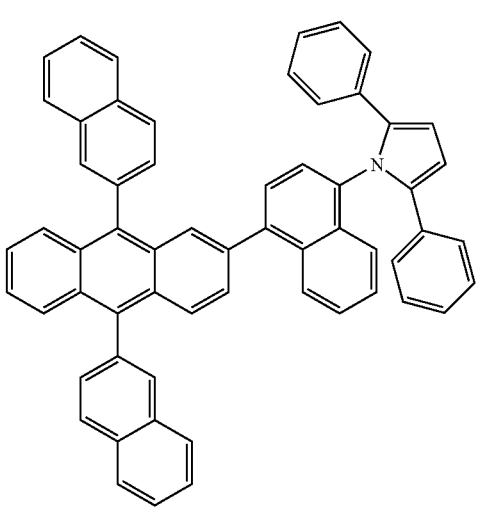
399

-continued
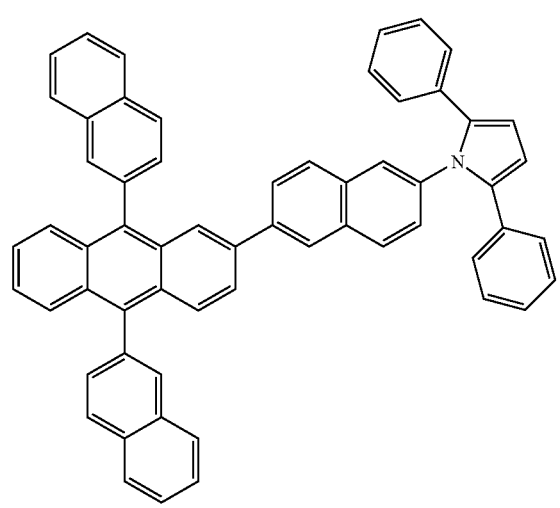
400
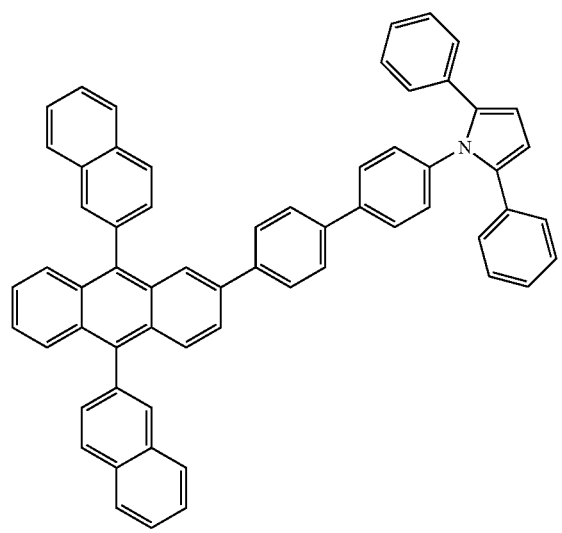
401
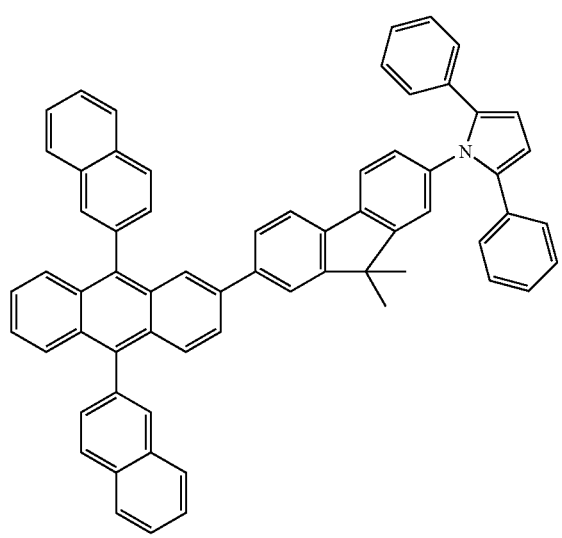
402
-continued
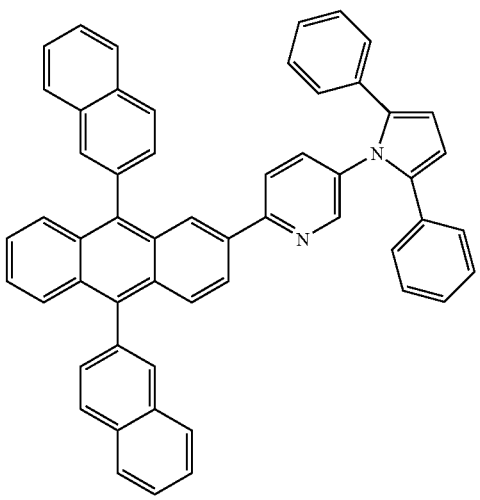
403
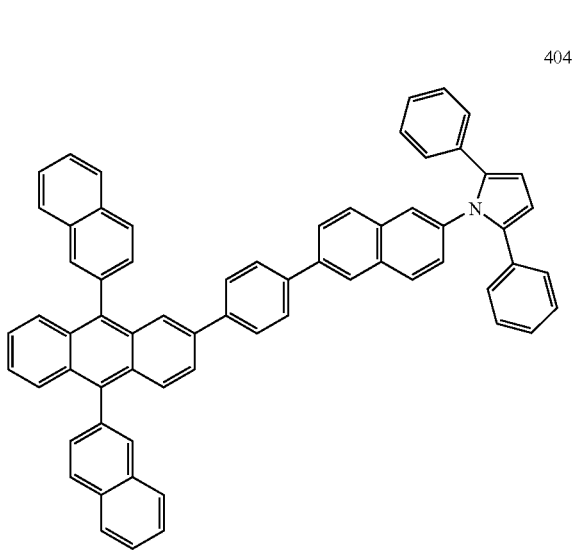
404
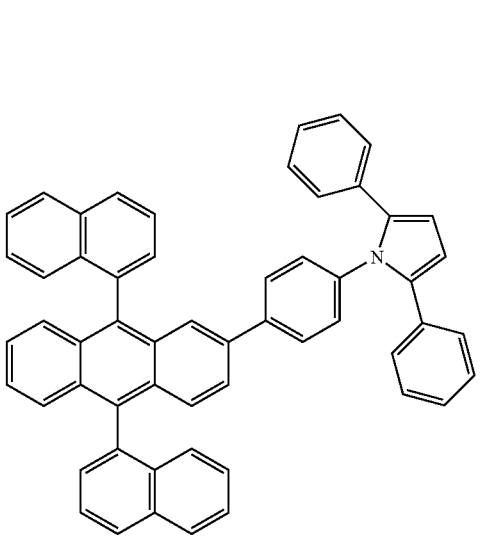
405

-continued
406
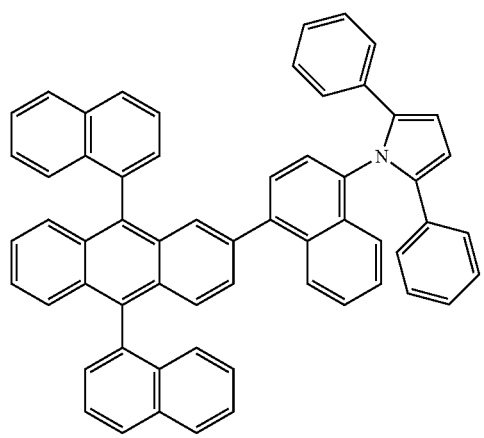
407
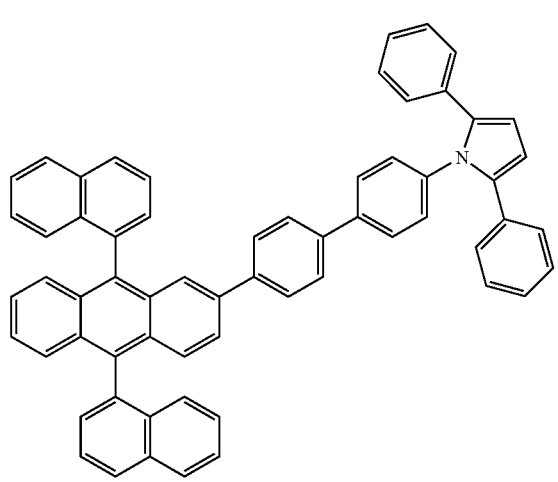
408
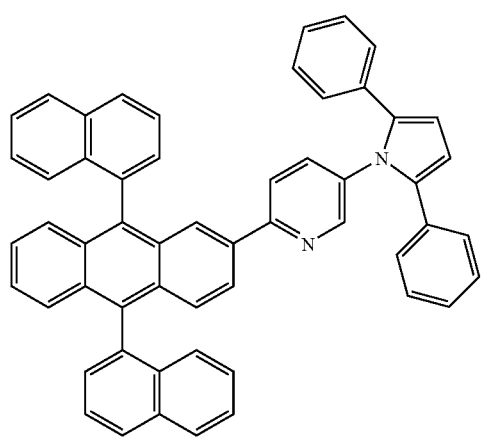
-continued
409
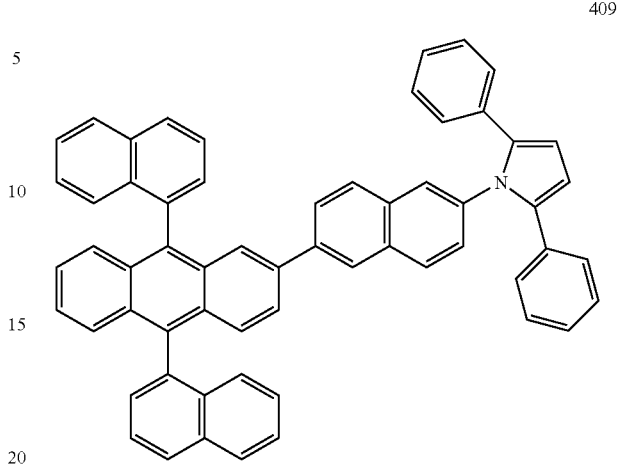
410
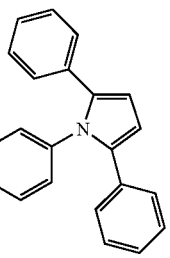
411
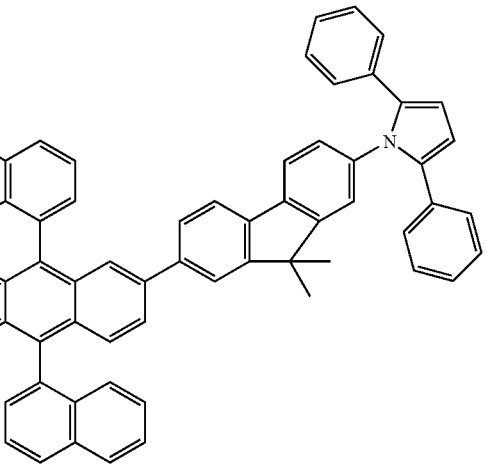

412
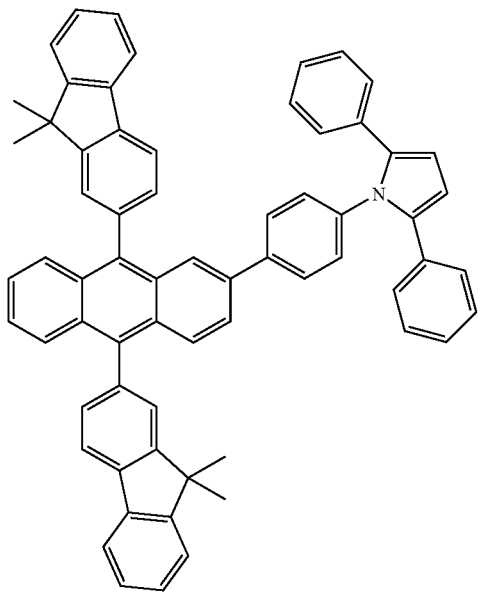
413
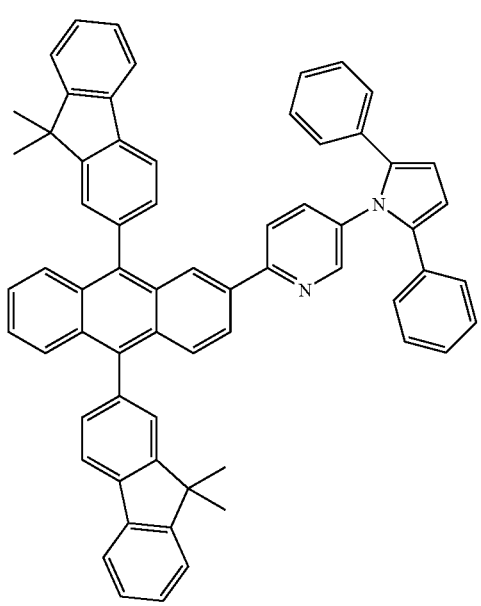
414
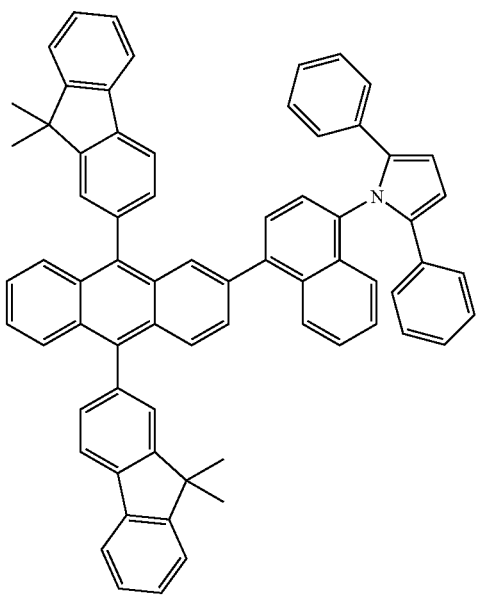
415
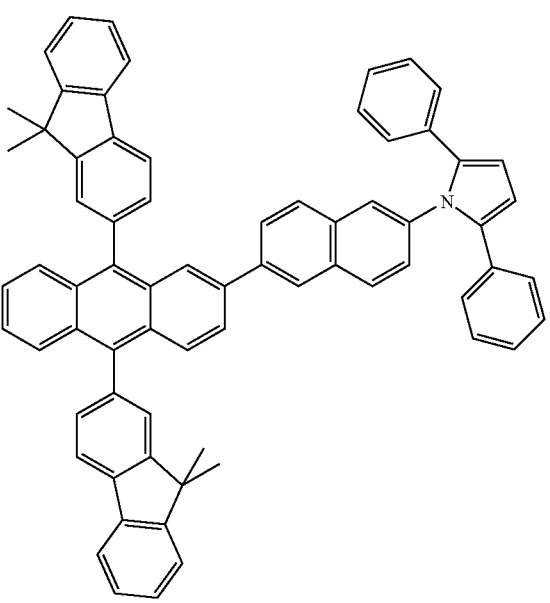

-continued
416
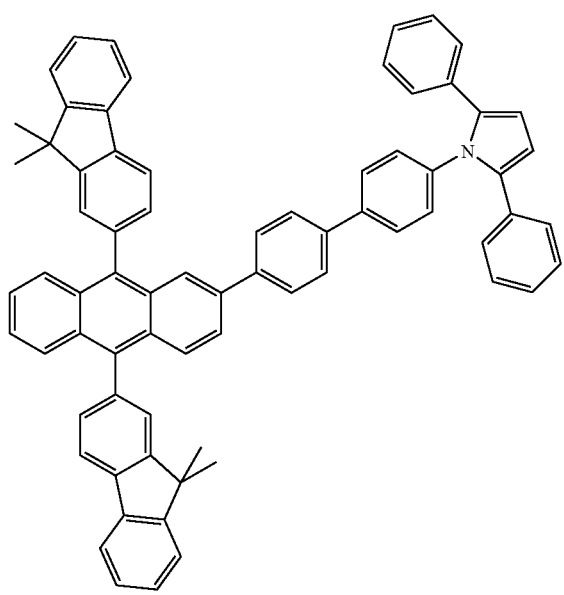
417
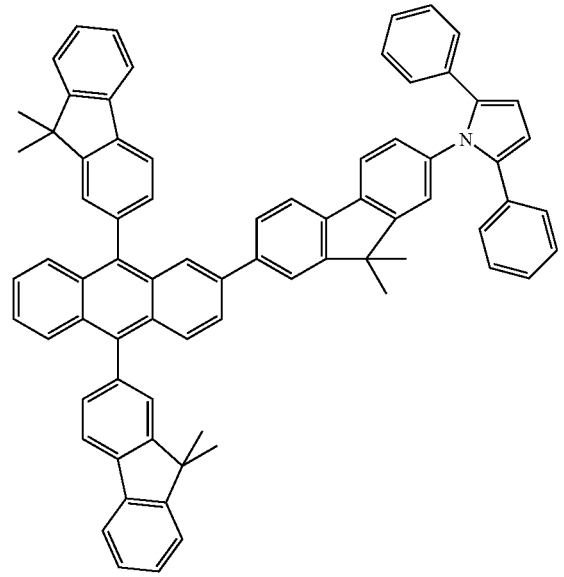
418
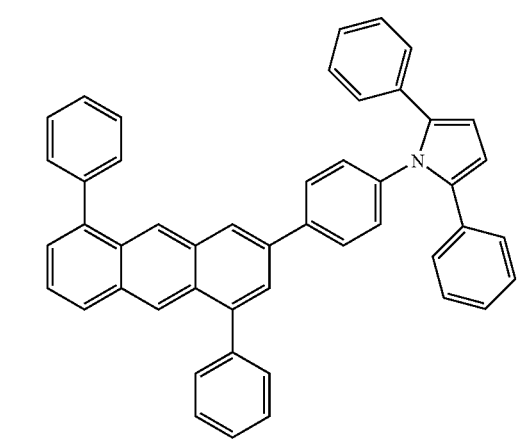
-continued
419
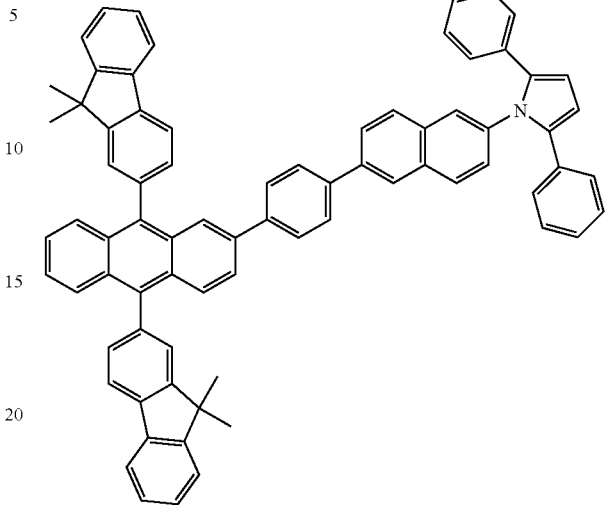
420
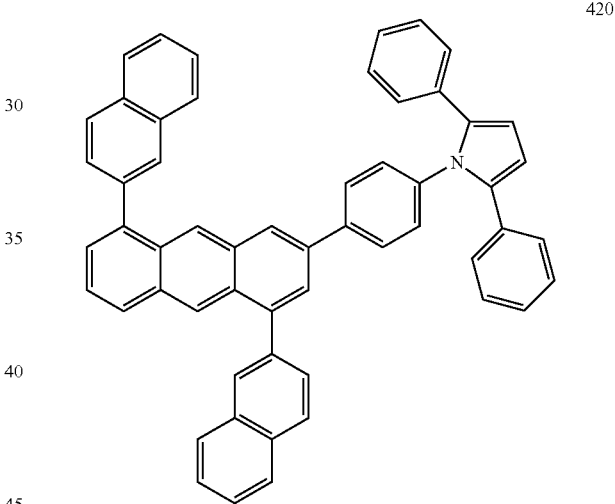
421
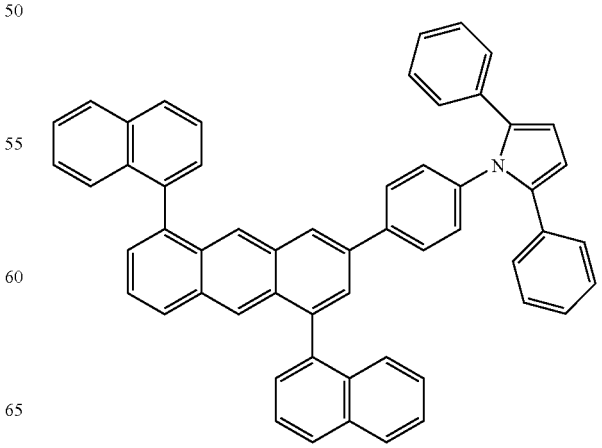

-continued
422
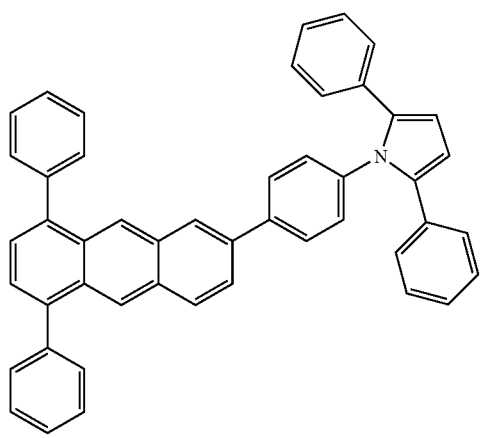
423
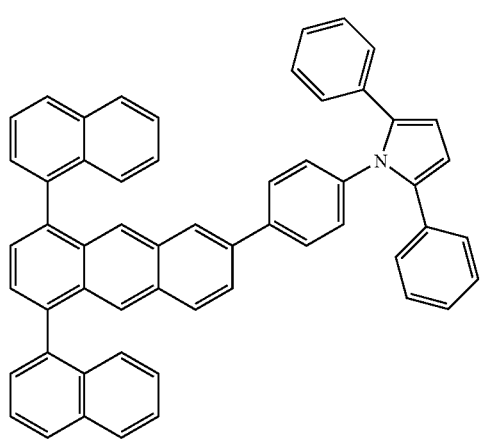
424
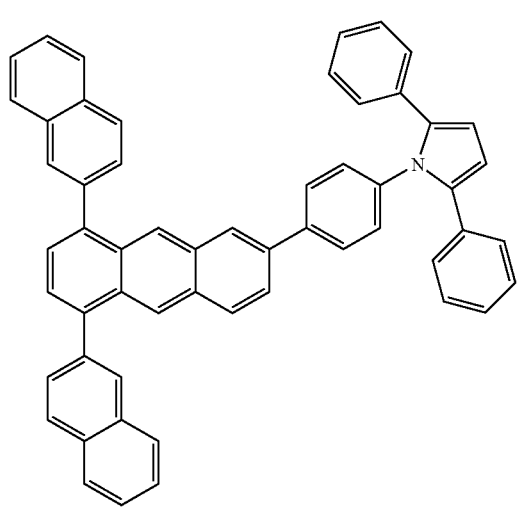
-continued
425
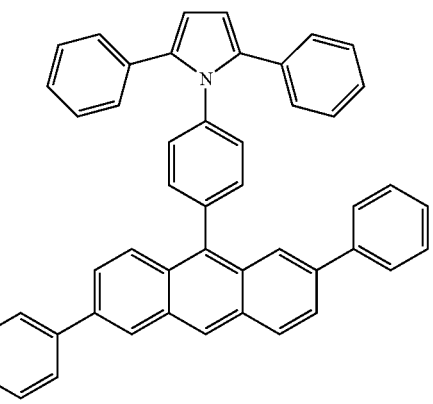
426
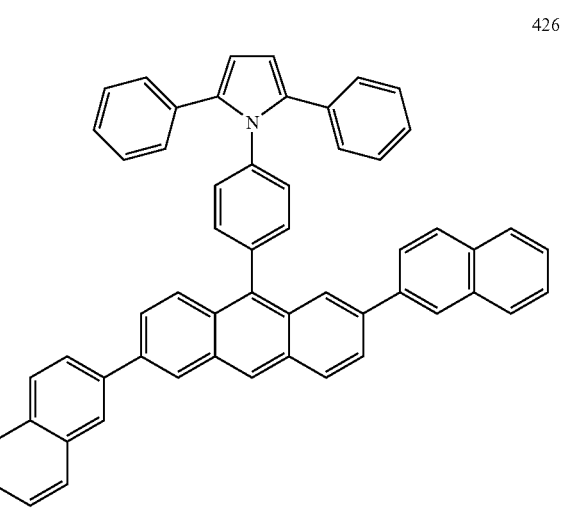
427
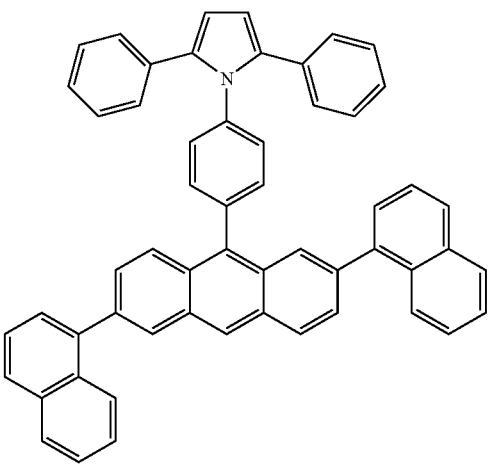

-continued
428
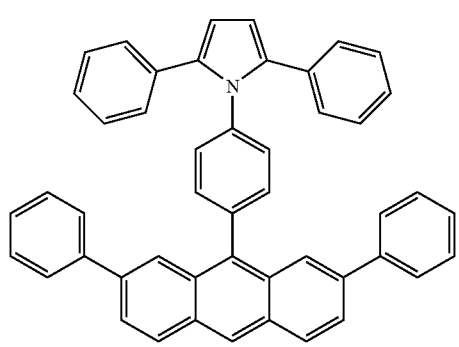
429
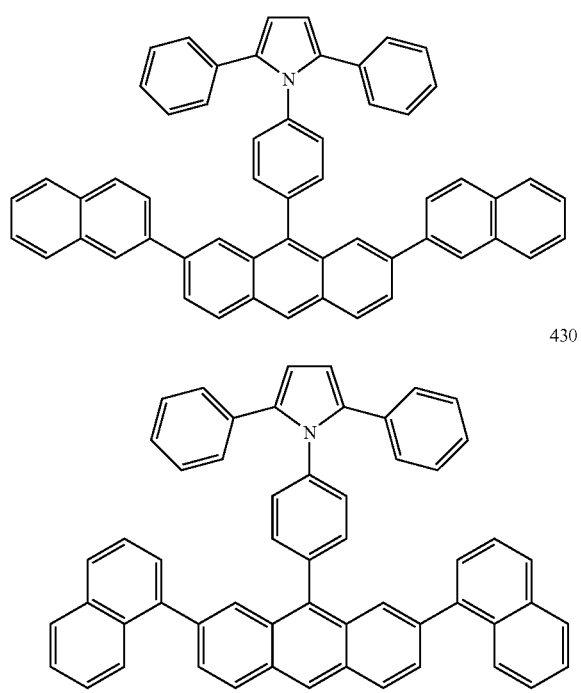
430
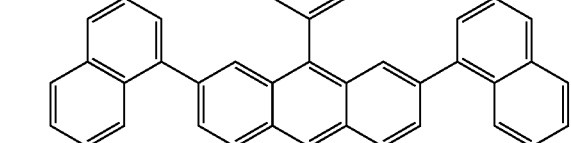
431
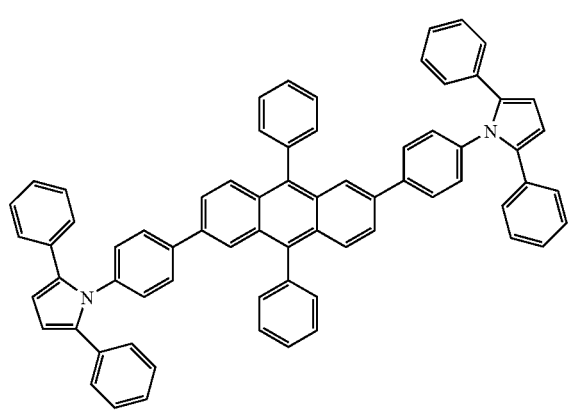
-continued
432
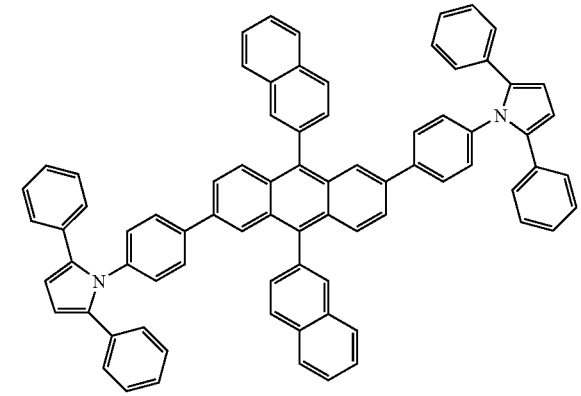
433
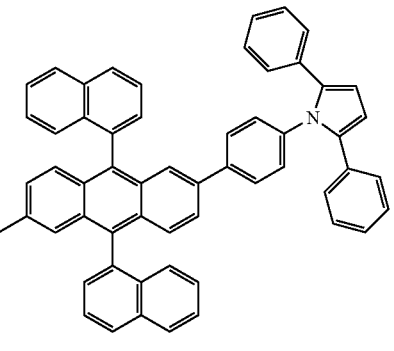
434
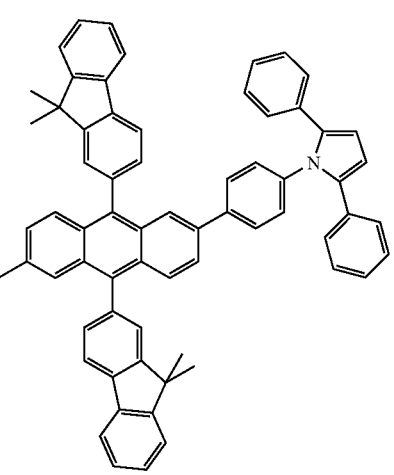

-continued
435
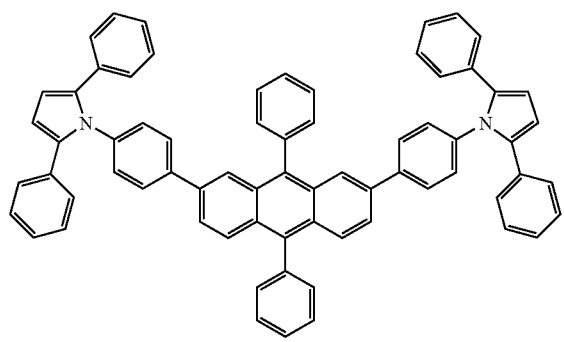
436
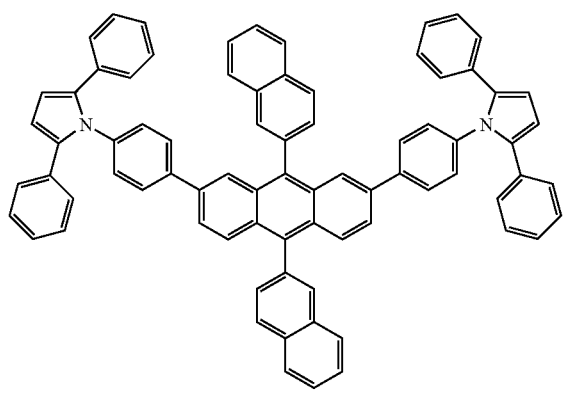
437
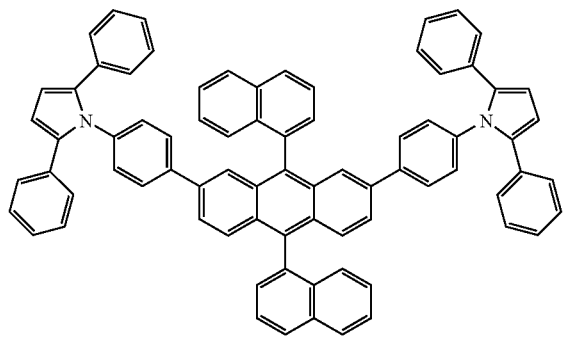
438
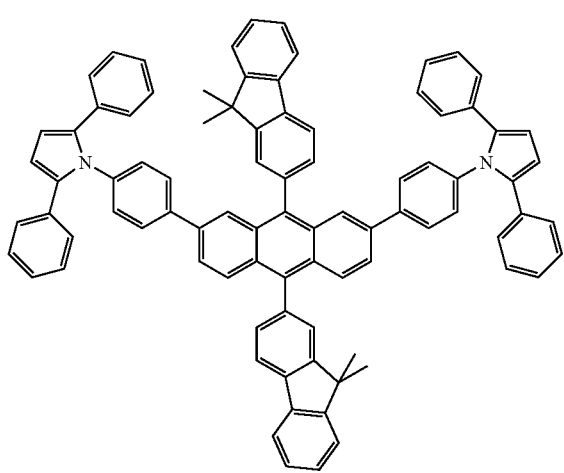
-continued
439
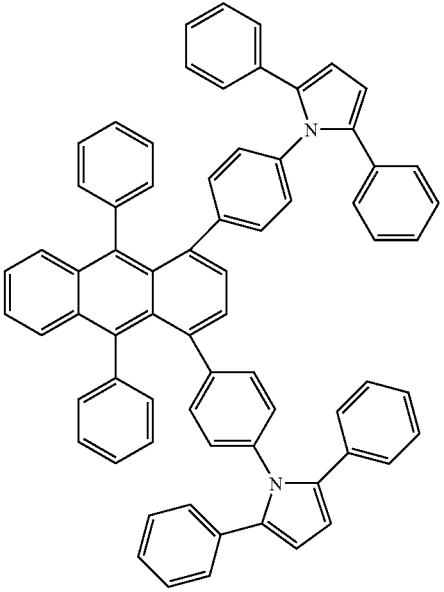
440
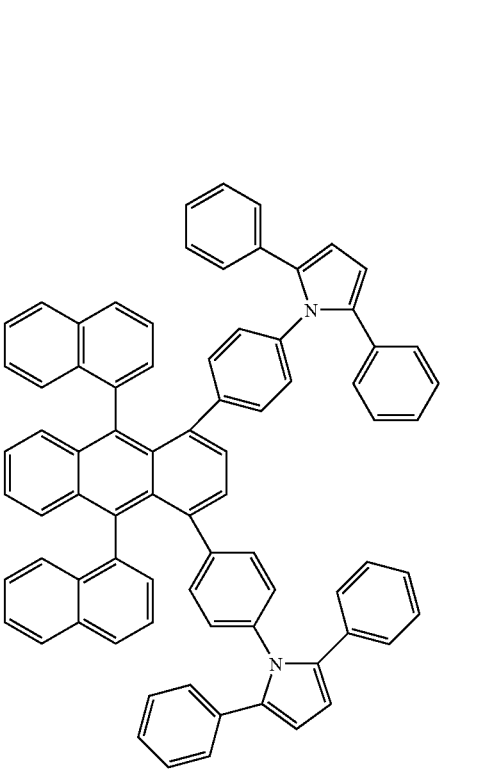

-continued
441
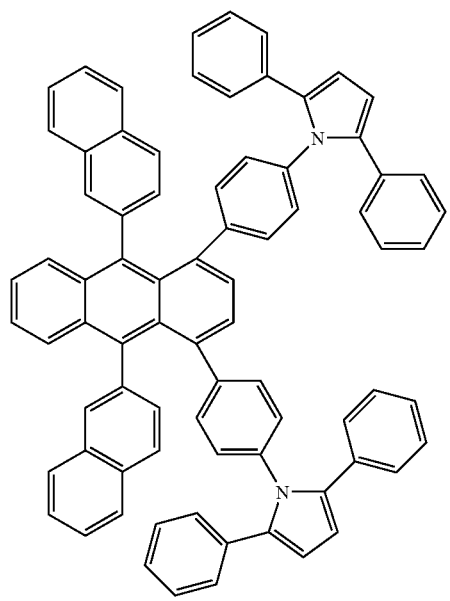
442
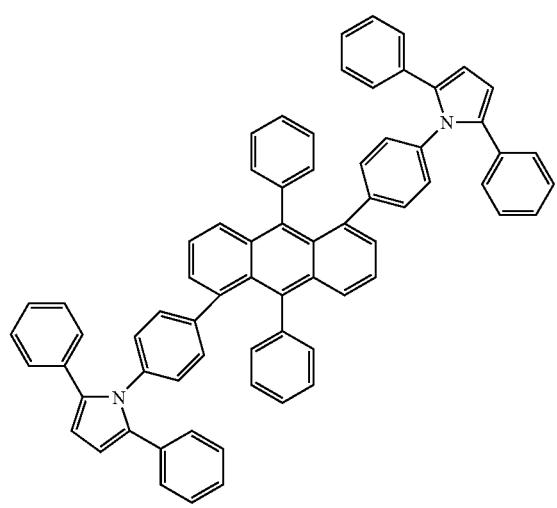
443
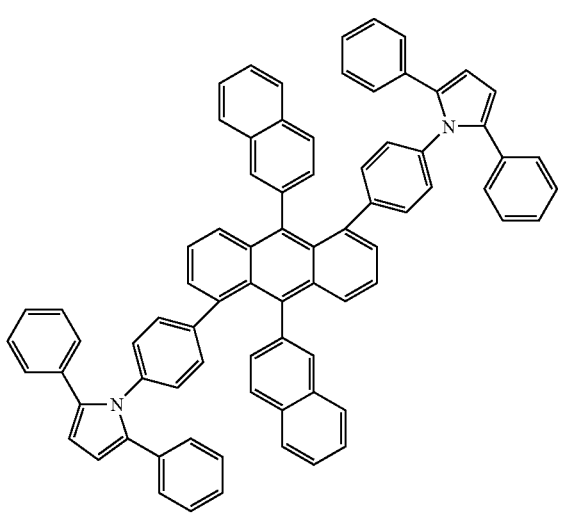
-continued
444
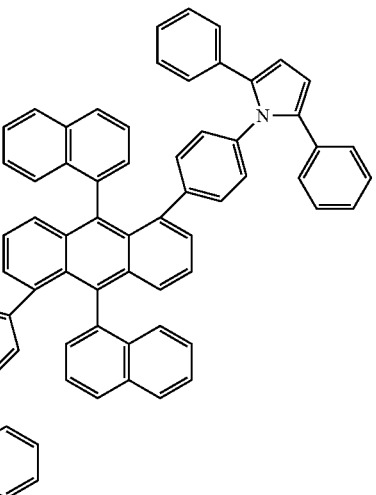
445
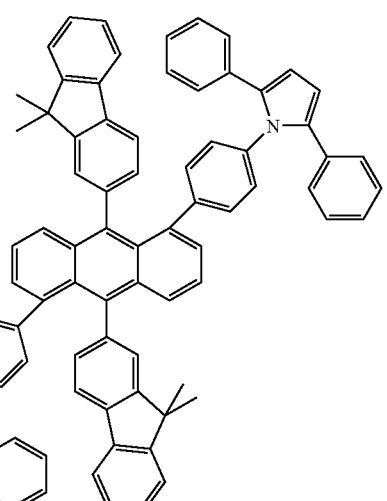
446
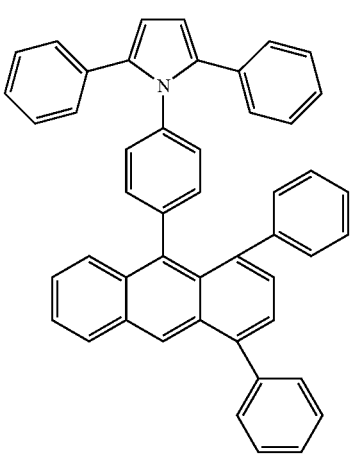

-continued
447
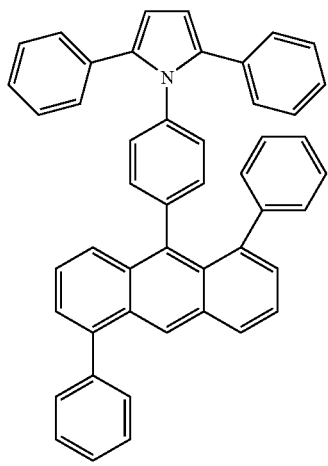
448
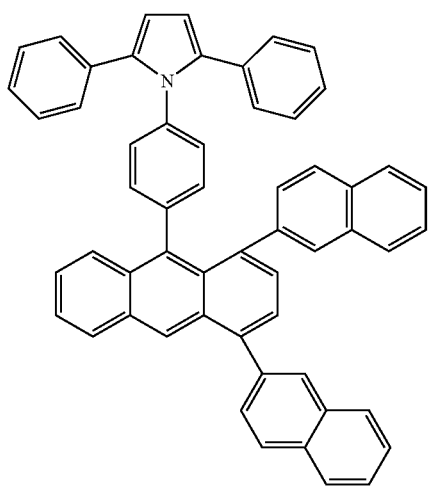
449
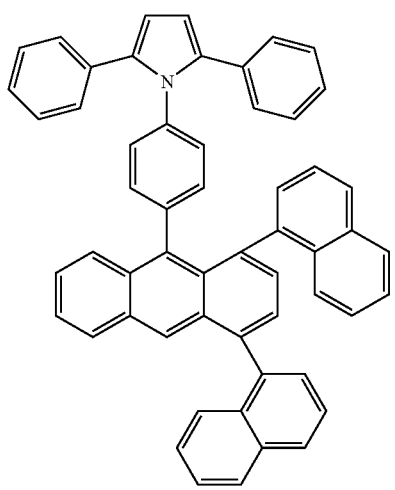
-continued
450
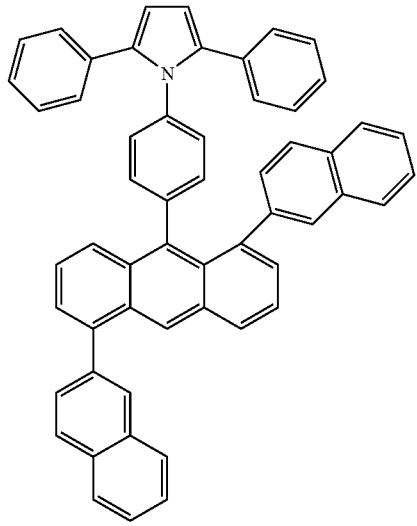
451
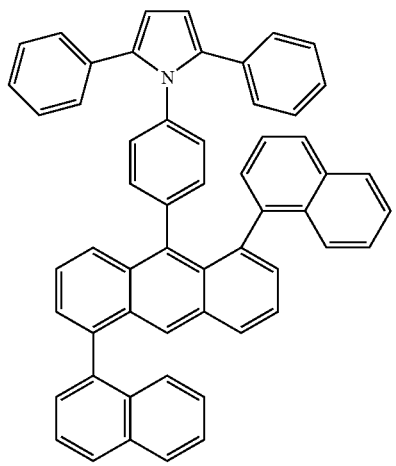
452
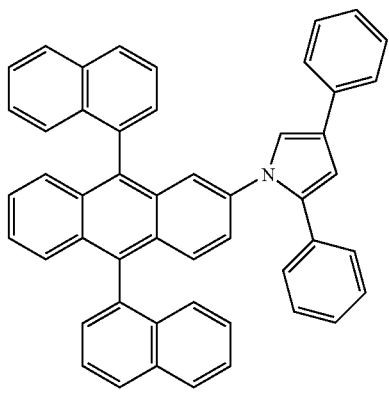

-continued

453

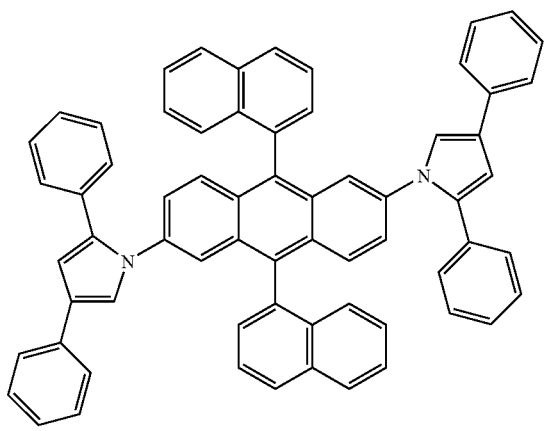

The compounds for electronic material according to the present invention can be prepared, as illustrated by Reaction Scheme (1), by the reaction of anthracene halide compound with pyrrole compound. The process for preparation is not restricted thereto, but various conventional processes of organic synthesis can be employed. Incorporation of substituents to the anthracene halide compound (the starting material) may be also carried out by various processes of organic synthesis.

Reaction Scheme 1

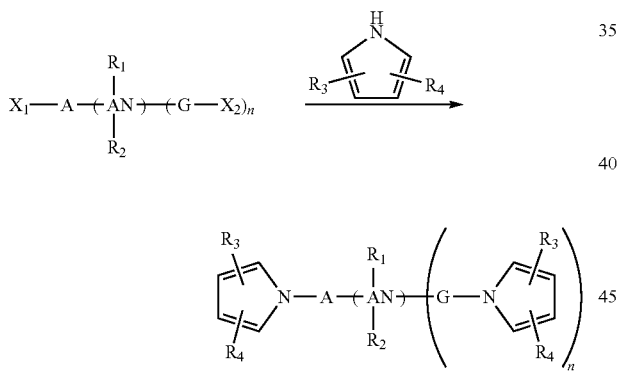

In Reaction Scheme (1), AN, A, G, $R_1$ through $R_4$ and n are defined as in Chemical Formula (1), and $X_1$ and $X_2$ are selected from halogen.

In addition, the present invention provides organic solar cells, which comprise one or more organic compounds for electronic material represented by Chemical Formula (1).

The present invention also provides an organic electroluminescent device which is comprised of a first electrode; a second electrode; and at least one organic layer(s) interposed between the first electrode and the second electrode; wherein the organic layer comprises one or more compounds for electronic material represented by Chemical Formula (1).

The organic electroluminescent device according to the present invention is characterized in that the organic layer comprises an electroluminescent layer, which contains one or more organic compound(s) for electronic material represented by Chemical Formula (1) as electroluminescent dopant, and one or more host(s). When the electroluminescent layer comprises the compound for electronic material according to the present invention as blue dopant, noticeable improvement in device life as well as luminous efficiency is resulted due to excellent hole and electron conductivity and stability of the material.

If the compound for electronic material represented by Chemical Formula (1) according to the present invention is employed as blue dopant, the host is not particularly restrictive, but preferably selected from the compounds represented by Chemical Formula (20) or (21):

  Chemical Formula 20

  Chemical Formula 21 wherein, X represents (C6-C60)arylene or (C4-C60)heteroarylene;

Y represents anthracenylene;

$Ar_{10}$ through $Ar_{40}$ are independently selected from hydrogen, (C1-C60)alkyl, (C1-C60)alkoxy, halogen, (C4-C60)heteroaryl, (C5-C60)cycloalkyl and (C6-C60)aryl; the cycloalkyl, aryl or heteroaryl of $Ar_{10}$ through $Ar_{40}$ may be further substituted by one or more substituent(s) selected from a group consisting of (C6-C60)aryl or (C4-C60)heteroaryl with or without one or more substituent(s) selected from a group consisting of (C1-C60)alkyl with or without halogen substituent(s), (C1-C60)alkoxy, (C3-C60)cycloalkyl, halogen, cyano, tri(C1-C60)alkylsilyl, di(C1-C60)alkyl(C6-C60)arylsilyl and tri(C6-C60)arylsilyl; (C1-C60)alkyl with or without halogen substituent(s), (C1-C60)alkoxy, (C3-C60)cycloalkyl, halogen, cyano, tri(C1-C60)alkylsilyl, di(C1-C60)alkyl(C6-C60)arylsilyl and tri(C6-C60)arylsilyl; and a, b, c and d independently represent an integer from 0 to 4.

The host of Chemical Formula (20) can be exemplified by anthracene derivatives and benz[a]anthracene derivatives represented by one of Chemical Formulas (22) to (24):

Chemical Formula 22

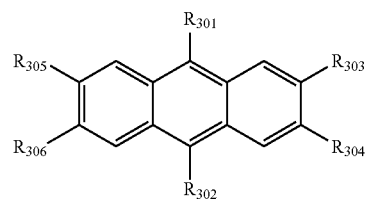

Chemical Formula 23

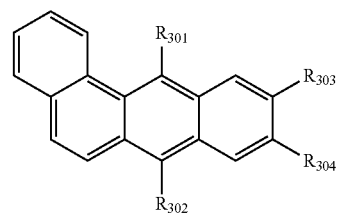

-continued

Chemical Formula 24

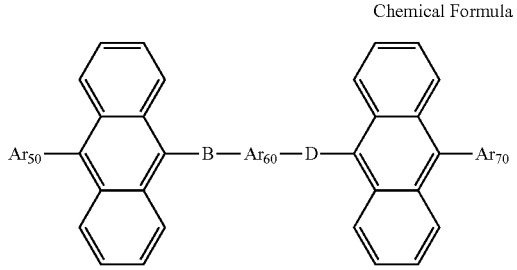

wherein, $R_{301}$ and $R_{302}$ independently represent (C6-C60) aryl, (C4-C60)heteroaryl, 5- or 6-membered heterocycloalkyl containing one or more heteroatom(s) selected from N, O and S, or (C3-C60)cycloalkyl; and the aryl or heteroaryl of $R_{301}$ and $R_{302}$ may be further substituted by one or more substituent(s) selected from a group consisting of (C6-C60) aryl or (C4-C60)heteroaryl with or without one or more substituent selected from a group consisting of (C1-C60)alkyl with or without halogen substituent(s), (C1-C60)alkoxy, (C3-C60)cycloalkyl, halogen, cyano, tri(C1-C60)alkylsilyl, di(C1-C60)alkyl(C6-C60)arylsilyl and tri(C6-C60)arylsilyl; (C1-C60)alkyl with or without halogen substituent(s), (C1-C60)alkoxy, (C3-C60)cycloalkyl, halogen, cyano, tri(C1-C60)alkylsilyl, di(C1-C60)alkyl(C6-C60)arylsilyl and tri(C6-C60)arylsilyl;

$R_{303}$ through $R_{306}$ represent hydrogen, (C1-C60)alkyl, (C1-C60)alkoxy, halogen, (C4-C60)heteroaryl, (C5-C60)cycloalkyl or (C6-C60)aryl; and the heteroaryl, cycloalkyl or aryl of $R_{303}$ through $R_{306}$ may be further substituted by one or more substituent(s) selected from a group consisting of (C1-C60)alkyl with or without halogen substituent(s), (C1-C60) alkoxy, (C3-C60)cycloalkyl, halogen, cyano, tri(C1-C60) alkylsilyl, di(C1-C60)alkyl(C6-C60)arylsilyl and tri(C6-C60)arylsilyl;

B and D independently represent a chemical bond, or (C6-C60)arylene with or without one or more substituent(s) selected from (C1-C60)alkyl, (C1-C60)alkoxy, (C6-C60) aryl, (C4-C60)heteroaryl and halogen;

$Ar_{50}$ and $Ar_{70}$ represent aryl selected from the following structures, or (C4-C60)heteroaryl; the aryl or heteroaryl of $Ar_{50}$ and $Ar_{70}$ may be substituted by one or more substituent(s) selected from (C1-C60)alkyl, (C1-C60)alkoxy, (C6-C60)aryl and (C4-C60)heteroaryl:

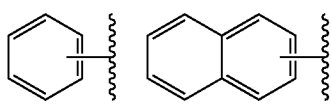

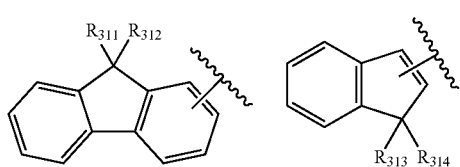

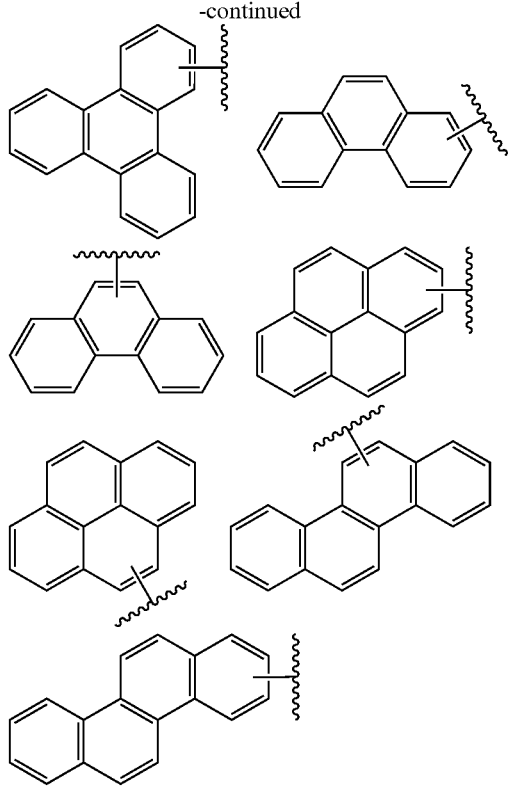

$Ar_{60}$ represents (C6-C60)arylene or (C4-C60)heteroarylene, preferably selected from phenylene, naphthylene, anthrylene, fluorenylene, phenanthrylene, tetracenylene, naphthacenylene, chrysenylene, pentacenylene, pyrenylene, heteroarylene, or a compound represented by the following structural formula; the arylene or heteroarylene of $Ar_{20}$ may be substituted by one or more substituent(s) selected from (C1-C60)alkyl, (C1-C60)alkoxy, (C6-C60)aryl, (C4-C60) heteroaryl or halogen:

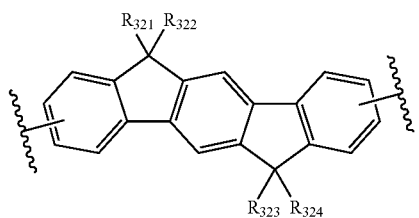

$R_{311}$ through $R_{314}$ independently represent hydrogen, (C1-C60)alkyl or (C6-C60)aryl, or each of them may be linked to an adjacent substituent via (C3-C60)alkylene or (C3-C60) alkenylene with or without a fused ring to form an alicyclic ring, or a monocyclic or polycyclic aromatic ring; and $R_{321}$ through $R_{324}$ independently represent hydrogen, (C1-C60)alkyl, (C1-C60)alkoxy, (C6-C60)aryl, (C4-C60)heteroaryl or halogen, or each of them may be linked to an adjacent substituent via (C3-C60)alkylene or (C3-C60)alkenylene with or without a fused ring to form an alicyclic ring, or a monocyclic or polycyclic aromatic ring.

The host compounds represented by one of Chemical Formulas (22) to (24) can be exemplified by the following compounds, but are not restricted thereto.

181
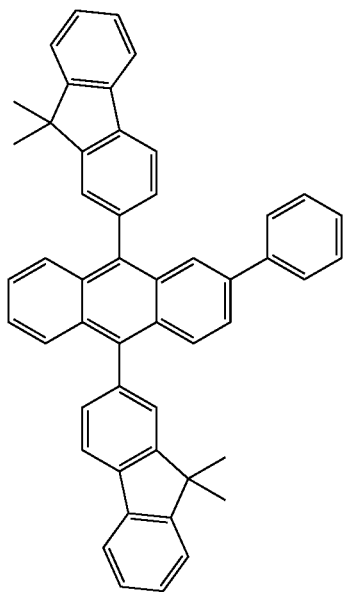
182
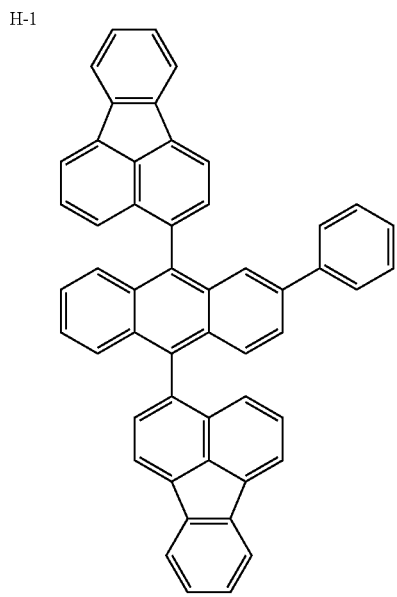
H-1
H-2
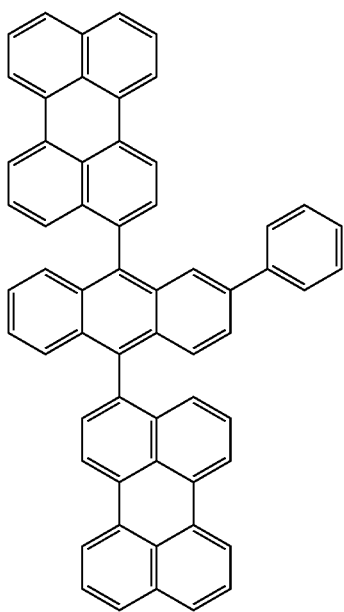
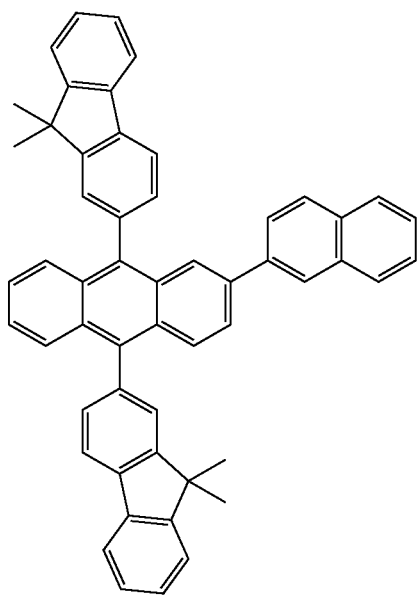
H-3
H-4

-continued
H-5
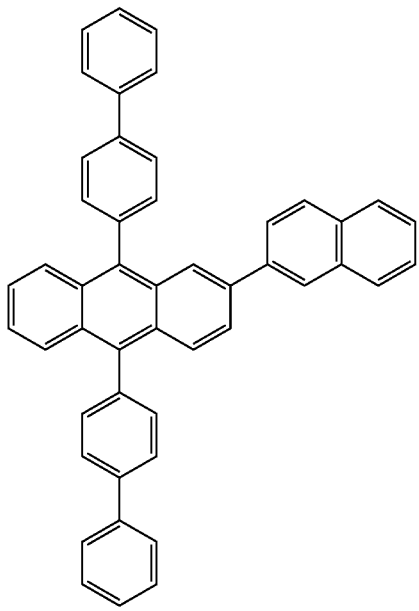
H-6
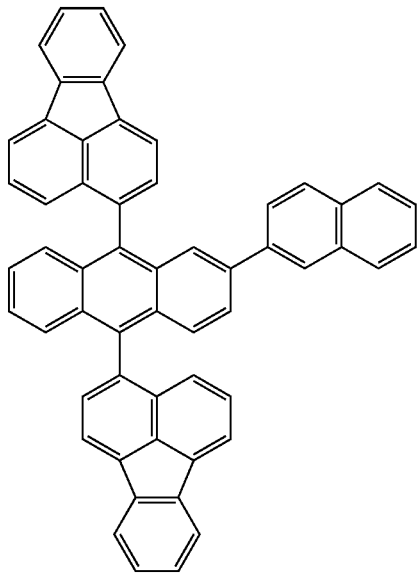
H-7
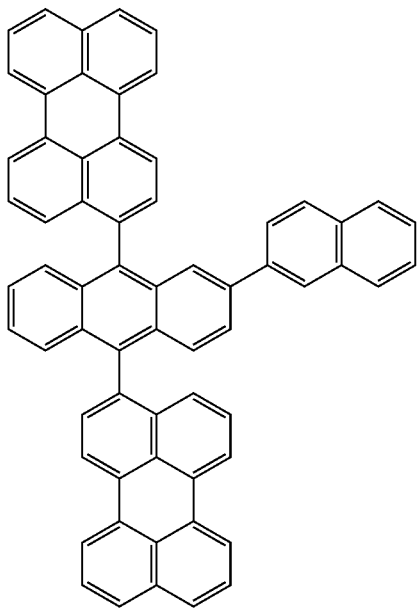
H-8
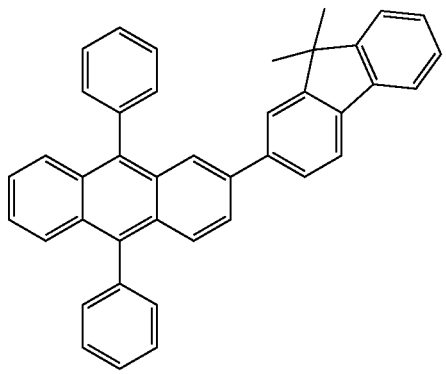

-continued
H-9
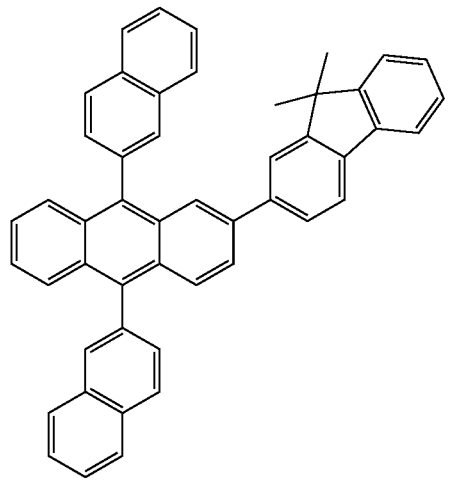
H-10
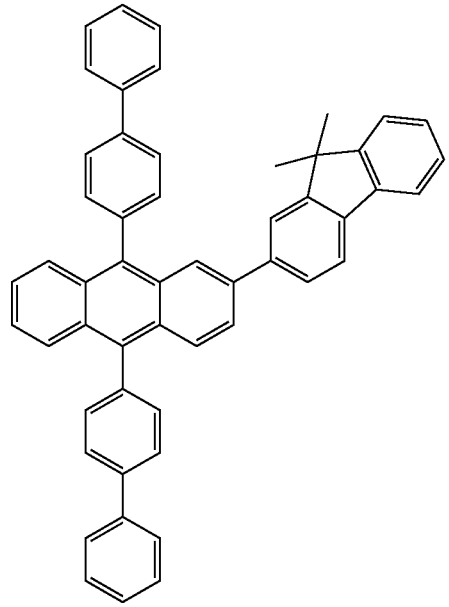
H-11
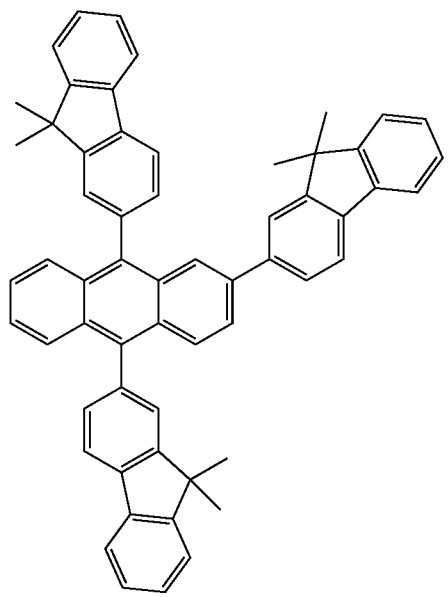
H-12
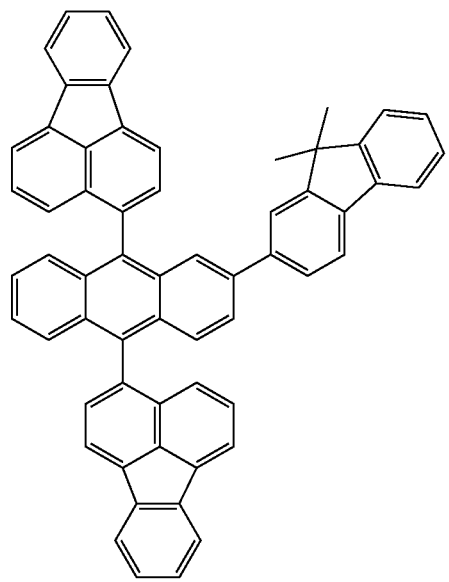

-continued
H-13
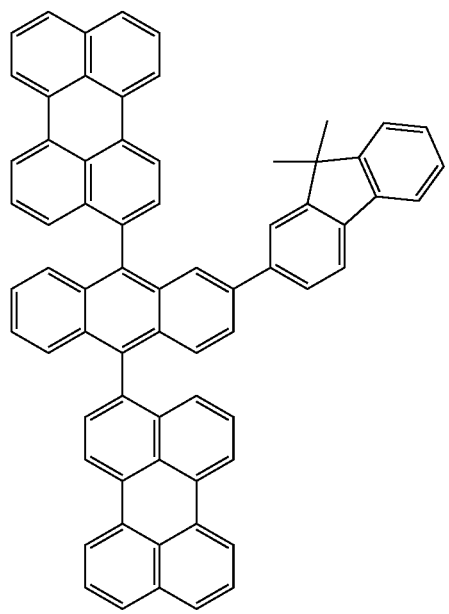
H-14
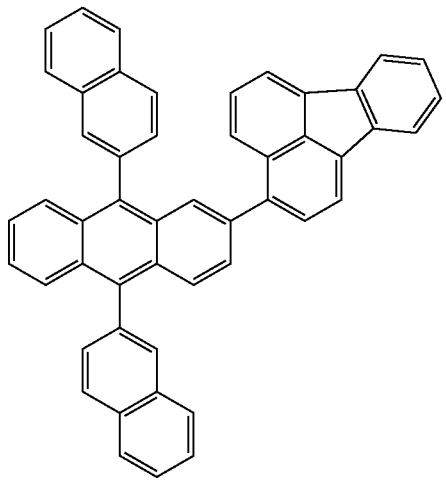
H-15
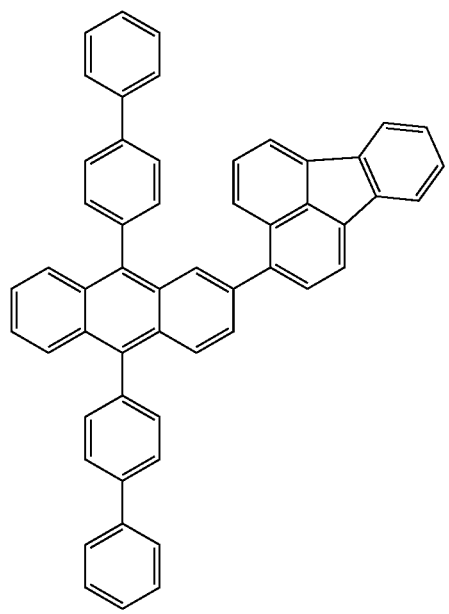
H-16
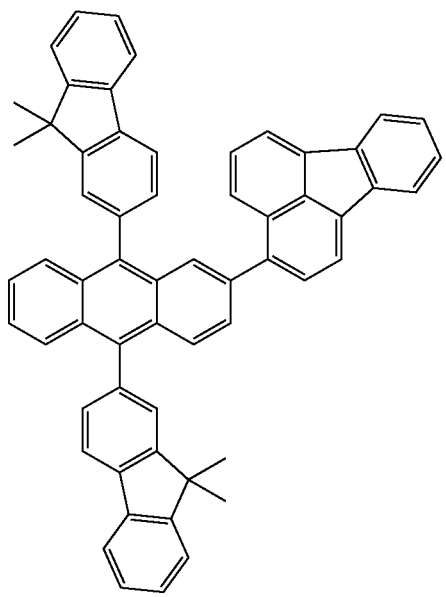

-continued
H-17
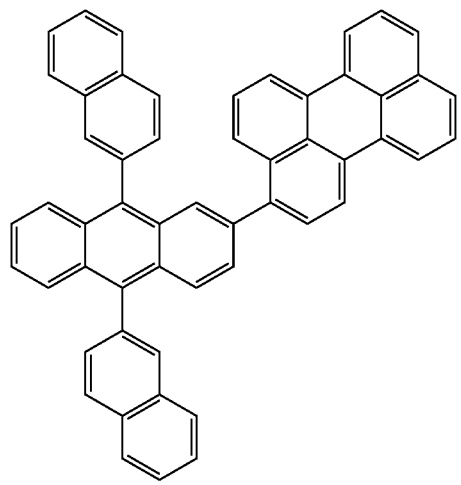
H-18
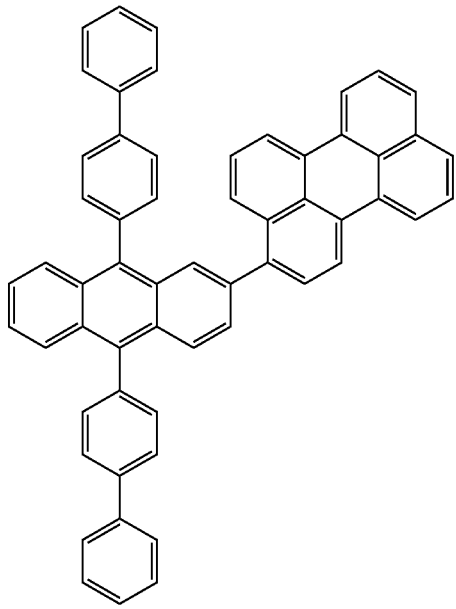
H-19
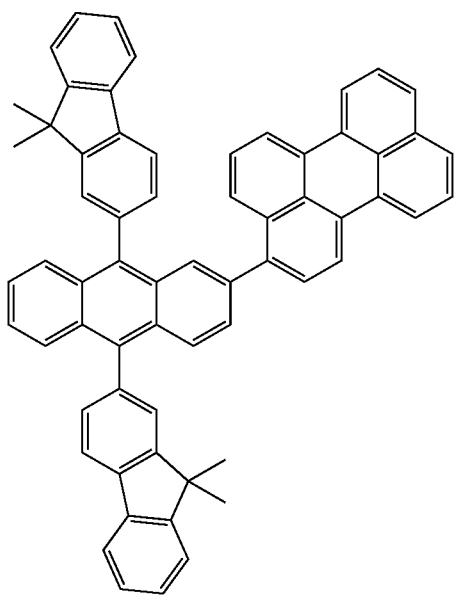
H-20
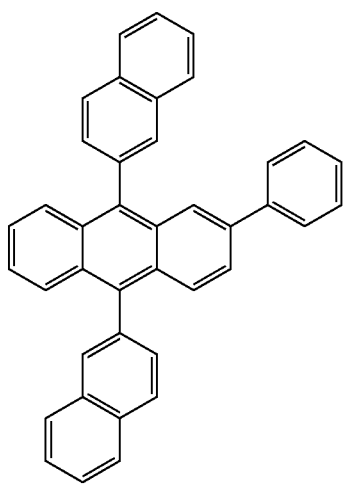

-continued
H-21
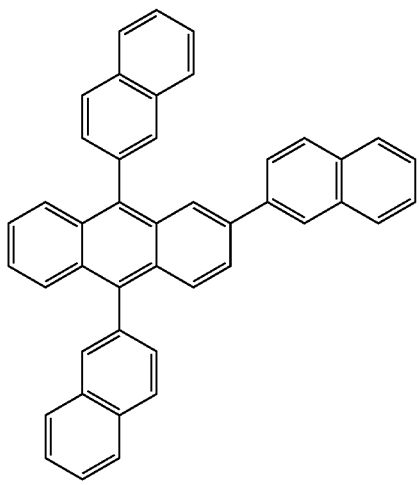
H-22
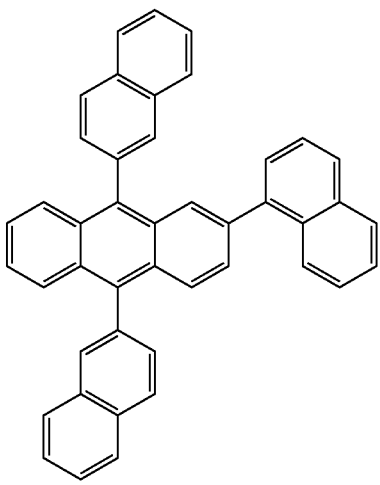
H-23
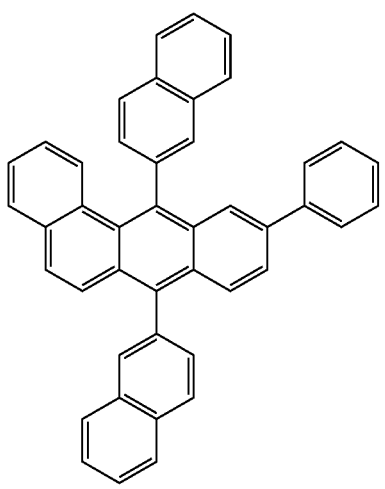
H-24
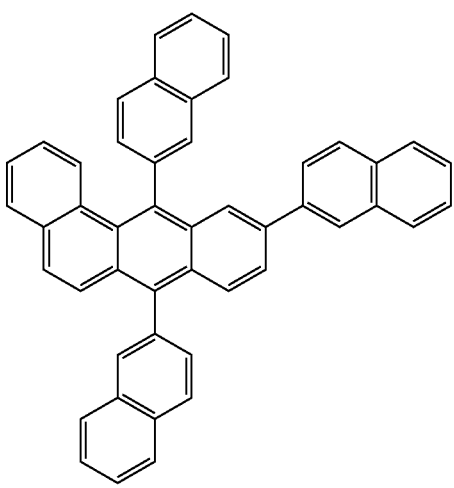
H-25
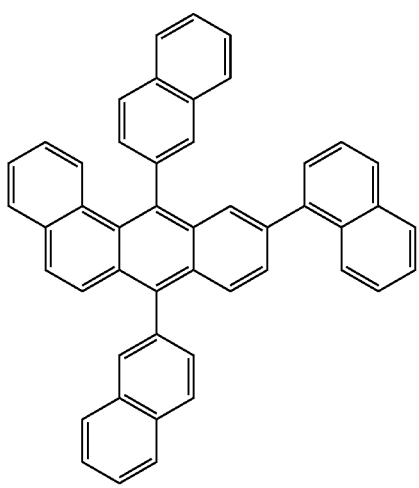
H-26
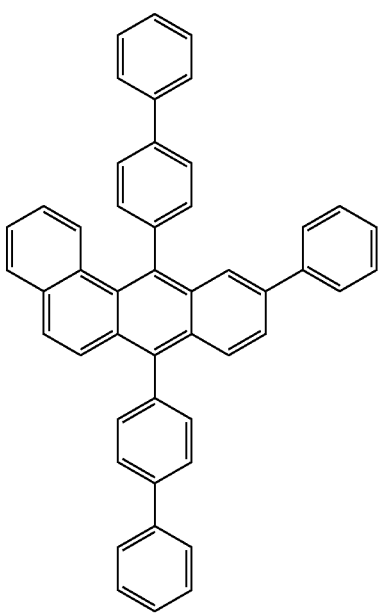

-continued
H-27
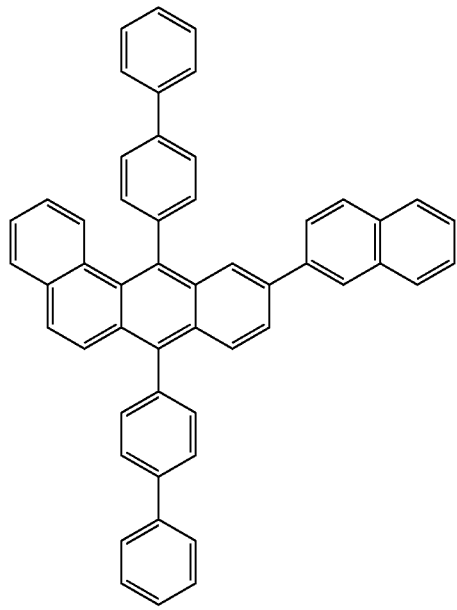
H-28
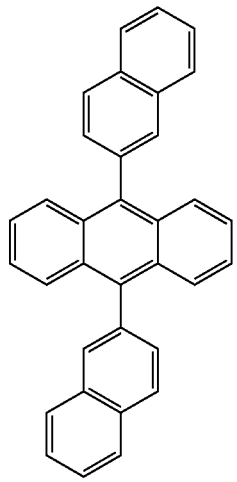
H-29
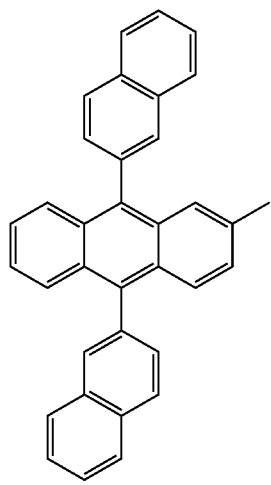
H-30
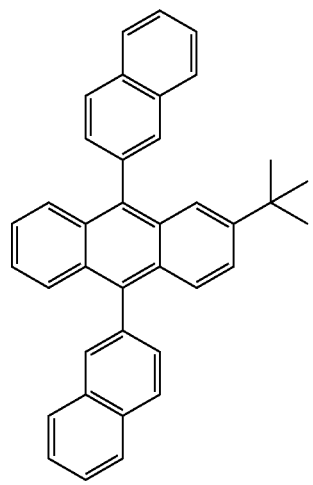

-continued
H-31
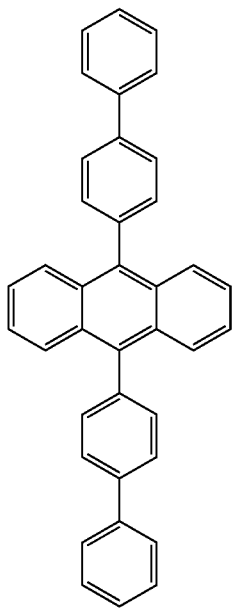
H-32
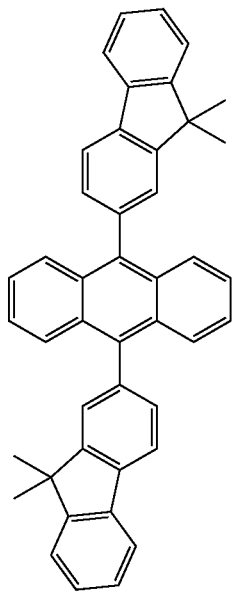
H-33
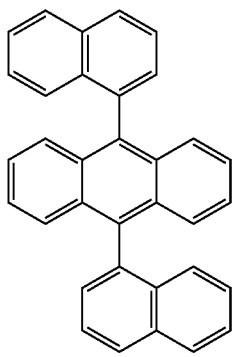
H-34
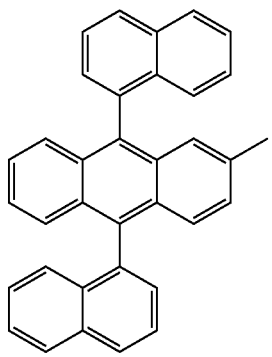
H-35
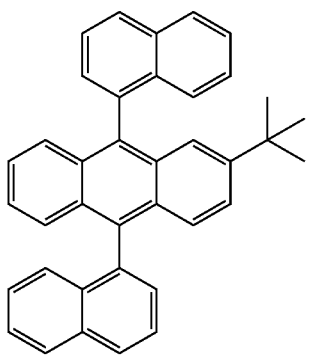
H-36
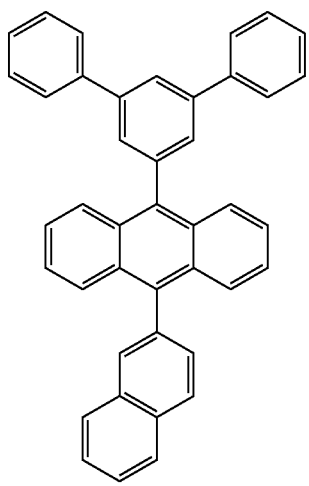

-continued
H-37
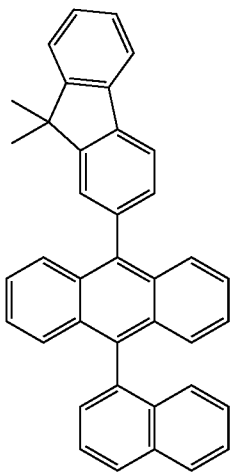
H-38
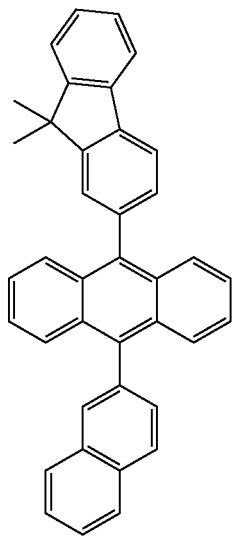
H-39
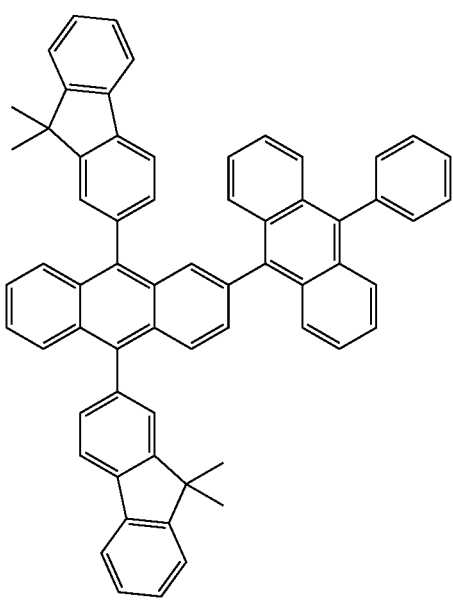
H-40
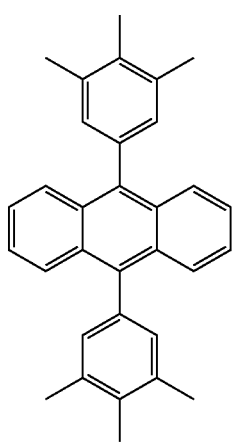
H-41
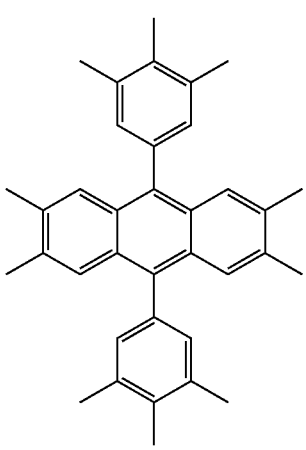
H-42
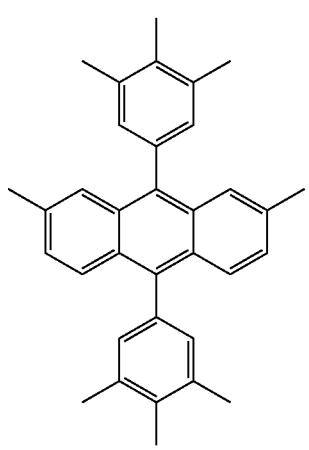

-continued
H-43
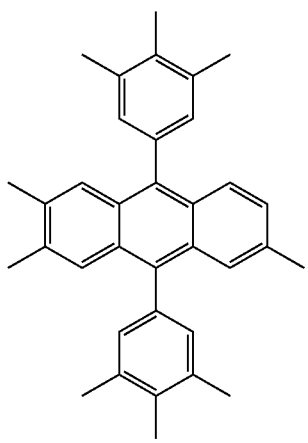
H-44
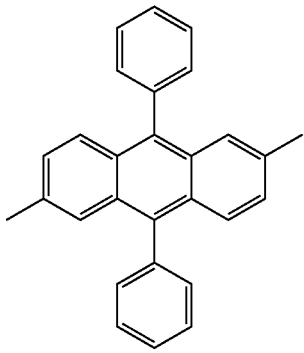
H-45
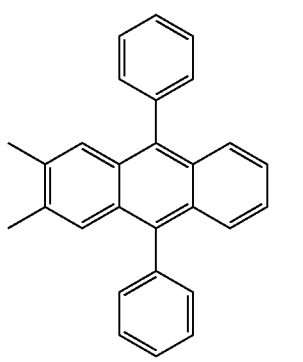
H-46
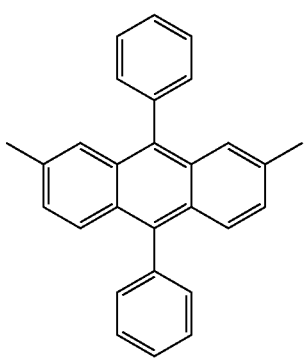
H-47
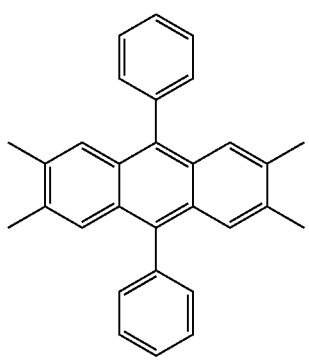
H-48
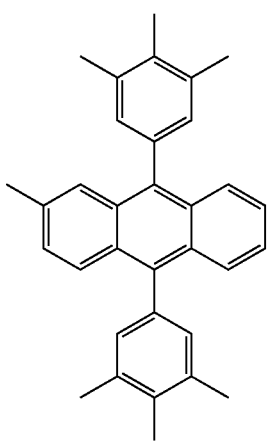
H-49
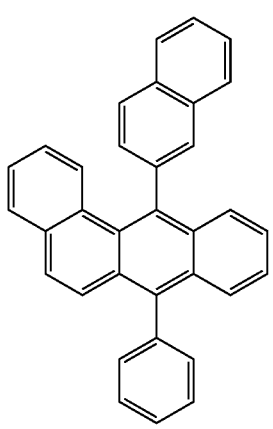
H-50
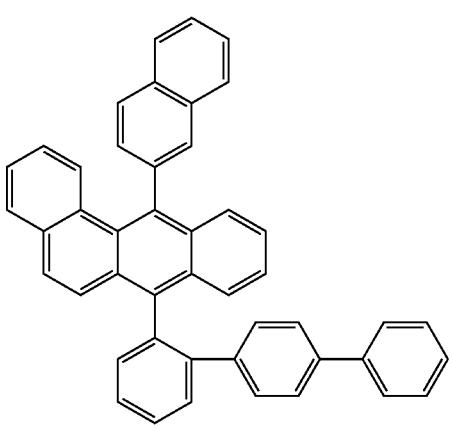

-continued
H-51
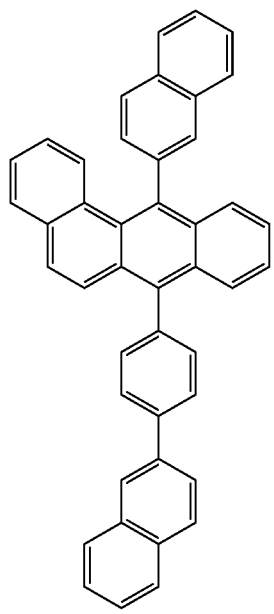
H-52
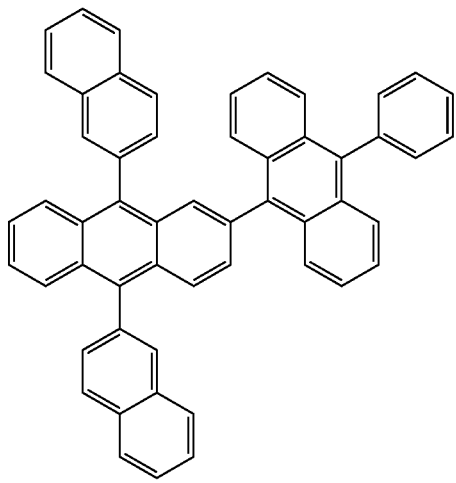
H-53
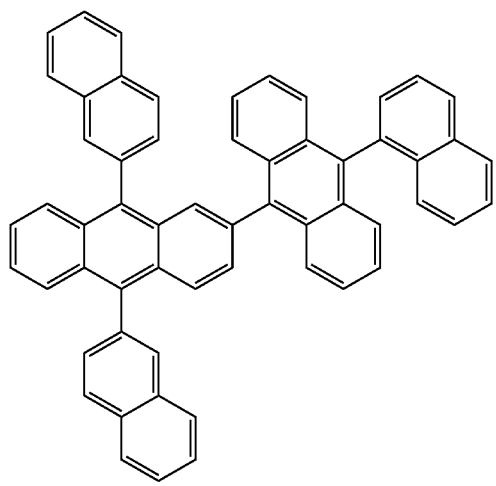
H-54
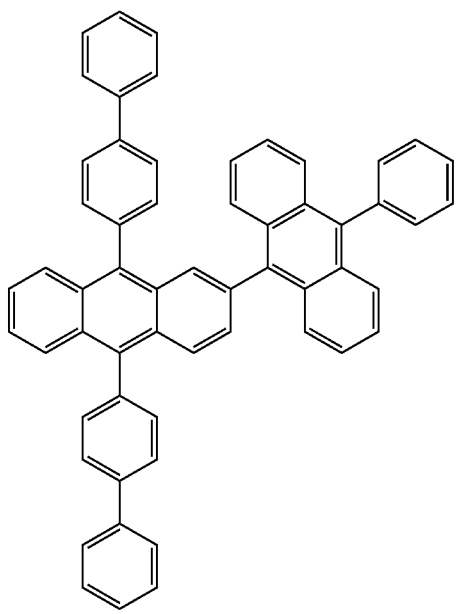

-continued
H-55
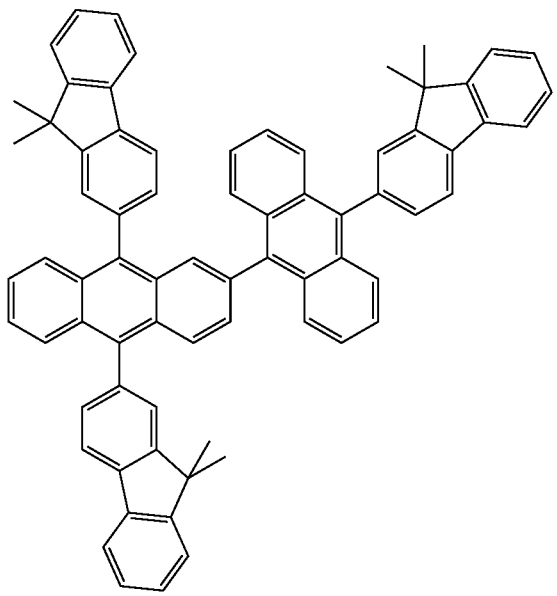
H-56
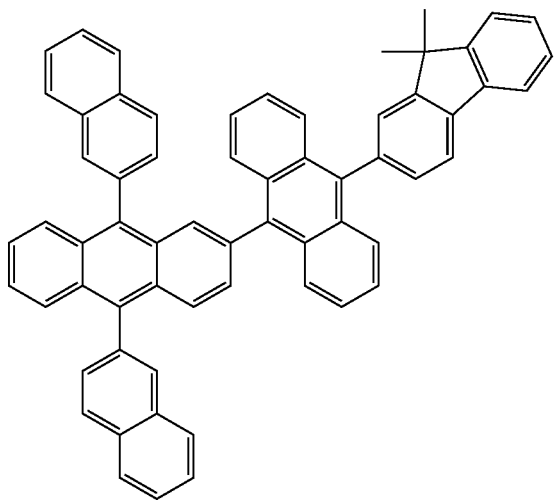
H-57
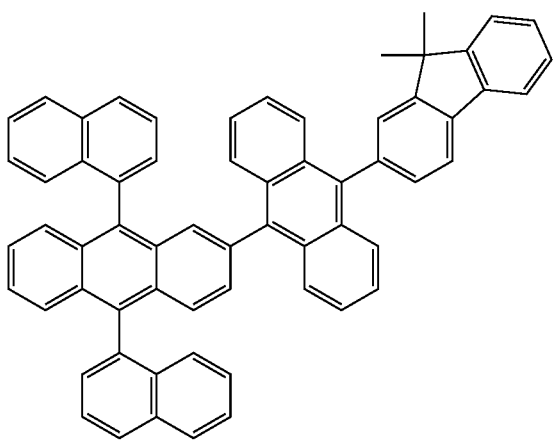
H-58
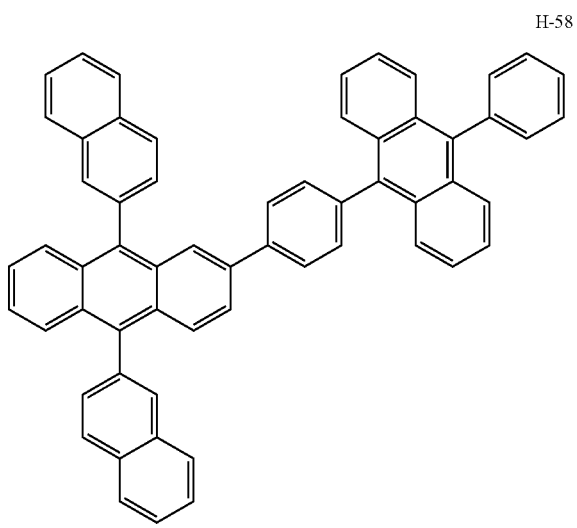

-continued
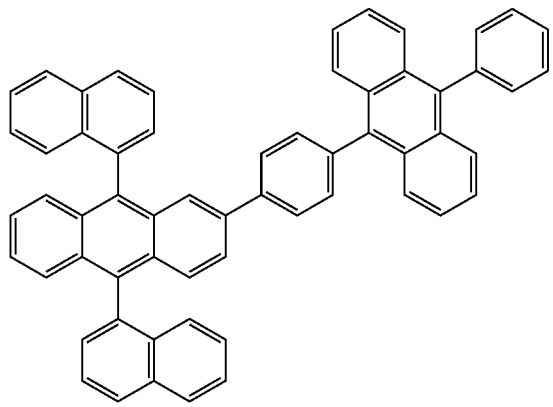

-continued
H-67
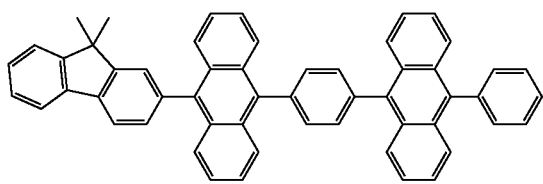
H-68
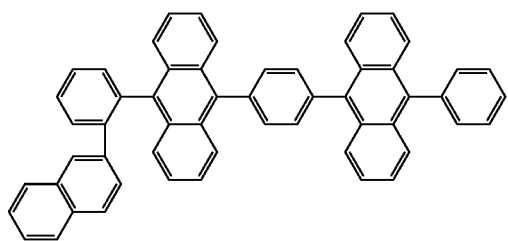
H-69
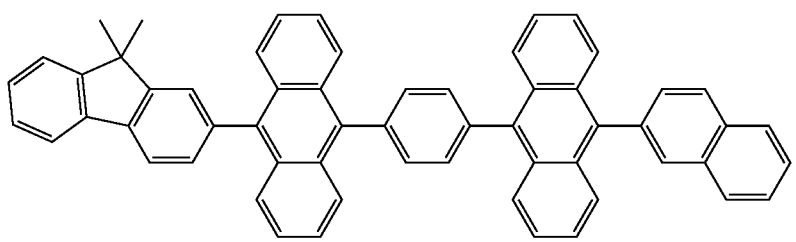
H-70
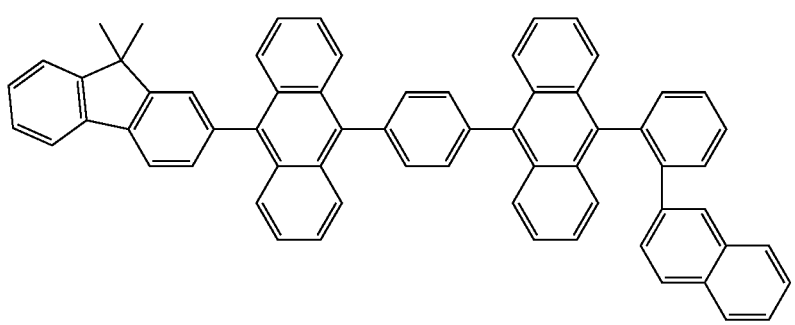
H-71
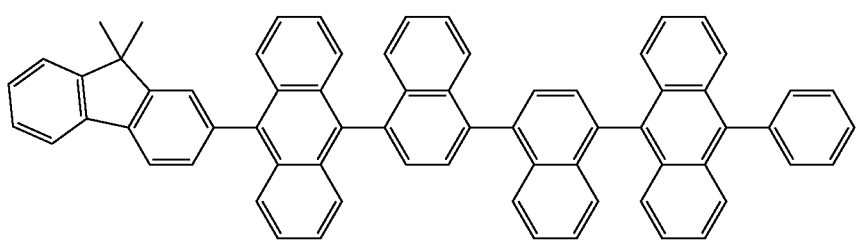
H-72
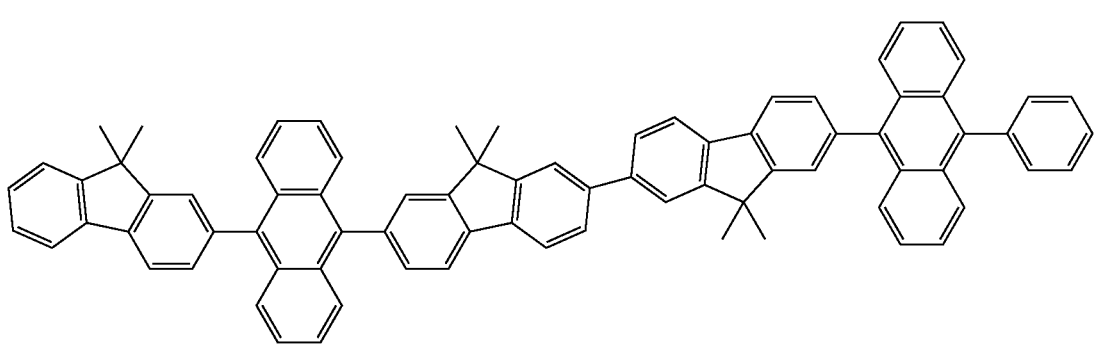

-continued
H-73
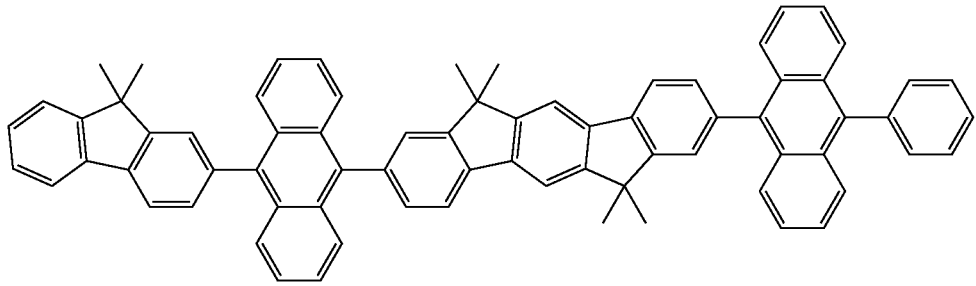
H-74
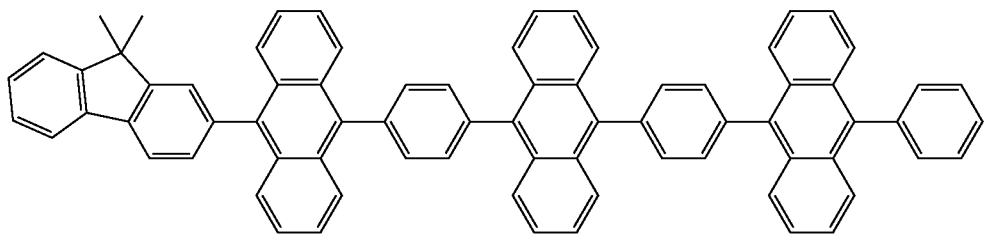
H-75
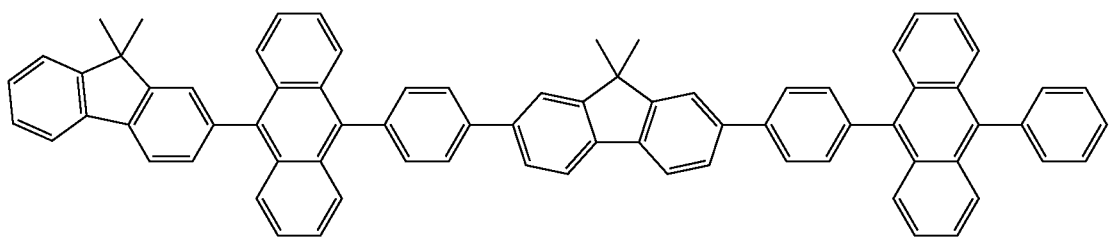
H-76
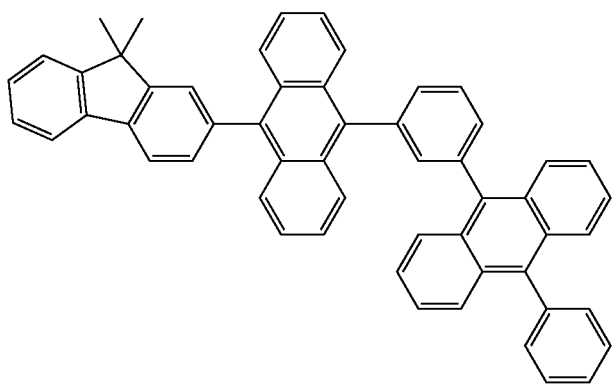
H-77
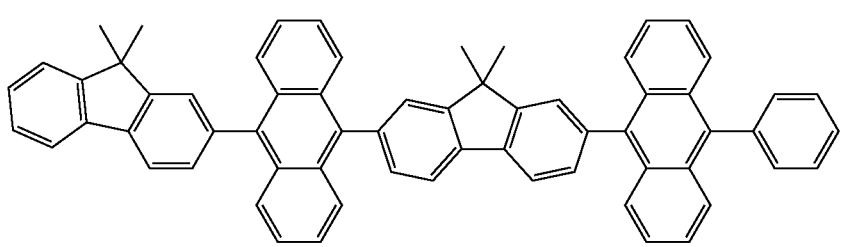

-continued
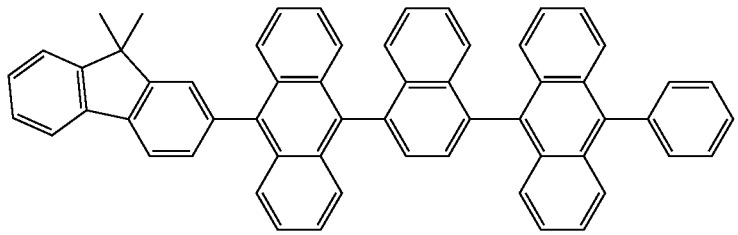
H-78
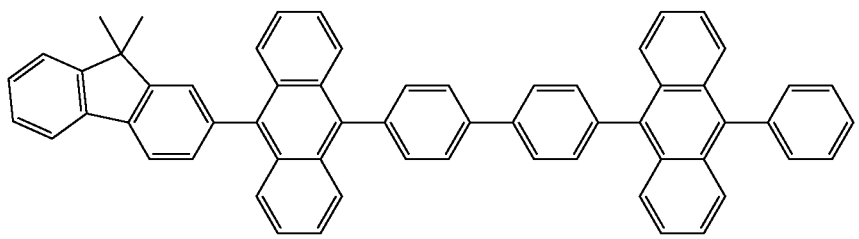
H-79
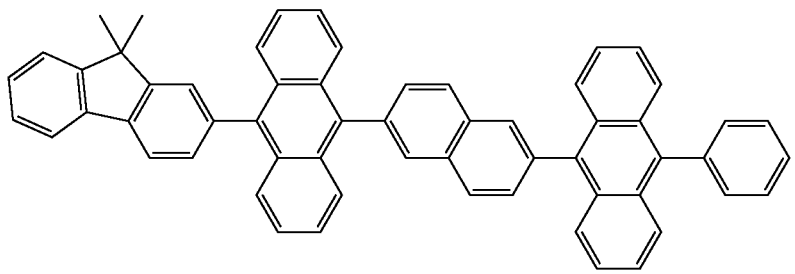
H-80
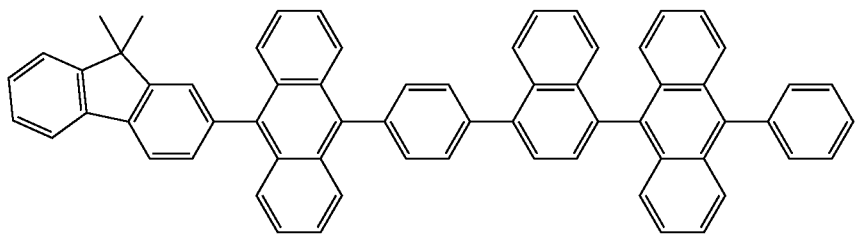
H-81
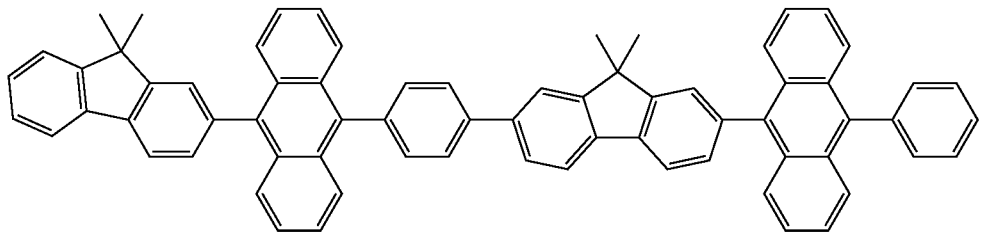
H-82
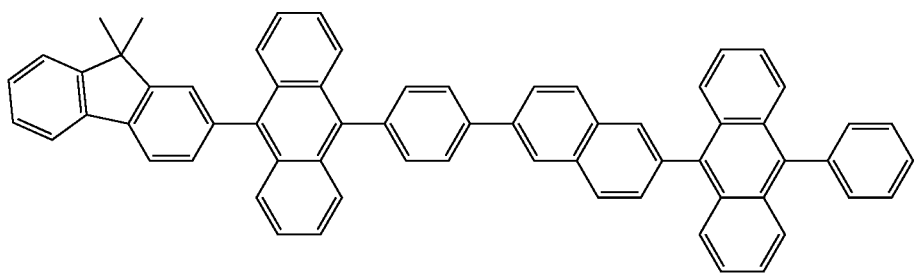
H-83

-continued

H-84

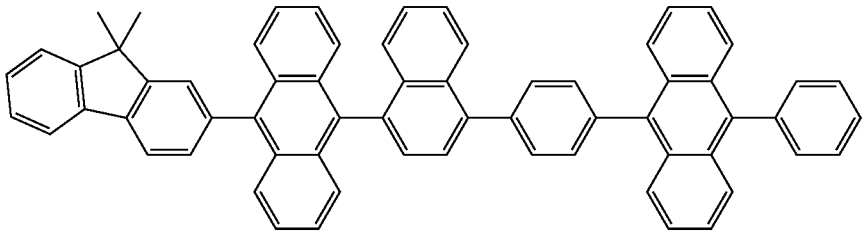

H-85

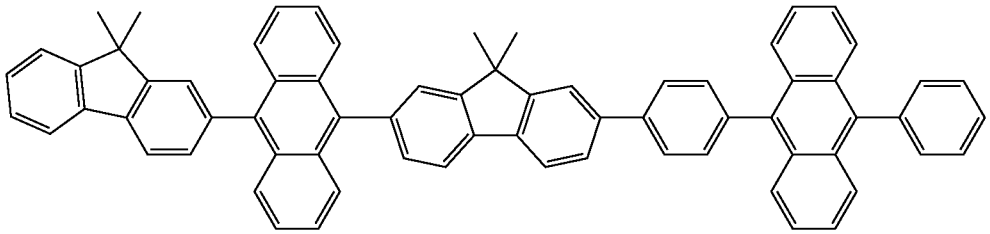

H-86

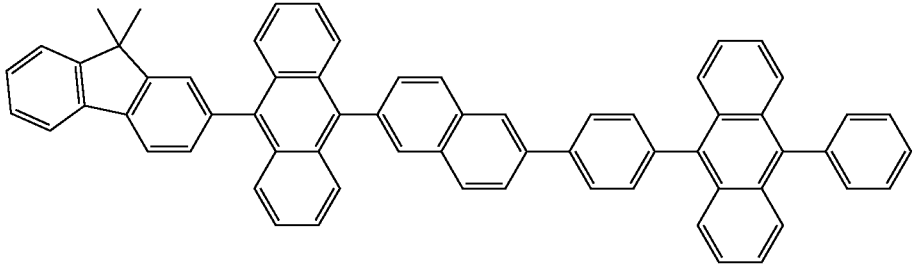

The organic electroluminescent device according to the invention is characterized in that the organic layer is employed as an electron transport layer. When the compound represented by Chemical Formula (1) according to the invention is employed in the electron transport layer, the operation voltage is lowered to result in noticeably decreased power consumption of an OLED, with excellent luminous efficiency.

In an organic electroluminescent device according to the invention, the organic layer comprises an electroluminescent layer, which contains one or more organic compounds for electronic material represented by Chemical Formula (1) as an phosphorescent host, and one or more dopant(s). The dopant to be applied to an electroluminescent device according to the present invention is not particularly restrictive, but preferably selected from the compounds represented by Chemical Formula (25):

$$M^3L^{31}L^{32}L^{33}$$   Chemical Formula 25 wherein, $M^3$ is selected from metals from Group 7, 8, 9, 10, 11, 13, 14, 15 and 16 in the Periodic Table of Elements, and ligands $L^{31}$, $L^{32}$ and $L^{33}$ are independently selected from the following structures:

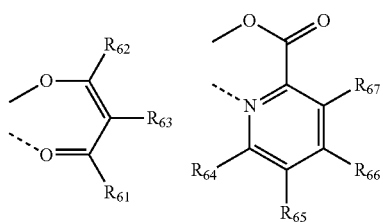

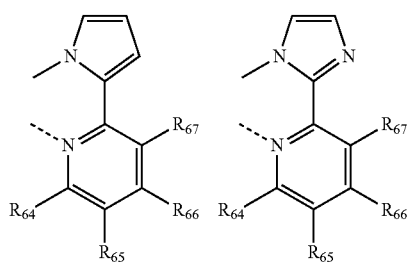

-continued
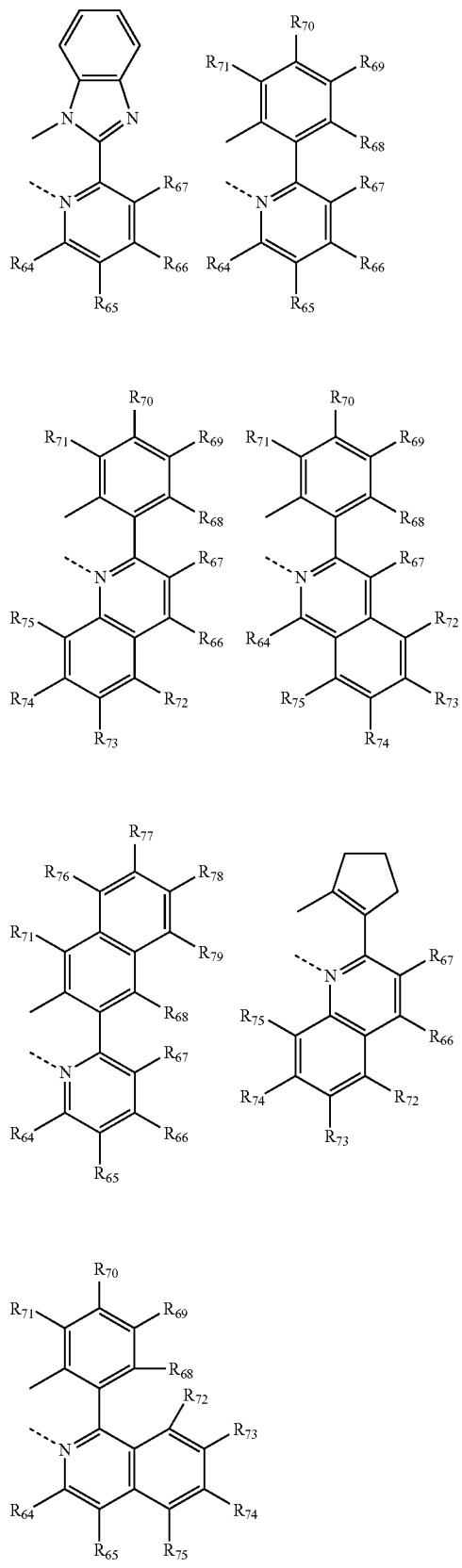
-continued
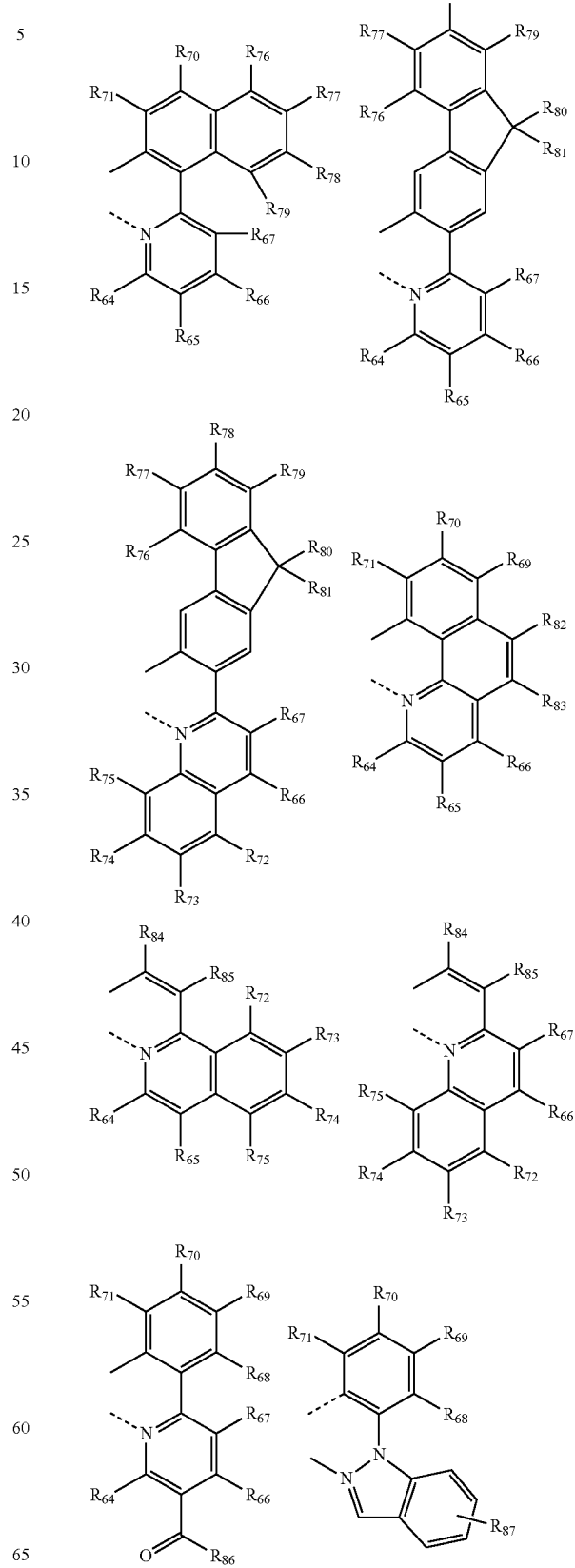

-continued

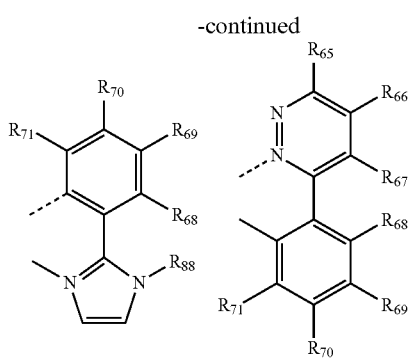

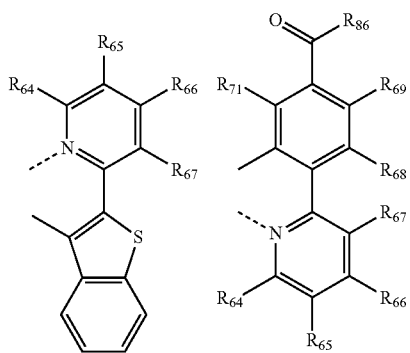

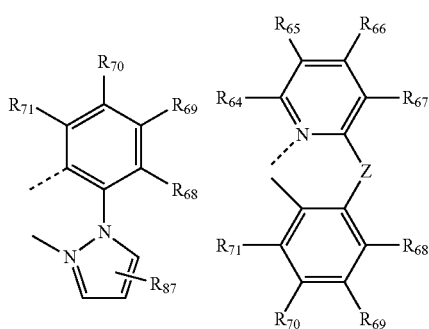

wherein, $R_{61}$ and $R_{62}$ independently represent hydrogen, (C1-C20)alkyl with or without halogen substituent(s), phenyl with or without (C1-C20)alkyl substituent(s), or halogen;

$R_{64}$ through $R_{79}$, $R_{82}$ and $R_{83}$ independently represent hydrogen, (C1-C20)alkyl with or without halogen substituent(s), (C1-C20)alkoxy, phenyl with or without (C1-C20)alkyl substituent(s), SF$_5$, tri(C1-C20)alkylsilyl or halogen;

$R_{80}$, $R_{81}$, $R_{84}$ and $R_{85}$ independently represent hydrogen, (C1-C20)alkyl, phenyl with or without (C1-C20)alkyl substituent;

$R_{86}$ represent (C1-C20)alkyl, phenyl with or without (C1-C20)alkyl substituent, or halogen;

$R_{87}$ and $R_{88}$ represent hydrogen, (C1-C20)alkyl with or without halogen, phenyl with or without (C1-C20)alkyl substituent, or halogen;

Z represents

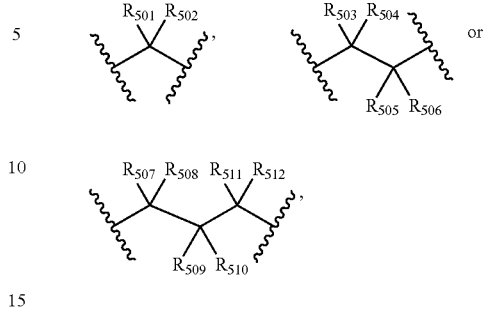

and $R_{501}$ through $R_{512}$ independently represent hydrogen, (C1-C20)alkyl with or without halogen substituent(s), alkoxy, halogen, phenyl, ketone, cyano or (C5-C7)cycloalkyl, or each of $R_{501}$ through $R_{512}$ may be linked to an adjacent substituent via alkylene or alkenylene to form a (C5-C7) spiro-ring or a (C5-C9) fused ring, or each of them may be linked to $R_{67}$ or $R_{68}$ via alkylene or alkenylene to form a (C5-C7) fused ring.

In Chemical Formula (25), M$^3$ may be selected from Ir, Pt, Pd, Rh, Re, Os, Tl, Pb, Bi, In, Sn, Sb, Te, Au and Ag, and the compounds of Chemical Formula (25) can be specifically exemplified by the compounds represented by one of the following structural formulas, but they are not restricted thereto.

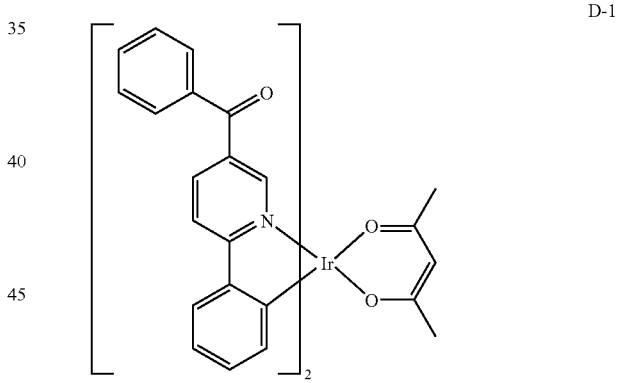

D-1

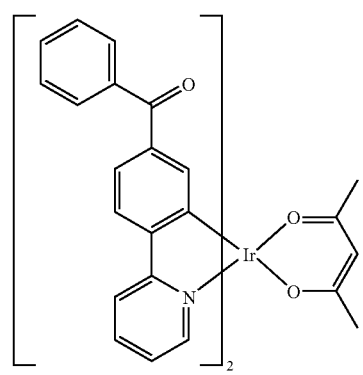

D-2

-continued
D-3
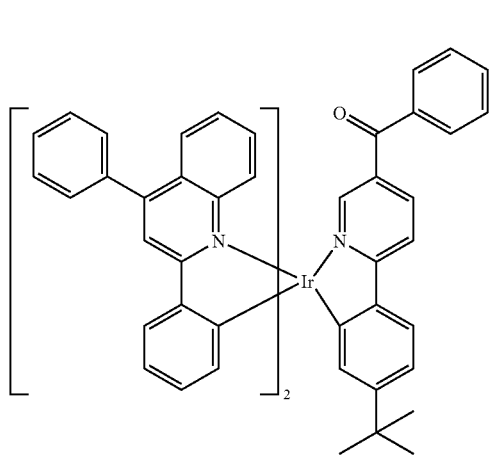
D-4
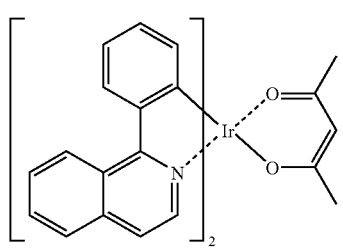
D-5
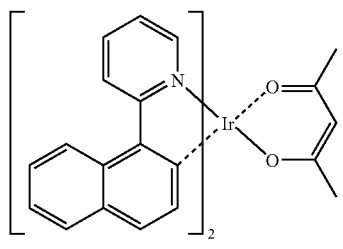
D-6
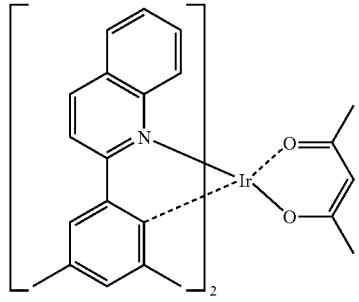
D-7
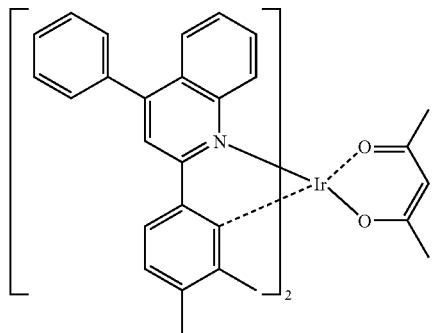
-continued
D-8
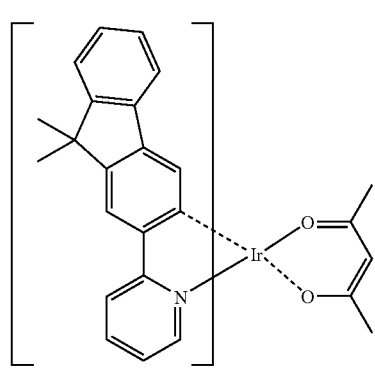
D-9
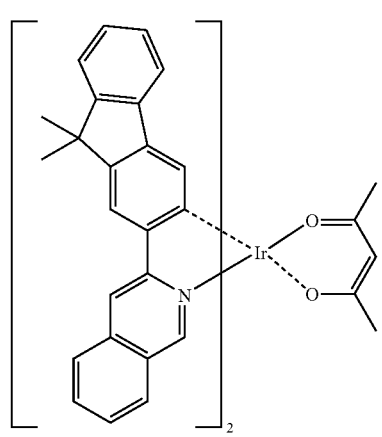
D-10
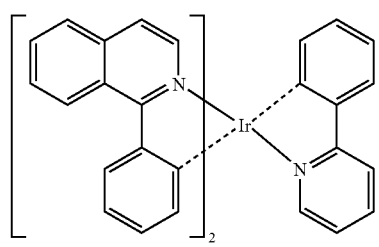
D-11
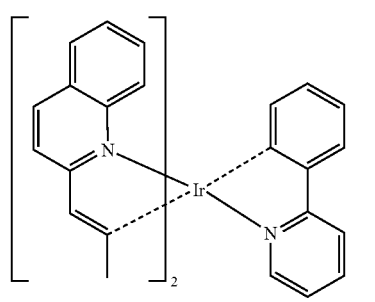
D-12
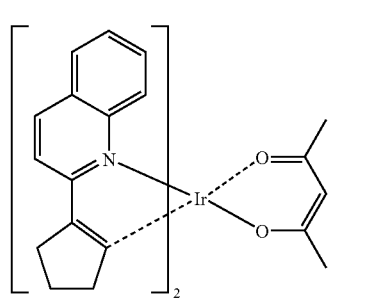

-continued
D-13
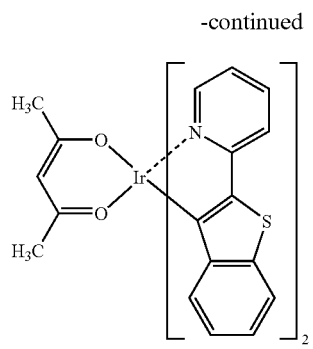
D-14
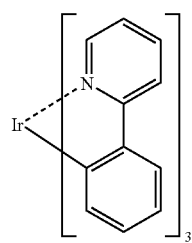
D-15
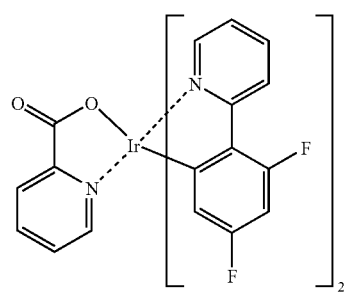
D-16
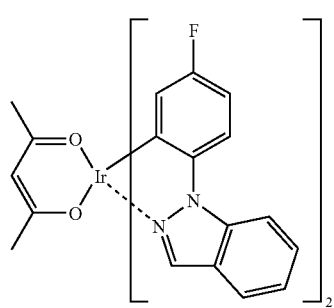
D-17
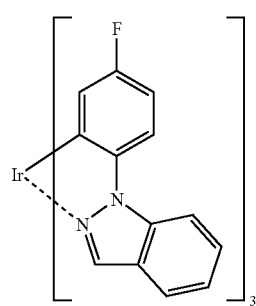
-continued
D-18
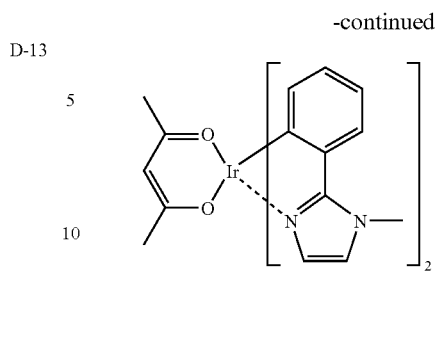
D-19
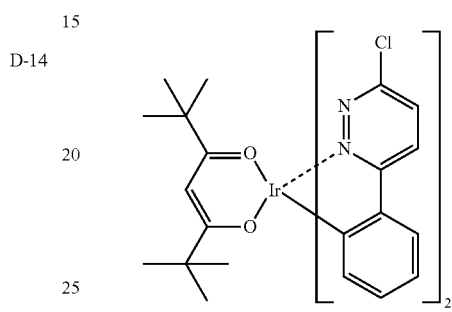
D-20
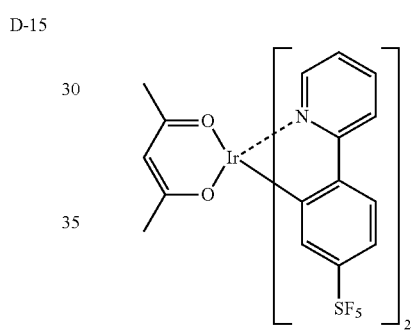
D-21
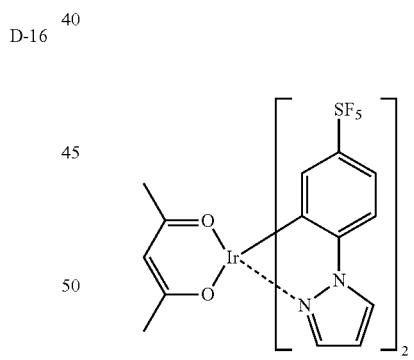
D-22
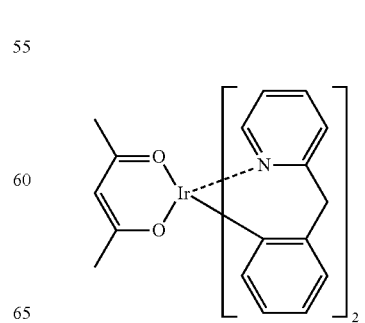

-continued
D-23
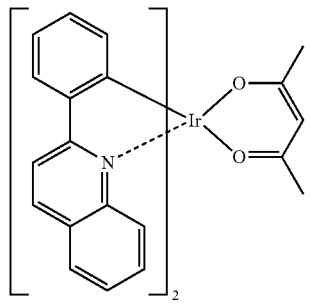
D-24
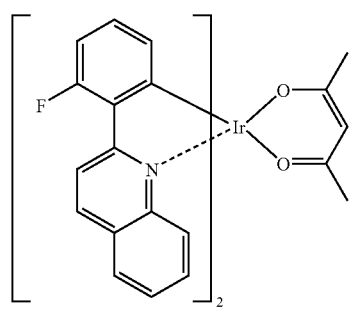
D-25
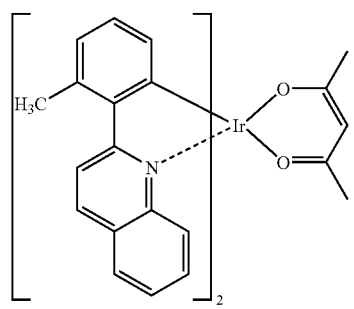
D-27
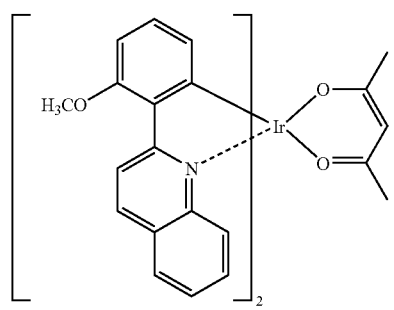
D-27
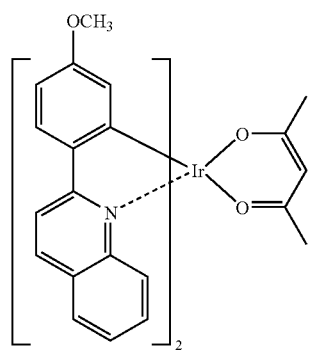
D-28
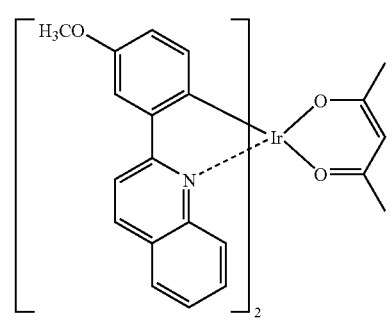
D-29
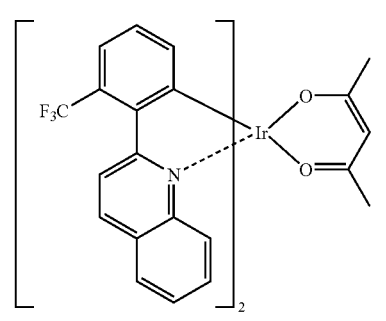
D-30
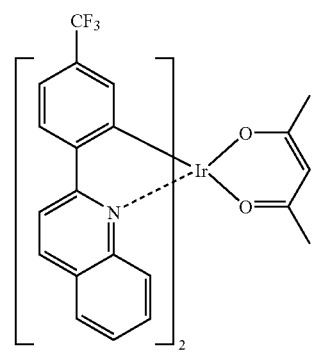
D-31
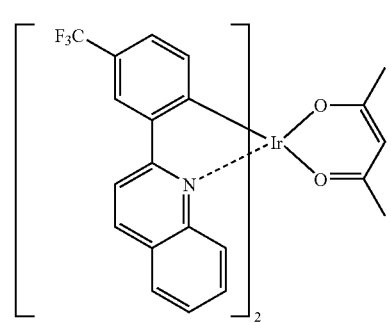
D-32
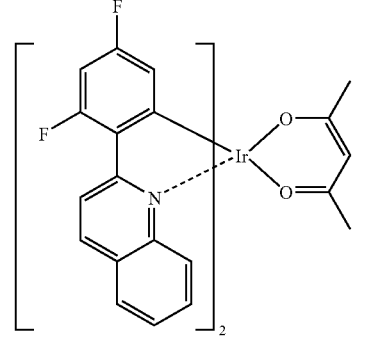

D-33
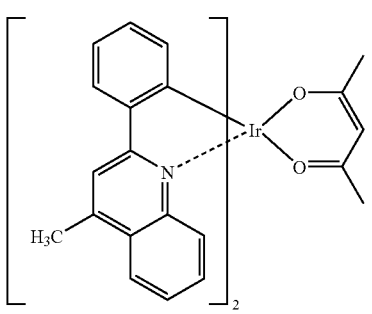

D-34
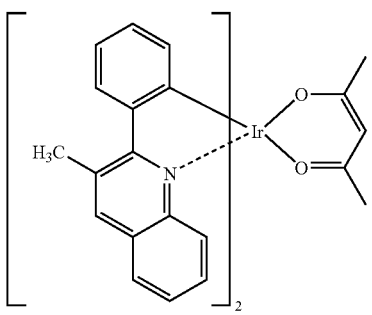

D-35
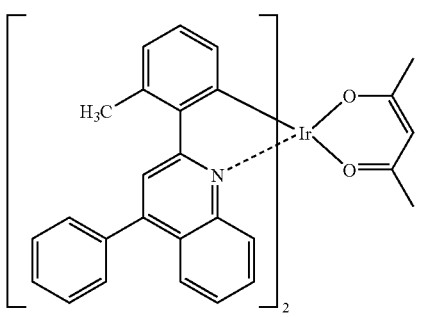

D-36
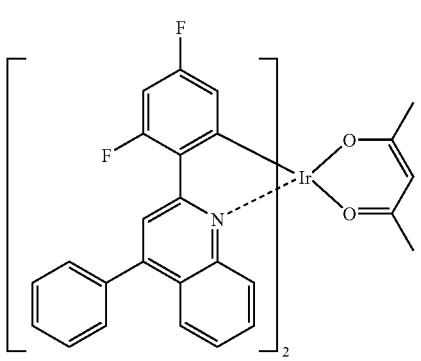

When the compound for electronic material according to the present invention is contained in an electroluminescent layer of a phosphor, noticeable decrease of power consumption due to lowered operation voltage can be obtained as well as at least comparable luminous efficiency, as compared to the device employing conventional phosphorescent host.

The electroluminescent layer means the layer where electroluminescence occurs, and it may be a single layer or a multi-layer consisting of two or more layers laminated. When a mixture of host-dopant is used according to the constitution of the present invention, the doping concentration of the dopant may be from 0.5 to 20% by weight.

The organic electroluminescent device according to the present invention may further comprise one or more compound(s) selected from a group consisting of arylamine compounds and styrylarylamine compounds, as well as the compound for electronic material represented by Chemical Formula (1). Examples of the arylamine or styrylarylamine compounds include the compounds represented by Chemical Formula (26), but they are not restricted thereto:

Chemical Formula 26

wherein, $Ar_{100}$ and $Ar_{200}$ independently represent (C1-C60)alkyl, (C6-C60)aryl, (C4-C60)heteroaryl, (C6-C60)arylamino, (C1-C60)alkylamino, morpholino or thiomorpholino, 5- or 6-membered heterocycloalkyl containing one or more heteroatom(s) selected from N, O and S, or (C3-C60)cycloalkyl, or $Ar_{100}$ and $Ar_{200}$ may be linked via (C3-C60)alkylene or (C3-C60)alkenylene with or without a fused ring to form an alicyclic ring, or a monocyclic or polycyclic aromatic ring; the aryl, heteroaryl, arylamino or heterocycloalkyl of $Ar_{100}$ and $Ar_{200}$ may be further substituted by one or more substituent(s) selected from halogen, (C1-C60)alkyl, (C2-C60)alkenyl, (C2-C60)alkynyl, (C6-C60)aryl, (C4-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C1-C60)alkyloxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl;

$Ar_{300}$ represents (C6-C60)aryl, (C5-C60)heteroaryl or (C6-C60)arylamino; the aryl, heteroaryl or arylamino of Y may be further substituted by one or more substituent(s) selected from halogen, (C1-C60)alkyl, (C6-C60)aryl, (C4-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl (C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; and g is an integer from 1 to 4.

The arylamine compounds or styrylarylamine compounds can be more specifically exemplified by the following compounds, but they are not restricted thereto.

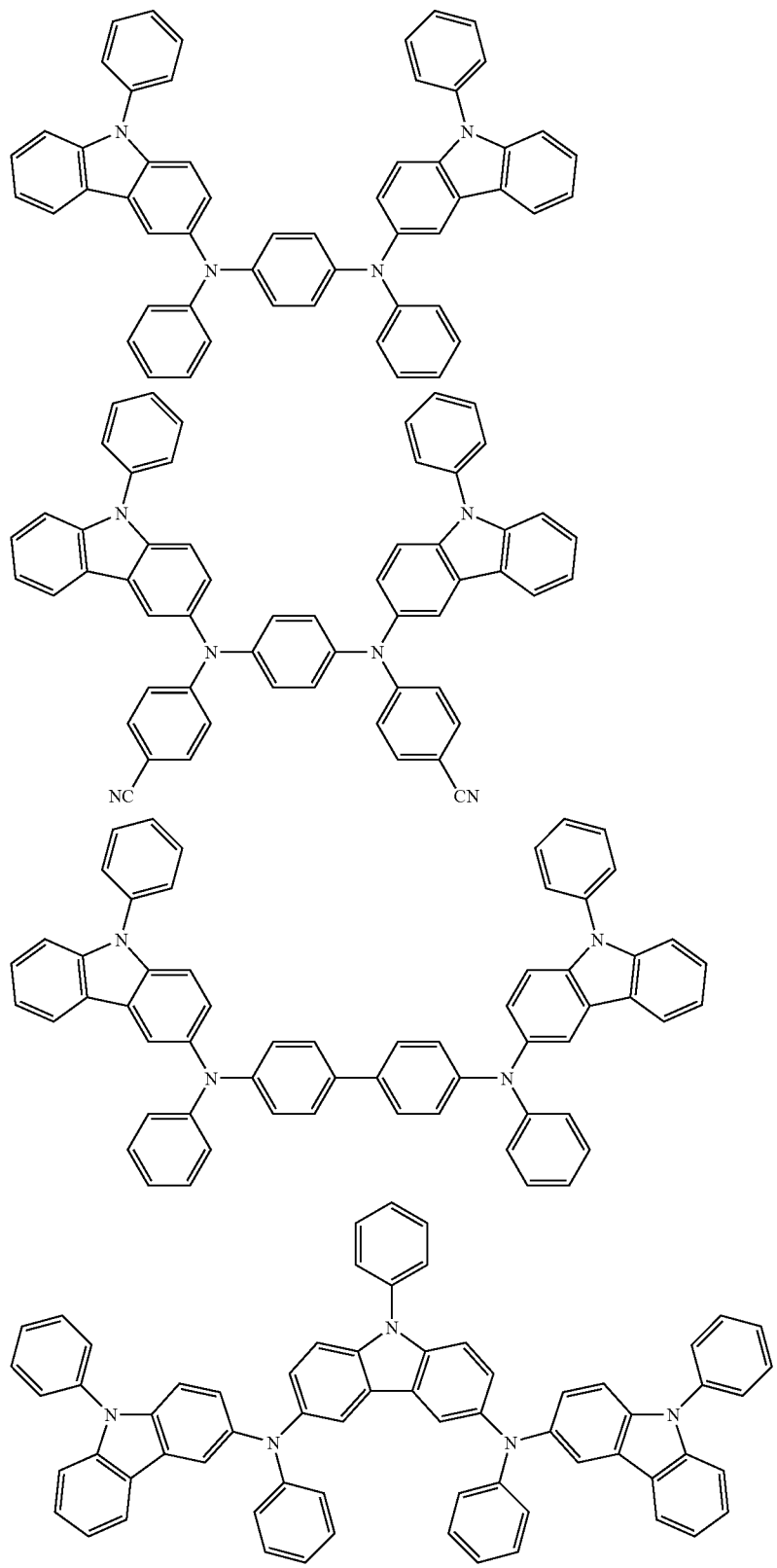

-continued
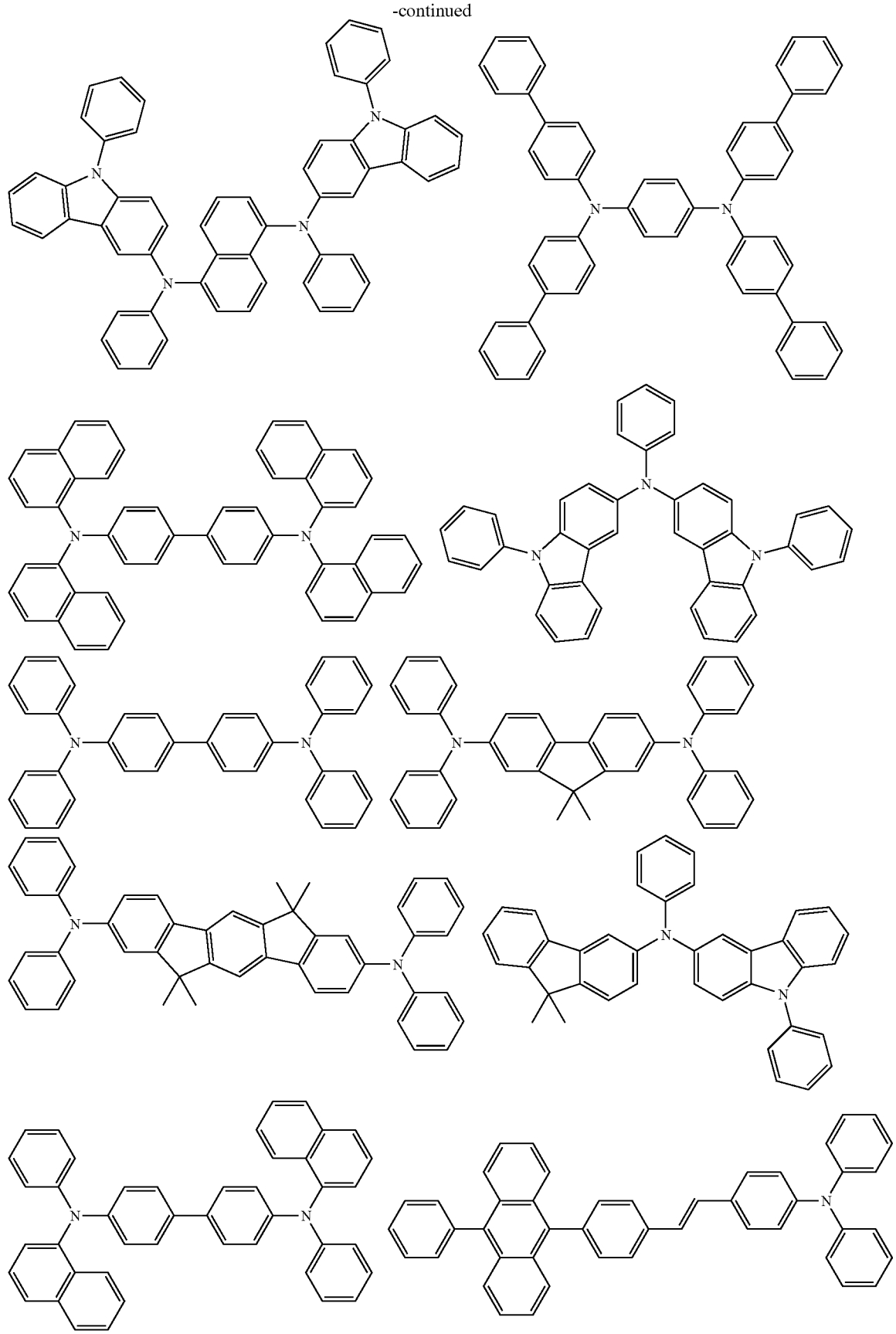

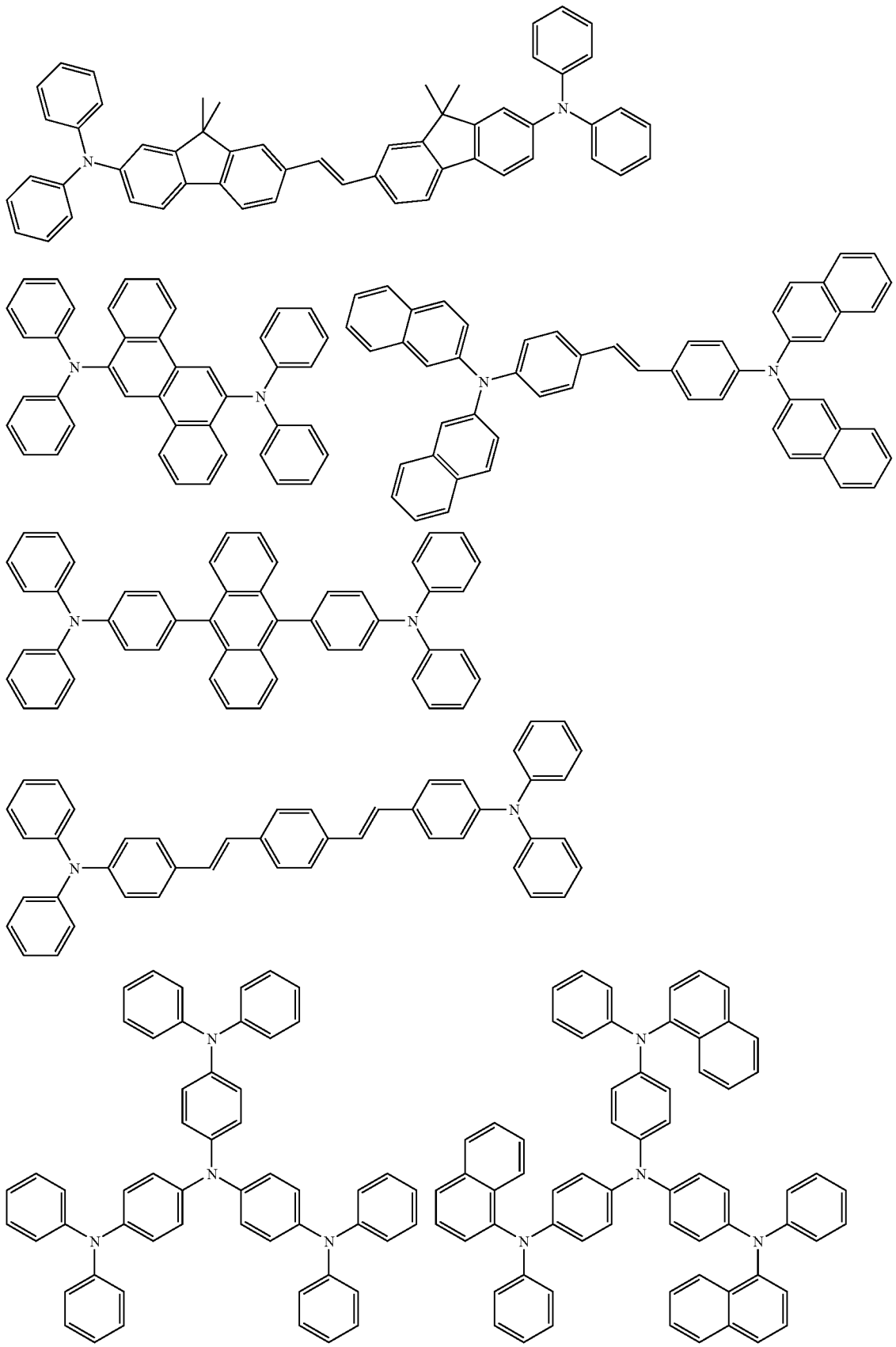

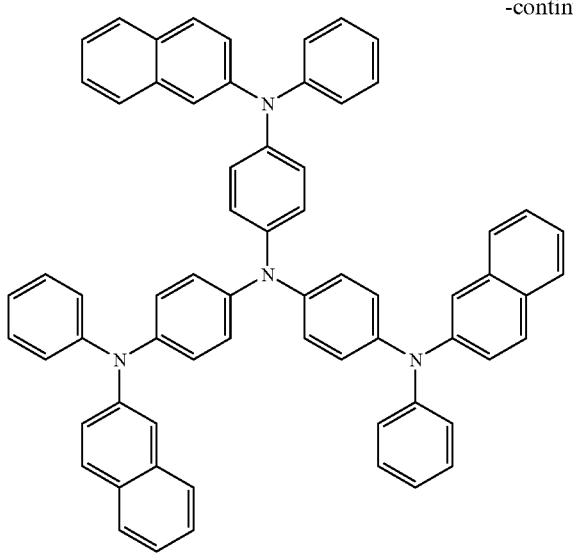

In an organic electroluminescent device according to the present invention, the organic layer may further comprise one or more metal(s) selected from a group consisting of organic metals of Group 1, Group 2, 4$^{th}$ period and 5$^{th}$ period transition metals, lanthanide metals and d-transition elements in the Periodic Table of Elements, as well as the compound for electronic material represented by Chemical Formula (1). The organic layer may comprise a charge generating layer, in addition to an electroluminescent layer.

The present invention can realize an organic electroluminescent device having a pixel structure of independent light-emitting mode, which comprises an organic electroluminescent device containing the compound for electronic material represented by Chemical Formula (1) as a sub-pixel, and one or more sub-pixel(s) comprising one or more metallic compound(s) selected from a group consisting of Ir, Pt, Pd, Rh, Re, Os, Tl, Pb, Bi, In, Sn, Sb, Te, Au and Ag, patterned in parallel at the same time.

Further, the organic layer may comprise compounds having the electroluminescent peak of wavelength of 480 to 560 nm, or those having the electroluminescent peak of wavelength of not less than 560 nm, at the same time. Those compounds can be exemplified by the compounds represented by one of Chemical Formulas (27) to (33).

Chemical Formula 27

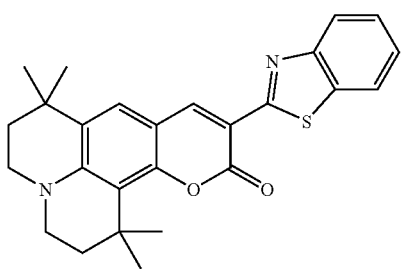

Chemical Formula 28

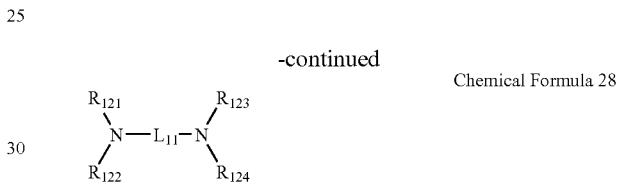

In Chemical Formula (28), $L_{11}$ represents (C6-C60)arylene with or without one or more substituent(s) selected from halogen, (C1-C60)alkyl, (C6-C60)aryl, (C4-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; the alkyl, cycloalkyl, heterocycloalkyl, aryl, heteroaryl, arylsilyl, alkylsilyl, alkylamino or arylamino as a substituent on the arylene may be further substituted by one or more substituent(s) selected from halogen, (C1-C60)alkyl, (C6-C60)aryl, (C4-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri (C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60) alkoxycarbonyl, carboxyl, nitro and hydroxyl;

$R_{121}$ through $R_{124}$ independently represent (C1-C60)alkyl, (C6-C60)aryl, (C4-C60)heteroaryl, (C6-C60)arylamino, (C1-C60)alkylamino, 5- or 6-membered heterocycloalkyl containing one or more heteroatom(s) selected from N, O and S, or (C3-C60)cycloalkyl, or each of $R_{121}$ through $R_{124}$ may be linked to an adjacent substituent via (C3-C60)alkylene or (C3-C60)alkenylene with or without a fused ring to form an alicyclic ring, or an monocyclic or polycyclic aromatic ring; and the alkyl, aryl, heteroaryl, arylamino, alkylamino, cycloalkyl or heterocycloalkyl of $R_{121}$ through $R_{124}$ may be further substituted by one or more substituent(s) selected from halogen, (C1-C60)alkyl, (C6-C60)aryl, (C4-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl.

$$M^1L^1L^2L^3 \qquad \text{Chemical Formula 29}$$

In Chemical Formula (29), $M^1$ is selected from metals of Group 7, 8, 9, 10, 11, 13, 14, 15 and 16 in the Periodic Table of Elements, and ligands $L^1$, $L^2$ and $L^3$ are independently selected from the following structures:

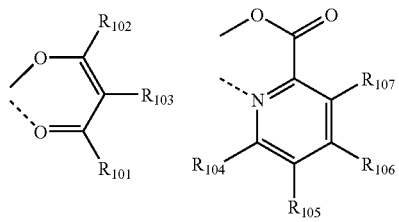

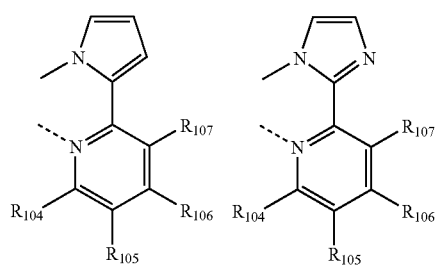

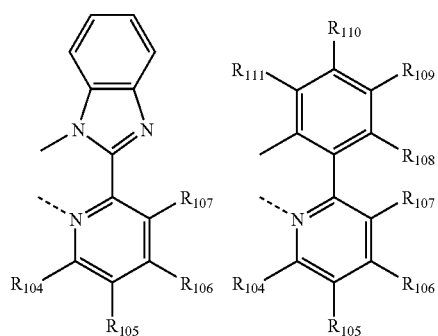

-continued

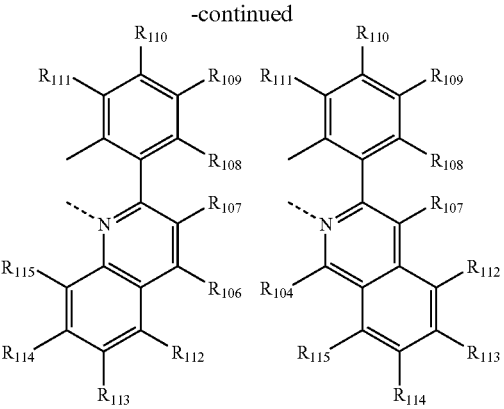

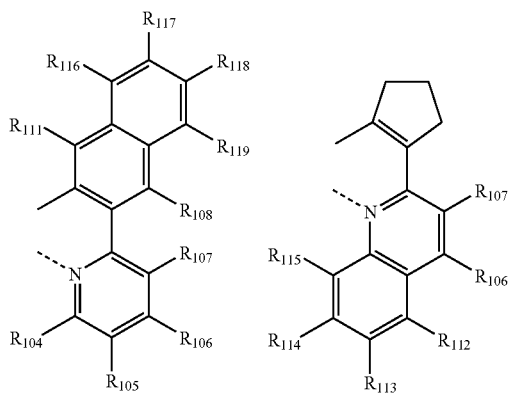

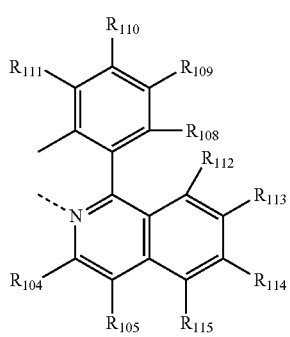

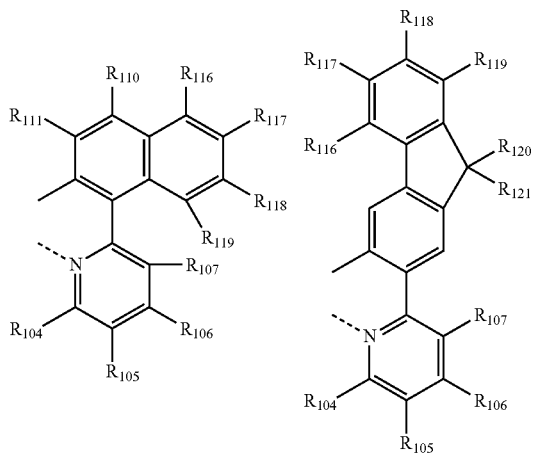

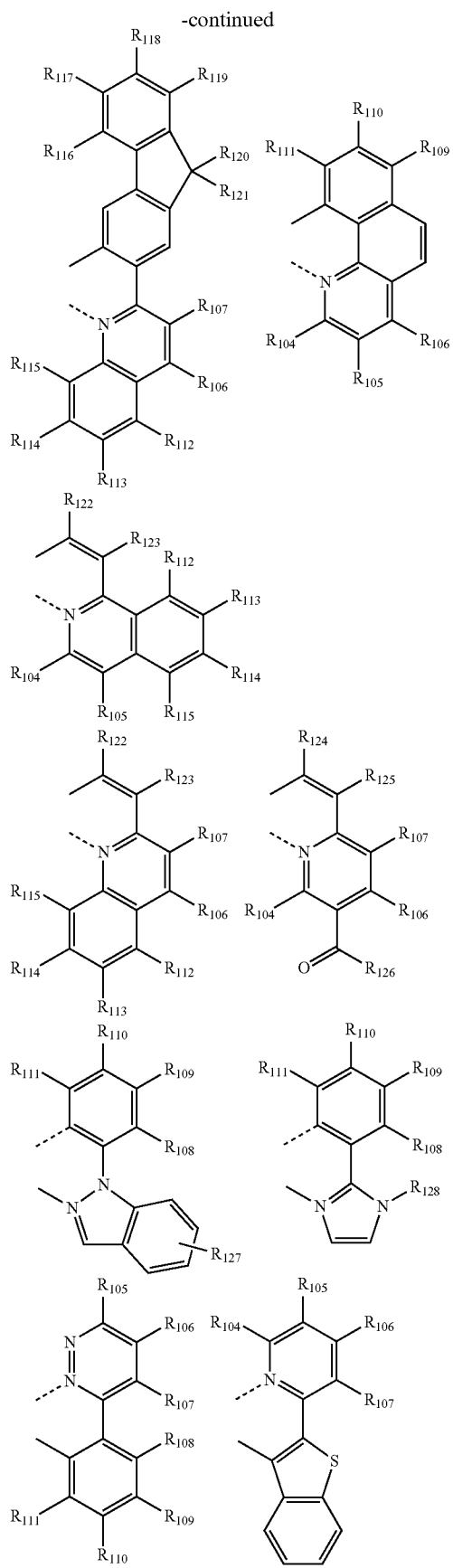
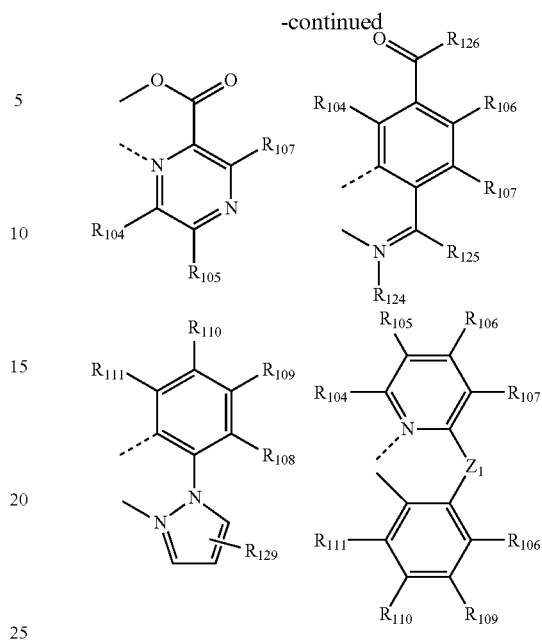

wherein, $R_{101}$ through $R_{103}$ independently represent hydrogen, (C1-C60)alkyl with or without halogen substituent(s), (C6-C60)aryl with or without (C1-C60)alkyl substituent(s), or halogen;

$R_{104}$ through $R_{119}$ independently represent hydrogen, (C1-C60)alkyl, (C1-C30)alkoxy, (C3-C60)cycloalkyl, (C2-C30)alkenyl, (C6-C60)aryl, mono or di(C1-C30)alkylamino, mono or di(C6-30)arylamino, $SF_5$, tri(C1-C30)alkylsilyl, di(C1-C30)alkyl(C6-C30)arylsilyl, tri(C6-C30)arylsilyl, cyano or halogen; $R_{110}$ and $R_{116}$ may be linked to an adjacent substituent via (C2-C12)alkylene or (C2-C12)alkenylene to form a fused ring or a multi-fused ring; the alkyl, cycloalkyl, alkenyl or aryl of $R_{104}$ through $R_{119}$, or the fused ring or the multi-fused ring formed from $R_{110}$ and $R_{116}$ via alkylene or alkenylene may be further substituted by one or more substituent(s) selected from (C1-C60)alkyl, (C6-C60)aryl and halogen;

$R_{120}$ through $R_{123}$ independently represent hydrogen, (C1-C60)alkyl with or without halogen substituent(s), or (C6-C60)aryl with or without (C1-C60)alkyl substituent(s);

$R_{124}$ and $R_{125}$ independently represent hydrogen, linear or branched (C1-C60)alkyl, (C6-C60)aryl or halogen, or $R_{124}$ and $R_{125}$ may be linked via (C3-C12)alkylene or (C3-C12)alkenylene with or without a fused ring to form an alicyclic ring, or a monocyclic or polycyclic aromatic ring; and the alkyl or aryl of $R_{124}$ and $R_{125}$, or the alicyclic ring, or the monocyclic or polycyclic aromatic ring formed therefrom via (C3-C12)alkylene or (C3-C12)alkenylene with or without a fused ring may be further substituted by one or more substituent(s) selected from linear or branched (C1-C60)alkyl with or without halogen substituent(s), (C1-C30)alkoxy, halogen, tri(C1-C30)alkylsilyl, tri(C6-C30)arylsilyl and (C6-C60)aryl;

$R_{126}$ represents (C1-C60)alkyl, (C6-C60)aryl, (C5-C60)heteroaryl or halogen;

$R_{127}$ through $R_{129}$ independently represent hydrogen, (C1-C60)alkyl, (C6-C60)aryl or halogen, and the alkyl or aryl of $R_{126}$ through $R_{129}$ may be further substituted by halogen or (C1-C60)alkyl;

$Z_1$ represents

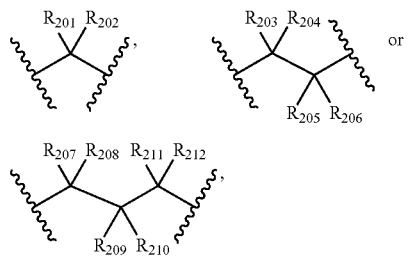

and $R_{201}$ through $R_{212}$ independently represent hydrogen, (C1-C60)alkyl with or without halogen substituent(s), (C1-C30)alkoxy, halogen, (C6-C60)aryl, cyano or (C5-C60)cycloalkyl, or each of $R_{201}$ through $R_{212}$ may be linked to an adjacent substituent via alkylene or alkenylene to form a (C5-C7) spiro-ring or a (C5-C9) fused ring, or each of them may be linked to $R_{107}$ or $R_{108}$ via alkylene or alkenylene to form a (C5-C7) fused ring.

Chemical Formula 30

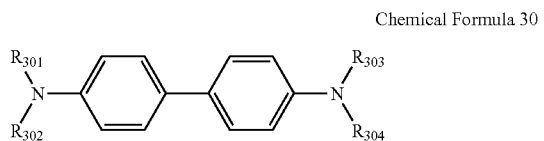

In Chemical Formula (30), $R_{301}$ through $R_{304}$ independently represent (C1-C60)alkyl or (C6-C60)aryl, or each of them may be linked to an adjacent substituent via (C3-C60)alkylene or (C3-C60)alkenylene with or without a fused ring to form an alicyclic ring, or a monocyclic or polycyclic aromatic ring; and the alkyl or aryl of $R_{301}$ through $R_{304}$, or the alicyclic ring, or the monocyclic or polycyclic aromatic ring formed therefrom by linkage via (C3-C60)alkylene or (C3-C60)alkenylene with or without a fused ring may be further substituted by one or more substituent(s) selected from (C1-C60)alkyl with or without halogen substituent(s), (C1-C60)alkoxy, halogen, tri(C1-C60)alkylsilyl, tri(C6-C60)arylsilyl and (C6-C60)aryl.

Chemical Formula 31

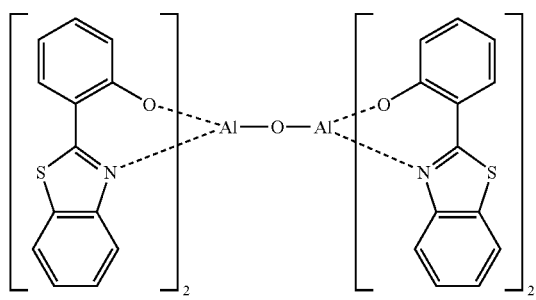

Chemical Formula 32

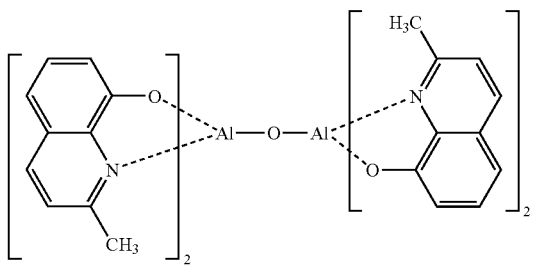

Chemical Formula 33

$L^6L^7M^2(Q)_d$

In Chemical Formula (33), the ligands, $L^6$ and $L^7$ are independently selected from the following structures:

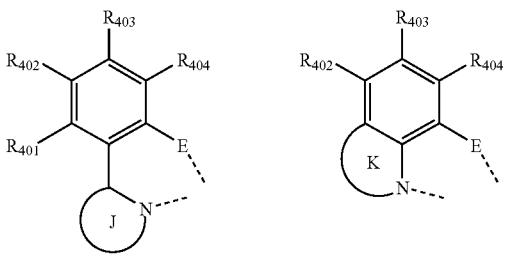

wherein, $M^2$ is a bivalent or trivalent metal;

d is 0 when $M^2$ is a bivalent metal, while d is 1 when $M^2$ is a trivalent metal;

Q represents (C6-C60)aryloxy or tri(C6-C60)arylsilyl, and the aryloxy and triarylsilyl of Q may be further substituted by (C1-C60)alkyl or (C6-C60)aryl;

E represents O, S or Se;

ring J represents oxazole, thiazole, imidazole, oxadiazole, thiadiazole, benzoxazole, benzothiazole, benzimidazole, pyridine or quinoline;

ring K represents pyridine or quinoline, and ring K may be further substituted by (C1-C60)alkyl, or phenyl or naphthyl with or without (C1-C60)alkyl substituent(s);

$R_{401}$ through $R_{404}$ independently represent hydrogen, (C1-C60)alkyl, halogen, tri(C1-C60)alkylsilyl, tri(C6-C60)arylsilyl or (C6-C60)aryl, or each of them may be linked to an adjacent substituent via (C3-C60)alkylene or (C3-C60)alkenylene to form a fused ring, and the pyridine or quinoline may form a chemical bond with $R_{401}$ to form a fused ring; and ring J or the aryl group of $R_{401}$ through $R_{404}$ may be further substituted by (C1-C60)alkyl, halogen, (C1-C60)alkyl with halogen substituent(s), phenyl, naphthyl, tri(C1-C60)alkylsilyl, tri(C6-C60)arylsilyl or amino group.

The compounds having electroluminescent peak of wavelength of 480 to 560 nm, or those having electroluminescent peak of wavelength of not less than 560 nm, can be exemplified by the following compounds, but they are not restricted thereto.

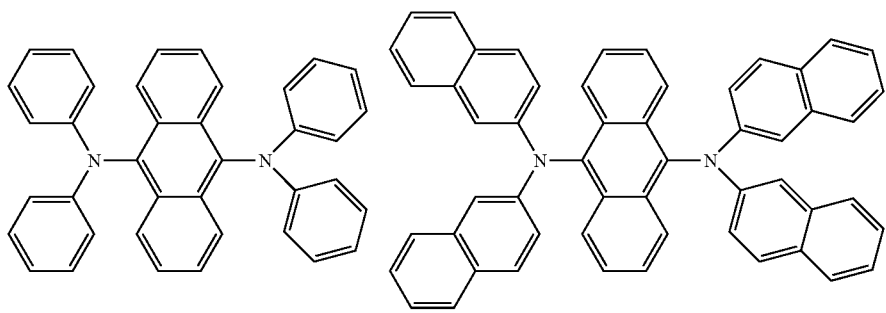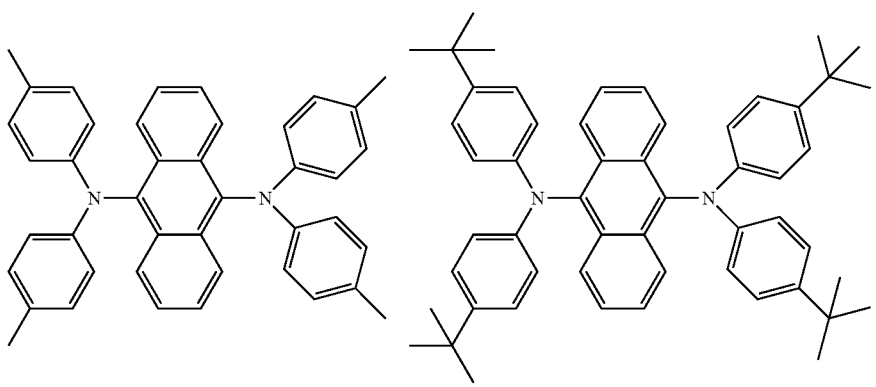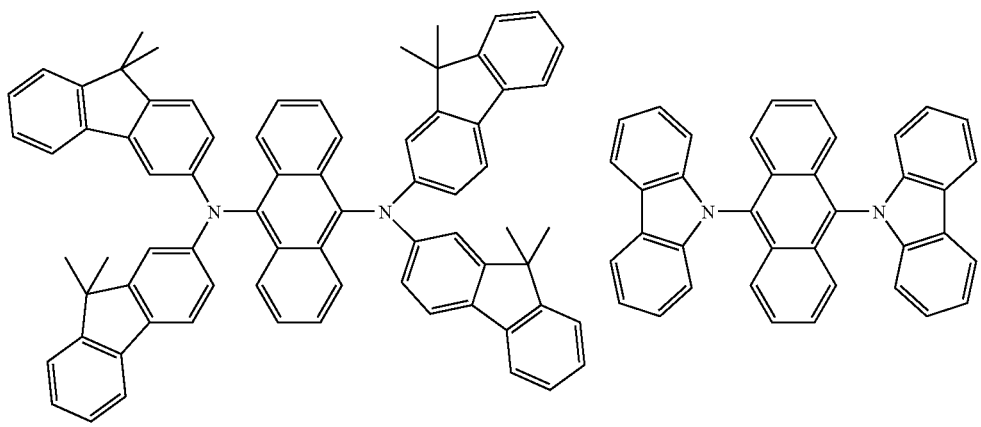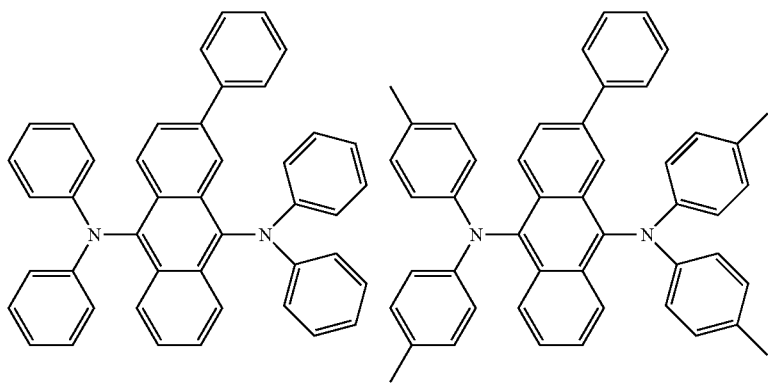

-continued
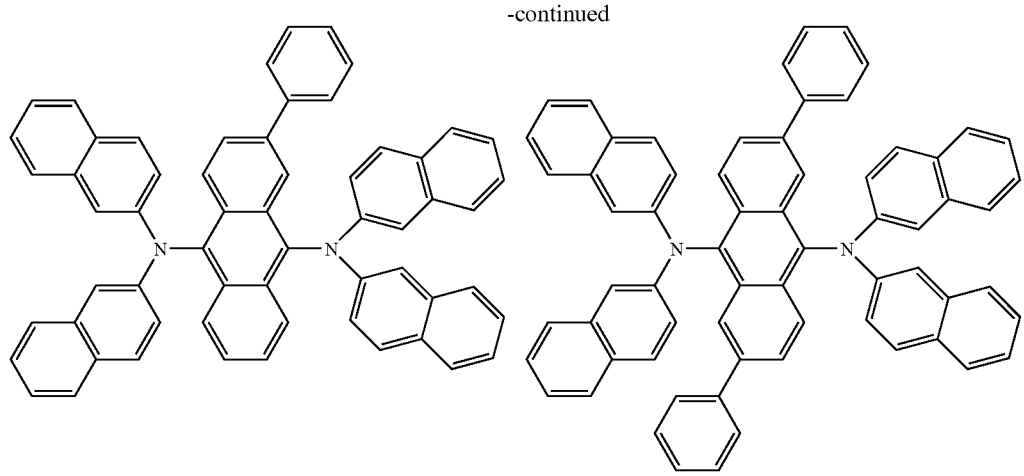
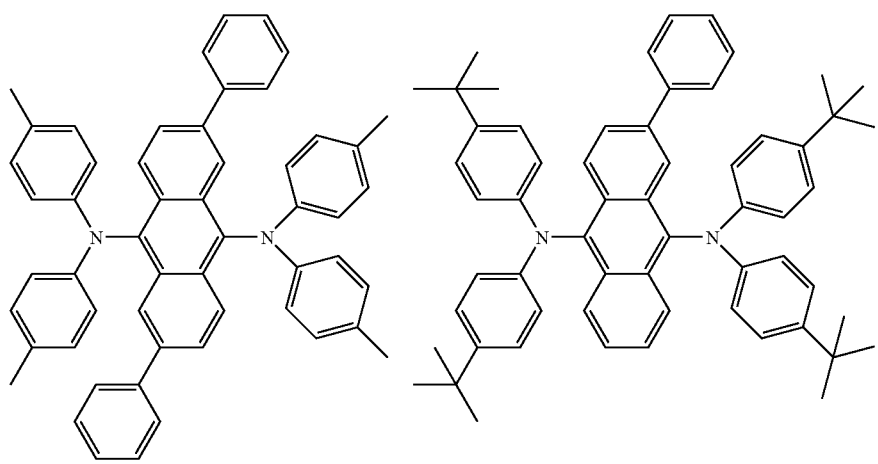
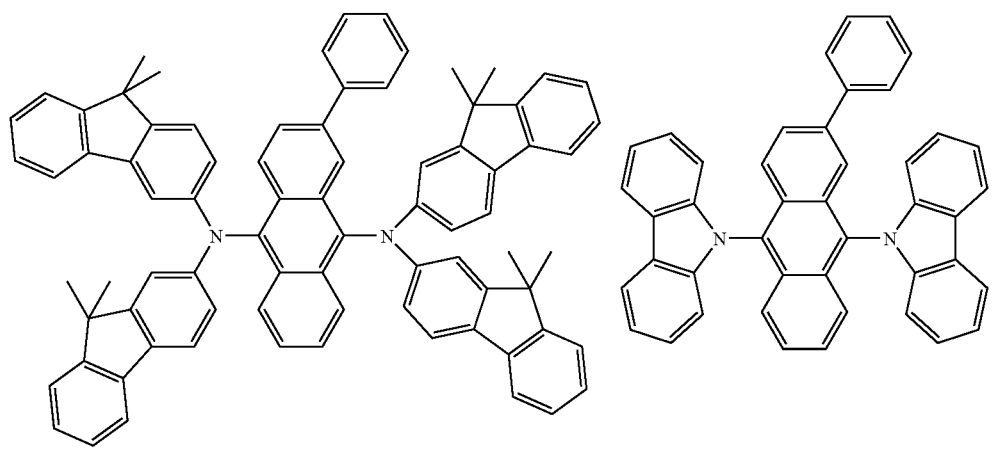

-continued
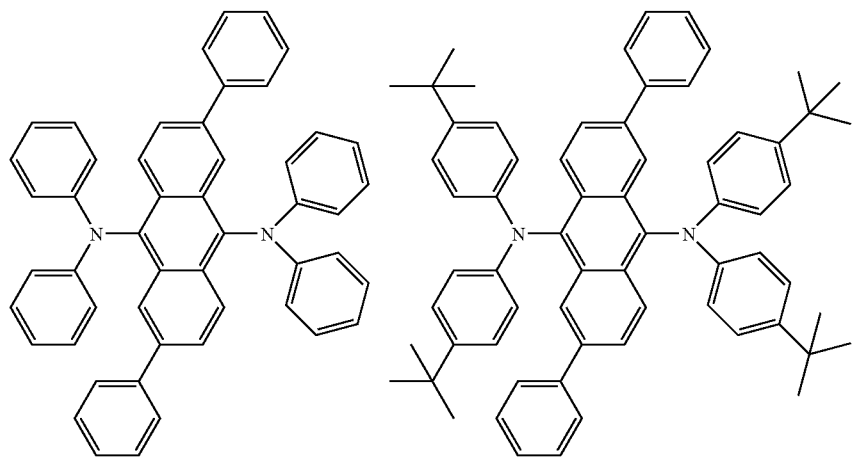
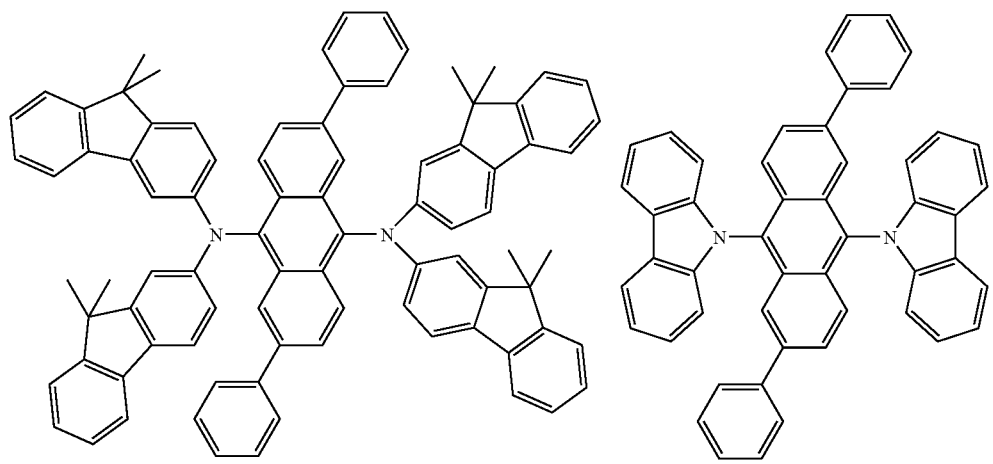
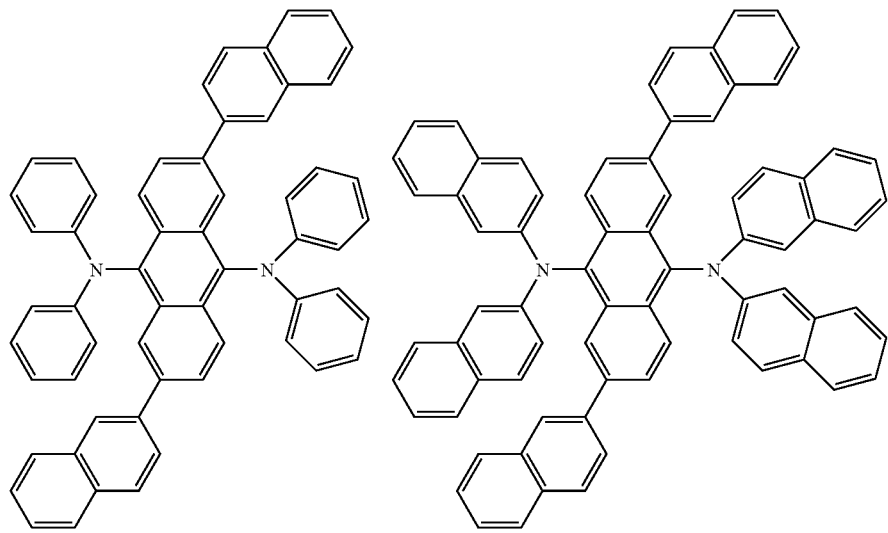

-continued
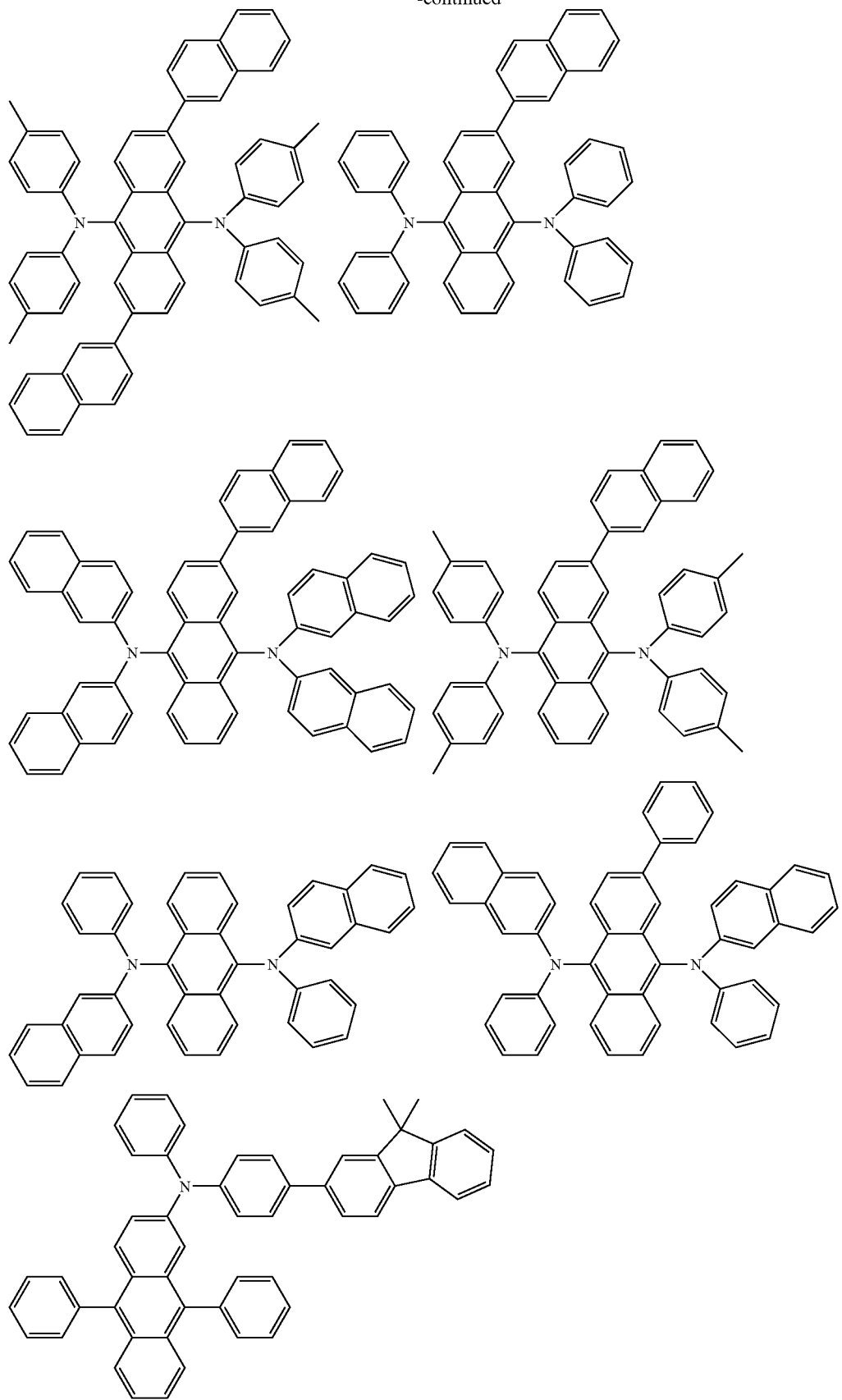

-continued
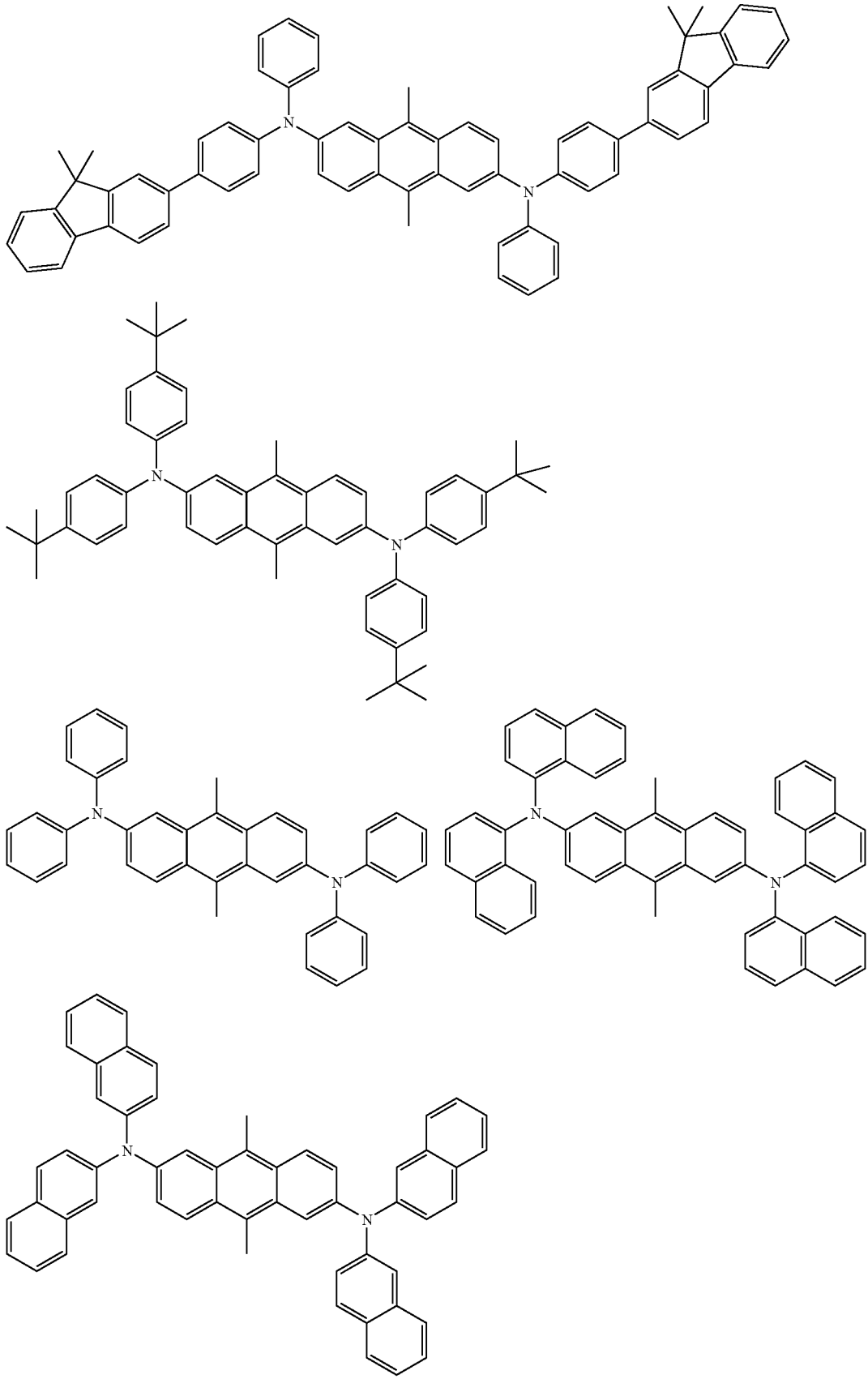

-continued
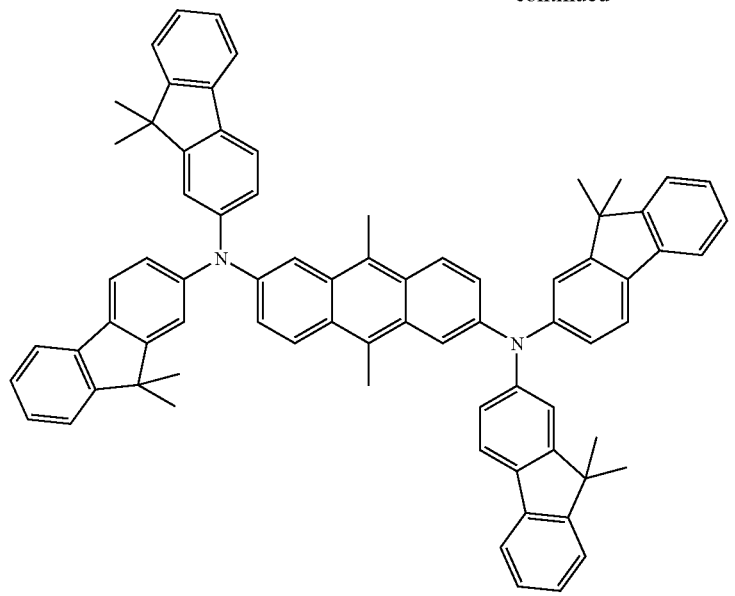
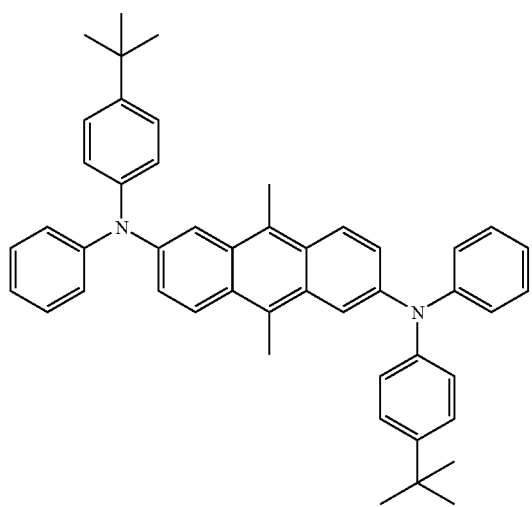
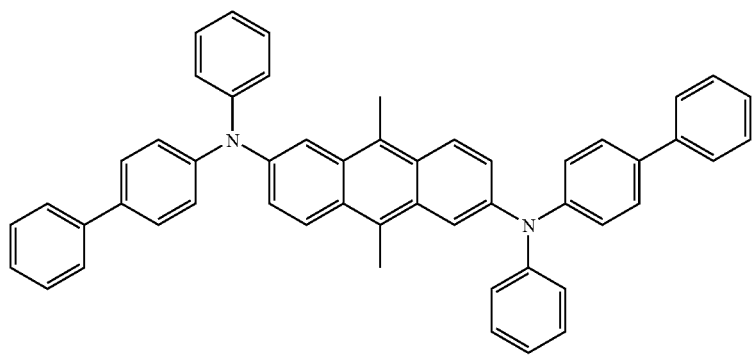

253
254
-continued
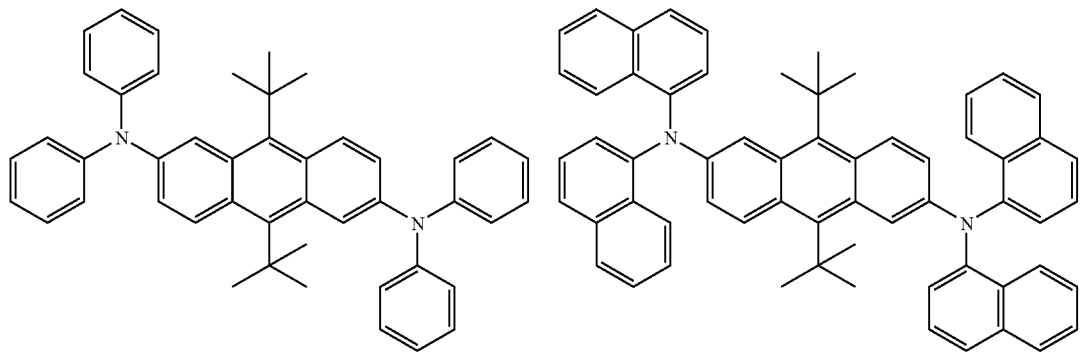
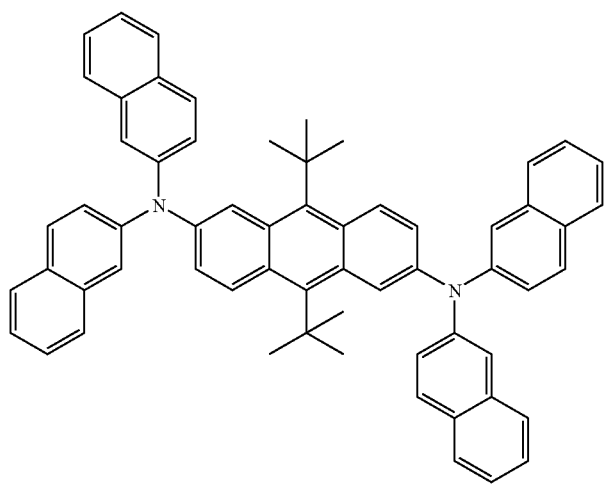
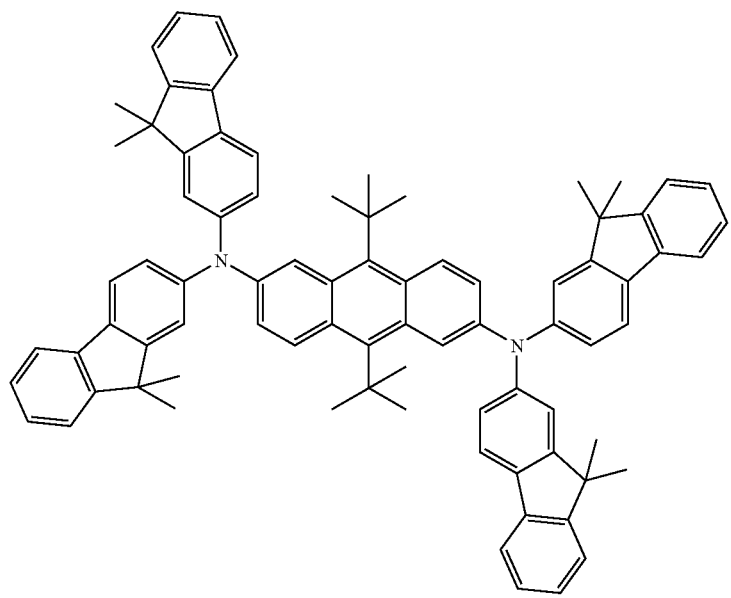

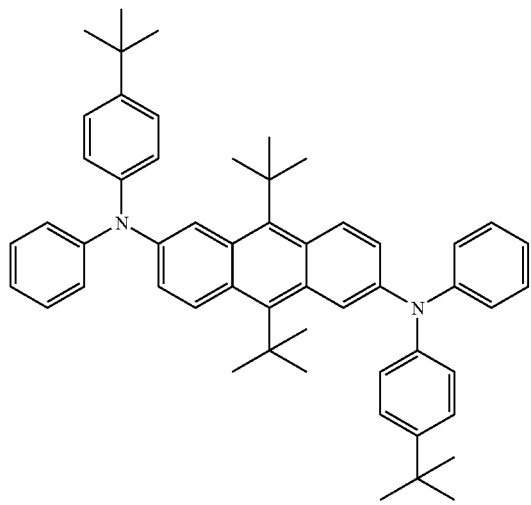
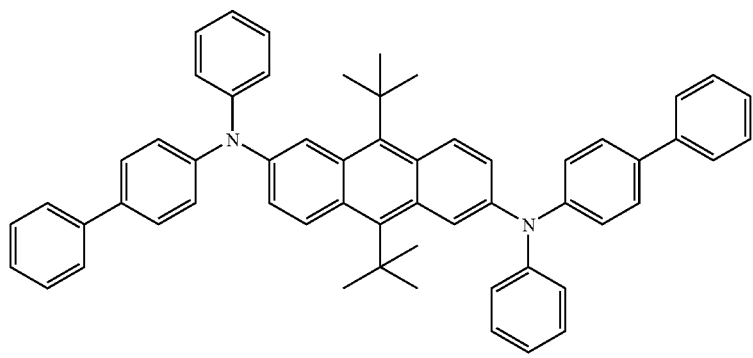
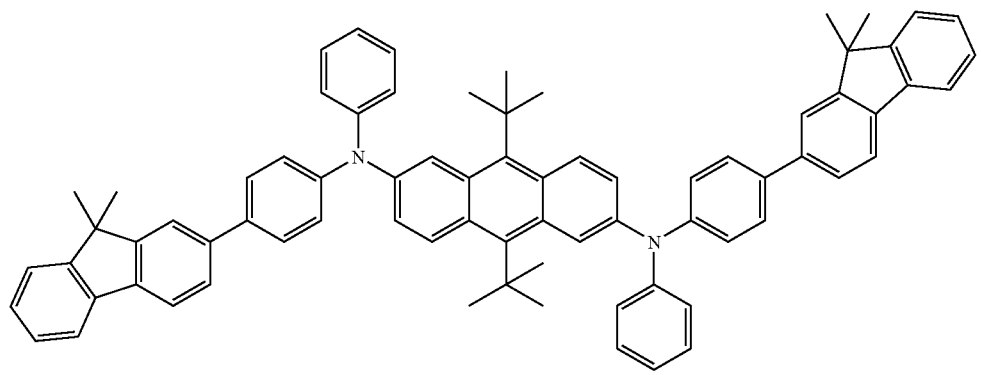

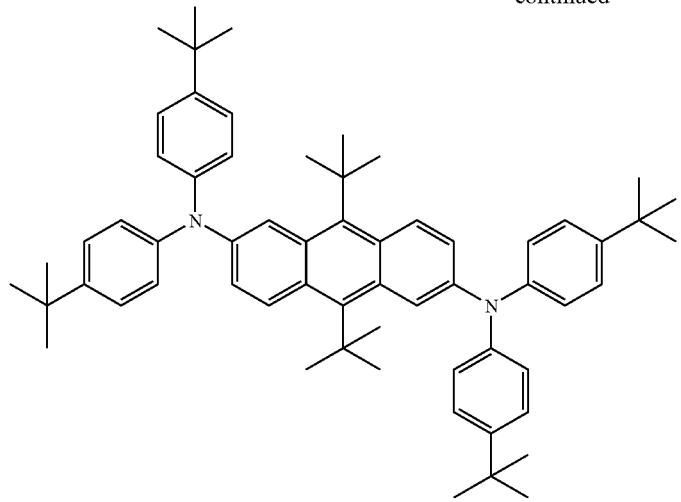
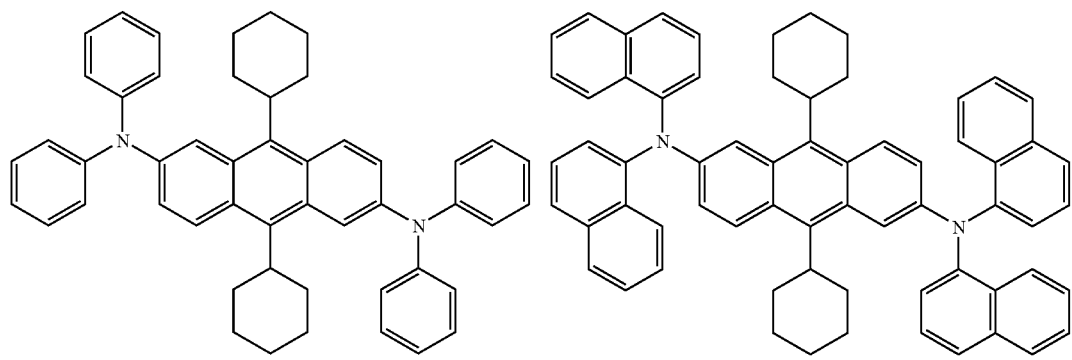
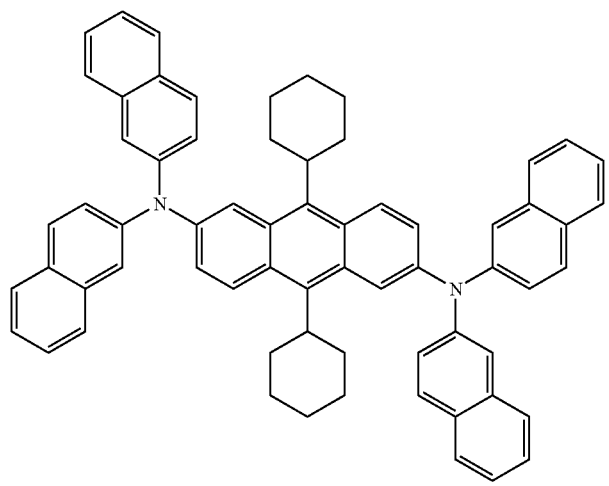

-continued
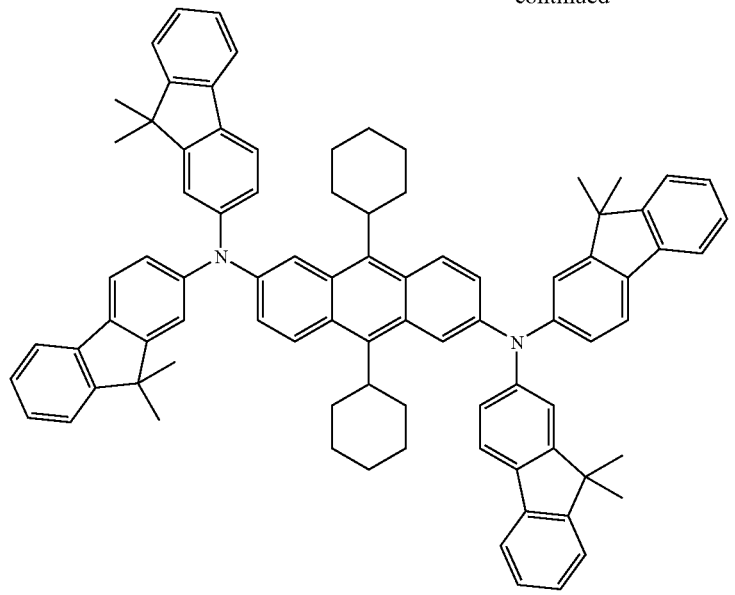
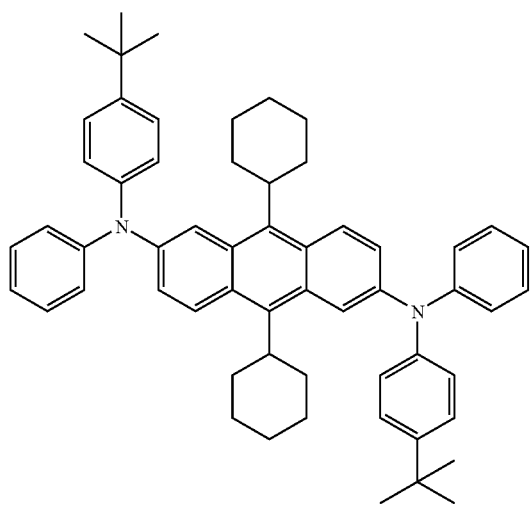
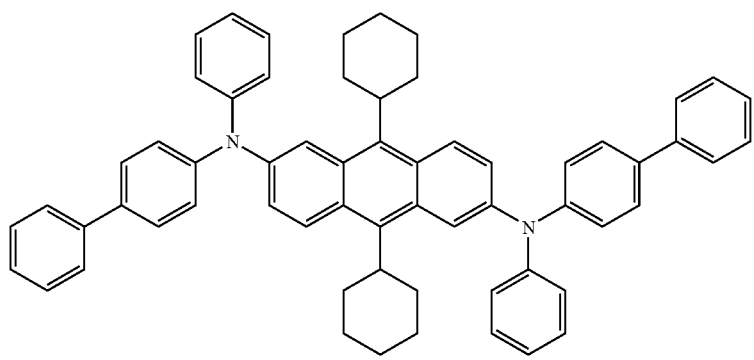

-continued
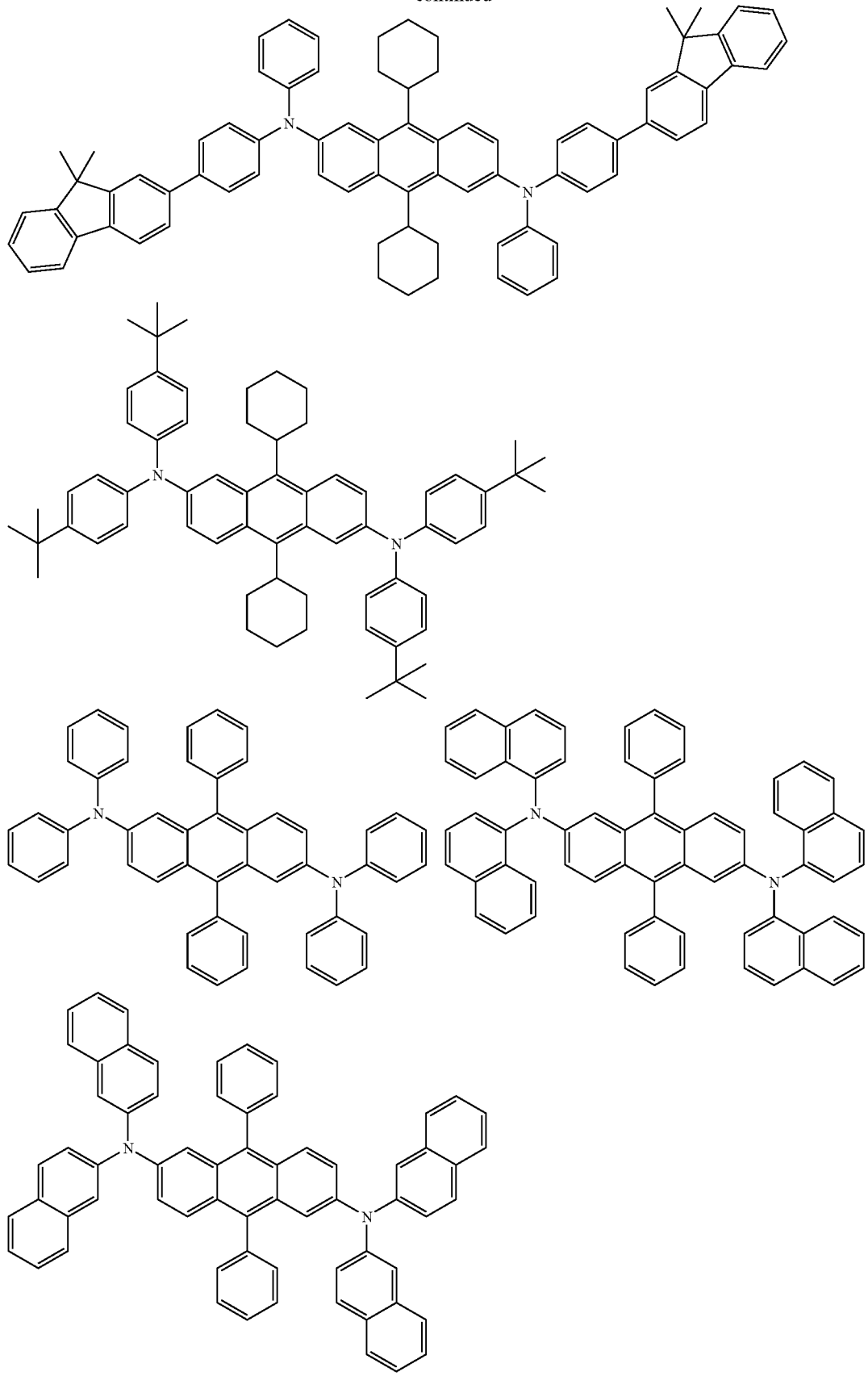

-continued
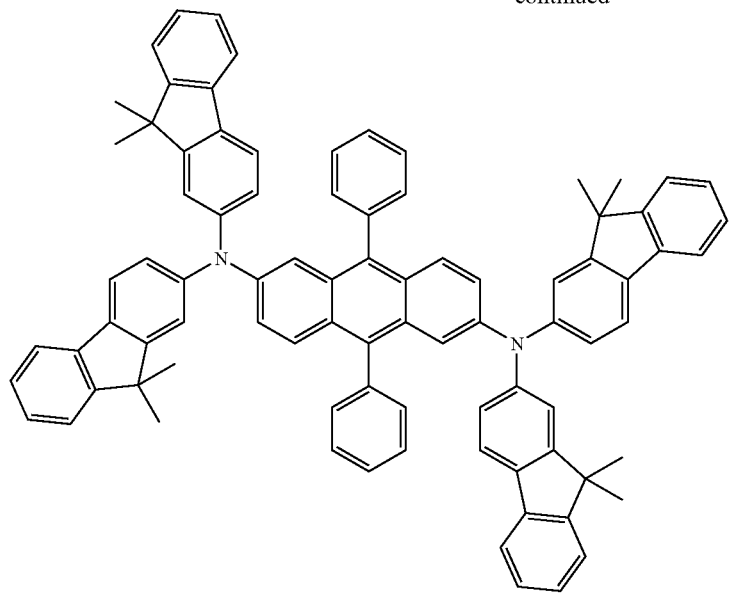
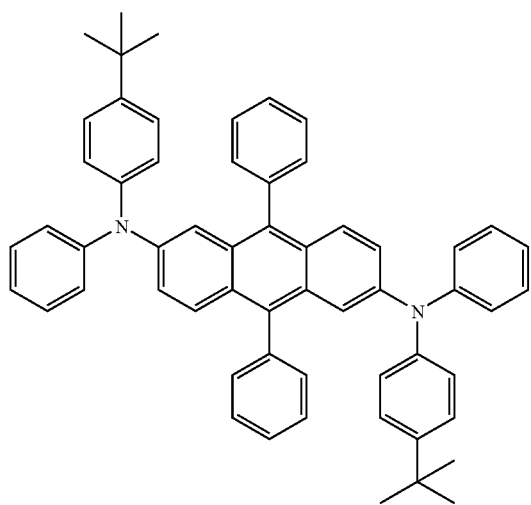
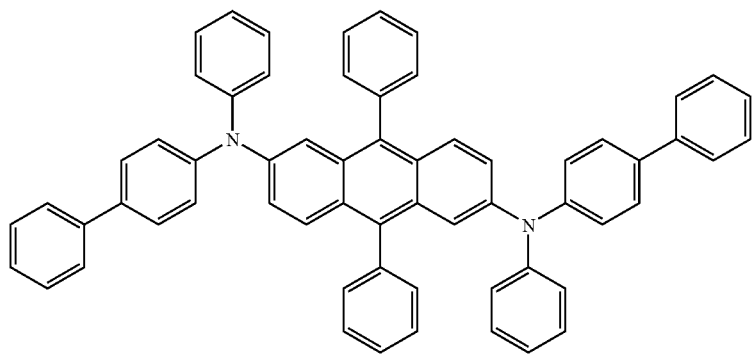

-continued
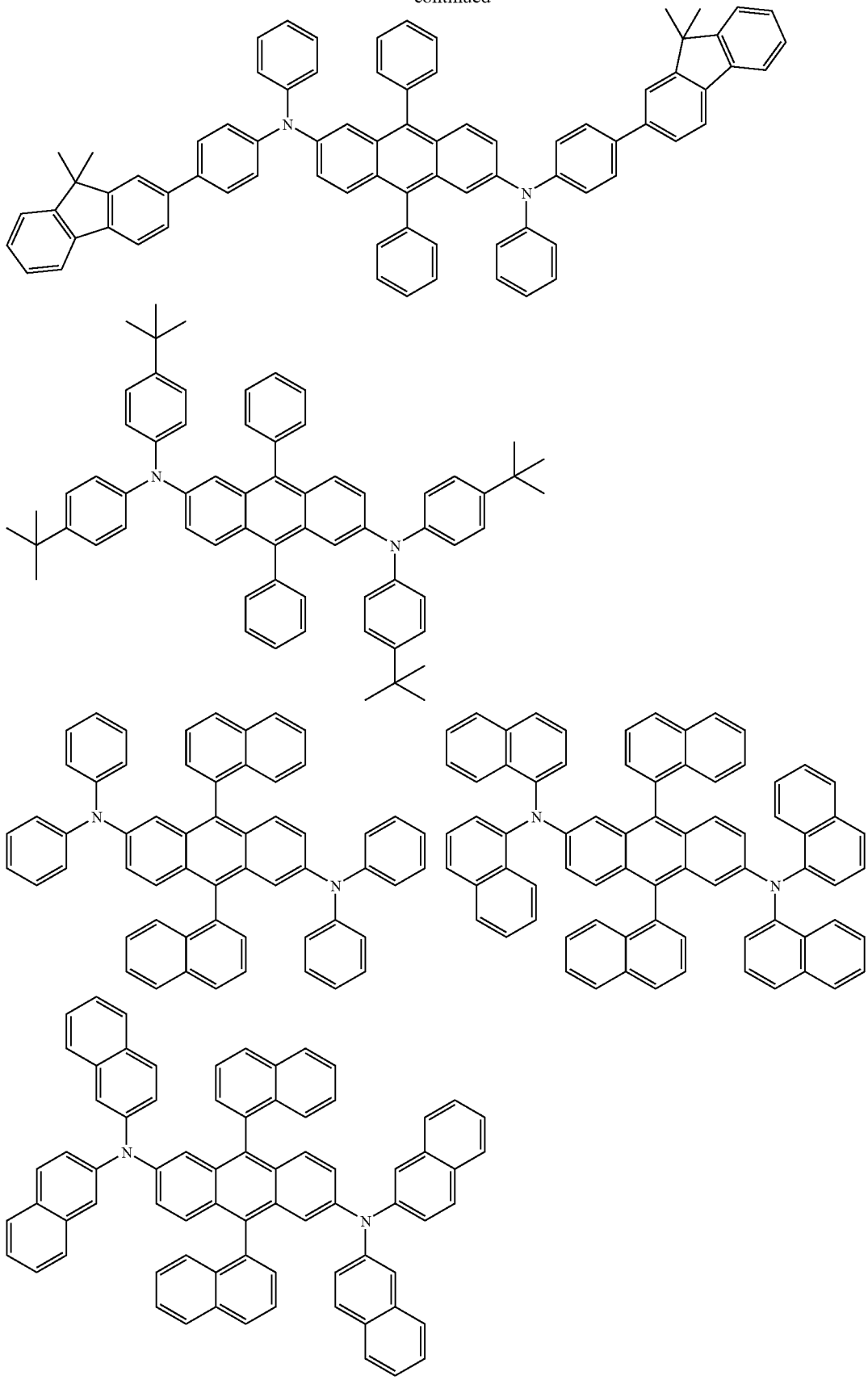

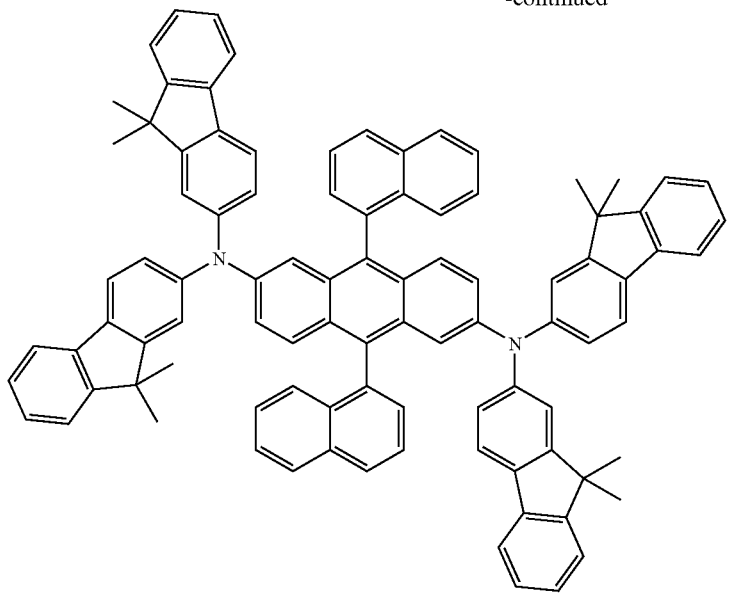
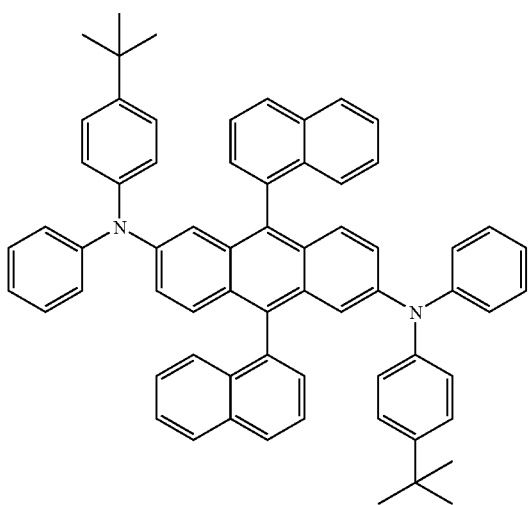
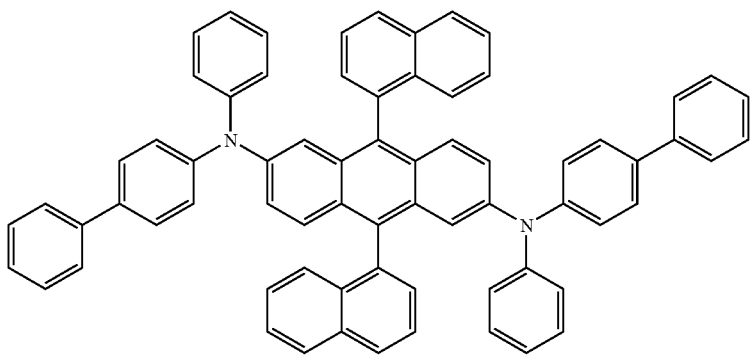

269
270
-continued
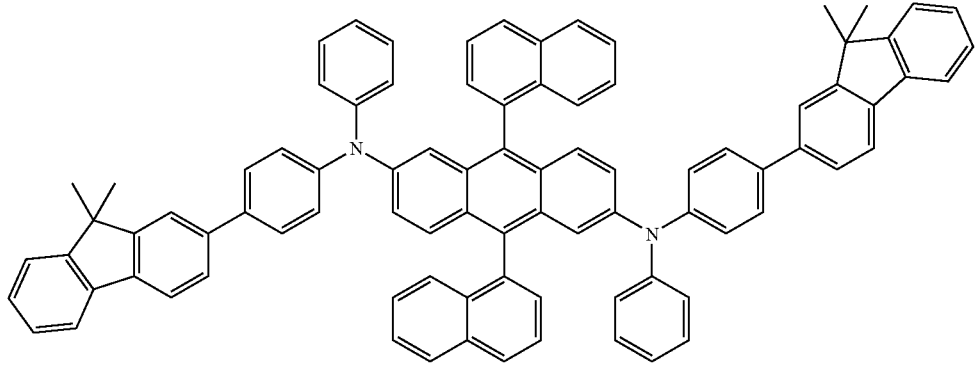
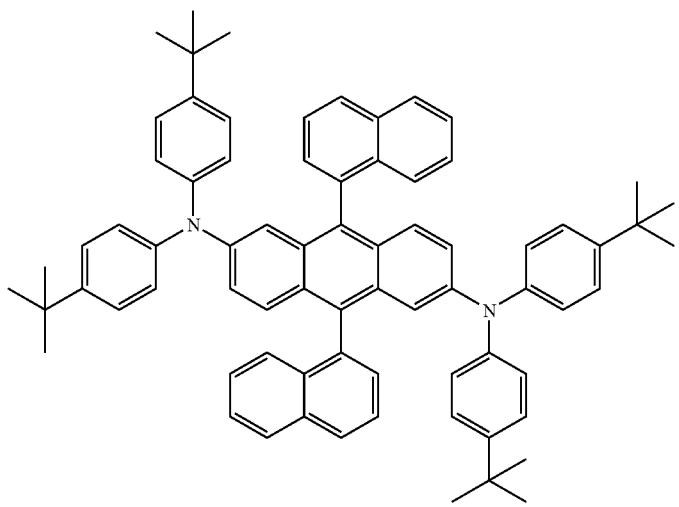
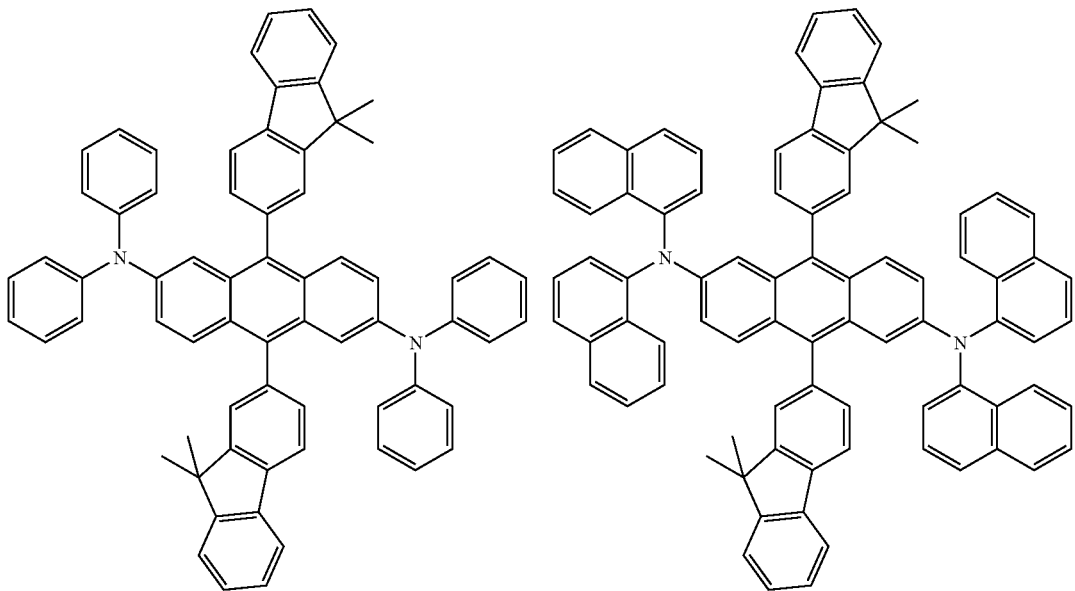

-continued
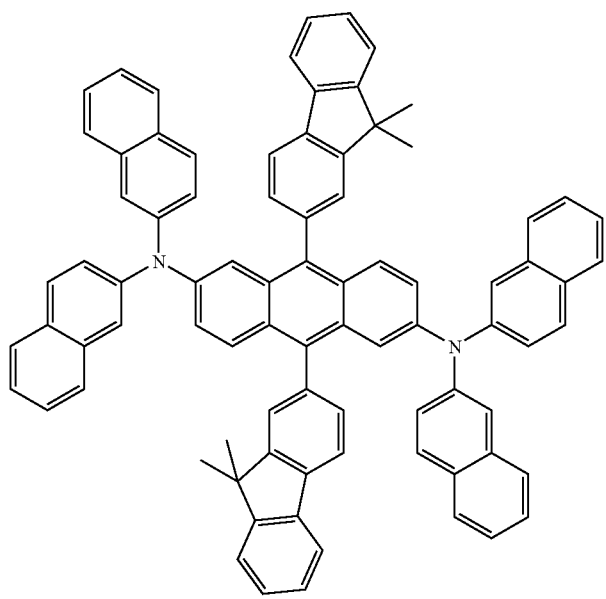
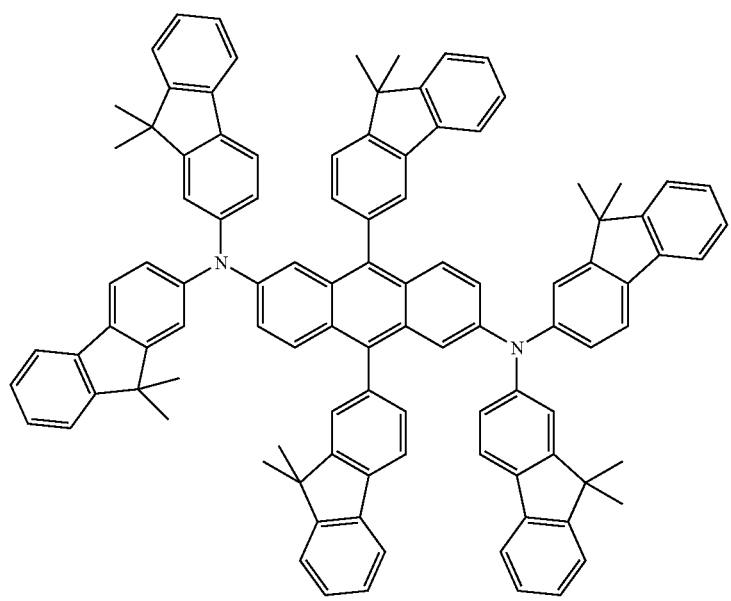

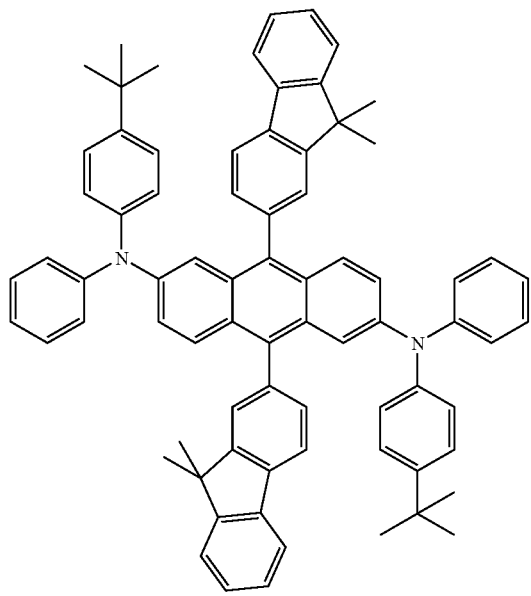
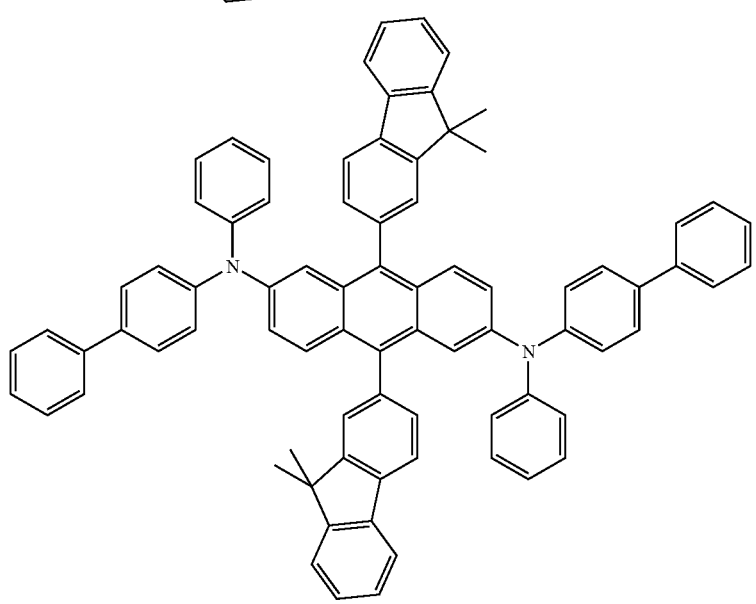
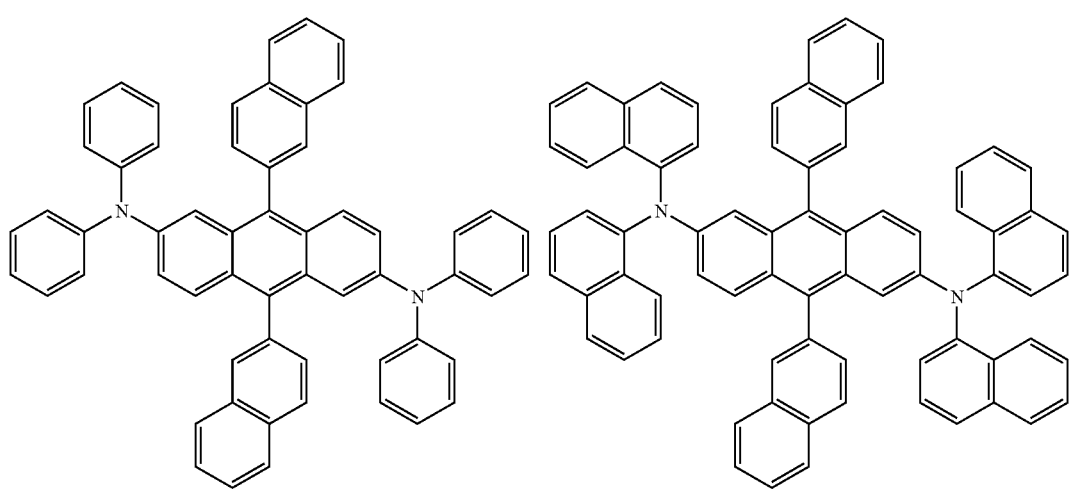

-continued
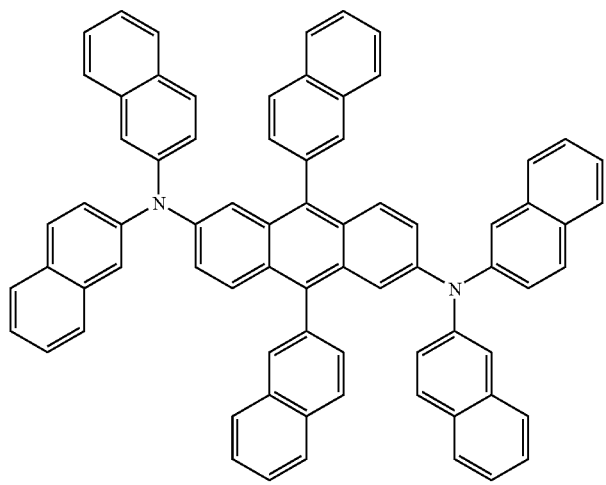
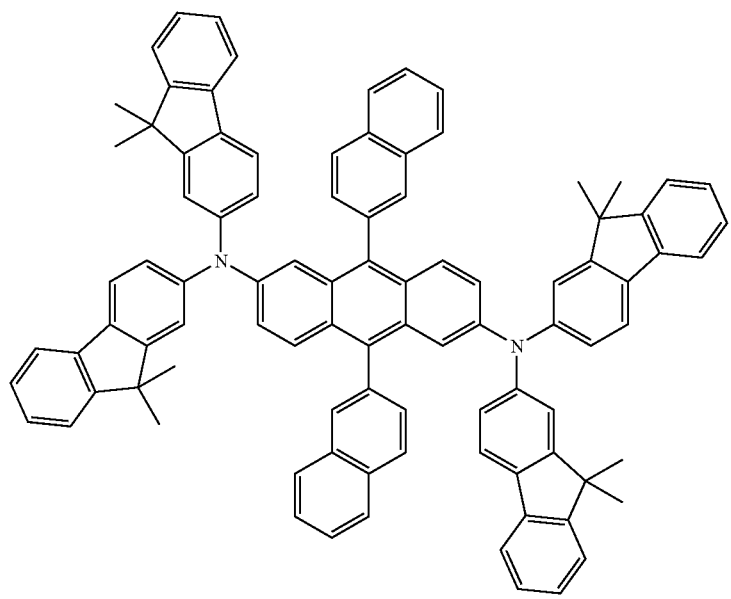
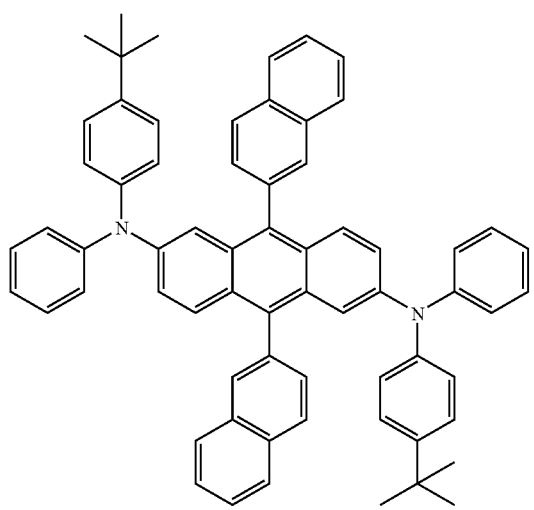

-continued
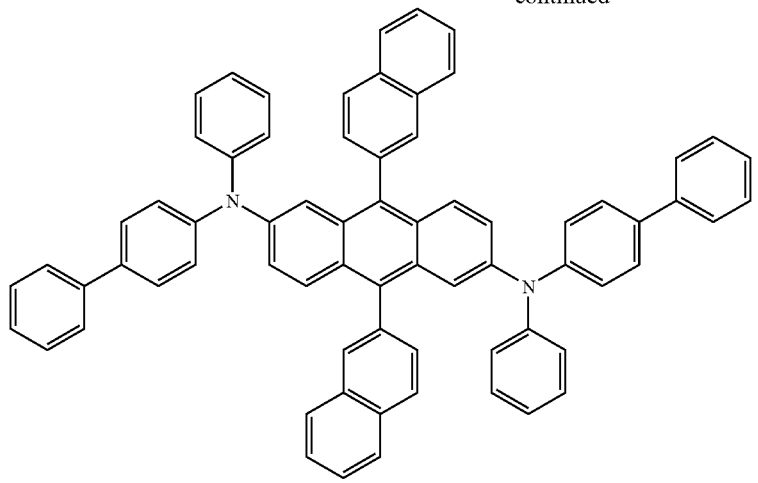
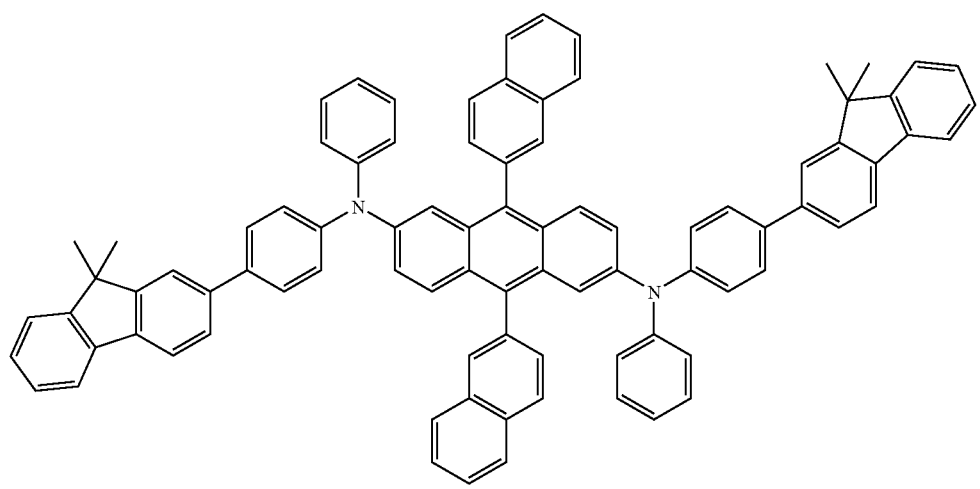
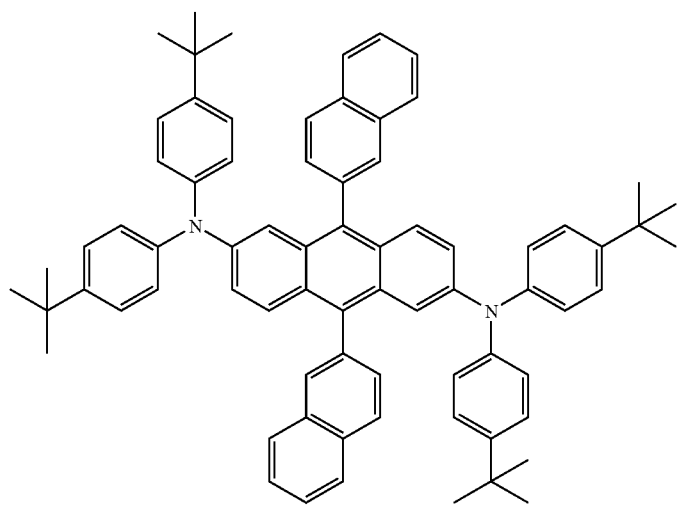

-continued
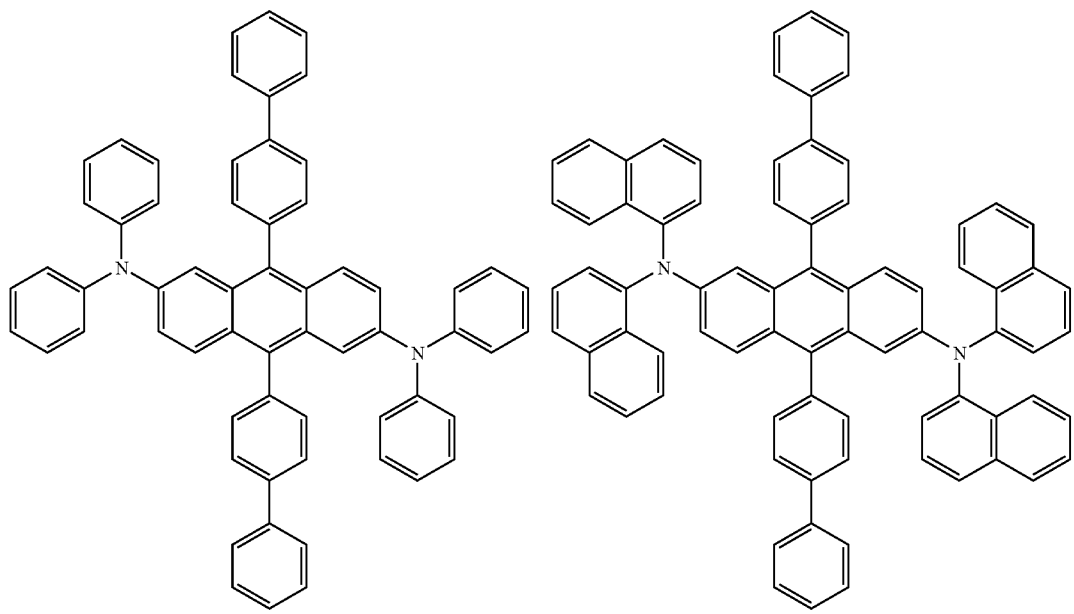
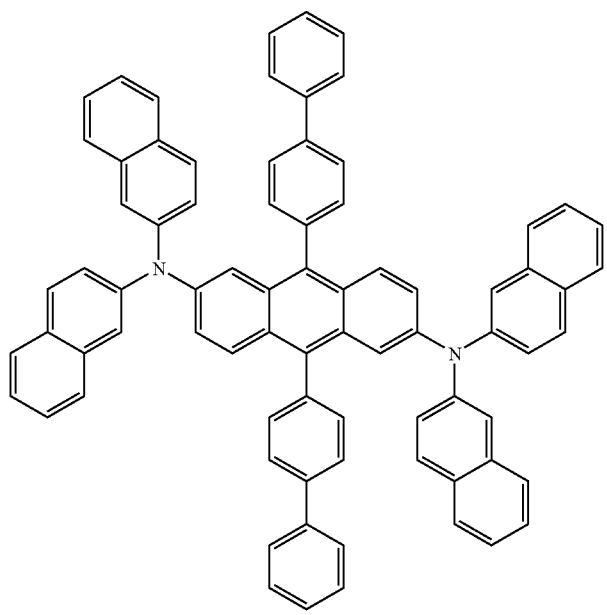

-continued
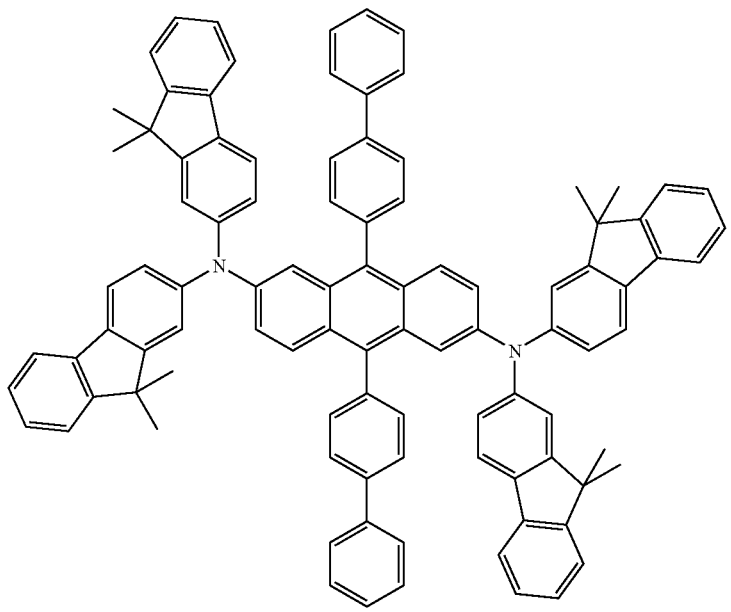
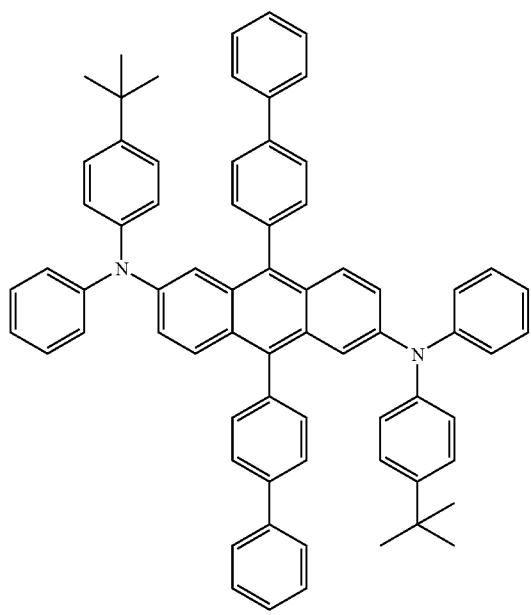

-continued
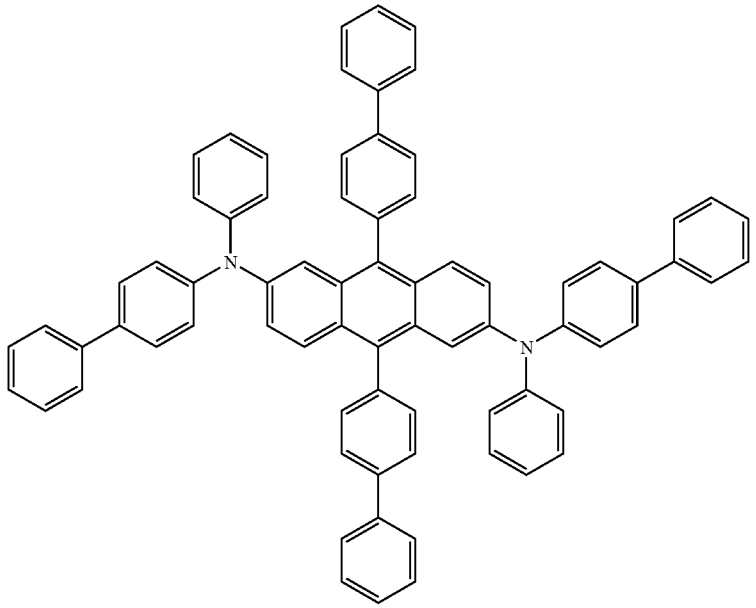
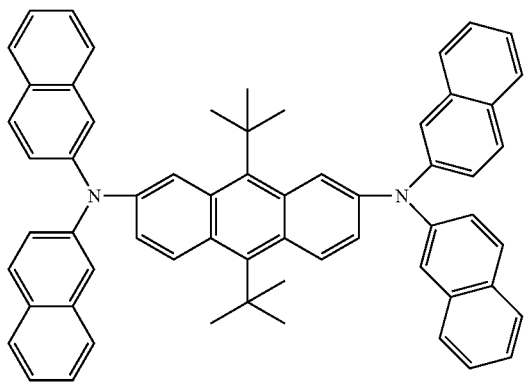
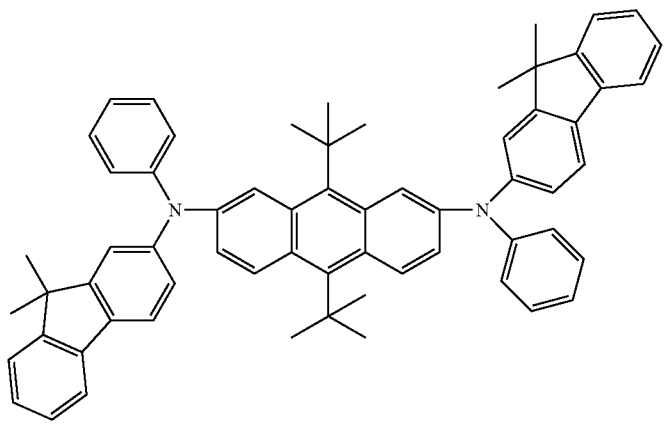
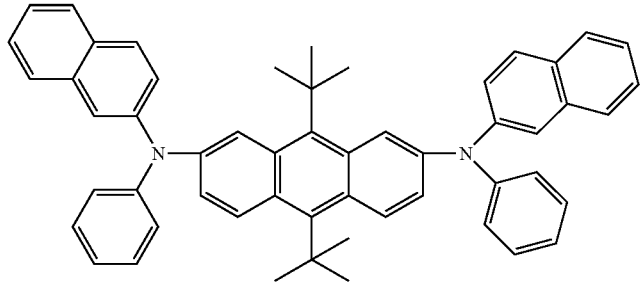

-continued
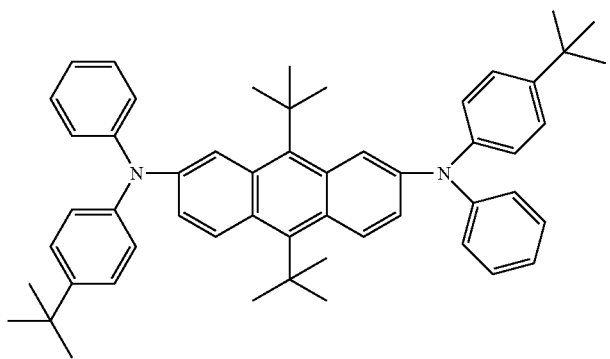
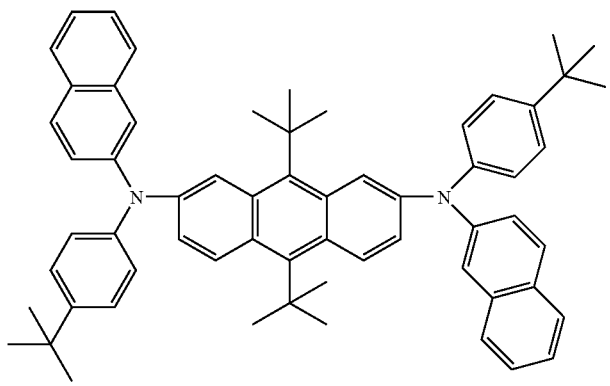
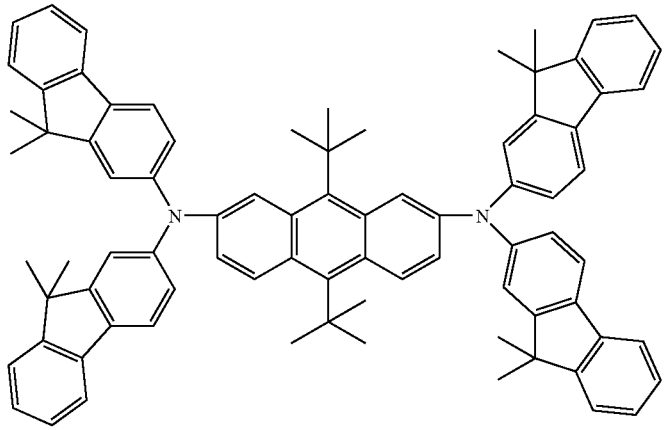
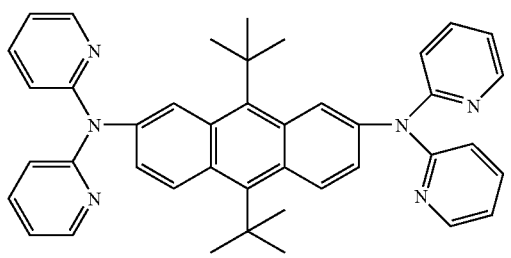

-continued
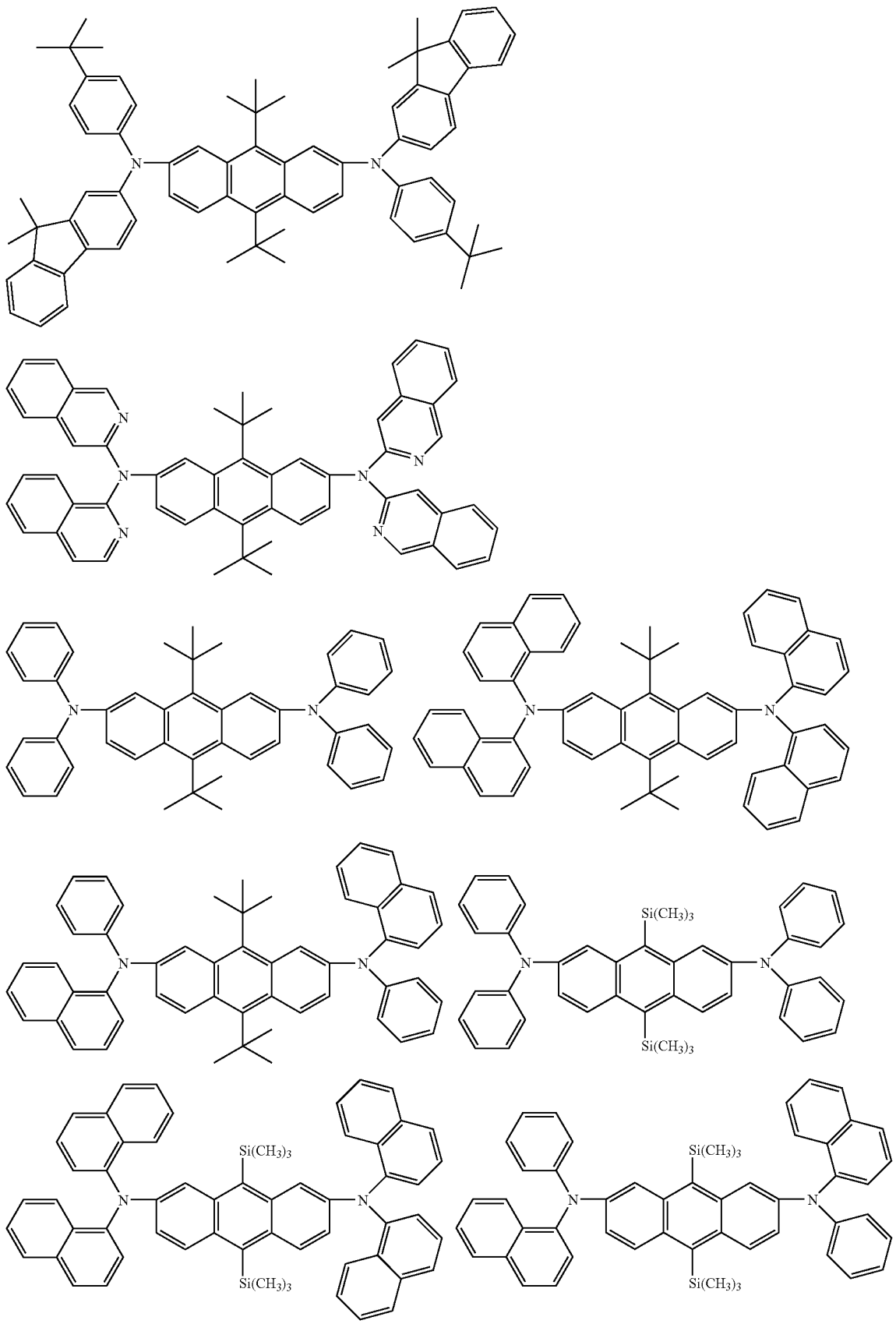

-continued
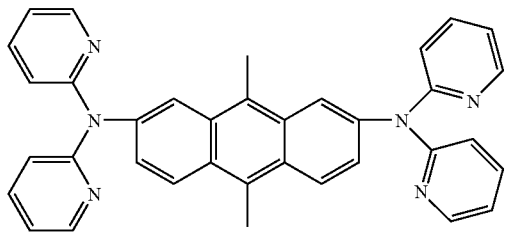
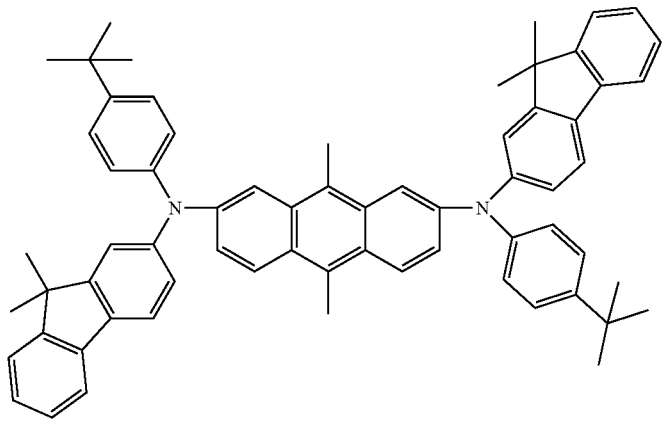
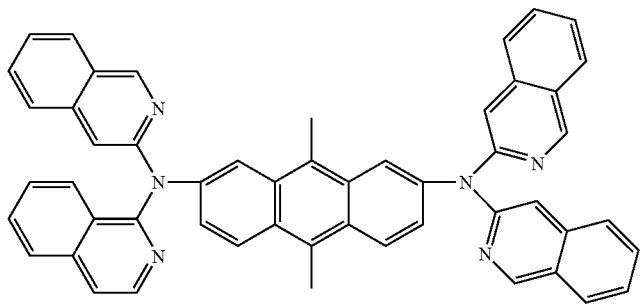
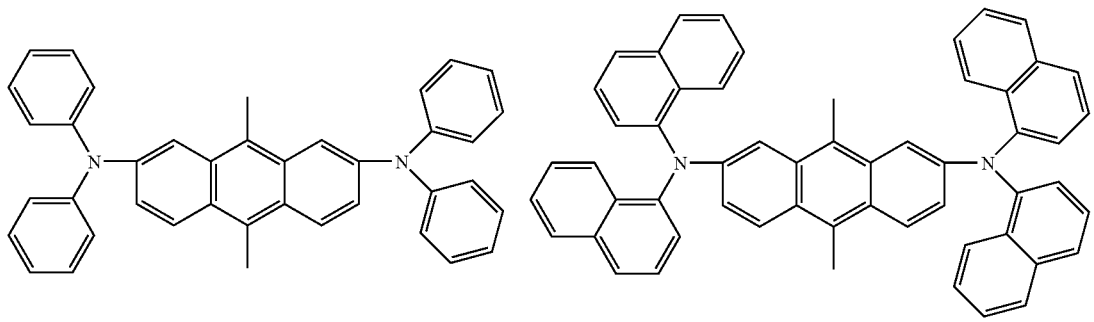
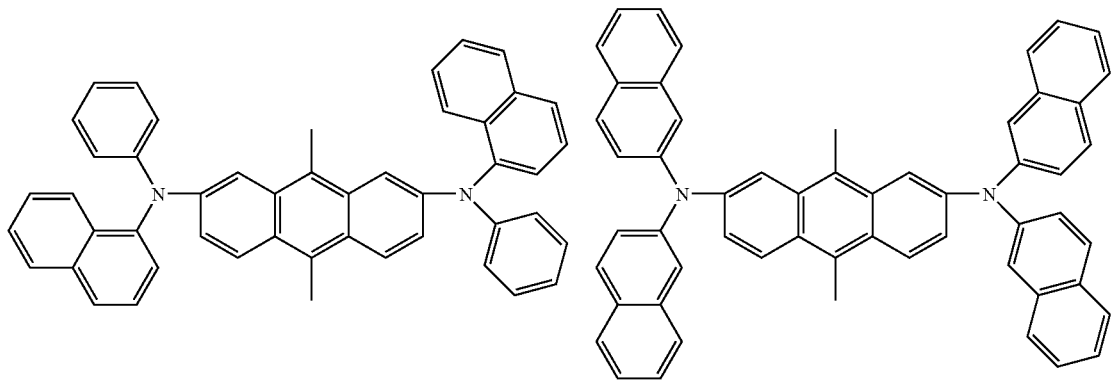

-continued
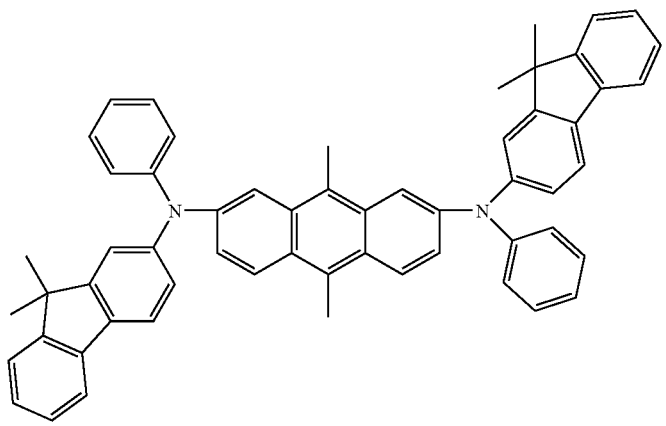
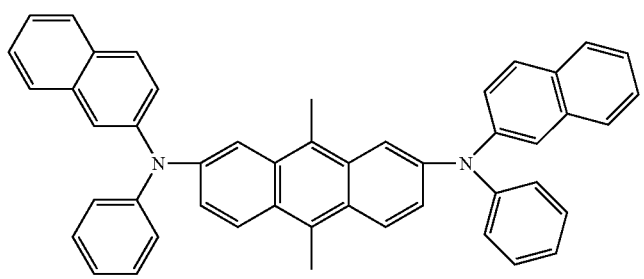
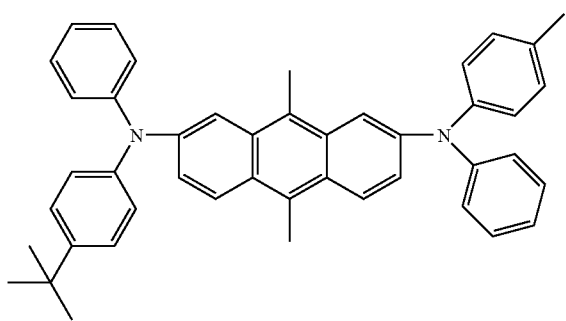
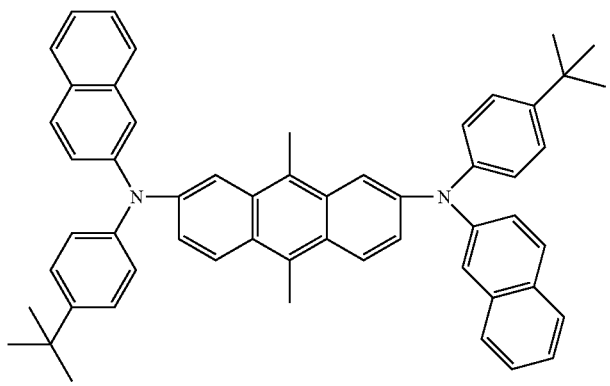

-continued
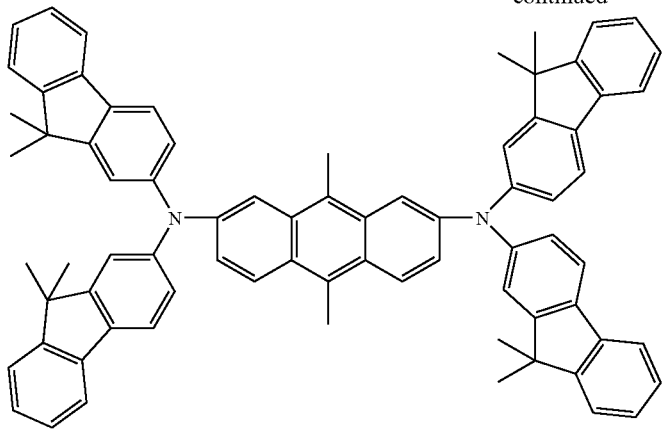
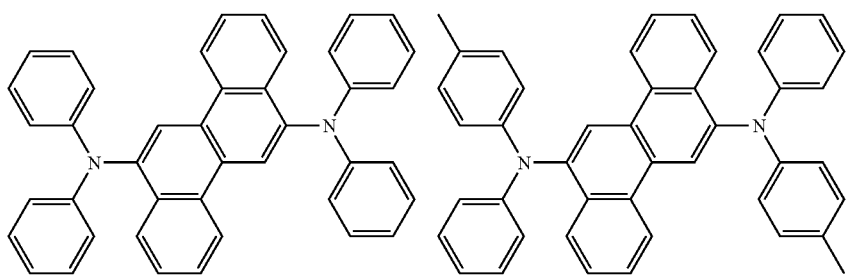
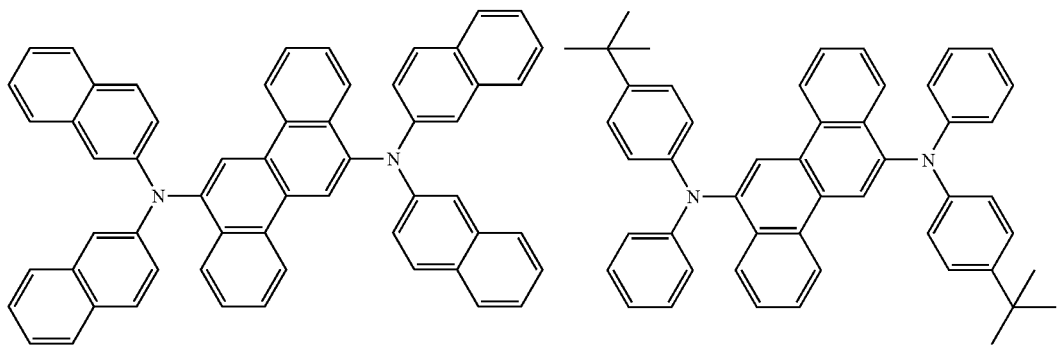
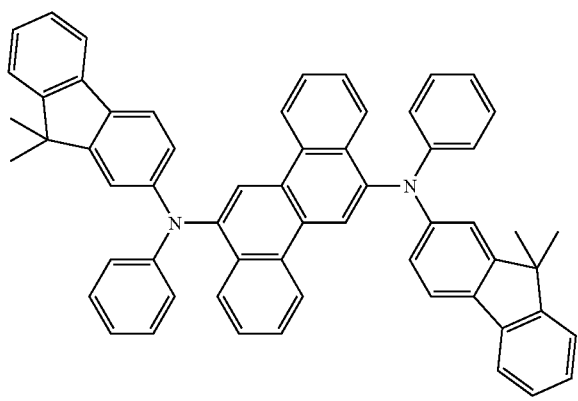

-continued
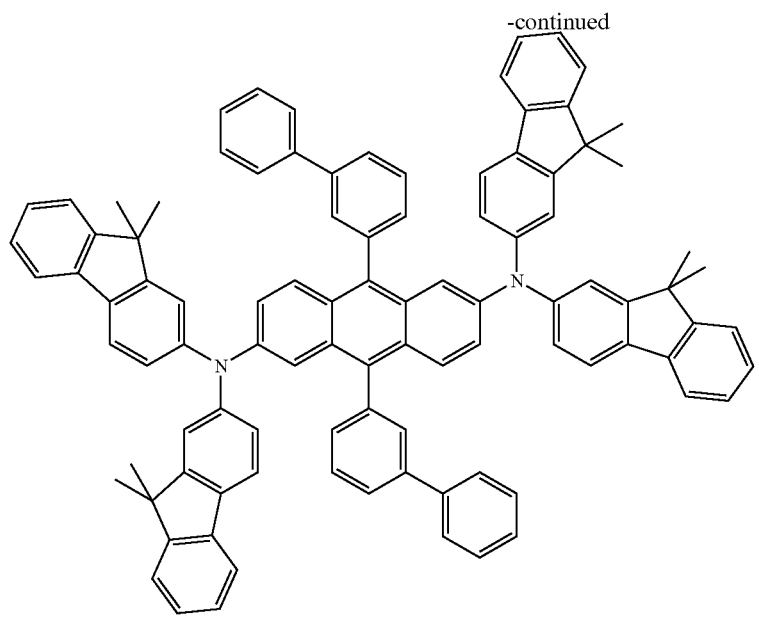
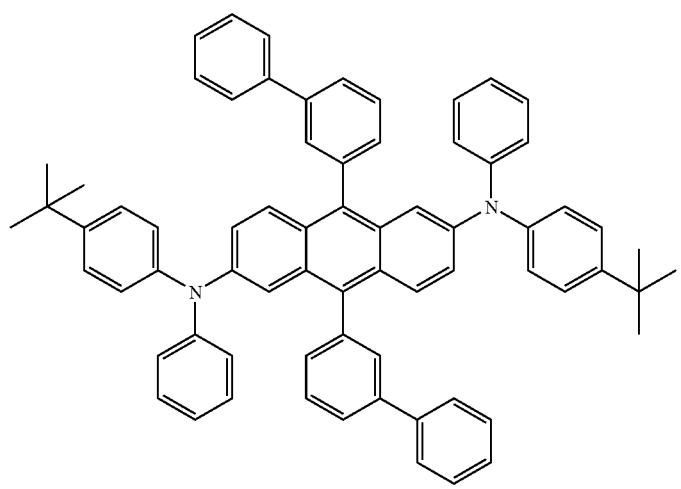
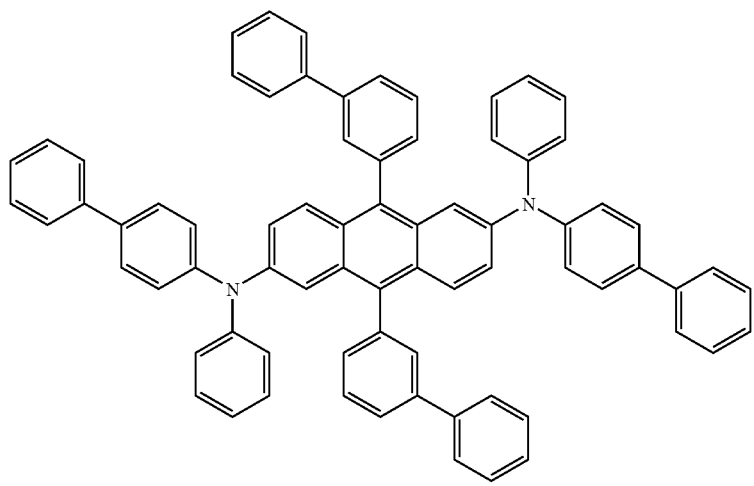

-continued
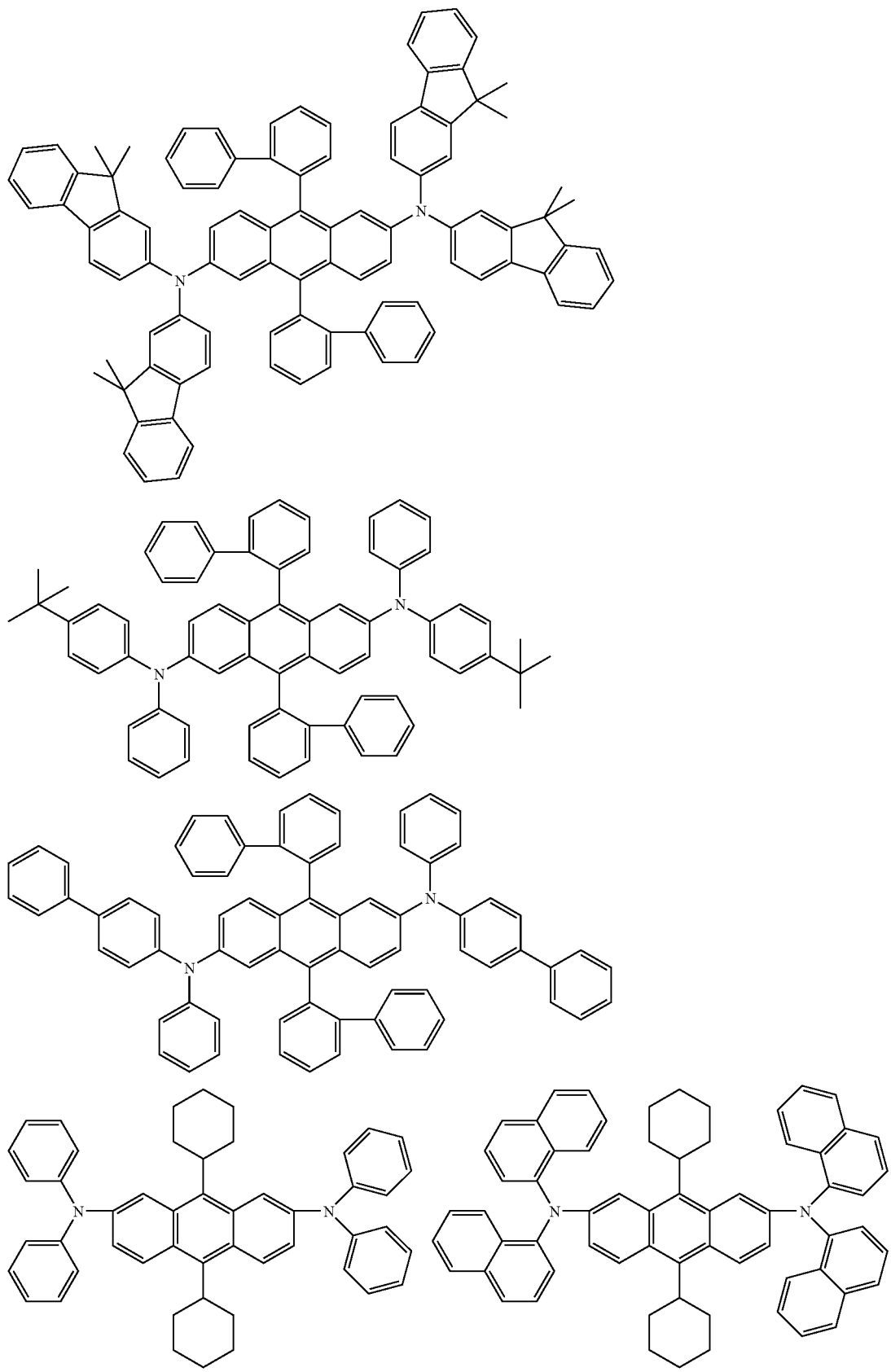

-continued
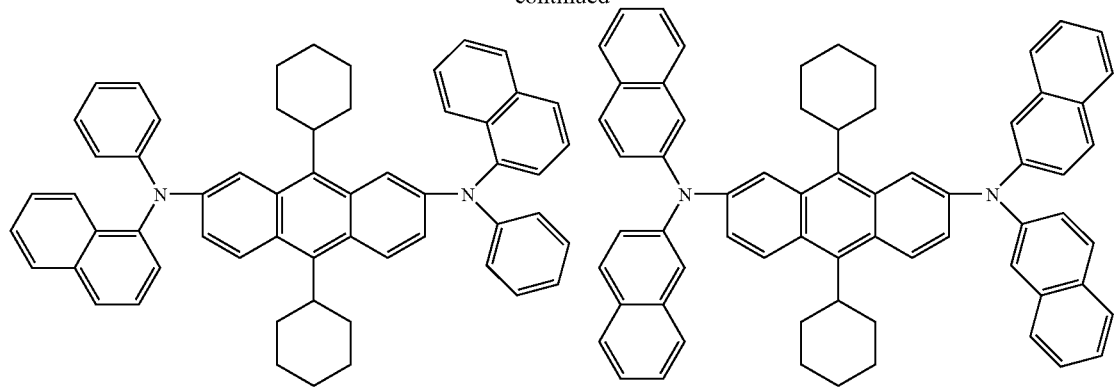
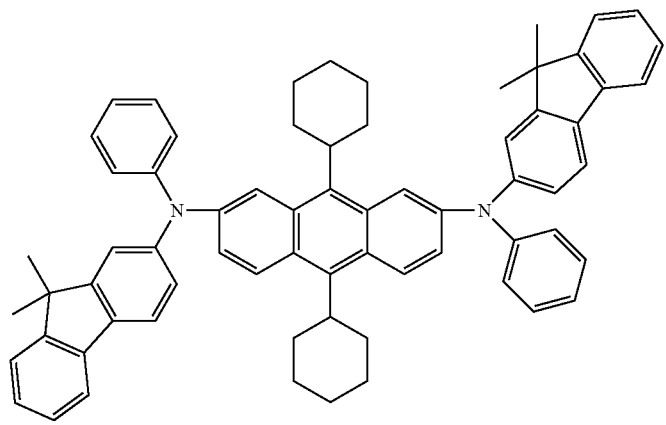
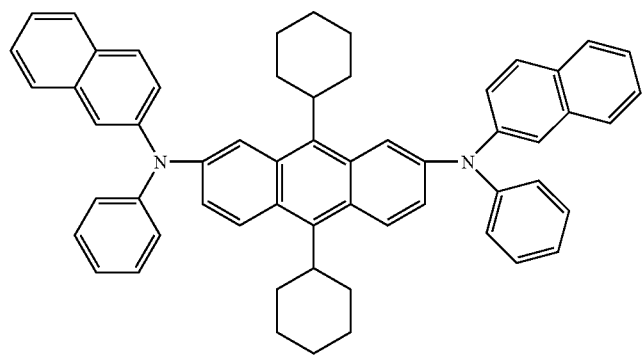
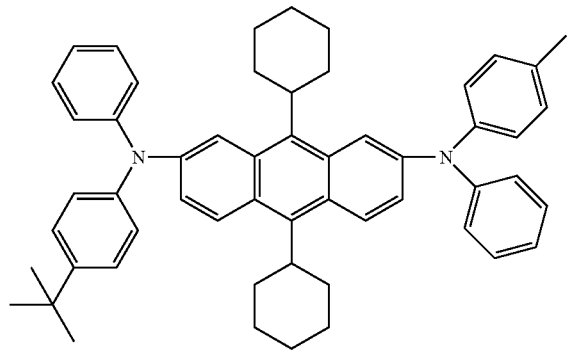

-continued
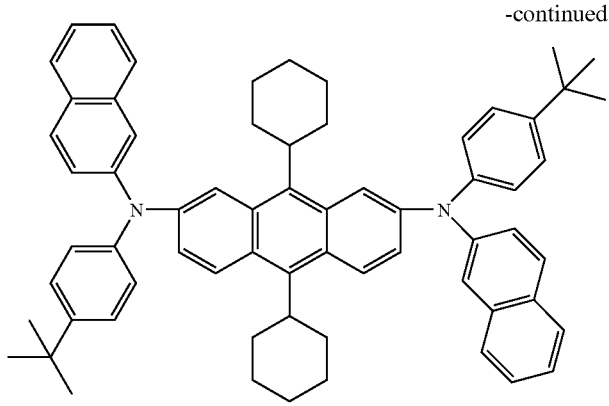
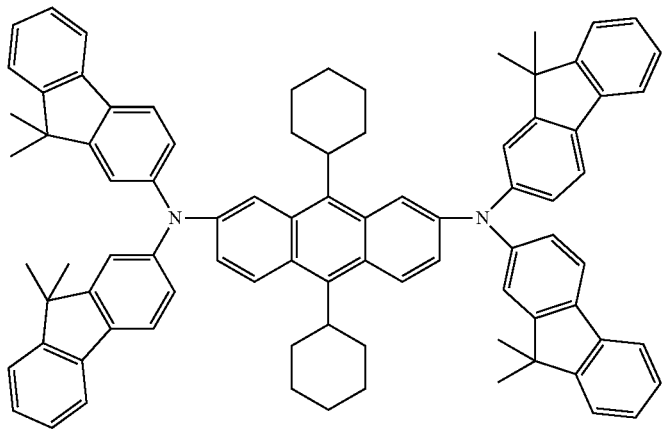
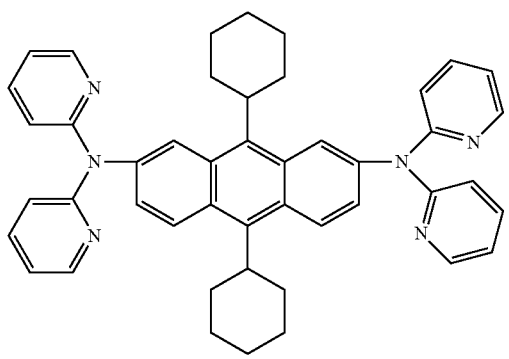
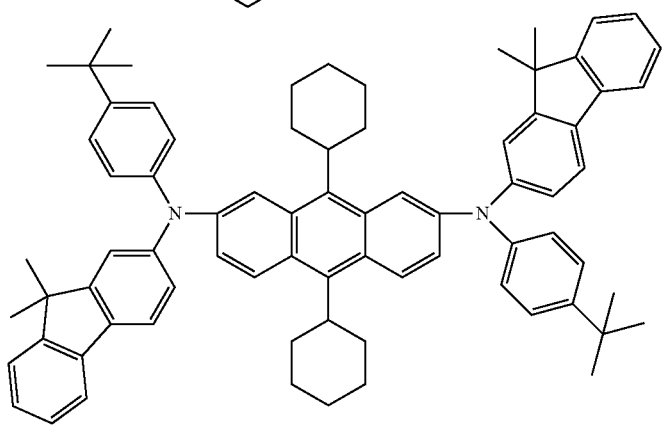

-continued
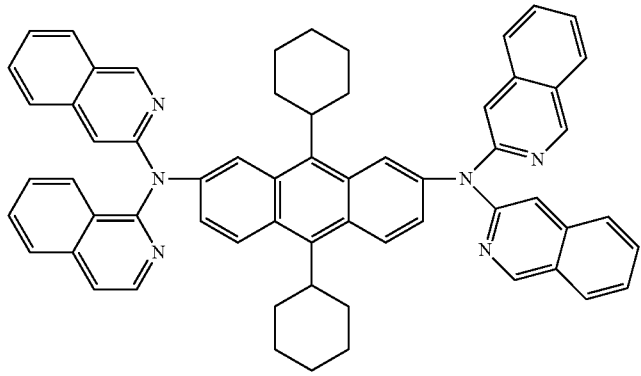 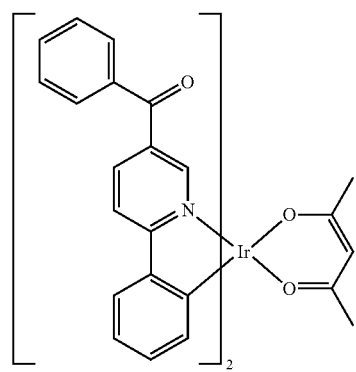
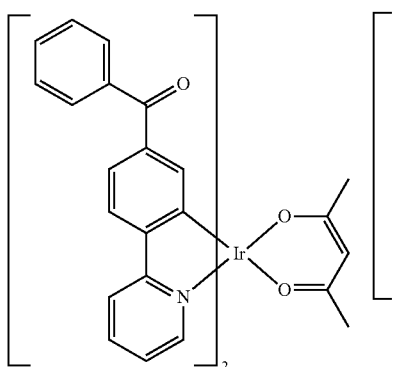 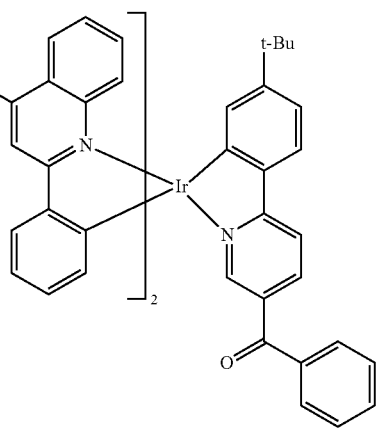
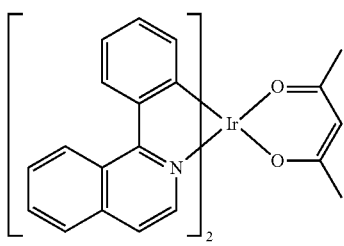 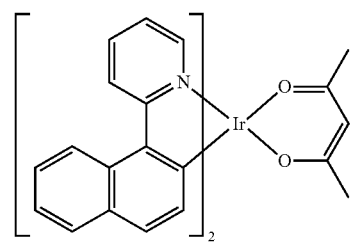 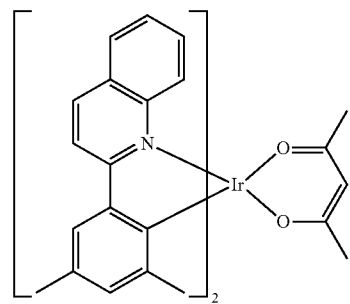
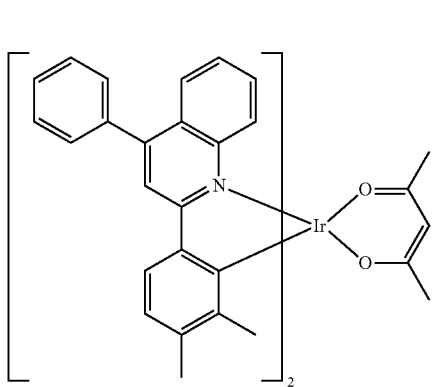 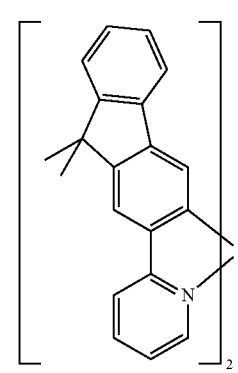 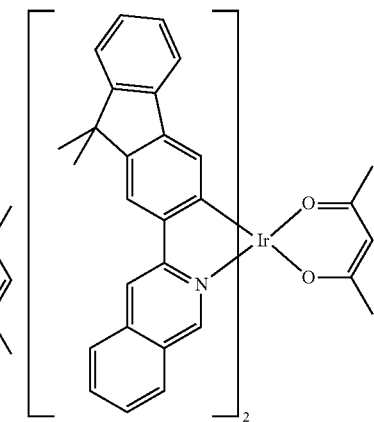

-continued
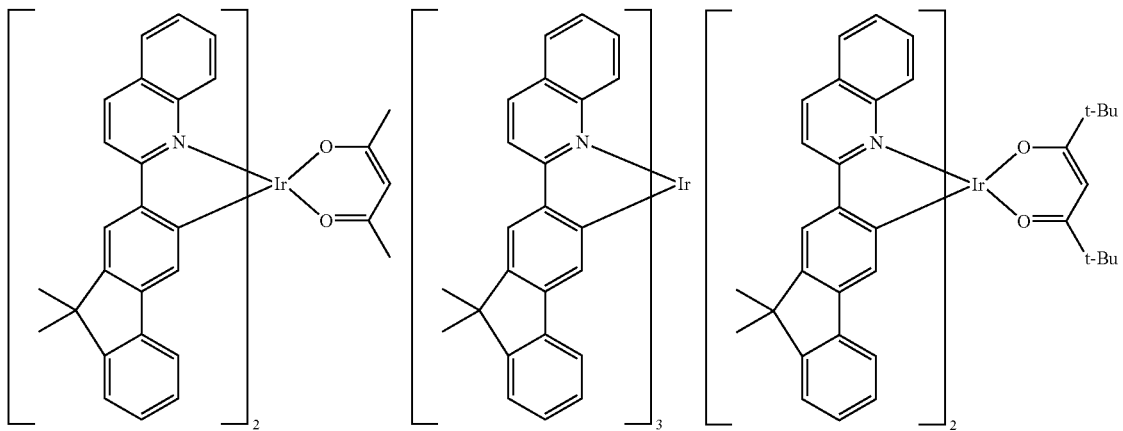
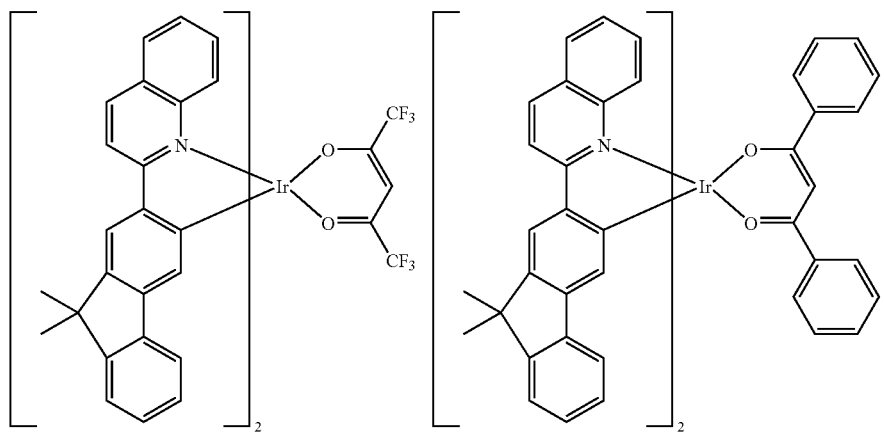
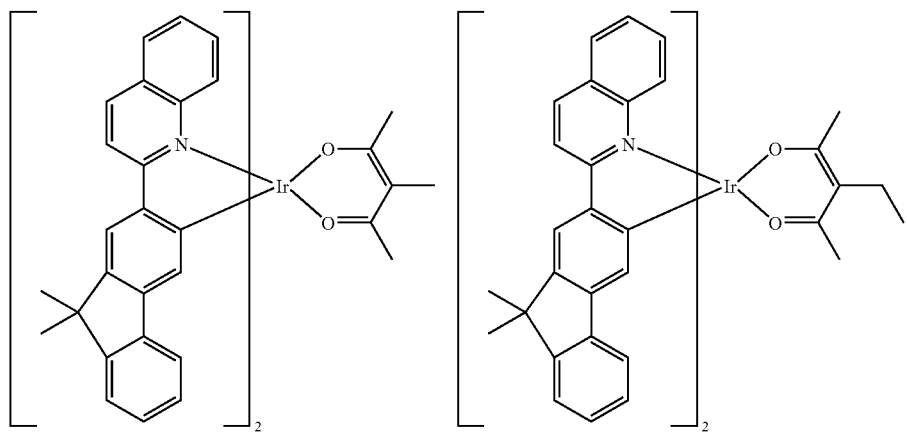

-continued
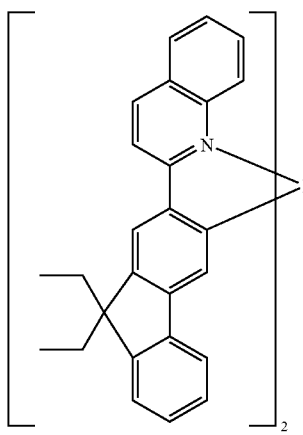 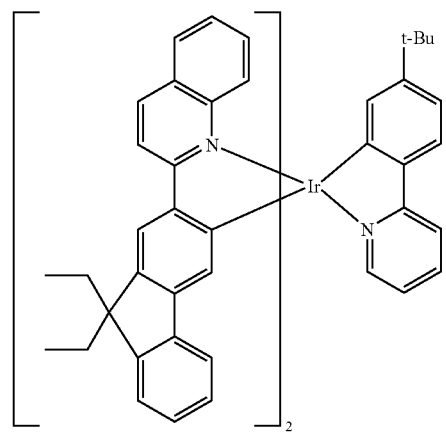
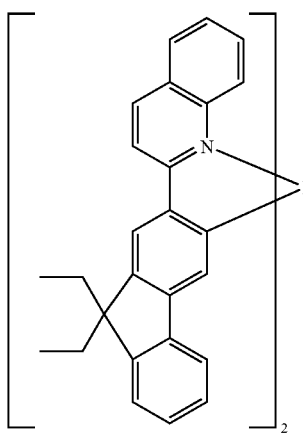 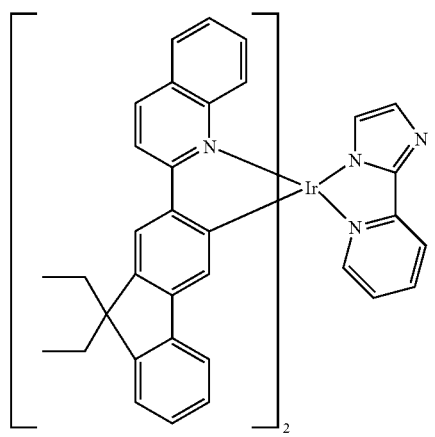
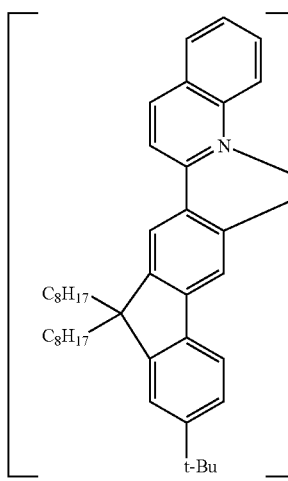 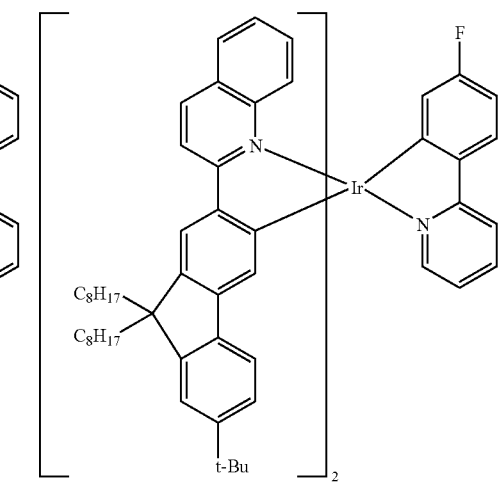

309
310
-continued
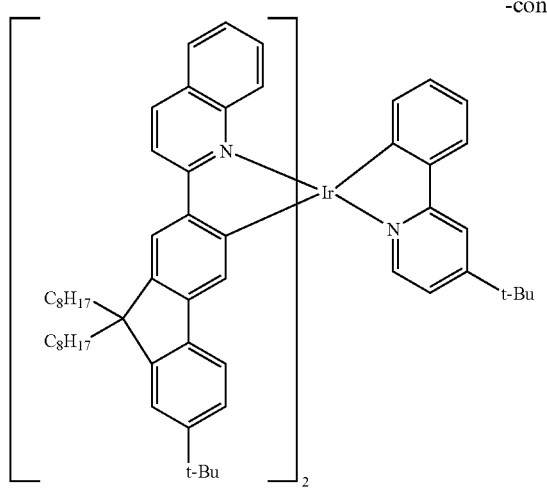
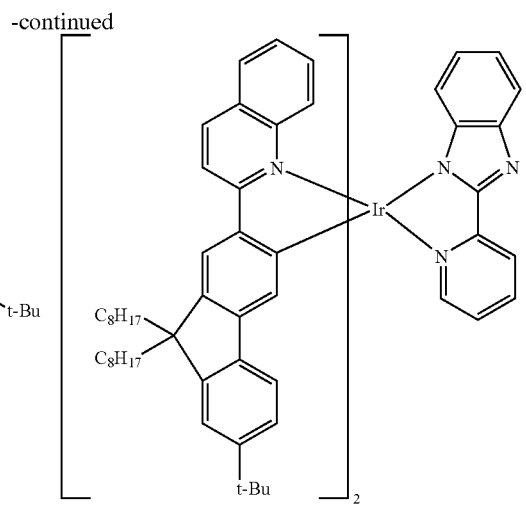
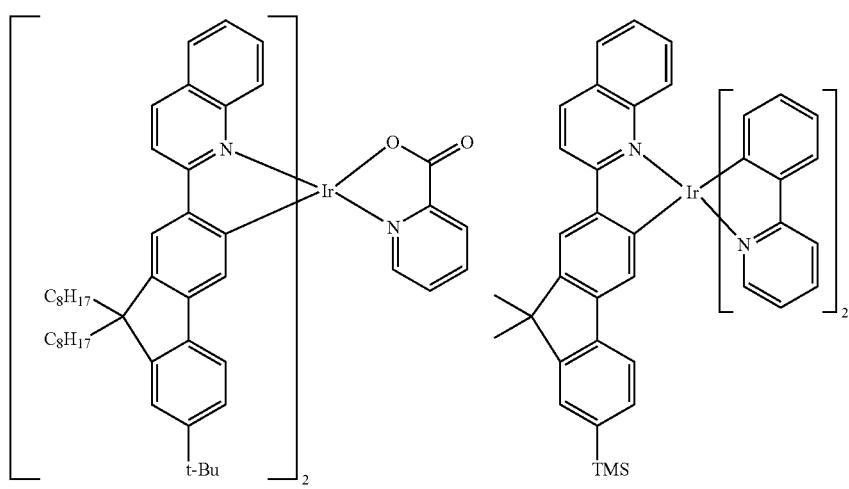
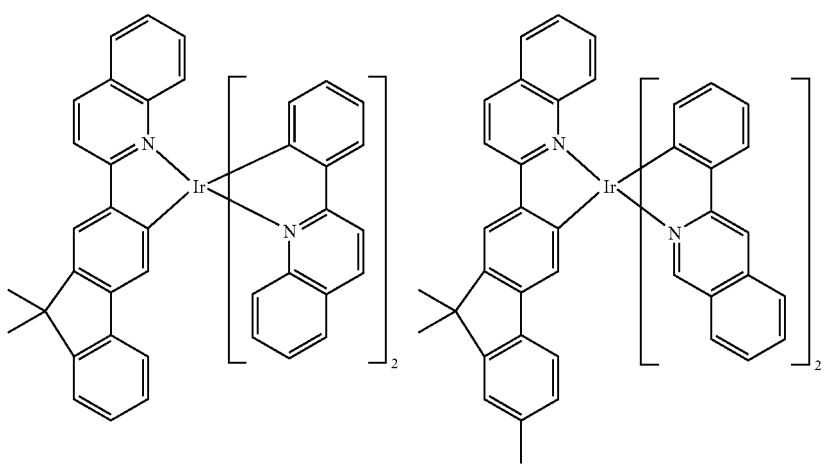

-continued
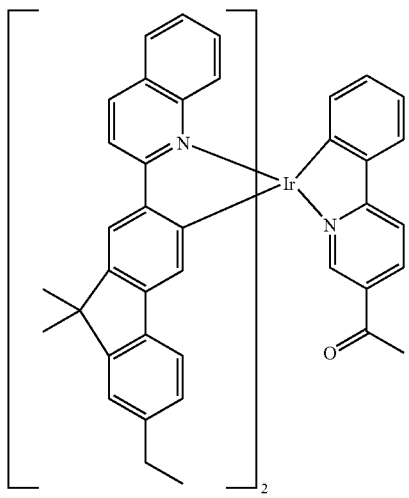
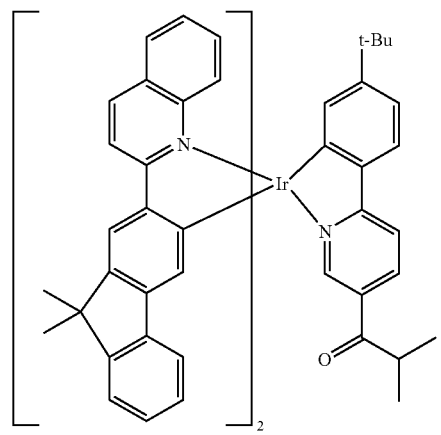
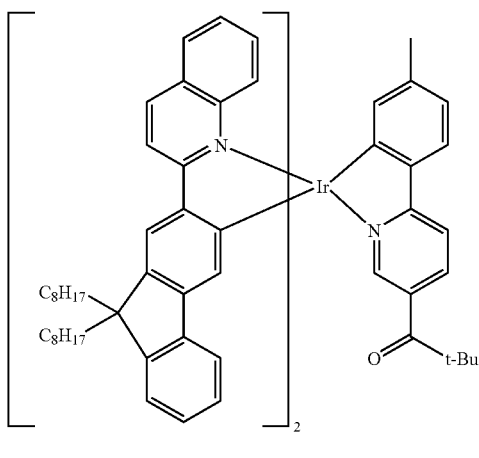
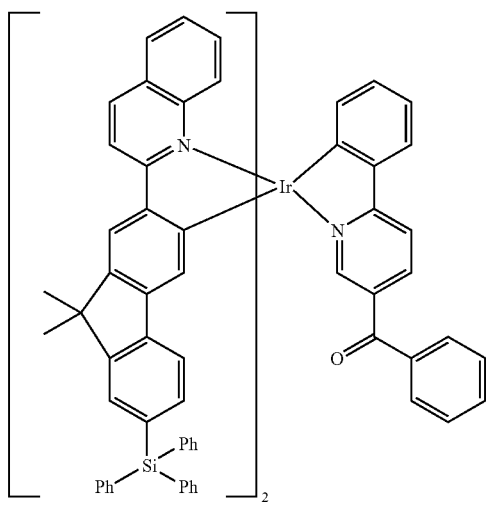
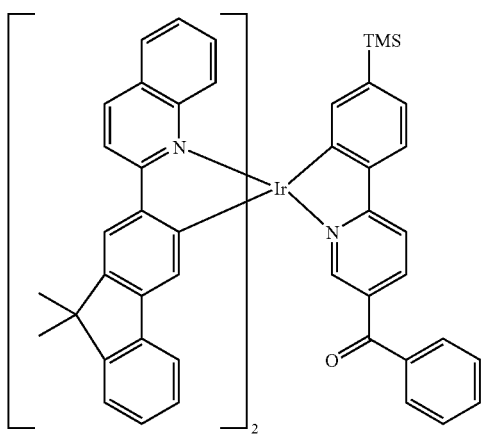
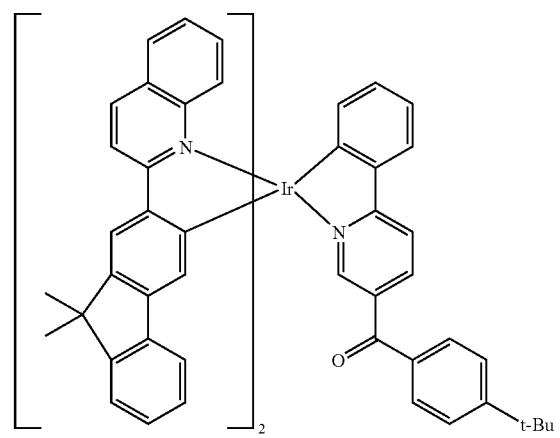

-continued
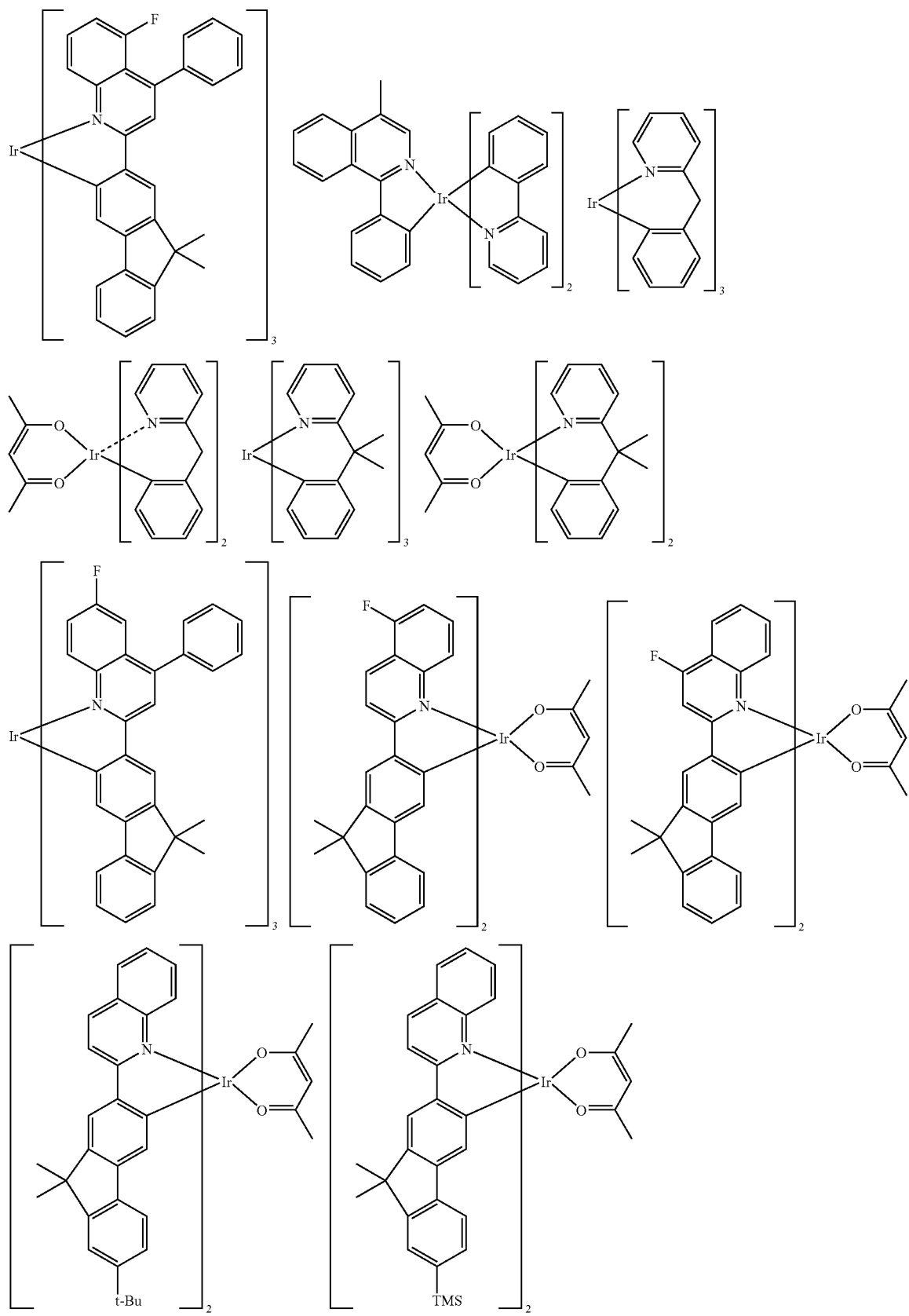

-continued
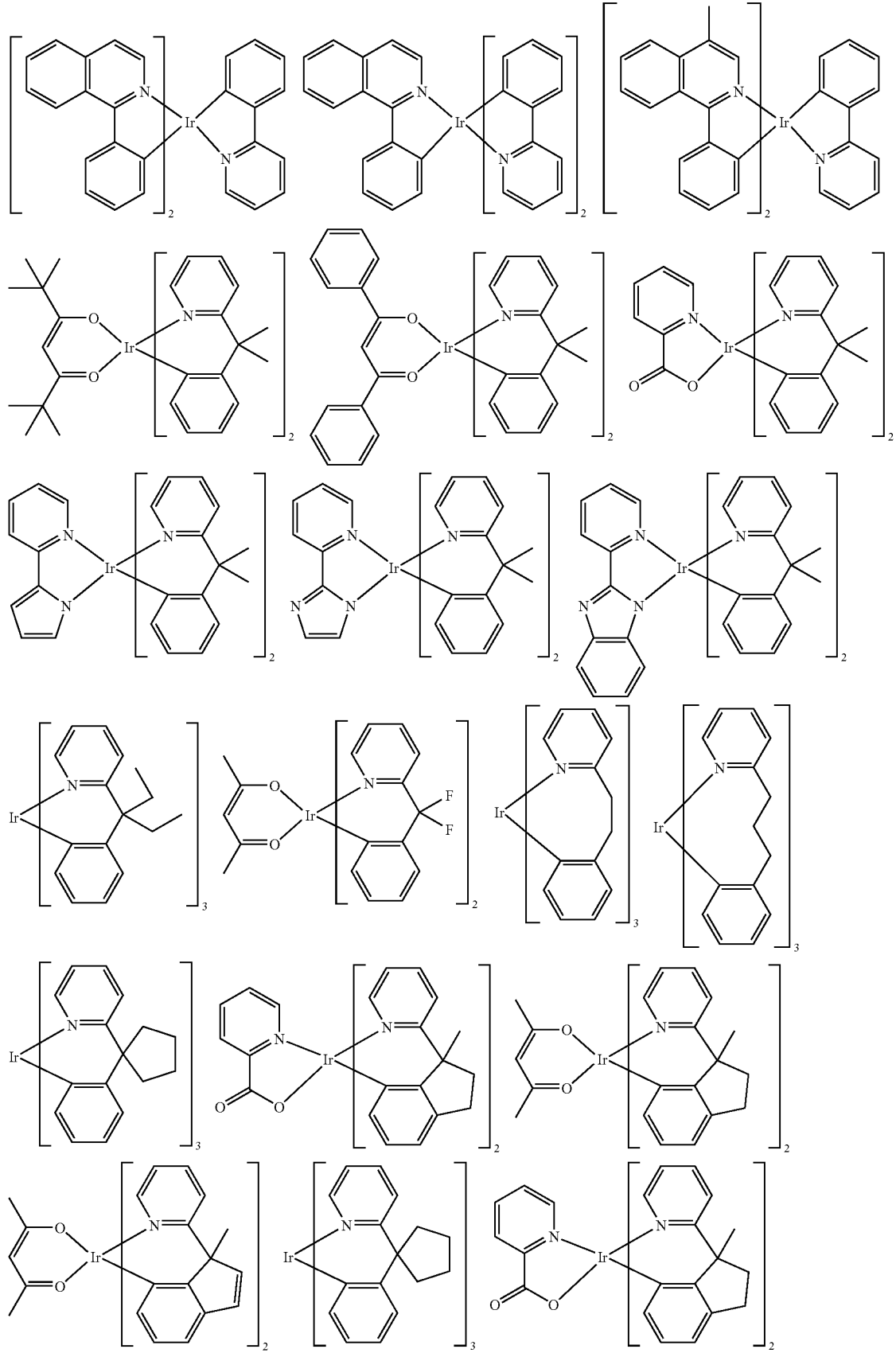

-continued
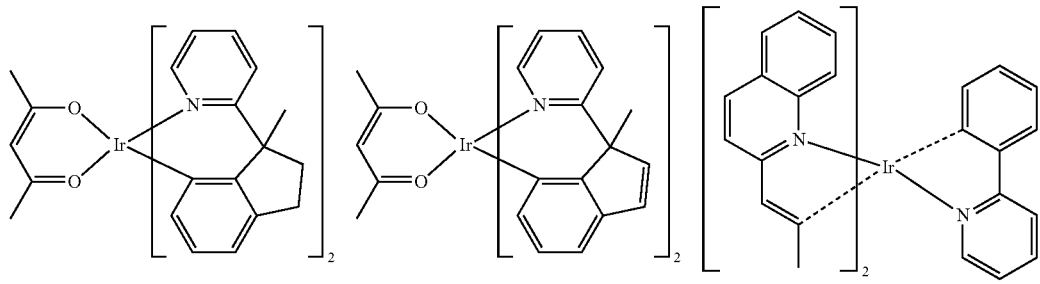
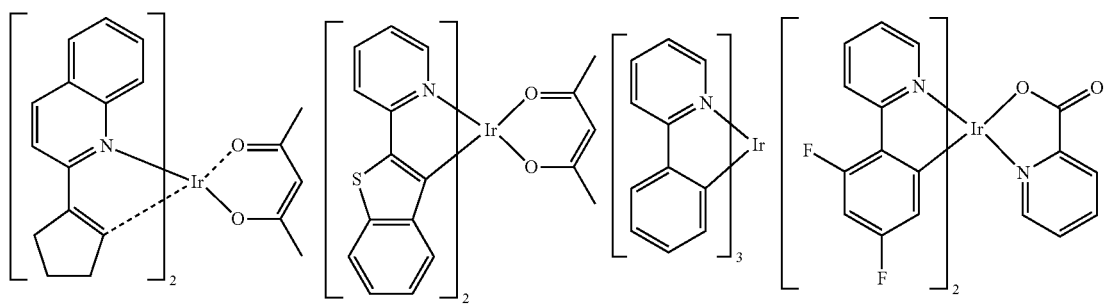
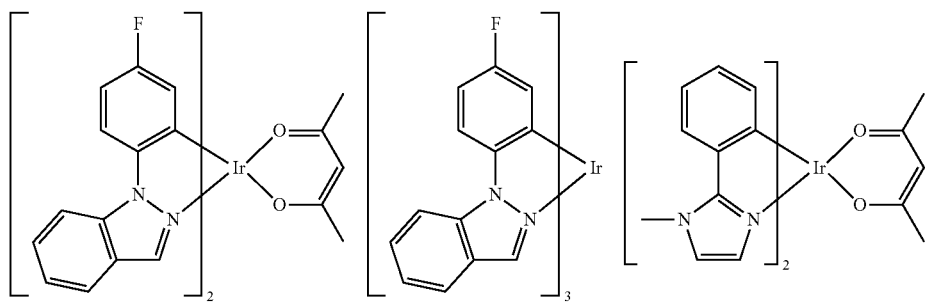
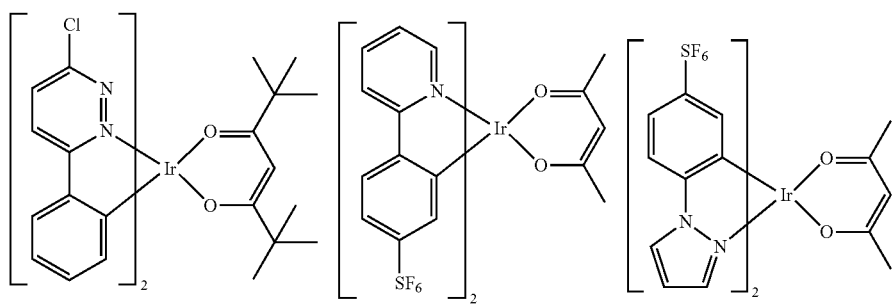
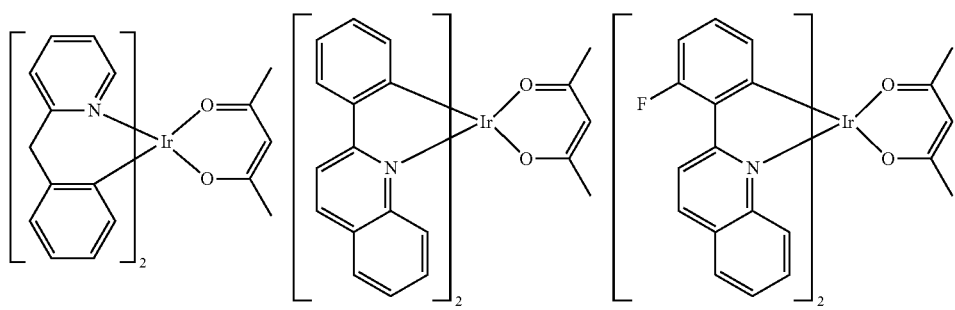

-continued
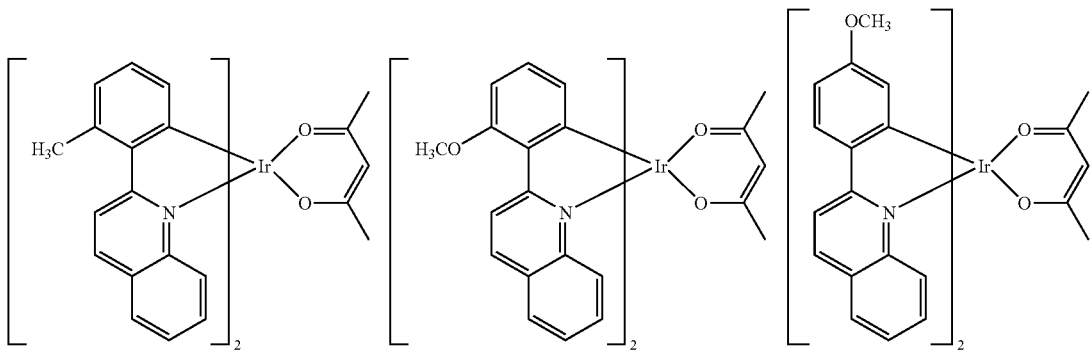
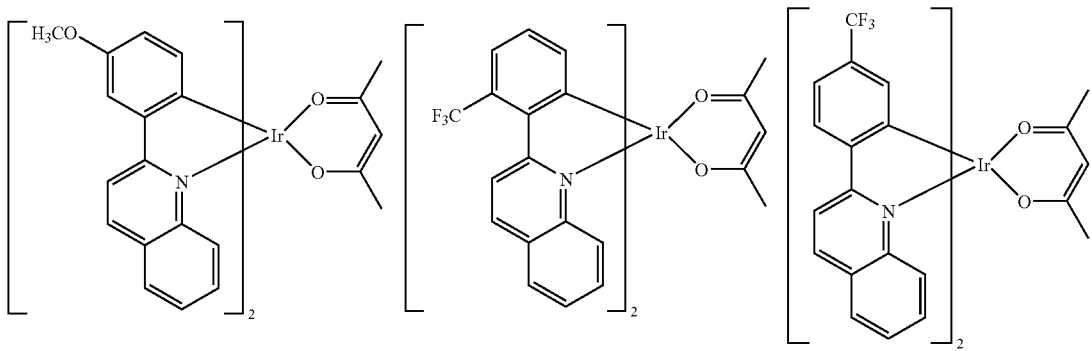
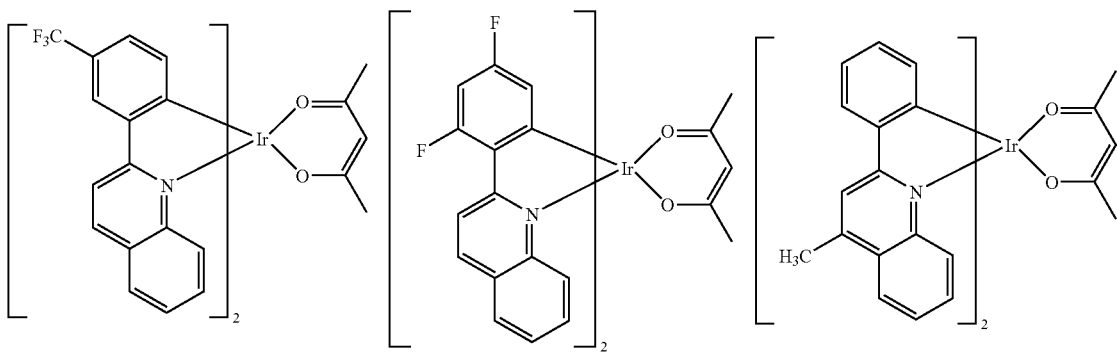
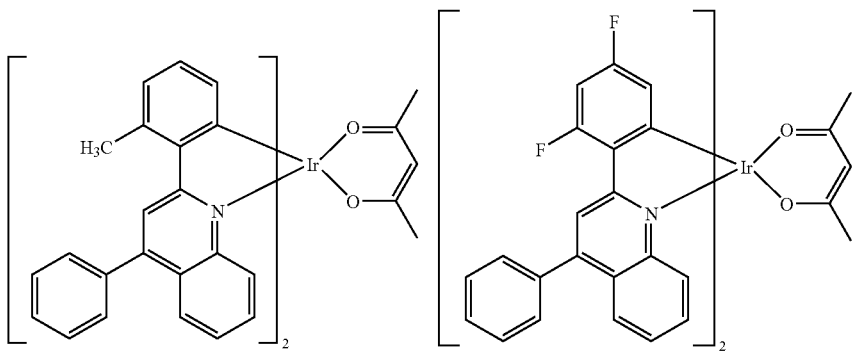

-continued
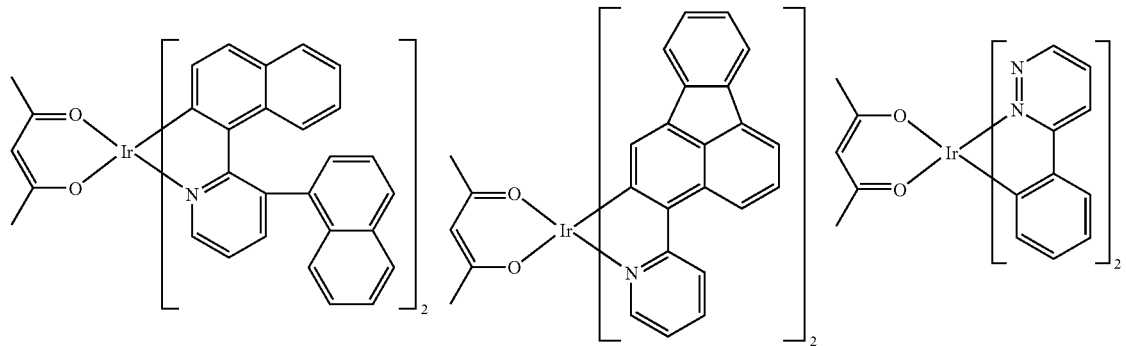
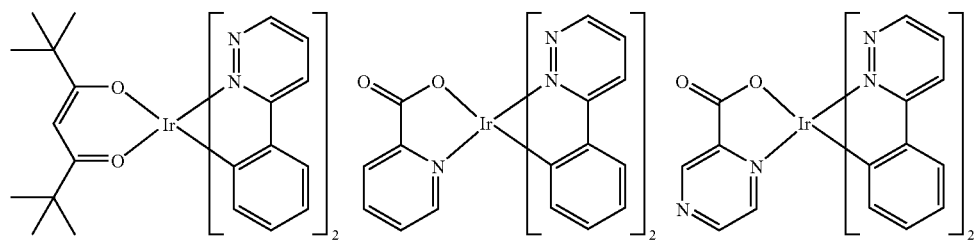
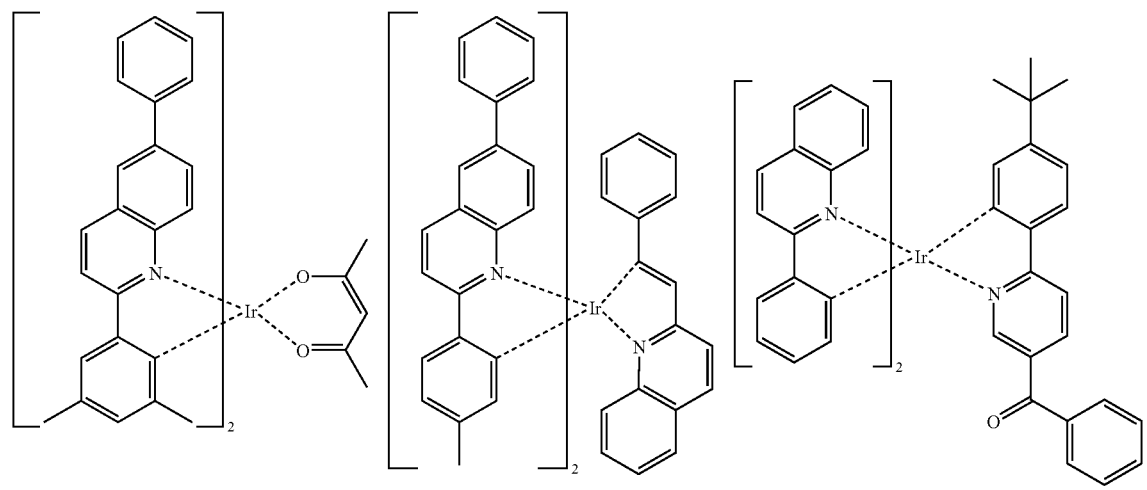
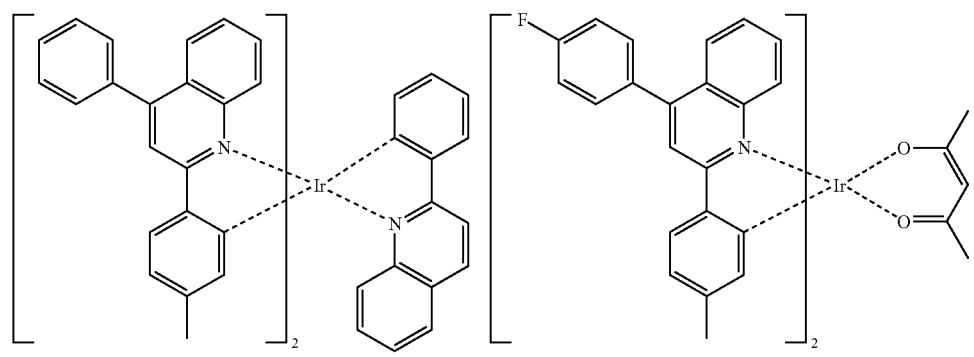

-continued
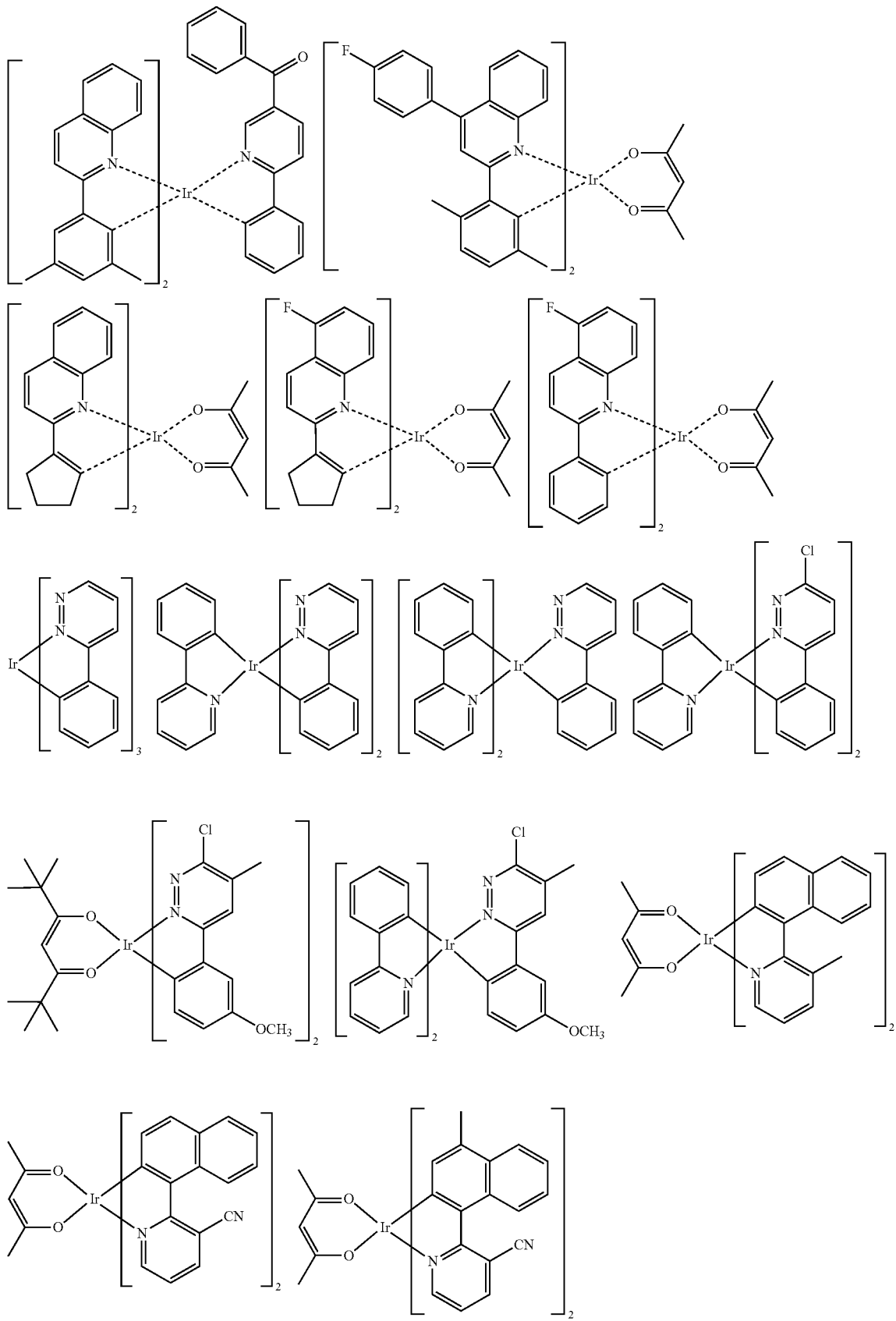

-continued
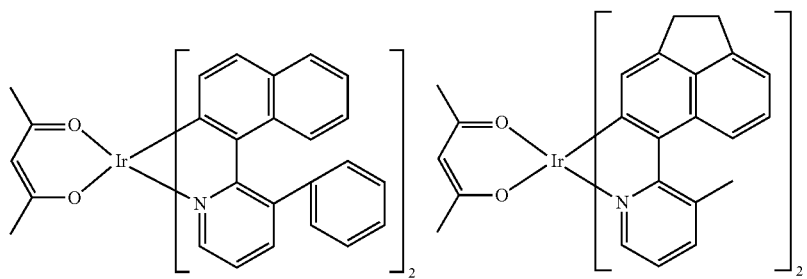
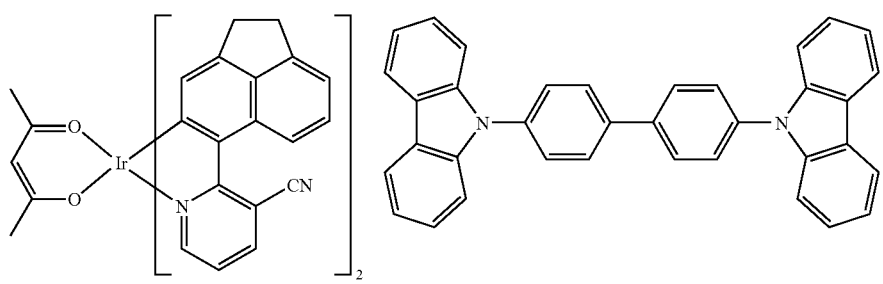
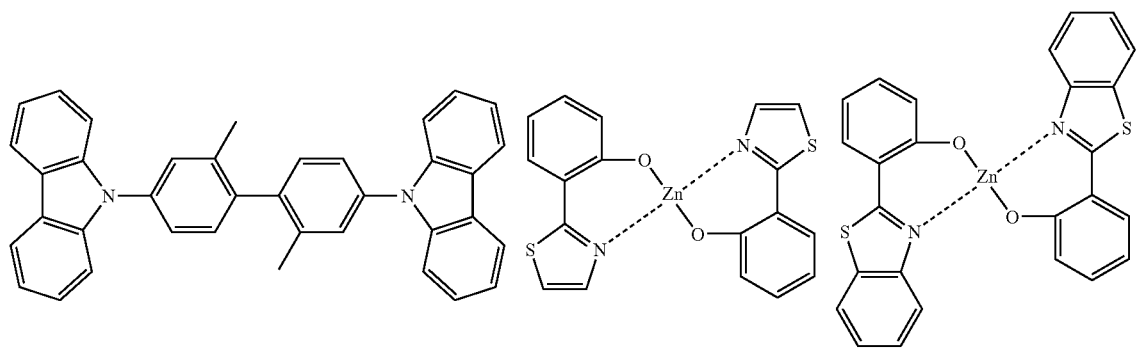
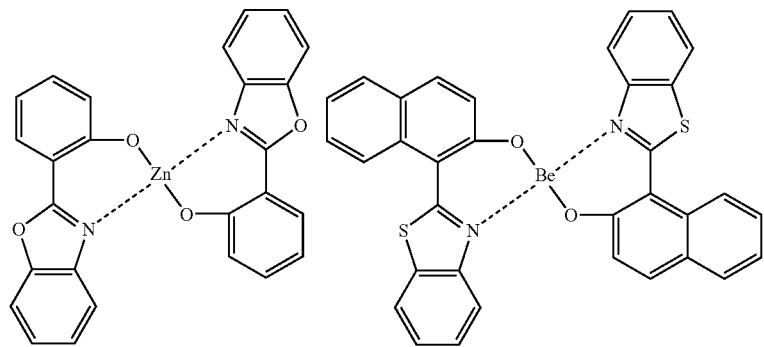
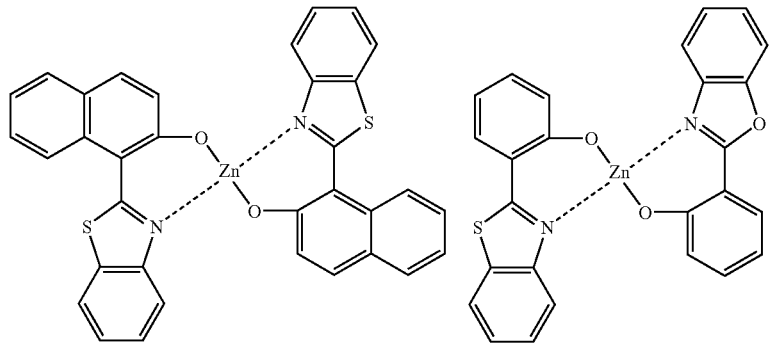

-continued
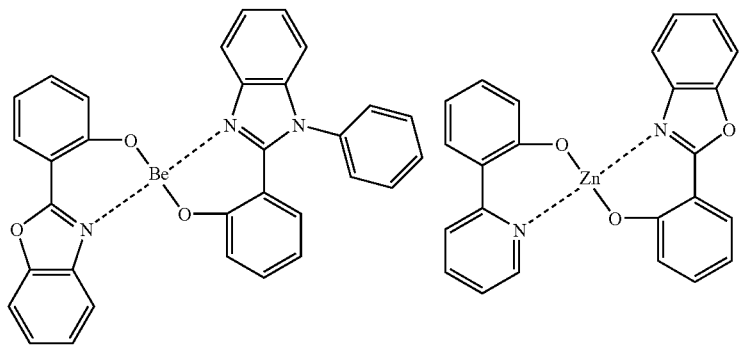
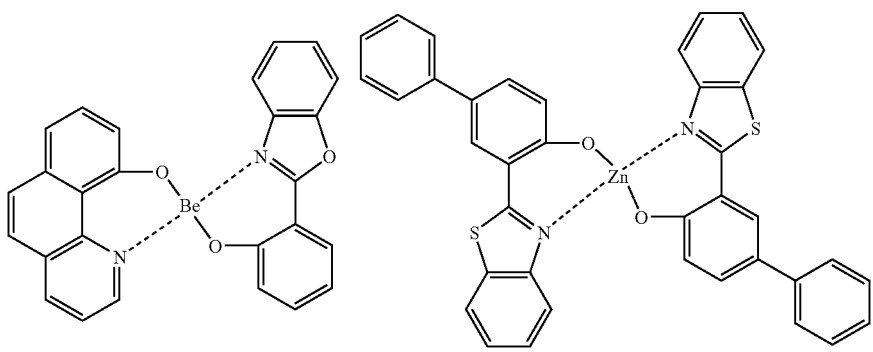
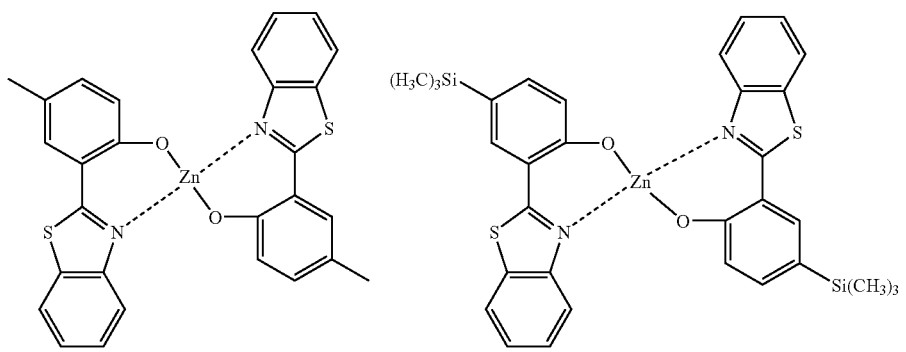
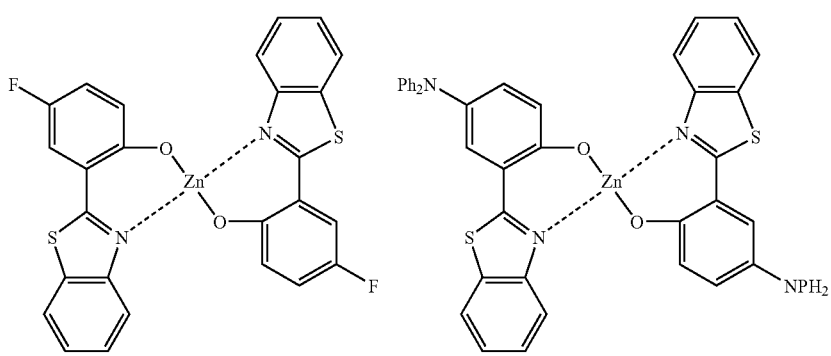

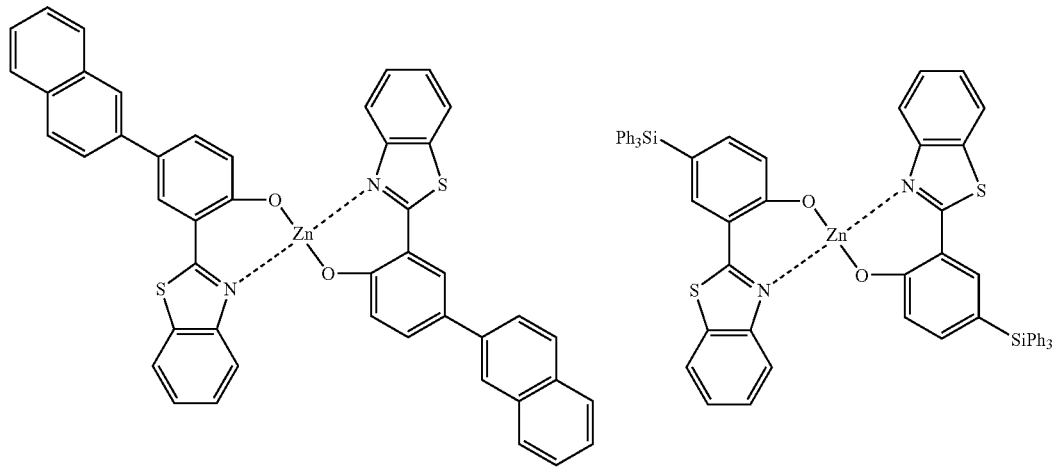
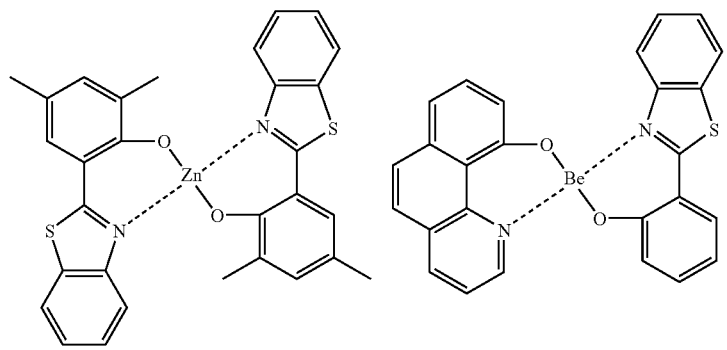
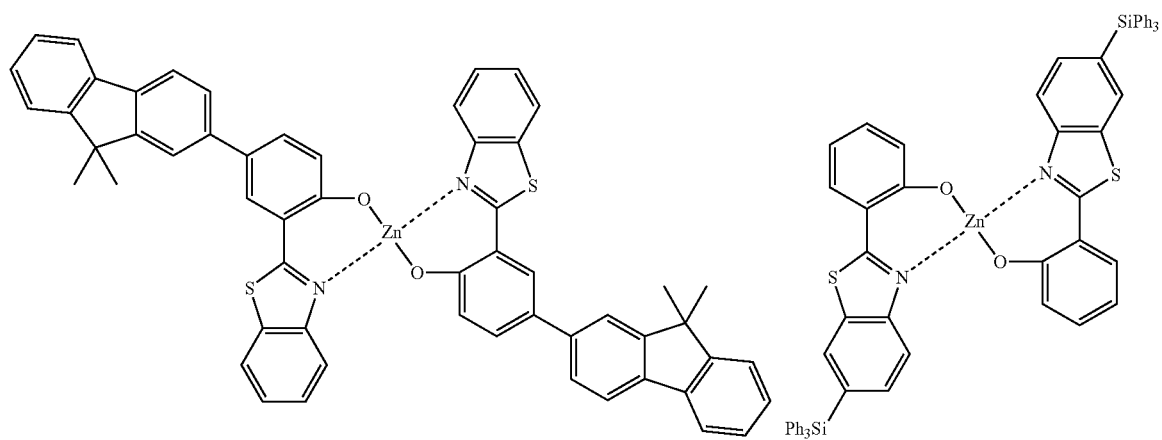

-continued
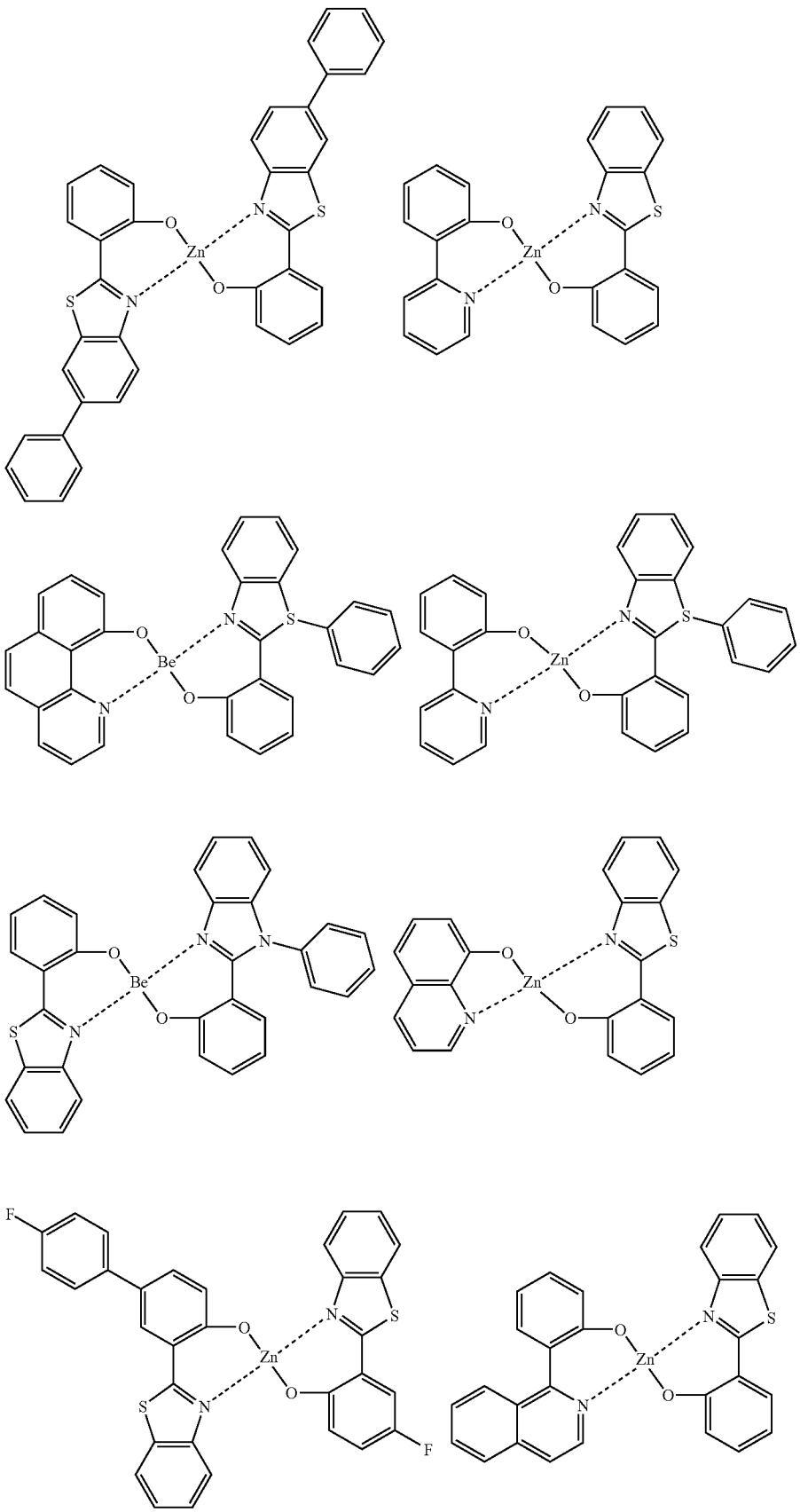

-continued
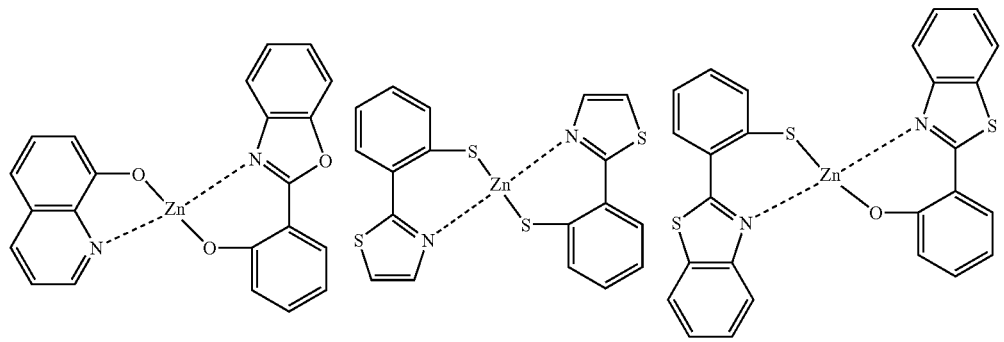
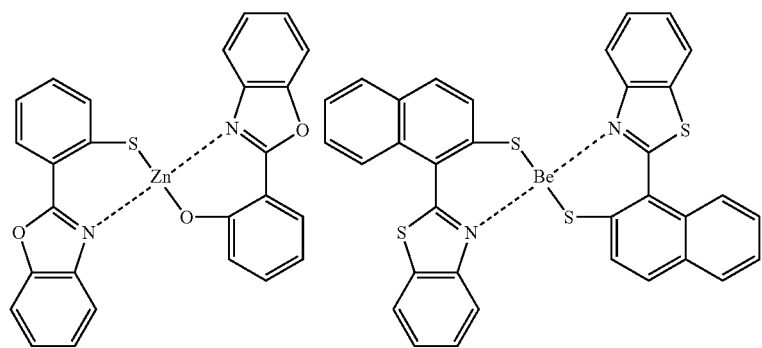
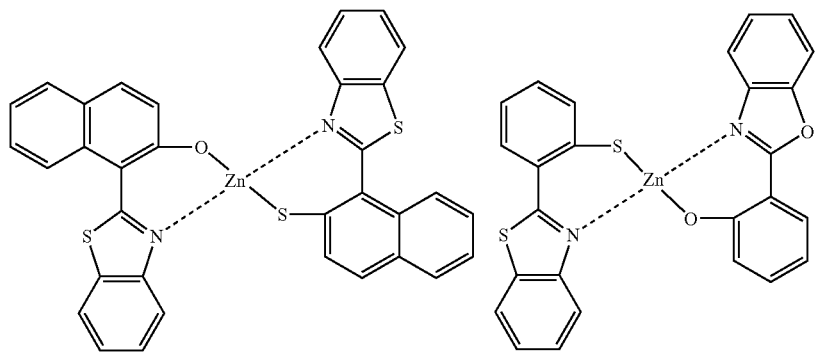
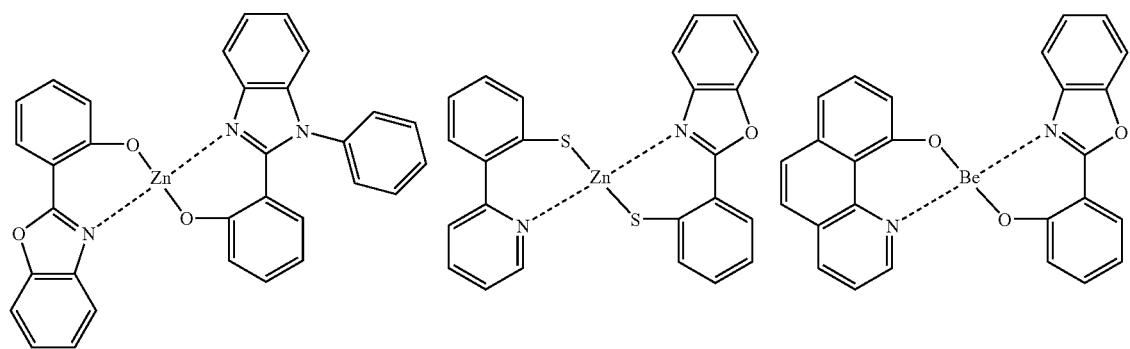

-continued
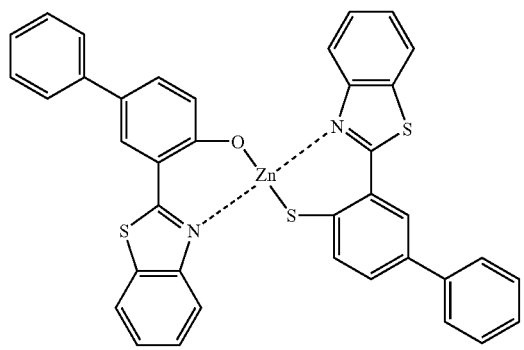
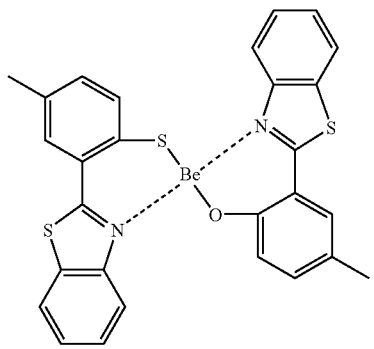
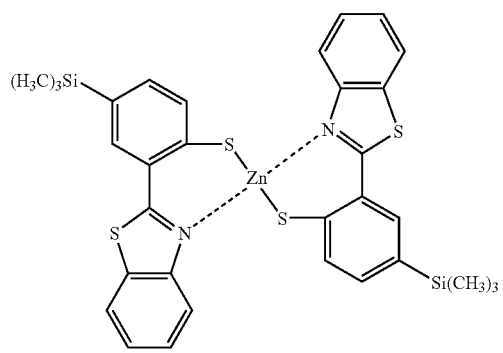
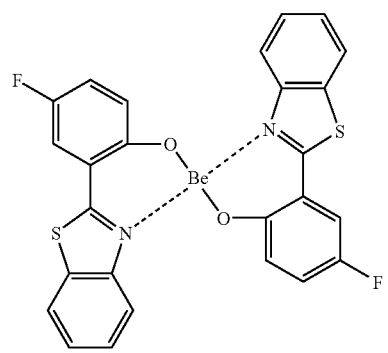
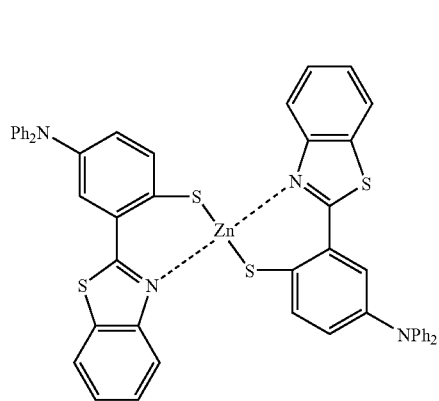
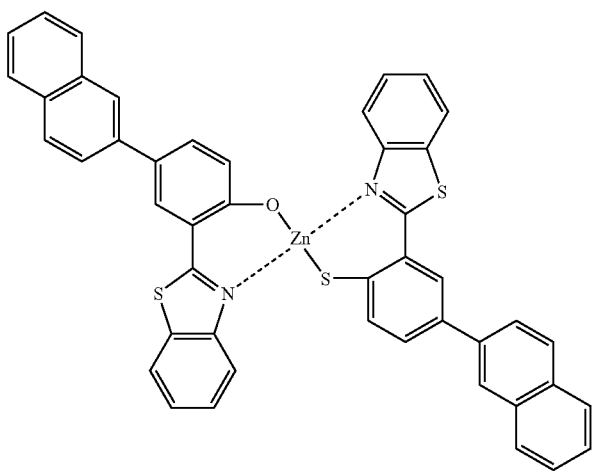
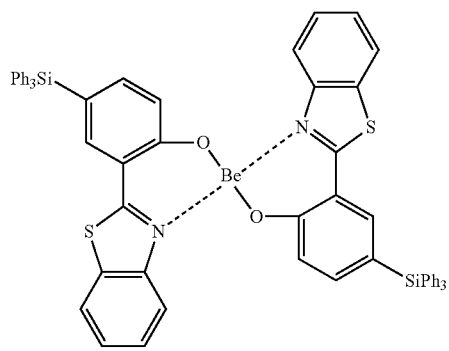
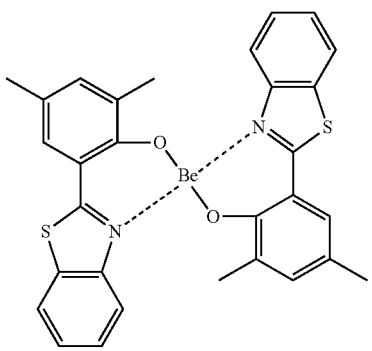

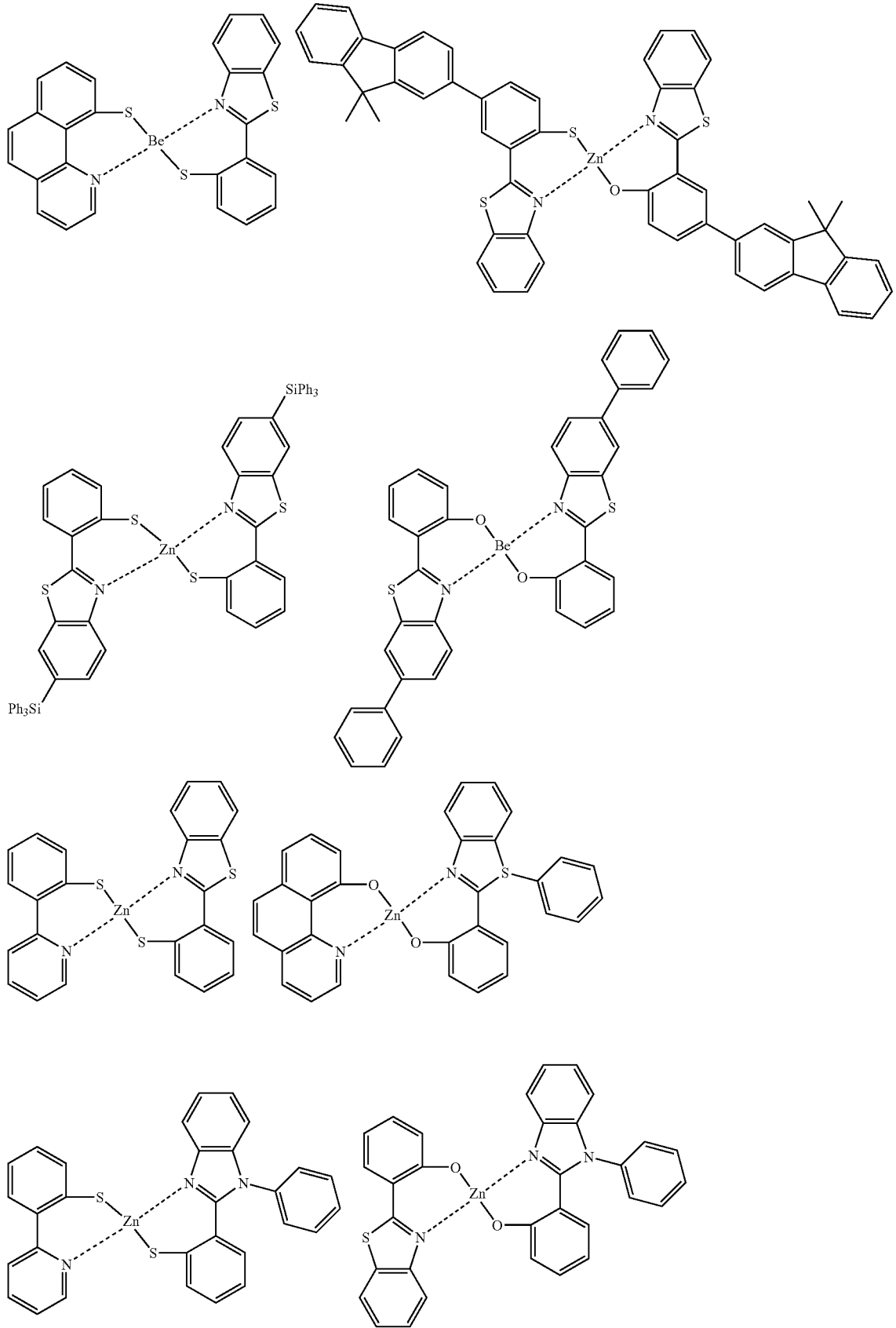

-continued
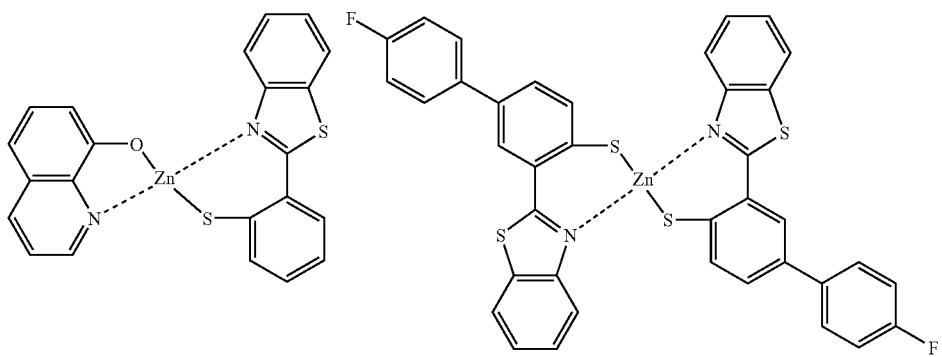
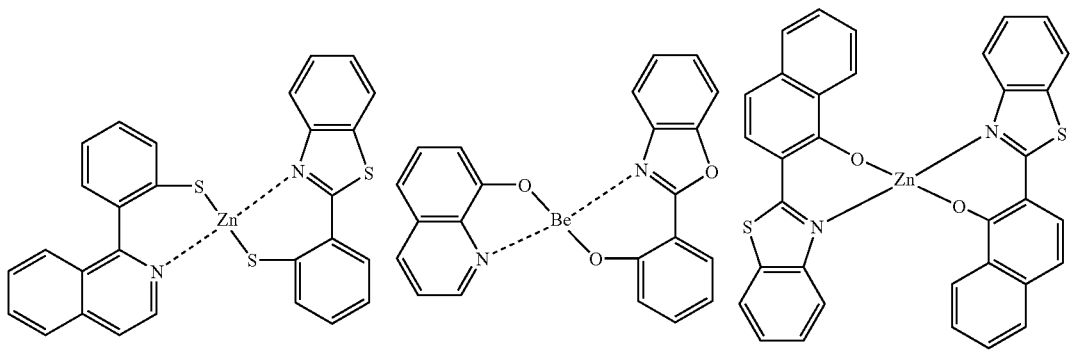
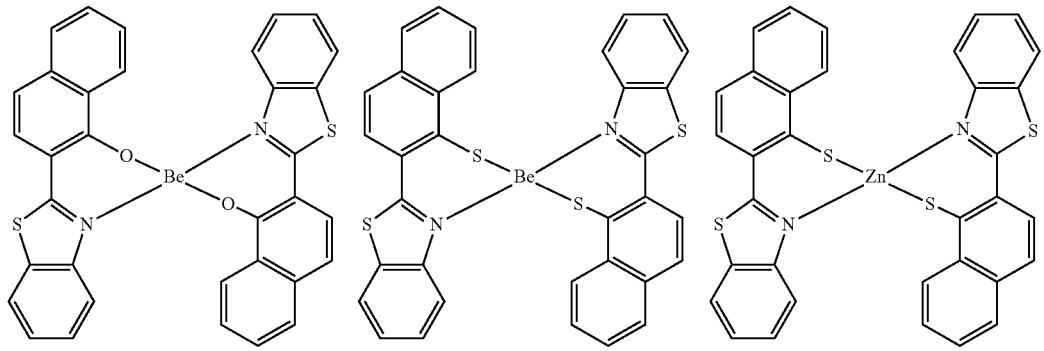
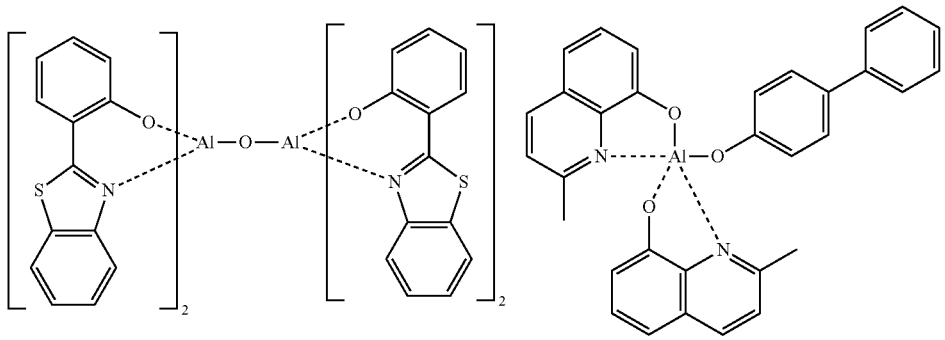

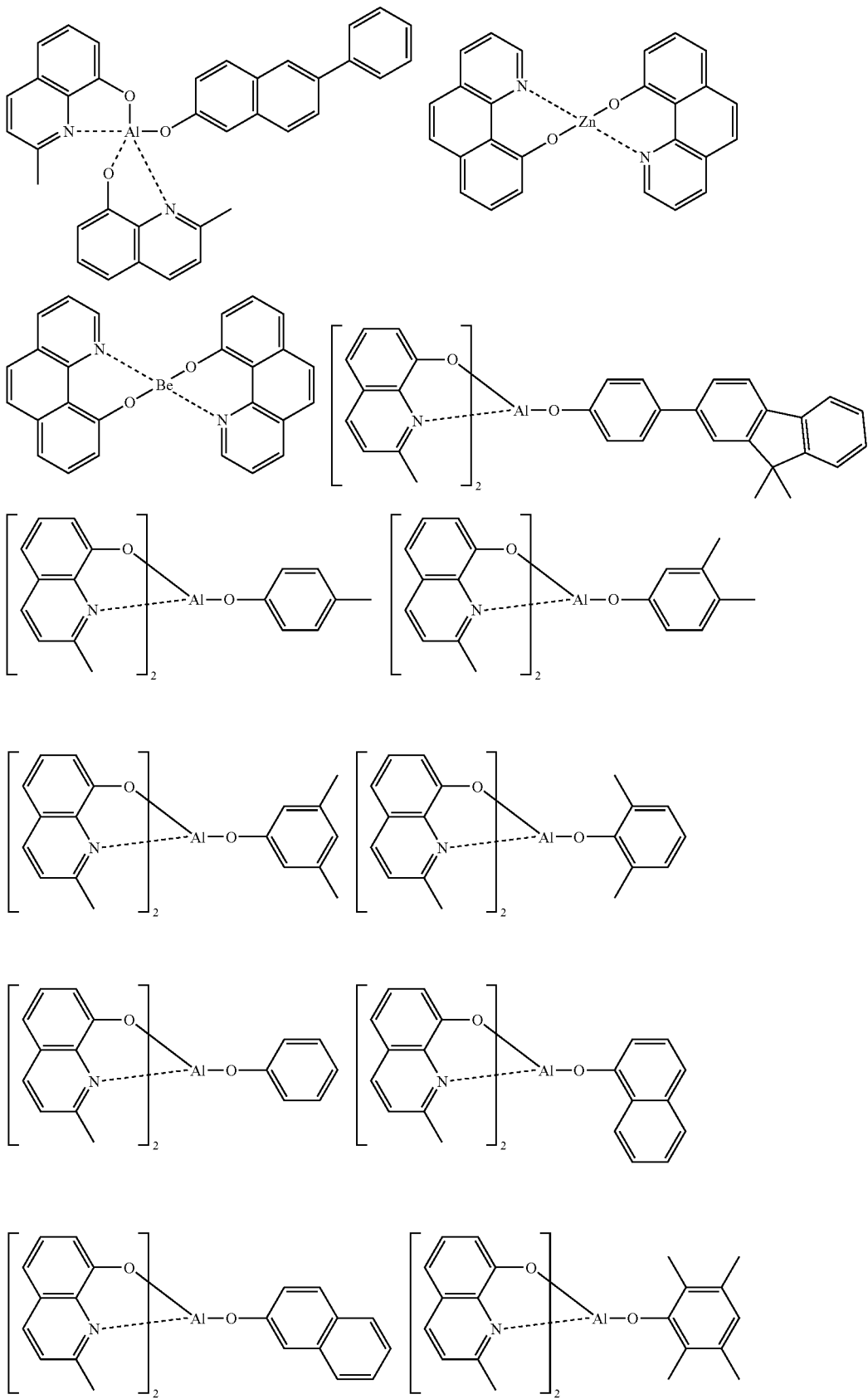

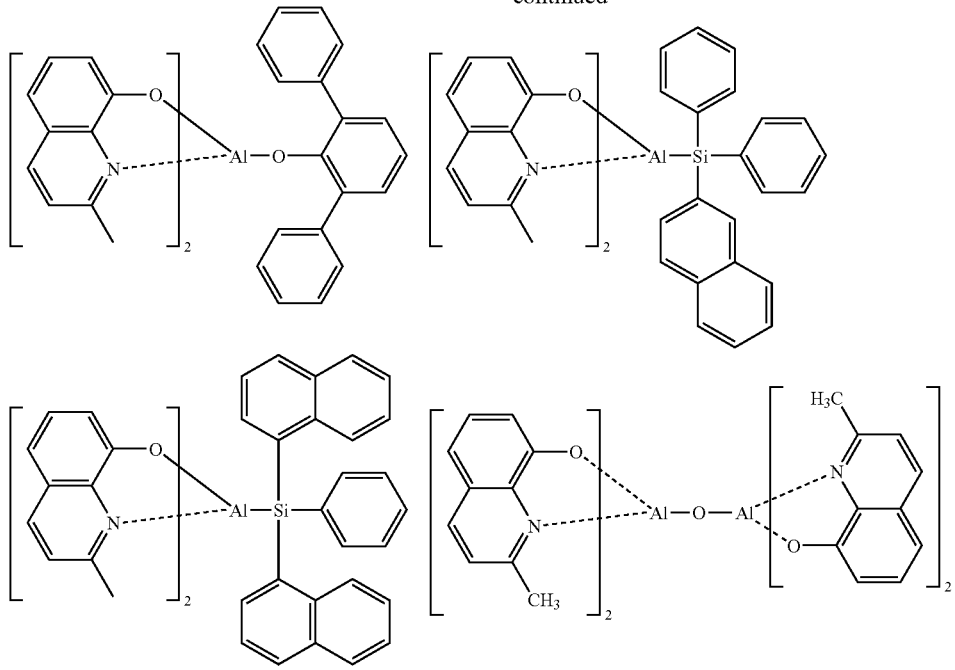

In an organic electroluminescent device according to the present invention, it is preferable to arrange one or more layer(s) (here-in-below, referred to as the "surface layer") selected from chalcogenide layers, metal halide layers and metal oxide layers, on the inner surface of at least one side of the pair of electrodes. Specifically, it is preferable to arrange a chalcogenide layer of silicon and aluminum metal (including oxides) on the anode surface of the EL medium layer, and a metal halide layer or a metal oxide layer on the cathode surface of the EL medium layer. As the result, stability in operation can be obtained.

Examples of chalcogenides preferably include $SiO_x$ ($1 \leq X \leq 2$), $AlO_x$ ($1 \leq X \leq 1.5$), SiON, SiAlON, or the like. Examples of metal halides preferably include LiF, $MgF_2$, $CaF_2$, fluorides of rare earth metal or the like. Examples of metal oxides preferably include $Cs_2O$, $Li_2O$, MgO, SrO, BaO, CaO, or the like.

In an electroluminescent device according to the present invention, it is also preferable to arrange, on at least one surface of the pair of electrodes thus manufactured, a mixed region of electron transport compound and a reductive dopant, or a mixed region of a hole transport compound with an oxidative dopant. Accordingly, the electron transport compound is reduced to an anion, so that injection and transportation of electrons from the mixed region to an EL medium are facilitated. In addition, since the hole transport compound is oxidized to form a cation, injection and transportation of holes from the mixed region to an EL medium are facilitated. Preferable oxidative dopants include various Lewis acids and acceptor compounds. Preferable reductive dopants include alkali metals, alkali metal compounds, alkaline earth metals, rare-earth metals, and mixtures thereof.

The novel compounds for electronic material according to the present invention, when being contained in an electroluminescent layer of an organic electroluminescent device, exhibit high luminous efficiency and excellent life property of material, so that an OLED having very good operation life can be manufactured therefrom.

Further, if the novel compound for electronic material according to the invention is employed as an electron transport layer or as a host for phosphor in an organic electroluminescent device, the operation voltage is lowered to result in noticeable decrease in power consumption while exhibiting at least comparable luminous efficiency.

Best Mode

The present invention is further described by referring to representative compounds with regard to the compounds for electronic material according to the invention, preparation thereof and luminescent properties of the devices manufactured therefrom, but those examples are provided for illustration of the embodiments only, not being intended to limit the scope of the invention by any means.

PREPARATION EXAMPLE 1

Preparation of Compound (6)

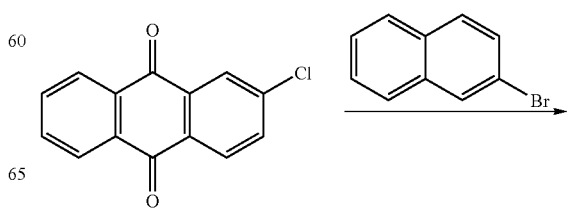

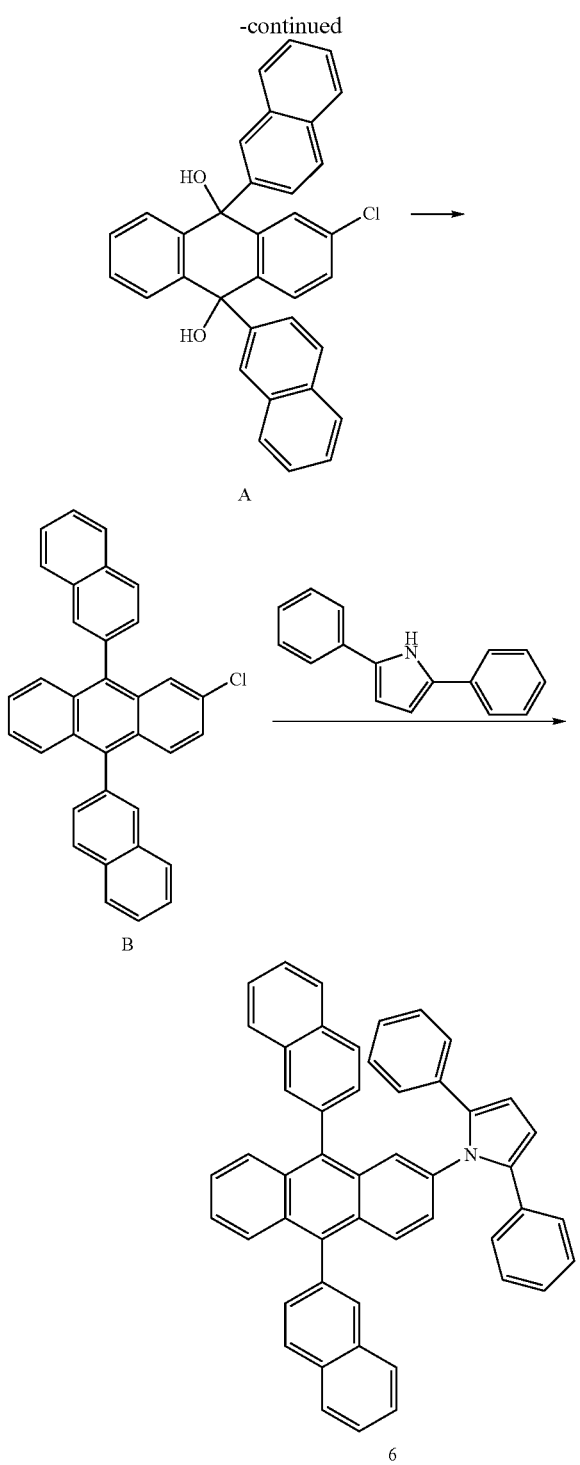

A

B

6

Preparation of Compound (A)

In a reaction vessel, 2-bromonaphthalene (819 g, 3.956 mol) was dissolved in tetrahydrofuran (5 L, 0.33 M) at room temperature with stirring for 10 minutes to provide complete dissolution. After chilling the solution to −78° C., 1.6 M butyllithium (2.68 L, 4.285 mol) was slowly added dropwise thereto. After 1 hour, 2-chloroanthraquinone (400 g, 1.648 mol) was added thereto, and the resultant mixture was stirred for 26 hours, while slowly raising the temperature to room temperature. Saturated ammonium chloride solution was added thereto, and the resultant mixture was stirred for one hour, and then filtered under reduced pressure. The mixture was extracted with ethyl acetate, and the organic layer was dried over magnesium sulfate. After filtration, the organic layer was evaporated under reduced pressure. The solid obtained was recrystallized from dichloromethane (1 L) and n-hexane (2 L), filtered and dried to obtain Compound (A) (551 g, 67%).

Preparation of Compound (B)

In a reaction vessel, Compound (A) (551 g, 1.104 mol), potassium iodide (733 g, 4.417 mol), sodium phosphate monohydrate (937 g, 8.834 mol) and acetic acid (3.35 L, 0.33 M) were stirred under reflux. After 21 hours, the reaction mixture was cooled to room temperature, and filtered under reduced pressure. To the solid obtained, added was a small amount of potassium carbonate and distilled water to neutralize the mixture. After stirring for 2 hours, the mixture was extracted with dichloromethane solvent, and the extract was dried over magnesium sulfate. After isolating the organic layer, the compound was recrystallized from dichloromethane (1 L) and methanol (2 L). The solid obtained from filtration was dried to obtain Compound (B) (318 g, 62%).

Preparation of Compound (6)

A reaction vessel was charged with Compound (B) (10.0 g, 21.5 mmol), 2,5-diphenylpyrrole (5.66 g, 25.8 mmol), palladium acetate (0.096 g, 0.43 mmol), tri-tert-butylphosphine (0.17 g, 0.86 mmol) and cesium carbonate (10.5 g, 32.25 mmol) under nitrogen atmosphere. Toluene solvent (200 mL) was added thereto, and the mixture was stirred under reflux for 18 hours. After cooling to room temperature, methanol (300 mL) was poured to the reaction mixture to produce solid. After filtering the mixture under reduced pressure, dark brown solid thus obtained was purified via column chromatography by using dichloromethane and hexane to obtain Compound (6) (8.49 g, 61%).

PREPARATION EXAMPLE 2

Preparation of Compound (203)

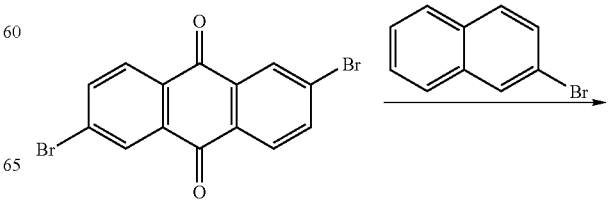

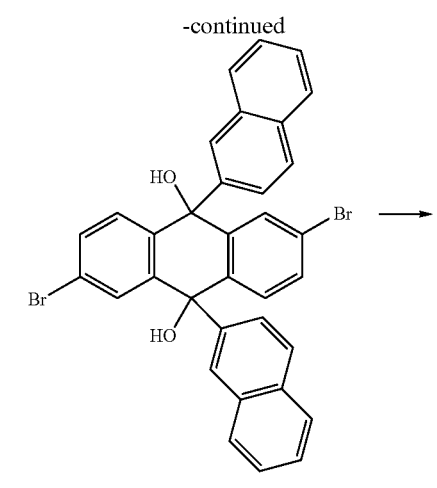

A

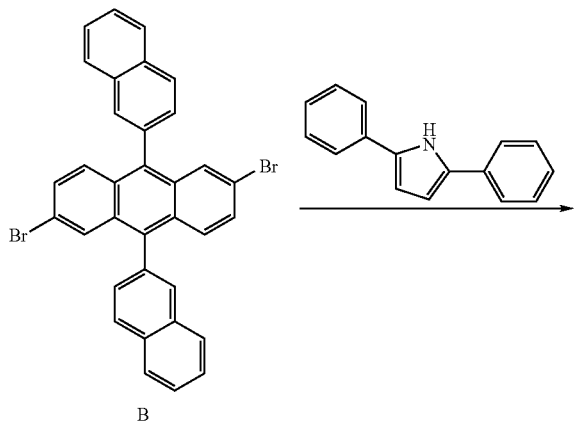

B

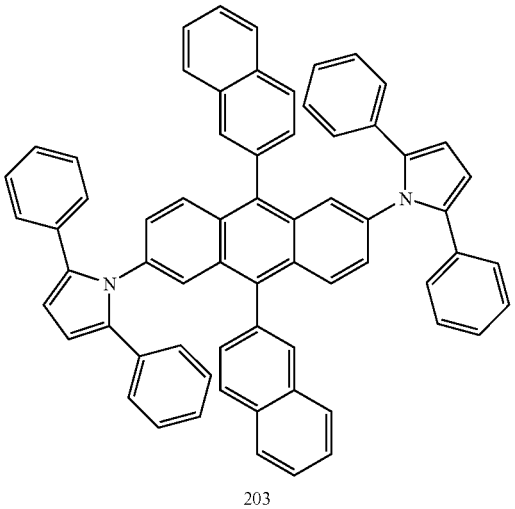

203

Preparation of Compound (A)

In a reaction vessel, 2-bromonaphthalene (27.16 g, 0.131 mol) was completely dissolved with stirring in tetrahydrofuran (1.2 L) at room temperature for 10 minutes. After chilling the solution to −78° C., 2.5 M butyllithium (68.2 mL, 0.17 mol) was slowly added dropwise thereto. After 1 hour, 2,6-dibromoanthraquinone (20 g, 0.055 mol) was added, and the resultant mixture was slowly warmed to room temperature with stirring for 20 hours. To the reaction mixture, 10% HCl solution (0.3 L) was added, and the resultant mixture was stirred for 2 hours and filtered under reduced pressure. The organic layer separated was evaporated, and the residue was recrystallized from ethyl acetate (100 mL) and n-hexane (500 mL). After filtration, the solid compound obtained was dried to obtain Compound (A) (22.44 g, 66%).

Preparation of Compound (B)

In a reaction vessel, Compound (A) (20 g, 32.14 mmol), potassium iodide (16.0 g, 96.42 mmol), sodium phosphate monohydrate (20.43 g, 192.8 mmol), and acetic acid (0.1 L, 0.3 M) were stirred under reflux for 18 hours. After cooling to room temperature, the mixture was filtered under reduced pressure. To the solid obtained, a small amount of potassium carbonate and distilled water were added to neutralize the mixture. After stirring for 1 hour, the organic layer was separated and evaporated to obtain dark brown solid, which was then purified via column chromatography (ethyl acetate:hexane=1:10) to obtain Compound (B) (9.83 g, 52%).

Preparation of Compound (203)

A reaction vessel was charged with Compound (B) (10.0 g, 0.017 mol), 2,5-diphenylpyrrole (11.18 g, 0.051 mol), palladium acetate (0.15 g, 0.68 mmol), tri-tert-butylphosphine (0.27 g, 1.36 mmol) and cesium carbonate (16.62 g, 51.0 mmol) under nitrogen atmosphere. Toluene solvent (200 mL) was added thereto, and the mixture was stirred under reflux for 18 hours. After cooling to room temperature, methanol (300 mL) was poured thereto to form solid. The reaction mixture was filtered under reduced pressure, and the dark brown solid obtained was purified via column chromatography by using dichloromethane and hexane to obtain Compound (203) (8.23 g, 56%).

The organic electroluminescent compounds (Compounds 1 to 453) were prepared according to the procedure described in Preparation Example 1 or 2, and the $^1$H NMR and MS/FAB data of organic electroluminescent compounds thus prepared are listed in Table 1.

TABLE 1

| | | MS/FAB | |
|---|---|---|---|
| compound | $^1$H NMR(CDCl$_3$, 200 MHz) | found | calculated |
| 1 | δ = 2.64(6H, s), 6.58(2H, m), 7.3(2H, m), 7.4~7.41(3H, m), 7.51(4H, m), 7.79(4H, m), 7.9(2H, m), 8(2H, m) | 423.55 | 423.20 |

TABLE 1-continued

| compound | $^1$H NMR(CDCl$_3$, 200 MHz) | MS/FAB found | MS/FAB calculated |
|---|---|---|---|
| 6 | δ = 6.58(2H, m), 7.4~7.41(5H, m), 7.51(4H, m), 7.58~7.59(6H, m), 7.73~7.79(6H, m), 7.9~7.92(6H, m), 8(4H, m) | 647.80 | 647.26 |
| 7 | δ = 6.58(2H, m), 7.4~7.41(5H, m), 7.51~7.55(8H, m), 7.61(2H, m), 7.79(4H, m), 7.9(4H, m), 8.04~8.08(4H, m), 8.42(2H, m), 8.55(2H, m) | 647.80 | 647.26 |
| 12 | δ = 1.35(18H, s), 6.58(2H, m), 7.37~7.41(13H, m), 7.51(4H, m), 7.79(4H, m), 7.9(4H, m) | 659.90 | 659.36 |
| 19 | δ = 2.34(6H, s), 6.58(2H, m), 7.29~7.33(8H, m), 7.4~7.41(5H, m), 7.51(4H, m), 7.79(4H, m), 7.9(4H, m) | 575.74 | 575.26 |
| 25 | δ = 6.58(2H, m), 7.4~7.41(9H, m), 7.51~7.52(20H, m), 7.66(6H, m), 7.79(4H, m), 7.9(4H, m) | 852.07 | 851.36 |
| 30 | δ = 6.58(2H, m), 7.4~7.41(5H, m), 7.5~7.52(8H, m), 7.79(4H, m), 7.86~7.9(6H, m), 7.98~8(6H, m), 8.45(2H, m) | 759.98 | 579.21 |
| 34 | δ = 1.72(12H, s), 6.58(2H, m), 7.28(2H, m), 7.38~7.41(7H, m), 7.51~7.55(6H, m), 7.63(2H, m), 7.77~7.79(6H, m), 7.87~7.93(8H, m) | 780.01 | 779.36 |
| 41 | δ = 6.58(2H, m), 7.25(8H, m), 7.4~7.41(5H, m), 7.51(4H, m), 7.58~7.59(6H, m), 7.73~7.79(6H, m), 7.9~7.92(6H, m), 8(4H, m) | 800.00 | 799.32 |
| 42 | δ = 6.58(2H, m), 7.25(8H, m), 7.4~7.41(5H, m), 7.51~7.55(8H, m), 7.61(2H, m), 7.79(4H, m), 7.9(4H, m), 8.04~8.08(4H, m), 8.42(2H, m), 8.55(2H, m) | 800.00 | 799.32 |
| 45 | δ = 6.58(2H, m), 7.4~7.41(6H, m), 7.51~7.52(8H, m), 7.58~7.59(3H, m), 7.73~7.79(5H, m), 7.9~7.92(5H, m), 8(2H, m) | 597.75 | 597.25 |
| 49 | δ = 1.35(9H, s), 6.58(2H, m), 7.37~7.41(10H, m), 7.51~7.52(8H, m), 7.79(4H, m), 7.9(4H, m) | 603.79 | 603.29 |
| 70 | δ = 1.72(6H, s), 6.58(2H, m), 7.28(1H, m), 7.38~7.41(7H, m), 7.51~7.55(9H, m), 7.63(1H, m), 7.77~7.79(5H, m), 7.87~7.93(6H, m) | 663.85 | 663.29 |
| 82 | δ = 6.58(2H, m), 7.4~7.41(5H, m), 7.51~7.61(10H, m), 7.73~7.79(5H, m), 7.9~7.92(5H, m), 8~8.08(4H, m), 8.42(1H, m), 8.55(1H, m) | 647.80 | 647.20 |
| 97 | δ = 6.58(2H, m), 7.4~7.41(7H, m), 7.51~7.52(12H, m), 7.58~7.59(3H, m), 7.66(3H, m), 7.73~7.79(5H, m), 7.9~7.92(5H, m), 8(2H, m) | 749.94 | 749.31 |
| 120 | δ = 6.58(2H, m), 7.4~7.41(5H, m), 7.51~7.55(6H, m), 7.61(1H, m), 7.79~7.93(13H, m), 8.04~8.12(4H, m), 8.42(1H, m), 8.55(1H, m), 8.93(2H, m) | 697.86 | 697.28 |
| 133 | δ = 6.58(2H, m), 7.25~7.33(3H, m), 7.4~7.41(5H, m), 7.5~7.55(7H, m), 7.61~7.63(2H, m), 7.79(4H, m), 7.9~7.94(5H, m), 8.04~8.12(3H, m), 8.42(1H, m), 8.55(2H, m) | 686.84 | 686.27 |
| 139 | δ = 1.72(6H, s), 6.58(2H, m), 7.28(1H, m), 7.38~7.41(6H, m), 7.51~7.55(7H, m), 7.61~7.63(2H, m), 7.77~7.79(5H, m), 7.87~7.93(6H, m), 8.04~8.08(2H, m), 8.42(1H, m), 8.55(1H, m) | 713.90 | 713.31 |
| 157 | δ = 6.58(2H, m), 7.41(4H, m), 7.5~7.51(9H, m), 7.6(2H, m), 7.79(8H, m), 7.9(2H, m), 8.3(2H, m) | 547.69 | 547.23 |
| 170 | δ = 6.58(2H, m), 7.4~7.41(3H, m), 7.51(4H, m), 7.58~7.59(6H, m), 7.7~7.79(8H, m), 7.9~7.92(4H, m), 8(4H, m), 8.3(2H, m) | 647.80 | 647.26 |
| 182 | δ = 6.58(2H, m), 7.41(4H, m), 7.51~7.52(12H, m), 7.6(2H, m), 7.79(4H, m), 8(2H, m), 8.1(2H, m), 8.3(1H, m) | 547.69 | 547.23 |
| 199 | δ = 6.58(4H, m), 7.4~7.41(8H, m), 7.51~7.52(16H, m), 7.79(8H, m), 7.9(4H, m) | 764.95 | 764.32 |
| 201 | δ = 6.58(4H, m), 7.4~7.41(6H, m), 7.51~7.55(12H, m), 7.61(2H, m), 7.79(8H, m), 7.9(4H, m), 8.04~8.8(4H, m), 8.42(2H, m), 8.55(2H, m) | 865.07 | 864.35 |
| 203 | δ = 6.58(4H, m), 7.4~7.41(6H, m), 7.51(8H, m), 7.58~7.59(6H, m), 7.73~7.79(10H, m), 7.9~7.92(6H, m), 8(4H, m) | 865.07 | 864.35 |
| 215 | δ = 2.34(6H, s), 6.58(4H, m), 7.19(2H, m), 7.33~7.41(10H, m), 7.51(8H, m), 7.79(10H, m), 7.9(4H, m) | 793.00 | 792.35 |
| 228 | δ = 1.72(12H, s), 6.58(4H, m), 7.28(2H, m), 7.38~7.41(8H, m), 7.51~7.55(10H, m), 7.63(2H, m), 7.77~7.79(10H, m), 7.87~7.93(8H, m) | 997.27 | 996.44 |
| 239 | δ = 6.58(4H, m), 7.4~7.41(7H, m), 7.51~7.52(12H, m), 7.58~7.59(3H, m), 7.73~7.79(9H, m), 7.9~7.92(5H, m), 8(2H, m) | 815.01 | 814.33 |

TABLE 1-continued

| compound | $^1$H NMR(CDCl$_3$, 200 MHz) | MS/FAB found | MS/FAB calculated |
|---|---|---|---|
| 271 | δ = 6.58(4H, m), 7.25(4H, m), 7.4~7.41(7H, m), 7.51~7.52(12H, m), 7.58~7.59(3H, m), 7.73~7.79(9H, m), 7.9~7.92(5H, m), 8(2H, m) | 891.11 | 890.37 |
| 275 | δ = 6.58(4H, m), 7.4~7.41(6H, m), 7.51~7.61(14H, m), 7.73~7.79(9H, m), 7.9~7.92(5H, m), 8~8.08(4H, m), 8.42(1H, m), 8.55(1H, m) | 865.07 | 864.35 |
| 277 | δ = 6.58(4H, m), 7.4~7.41(6H, m), 7.51(8H, m), 7.58~7.59(3H, m), 7.73~7.93(19H, m), 8(2H, m), 8.12(2H, m), 8.93(2H, m) | 915.13 | 914.37 |
| 287 | δ = 2.34(6H, s), 6.58(4H, m), 7.31(1H, m), 7.4~7.41(6H, m), 7.51(8H, m), 7.58~7.6(5H, m), 7.73~7.79(9H, m), 7.9~7.92(5H, m), 8(2H, m) | 843.06 | 842.37 |
| 292 | δ = 6.58(4H, m), 7.4~7.41(7H, m), 7.51(10H, m), 7.58~7.59(5H, m), 7.73~7.79(11H, m), 7.9~7.92(5H, m), 8(4H. m), 8.4(2H, m) | 941.16 | 940.38 |
| 299 | δ = 6.58(4H, m), 7.25(4H, m), 7.4~7.41(7H, m), 7.51~7.52(12H, m), 7.58~7.59(3H, m), 7.73~7.79(9H, m), 7.9~7.92(5H, m), 8(2H, m) | 891.11 | 890.37 |
| 301 | δ = 1.72(6H, s), 6.58(4H, m), 7.28(1H, m), 7.38~7.41(7H, m), 7.51~7.63(13H, m), 7.73~7.79(10H, m), 7.87~7.93(7H, m), 8(2H, m) | 931.17 | 930.40 |
| 303 | δ = 6.58(4H, m), 7.16~7.19(4H, m), 7.28(1H, m), 7.35~7.41(9H, m), 7.51~7.63(13H, m), 7.73~7.79(12H, m), 7.87~7.93(7H, m), 8(2H, m) | 1053.29 | 1052.41 |
| 307 | δ = 6.58(4H, m), 7.25(4H, m), 7.4~7.41(6H, m), 7.51(8H, m), 7.58~7.59(6H, m), 7.73~7.79(10H, m), 7.9~7.92(6H, m), 8(4H, m) | 941.16 | 940.38 |
| 308 | δ = 6.58(4H, m), 7.25(4H, m), 7.4~7.41(6H, m), 7.51~7.61(14H, m), 7.73~7.79(9H, m), 7.9~7.92(5H, m), 8~8.08(4H, m), 8.42(1H, m), 8.55(1H, m) | 941.16 | 940.38 |
| 309 | δ = 6.58(4H, m), 7.25(4H, m), 7.4~7.41(6H, m), 7.51(8H, m), 7.58~7.59(3H, m), 7.73~7.93(19H, m), 8(2H, m), 8.12(2H, m), 8.93(2H, m) | 991.22 | 990.40 |
| 313 | δ = 6.58(4H, m), 7.4~7.41(6H, m), 7.51~7.55(10H, m), 7.61(1H, m), 7.79~7.93(17H, m), 8.04~8.12(4H, m), 8.42(1H, m), 8.55(1H, m), 8.93(2H, m) | 915.13 | 914.37 |
| 326 | δ = 6.58(4H, m), 7.35~7.41(7H, m), 7.51~7.61(12H, m), 7.79~7.81(9H, m), 7.9(4H, m), 8.04~8.1(4H, m), 8.38~8.42(2H, m), 8.55(1H, m), 8.83(1H, m) | 917.10 | 916.36 |
| 334 | δ = 1.72(6H, s), 6.58(4H, m), 7.28(1H, m), 7.38~7.41(7H, m), 7.51~7.55(11H, m), 7.61~7.63(2H, m), 7.77~7.79(9H, m), 7.87~7.93(6H, m), 8.04~8.08(2H, m), 8.42(1H, m), 8.55(1H, m) | 931.17 | 930.40 |
| 348 | δ = 6.58(4H, m), 7.41(6H, m), 7.51(12H, m), 7.6(2H, m), 7.79(12H, m), 7.9(2H, m), 8.3(2H, m) | 764.95 | 794.32 |
| 361 | δ = 6.58(4H, m), 7.4~7.41(5H, m), 7.51(8H, m), 7.58~7.59(6H, m), 7.7(1H, s), 7.73~7.79(10H, m), 7.9~7.92(4H, m), 8(4H, m), 8.3(2H, m) | 865.07 | 684.35 |
| 377 | δ = 6.58(4H, m), 7.41(6H, m), 7.51~7.52(16H, m), 7.6(2H, m), 7.79(8H, m), 8(2H, m), 8.1(2H, m) | 794.95 | 794.32 |
| 392 | δ = 6.58(2H, m), 7.39~7.41(6H, m), 7.51~7.52(12H, m), 7.61(1H, m), 7.68(2H, m), 7.79(6H, m), 7.91~7.97(3H, m), 8.13(1H, m) | 623.78 | 623.26 |
| 397 | δ = 6.58(2H, m), 7.39~7.41(4H, m), 7.51(4H, m), 7.58~7.61 (7H, m), 7.68~7.79(10H, m), 7.91~8(9H, m), 8.13(1H, m) | 723.90 | 723.29 |
| 412 | δ = 1.72(12H, s), 6.58(2H, m), 7.28(2H, m), 7.38~7.41(6H, m), 7.51~7.55(6H, m), 7.61~7.68(5H, m), 7.77~7.79(8H, m), 7.87~7.97(7H, m), 8.13(1H, m) | 856.10 | 855.39 |
| 426 | δ = 6.58(2H, m), 7.41(2H, m), 7.51(4H, m), 7.58~7.61 (8H, m), 7.68~7.79(10H, m), 7.92~8(8H, m), 8.13(2H, m), 8.27(1H, m) | 723.90 | 723.29 |
| 431 | δ = 6.58(4H, m), 7.41(6H, m), 7.51~7.52(16H, m), 7.61(2H, m), 7.68(4H, m), 7.79(12H, m), 7.97(2H, m), 8.13(2H, m) | 917.14 | 916.38 |
| 432 | δ = 6.58(4H, m), 7.41(4H, m), 7.51(8H, m), 7.58~7.61(8H, m), 7.68~7.79(18H, m), 7.92~8(8H, m), 8.13(2H, m) | 1017.26 | 1016.41 |
| 433 | δ = 6.58(4H, m), 7.41(4H, m), 7.51~7.55(12H, m), 7.61(4H, m), 7.68(4H, m), 7.79(12H, m), 7.97(2H, m), 8.04~8.13(6H, m), 8.42(2H, m), 8.55(2H, m) | 1017.26 | 1016.41 |
| 434 | δ = 1.72(12H, s), 6.58(4H, m), 7.28(2H, m), 7.38~7.41(6H, m), 7.51~7.55(10H, m), 7.61~7.68(8H, m), 7.77~7.79(14H, m), 7.87~7.97(6H, m), 8.13(2H, m) | 1149.46 | 1148.51 |

TABLE 1-continued

| compound | $^1$H NMR(CDCl$_3$, 200 MHz) | MS/FAB found | MS/FAB calculated |
|---|---|---|---|
| 436 | δ = 6.58(4H, m), 7.41(4H, m), 7.51(8H, m), 7.58~7.61(8H, m), 7.68~7.79(18H, m), 7.92~8(8H, m), 8.13(2H, m) | 1017.26 | 1016.41 |
| 438 | δ = 1.72(12H, s), 6.58(4H, m), 7.28(2H, m), 7.38~7.41(6H, m), 7.51~7.55(10H, m), 7.61~7.68(8H, m), 7.77~7.79(14H, m), 7.87~7.97(6H, m), 8.13(2H, m) | 1149.46 | 1148.51 |
| 443 | δ = 6.58(4H, m), 7.41~7.51(14H, m), 7.58~7.61(8H, m), 7.68~7.79(18H, m), 7.87~7.92(4H, m), 8(4H, m) | 1017.26 | 1016.41 |
| 446 | δ = 6.58(2H, m), 7.39~7.41(6H, m), 7.51(8H, m), 7.67~7.68(4H, m), 7.79(10H, m), 7.91(2H, m), 8.27(1H, m) | 623.78 | 623.26 |
| 450 | δ = 6.58(2H, m), 7.41~7.51(8H, m), 7.58~7.61(8H, m), 7.68~7.79(10H, m), 7.87~7.92(4H, m), 8(4H, m), 8.27(1H, m) | 723.90 | 723.29 |
| 452 | δ = 6.47(1H, m), 7.4~7.41(5H, m), 7.51~7.55(10H, m), 7.61(3H, m), 7.79(2H, m), 7.9(4H, m), 8.04~8.08(4H, m), 8.42(2H, m), 8.55(2H, m) | 647.80 | 647.26 |
| 453 | δ = 6.47(2H, m), 7.4~7.41(6H, m), 7.51~7.55(16H, m), 7.61(4H, m), 7.79(4H, m), 7.9(4H, m), 8.04~8.08(4H, m), 8.42(2H, m), 8.55(2H, m) | 865.07 | 864.35 |

EXAMPLE 1

Manufacture of OLED's by Using the Organic Compounds for Electronic Material of the Invention An OLED device was manufactured by using a compound for electronic material according to the invention.

First, a transparent electrode ITO thin film (15Ω/□) (2) prepared from glass for OLED (1) (manufactured by Samsung-Corning) was subjected to ultrasonic washing with trichloroethylene, acetone, ethanol and distilled water, sequentially, and stored in isopropanol before use.

Then, an ITO substrate was equipped in a substrate folder of a vacuum vapor-deposit device, and 4,4',4''-tris(N,N-(2-naphthyl)-phenylamino)triphenylamine (2-TNATA) (of which the structure is shown below) was placed in a cell of the vacuum vapor-deposit device, which was then ventilated up to 10$^{-6}$ torr of vacuum in the chamber. Electric current was applied to the cell to evaporate 2-TNATA, thereby providing vapor-deposit of a hole injecting layer (3) having 60 nm thickness on the ITO substrate.

Then, to another cell of the vacuum vapor-deposit device, charged was N,N'-bis(α-naphthyl)-N,N'-diphenyl-4,4'-diamine (NPB) (of which the structure is shown below), and electric current was applied to the cell to evaporate NPB, thereby providing vapor-deposit of a hole transport layer (4) of 20 nm thickness on the hole injecting layer.

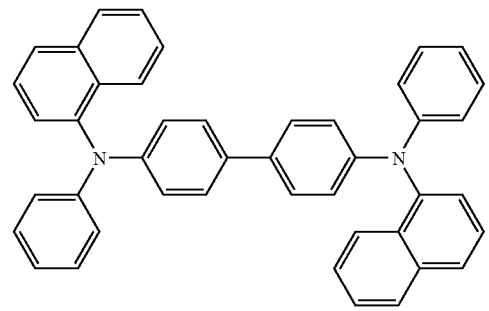

NPB

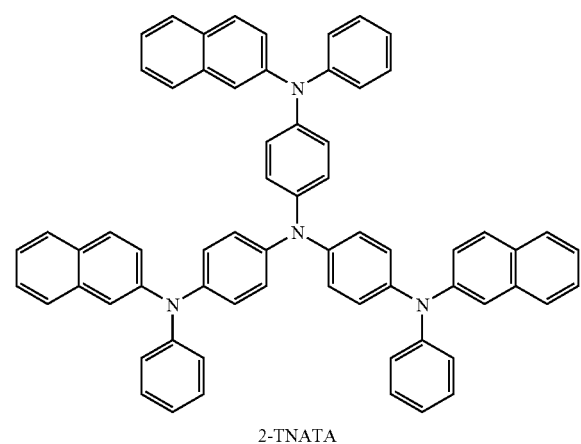

2-TNATA

After forming the hole injecting layer and the hole transport layer, an electroluminescent layer was vapor-deposited as follows. To one cell of a vacuum vapor-deposit device, charged was an anthracene-type host compound (H-29) (of which the structure is shown below) as a host, and a compound according to the invention (Compound 2) was charged to another cell as a dopant. The two substances were evaporated at different rates to give doping at 3% by weight on the basis of the host, to vapor-deposit an electroluminescent layer (5) with a thickness of 30 nm on the hole transport layer.

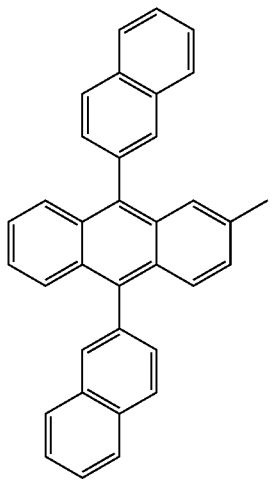

H-29

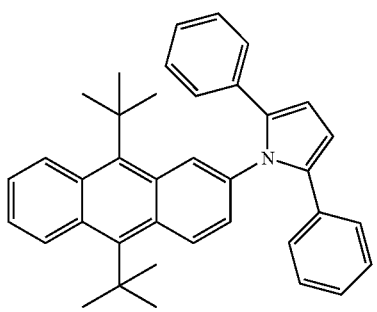

Then, tris(8-hydroxyquinoline)aluminum (III) (Alq) (of which the structure is shown below) was vapor-deposited as an electron transport layer (6) with a thickness of 20 nm, and lithium quinolate (Liq) (of which the structure shown below) was vapor-deposited as an electron injecting layer (7) with a thickness of 1 to 2 nm. Thereafter, an Al cathode (8) was vapor-deposited with a thickness of 150 nm by using another vacuum vapor-deposit device to manufacture an OLED.

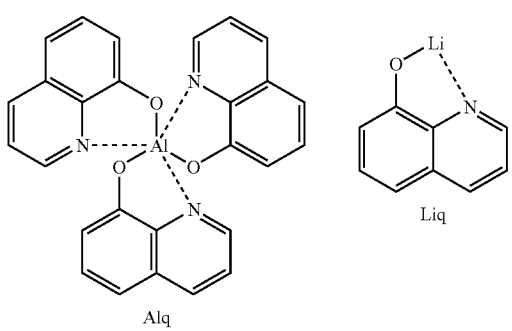

Alq    Liq

Each material employed for manufacturing an OLED was used as the electroluminescent material after purifying via vacuum sublimation at $10^{-6}$ torr.

COMPARATIVE EXAMPLE 1

Manufacture of an OLED by Using Conventional Compound for Electronic Material

After forming a hole injecting layer and a hole transport layer according to the same procedure as described in Example 1, dinaphthylanthracene (DNA) was charged to another cell of said vacuum vapor-deposit device as an electroluminescent host material, while perylene was charged to still another cell. The two substances were evaporated at different rates to carry out doping at a concentration of 3% by weight on the basis of the host, thereby vapor-depositing an electroluminescent layer with a thickness of 30 nm on the hole transport layer.

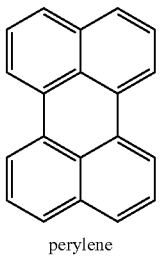

perylene

Then, an electron transport layer and an electron injecting layer were vapor-deposited according to the same procedure as in Example 1, and Al cathode was vapor-deposited by using another vacuum vapor-deposit device with a thickness of 150 nm, to manufacture an OLED.

TABLE 2

| No. | Host | Dopant | Efficiency (cd/A) @ 5,000 cd/m$^2$ | Color |
|---|---|---|---|---|
| 1 | H-29 | 2 | 5.8 | Blue |
| 2 | H-36 | 33 | 5.6 | Blue |
| 3 | H-38 | 102 | 6.5 | Blue |
| 4 | H-50 | 175 | 6.1 | Blue |
| 5 | H-66 | 197 | 6.8 | Blue |
| 6 | H-77 | 380 | 5.9 | Blue |
| 7 | H-79 | 435 | 5.4 | Blue |
| 8 | H-82 | 453 | 5.8 | Blue |
| Comp. 1 | DNA | perylene | 4.5 | Blue |

As can be seen from Table 2, Compound (H-66) with 3.0 wt % doping of Compound (197) showed the highest luminous efficiency.

EXAMPLE 2

Manufacture of an OLED by Using a Compound for Electronic Material According to the Invention After forming a hole injecting layer and a hole transport layer according to the same procedure as described in Example 1, an electroluminescent layer was vapor-deposited thereon as follows. One cell of the device was charged with tris(8-hydroxyquinoline)aluminum (III) (Alq) as an electroluminescent host material, while coumarin 545T (C545T) was charged to still another cell. The two substances were evaporated at different rates to carry out doping, thereby vapor-depositing an electroluminescent layer (5) with a thickness of 30 nm on the hole transport layer. The doping concentration is preferably 2% by weight on the basis of Alq.

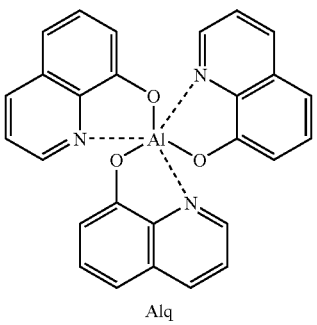

Alq

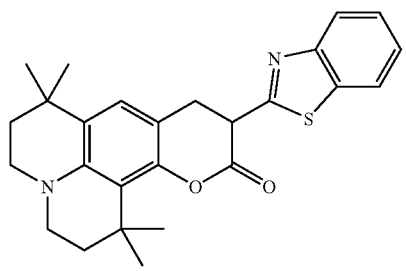

C545T

Then, a compound according to the invention (e.g., Compound 2) was vapor-deposited as an electron transport layer (6) with a thickness of 20 nm, and then lithium quinolate (Liq) (of which the structure is shown below) as an electron injecting layer (7) with a thickness of 1 to 2 nm. Al cathode was vapor-deposited by using another vacuum vapor-deposit device with a thickness of 150 nm, to manufacture an OLED.

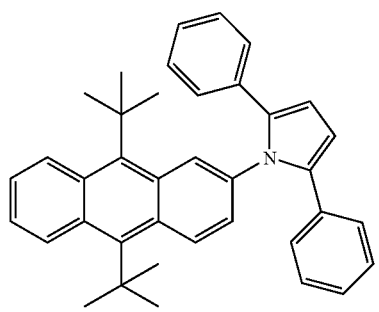

2

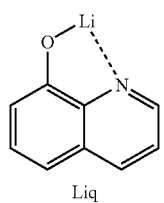

Liq

COMPARATIVE EXAMPLE 2

Manufacture of an OLED by Using Conventional Compound for Electronic Material

After forming a hole injecting layer (3), a hole transport layer (4) and an electroluminescent layer (5) according to the same procedure as described in Example 2, Alq (tris(8-hydroxyquinoline)-aluminum (III)) (of which the structure is shown below) was vapor-deposited as an electron transport layer (6) with a thickness of 20 nm, and then lithium quinolate (Liq) as an electron injecting layer (7) with a thickness of 1 to 2 nm. Thereafter, Al cathode (8) was vapor-deposited by using another vacuum vapor-deposit device with a thickness of 150 nm, to manufacture an OLED.

TABLE 3

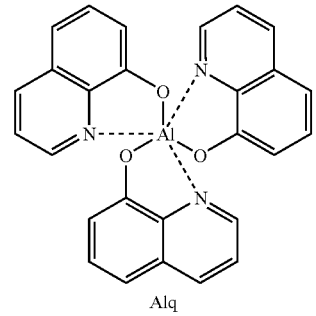

Alq

| No. | Material for electron transport layer | Operation voltage (V) @ 1,000 cd/m$^2$ | Luminous efficiency (cd/A) @ 1,000 cd/m$^2$ | Color |
|---|---|---|---|---|
| 1 | 2 | 5 | 11.7 | Green |
| 2 | 70 | 4.8 | 13.1 | Green |
| Comp. 2 | Alq | 6 | 11.6 | Green |

It is found that the compounds developed by the present invention exhibit enhanced properties in terms of performance as compared to the conventional material.

EXAMPLE 3

Manufacture of an OLED by Using a Compound for Electronic Material According to the Invention After forming a hole injecting layer and a hole transport layer according to the same procedure as described in Example 1, a compound according to the present invention (e.g., Compound 2) which had been purified by vacuum sublimation at 10$^{-6}$ torr was charged to one cell of the vacuum vapor-deposit device as host material, while an electroluminescent dopant (e.g., compound (piq)$_2$Ir(acac)) was charged to another cell. The two substances were evaporated at different rates to give doping at 8% by weight, to vapor-deposit an electroluminescent layer (5) with a thickness of 30 nm on the hole transport layer.

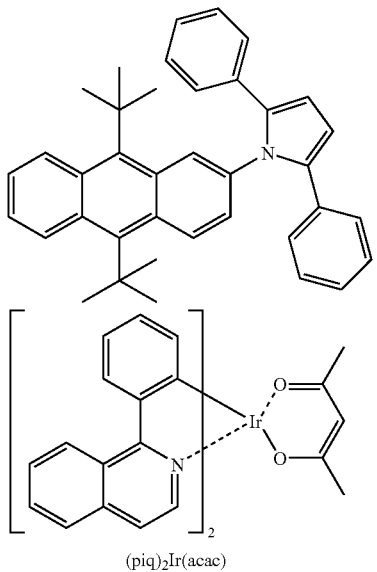

(piq)₂Ir(acac)

Then, tris(8-hydroxyquinoline)aluminum (III) (Alq) was vapor-deposited as an electron transport layer (6) with a thickness of 20 nm, and lithium quinolate (Liq) was vapor-deposited as an electron injecting layer (7) with a thickness of 1 to 2 nm. Thereafter, an Al cathode (8) was vapor-deposited with a thickness of 150 nm by using another vacuum vapor-deposit device to manufacture an OLED.

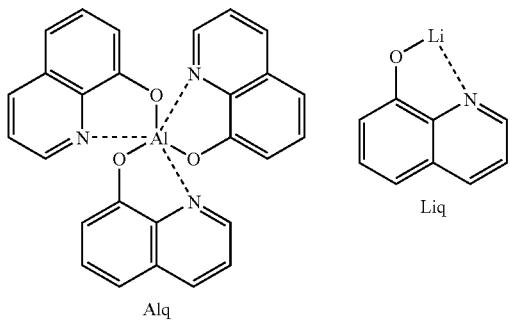

Alq

Liq

COMPARATIVE EXAMPLE 3

Manufacture of an OLED by Using Conventional Compound for Electronic Material After forming a hole injecting layer and a hole transport layer according to the same procedure as described in Example 3, an electroluminescent layer was vapor-deposited as follows. Another cell of the vacuum vapor-deposition device was charged with 4,4'-N,N'-dicarbazole-biphenyl (CBP) as an electroluminescent host material, while an electroluminescent dopant (e.g., compound (piq)₂Ir(acac)) was charged to another cell. The two substances were evaporated at different rates to carry out doping, thereby vapor-depositing an electroluminescent layer (5) with a thickness of 30 nm on the hole transport layer. The doping concentration is suitably 8% by weight on the basis of CBP.

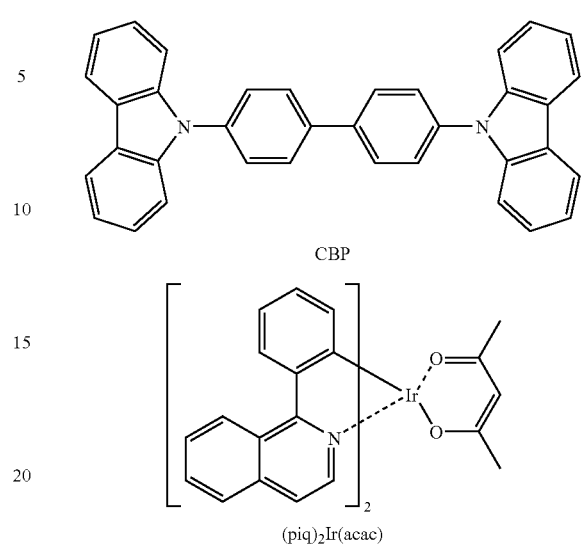

CBP (piq)₂Ir(acac)

On the electroluminescent layer, vapor-deposited were bis(2-methyl-8-quinolinato)(p-phenylphenolato)aluminum (III) (BAlq) as a hole blocking layer, and tris(8-hydroxyquinoline)-aluminum (III) (Alq) as an electron transport layer (6) with a thickness of 20 nm. Then lithium quinolate (Liq) was vapor-deposited as an electron injecting layer (7) with a thickness of 1 to 2 nm. An Al cathode (8) was vapor-deposited by using another vacuum vapor-deposit device with a thickness of 150 nm, to manufacture an OLED.

TABLE 4

BAlq

| No. | Material | Host | Hole blocking layer | EL color | Operation voltage | Max. luminous efficiency (cd/A) |
|---|---|---|---|---|---|---|
| 1 | D-4 | 2 | — | Red | 7.5 | 6.5 |
| 2 | D-6 | 29 | — | Red | 7.3 | 6.7 |
| 3 | D-10 | 137 | — | Red | 7.5 | 7.5 |
| 4 | D-15 | 220 | — | Red | 7.3 | 7.2 |
| 5 | D-21 | 432 | — | Red | 7.1 | 6.9 |
| Comp. 3 | (piq)₂Ir(acac) | CBP | BAlq | Red | 8.3 | 6.5 |

When using the host according to the invention, without using a hole blocking layer, the device shows at least comparable luminous efficiency as compared to CBP as conventional phosphorescent host, and lowered operation voltage by 0.8 to 1.2 V to result in noticeably lowered power consumption of the OLED.

The invention claimed is:

1. A compound for electronic material represented by Chemical Formula (1):

Chemical Formula 1

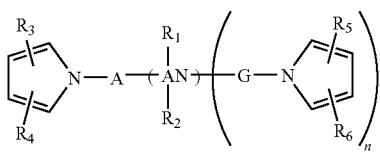

In Chemical Formula (1),

AN is an anthracene ring;

A and G independently represent a chemical bond, or they are selected from (C6-C60)arylene, (C3-C60)heteroarylene, 5- or 6-membered heterocycloalkylene containing one or more heteroatom(s) selected from N, O and S, (C3-C60)cycloalkylene, (C2-C60)alkenylene, (C2-C60)alkynylene, (C1-C60)alkylenoxy, (C6-C60)arylenoxy and (C6-C60)arylenethio;

$R_1$ through $R_6$ independently represent hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; or each of $R_1$ through $R_6$ may be linked to an adjacent substituent via (C3-C60)alkylene or (C3-C60)alkenylene with or without a fused ring to form an alicyclic ring, or a monocyclic or polycyclic aromatic ring; which may be represented by one of Compounds (A) to (C);

Compound (A)

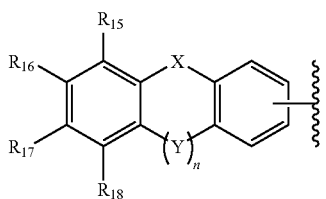

Compound (B)

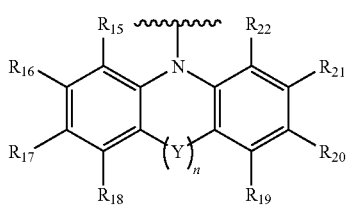

Compound (C)

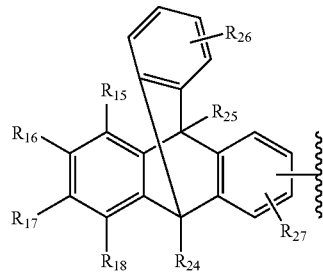

wherein, $R_{15}$ through $R_{27}$ are independently selected from hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl;

X and Y are independently selected from $CR_{28}R_{29}$, $NR_{30}$, S, O, $SiR_{30}R_{31}$, $PR_{32}$, CO, $BR_{33}$, $InR_{34}$, Se, $GeR_{35}R_{36}$, $SnR_{37}R_{38}$, $GaR_{39}$ and $R_{40}C=CR_{41}$; wherein $R_{28}$ through $R_{41}$ represent hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl, or each of $R_1$ through $R_6$ may be linked to an adjacent substituent via (C3-C60)alkylene or (C3-C60)alkenylene with or without a fused ring to form an alicyclic ring, or a monocyclic or polycyclic aromatic ring; n is an integer from 0 to 4; and the arylene, heteroarylene, heterocycloalkylene, cycloalkylene, alkenylene, alkynylene, alkylenoxy, arylenoxy, arylenethio of A and G; and the alkyl, alkenyl, alkynyl, cycloalkyl, heterocycloalkyl, aryl, heteroaryl, arylsilyl, alkylsilyl, alkylamino and arylamino group of $R_1$ through $R_6$, and $R_{15}$ through $R_{41}$ may be further substituted by halogen, (C1-C60)alkyl with or without halogen substituent(s), (C6-C60)aryl, (C3-C60)heteroaryl with or without (C6-C60)aryl substituent, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; or an alicyclic ring, or a monocyclic or polycyclic aromatic ring formed by linkage via (C3-C60)alkylene or (C3-C60)alkenylene with or without a fused ring.

2. The compound for electronic material according to claim 1, which is represented by one of Chemical Formulas (2) to (19):
Chemical Formula 2
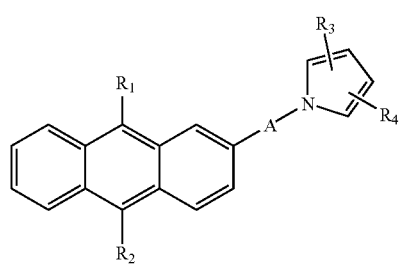
Chemical Formula 3
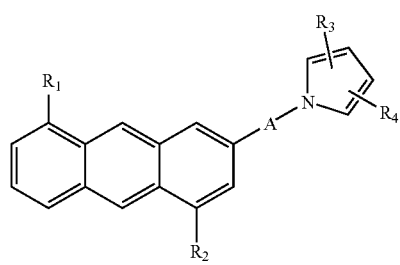
Chemical Formula 4
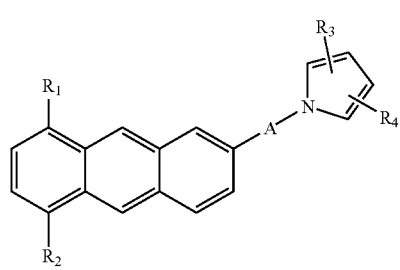
Chemical Formula 5
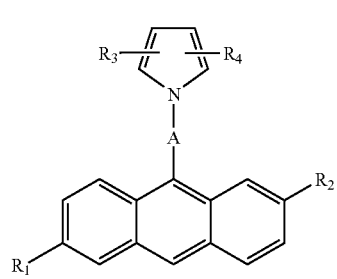
Chemical Formula 6
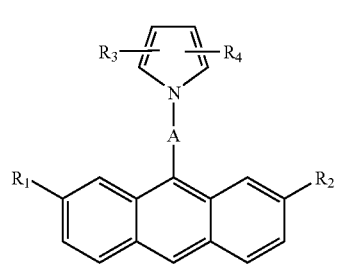
-continued
Chemical Formula 7
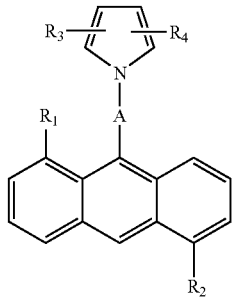
Chemical Formula 8
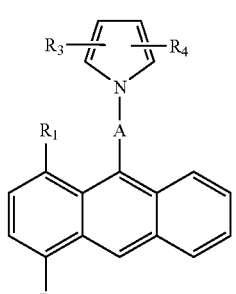
Chemical Formula 9
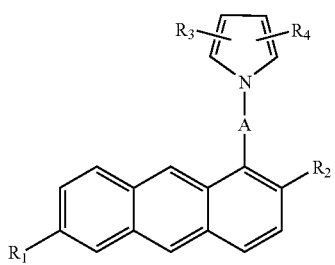
Chemical Formula 10
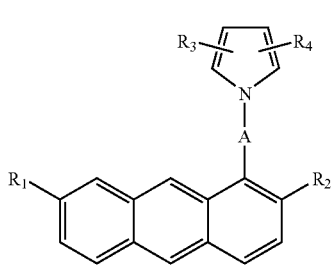
Chemical Formula 11
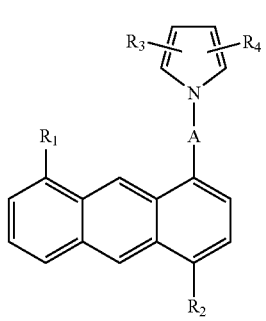

-continued
Chemical Formula 12
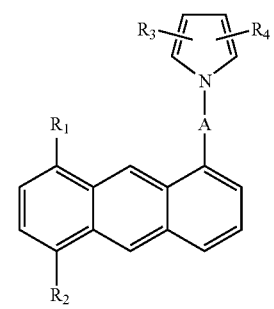
Chemical Formula 13
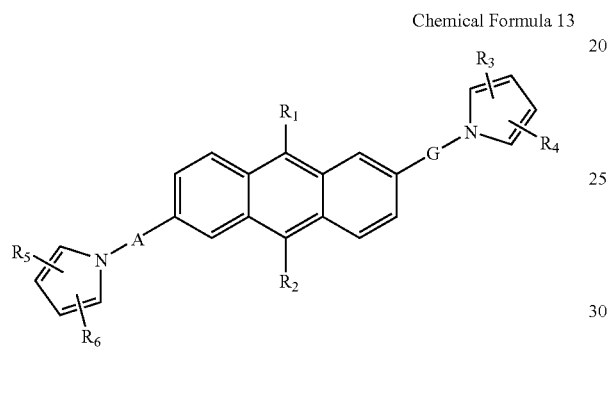
Chemical Formula 14
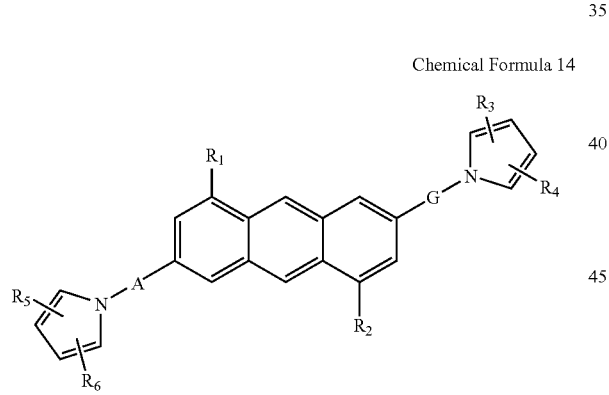
Chemical Formula 15
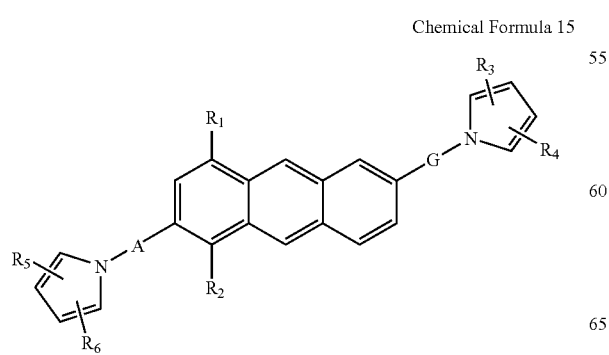
-continued
Chemical Formula 16
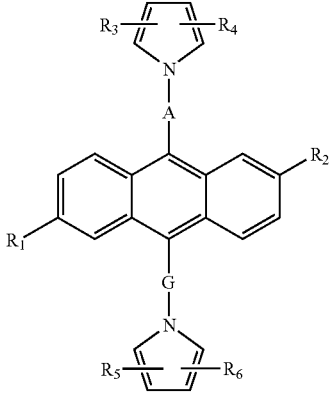
Chemical Formula 17
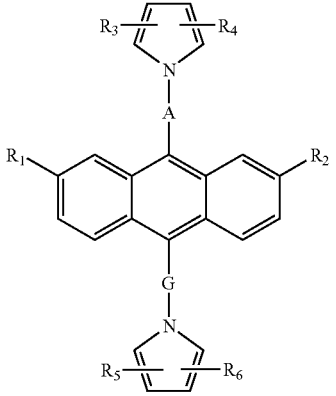
Chemical Formula 18
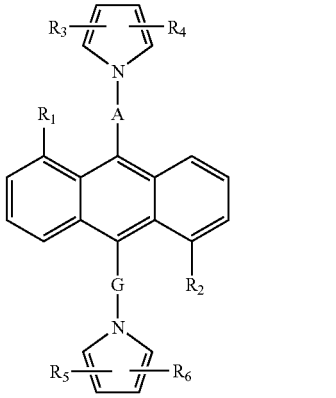
Chemical Formula 19
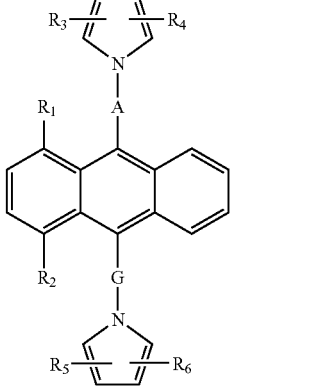
wherein, A, G and $R_1$ through $R_6$ are defined as in claim 1.

3. The compound for electronic material according to claim 2, wherein A and G in Chemical Formulas (2) to (19) represent a chemical bond, or they are selected from the following structures:
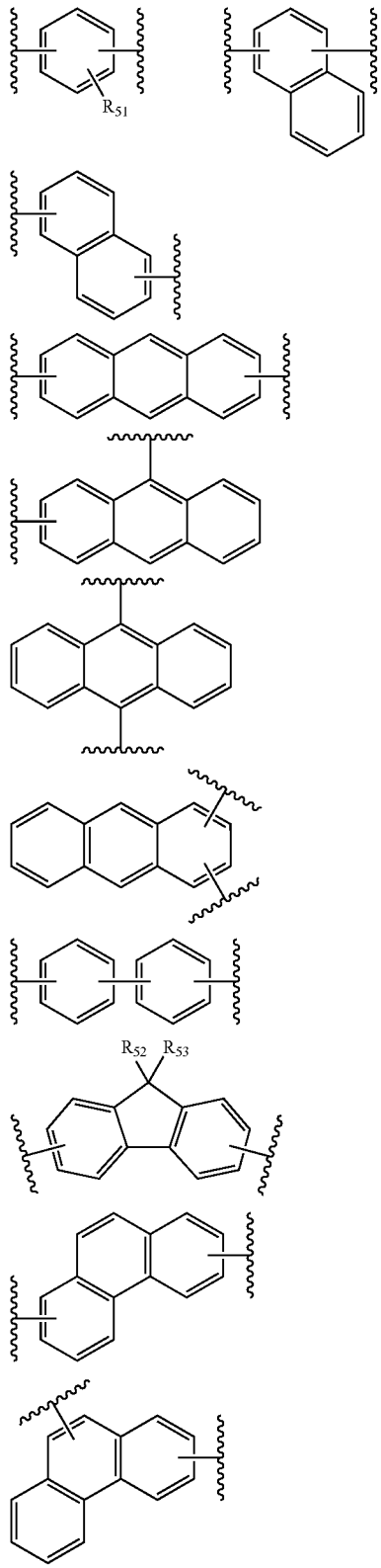
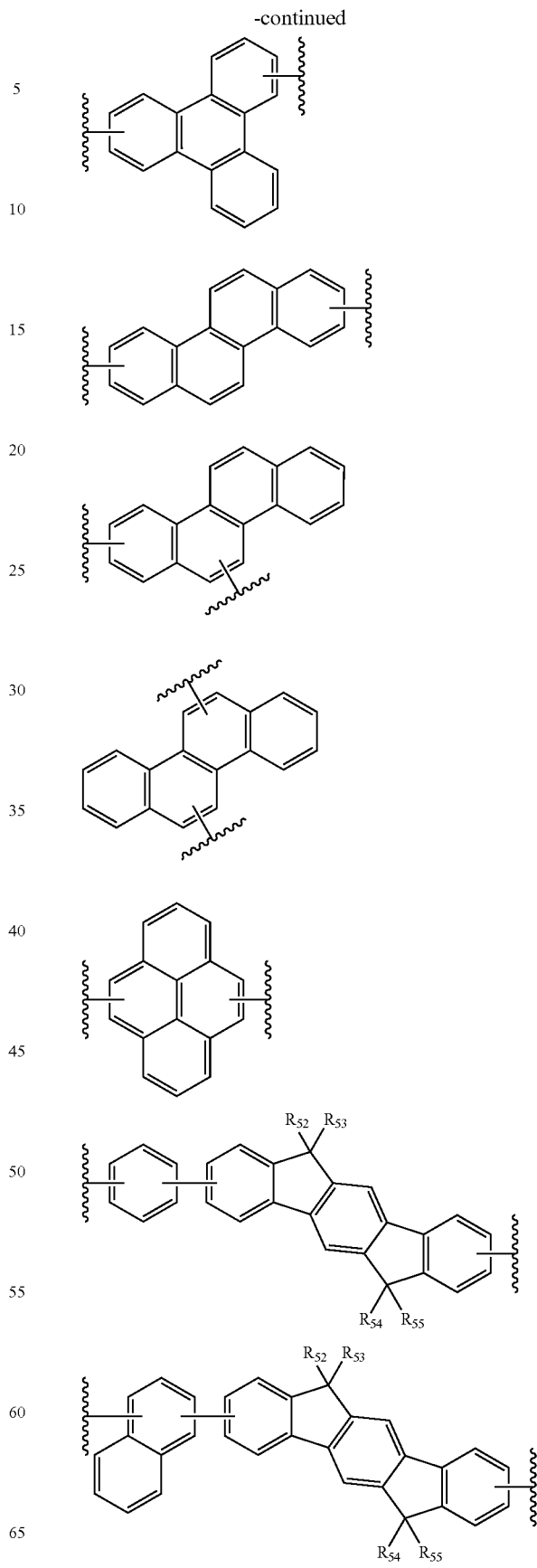

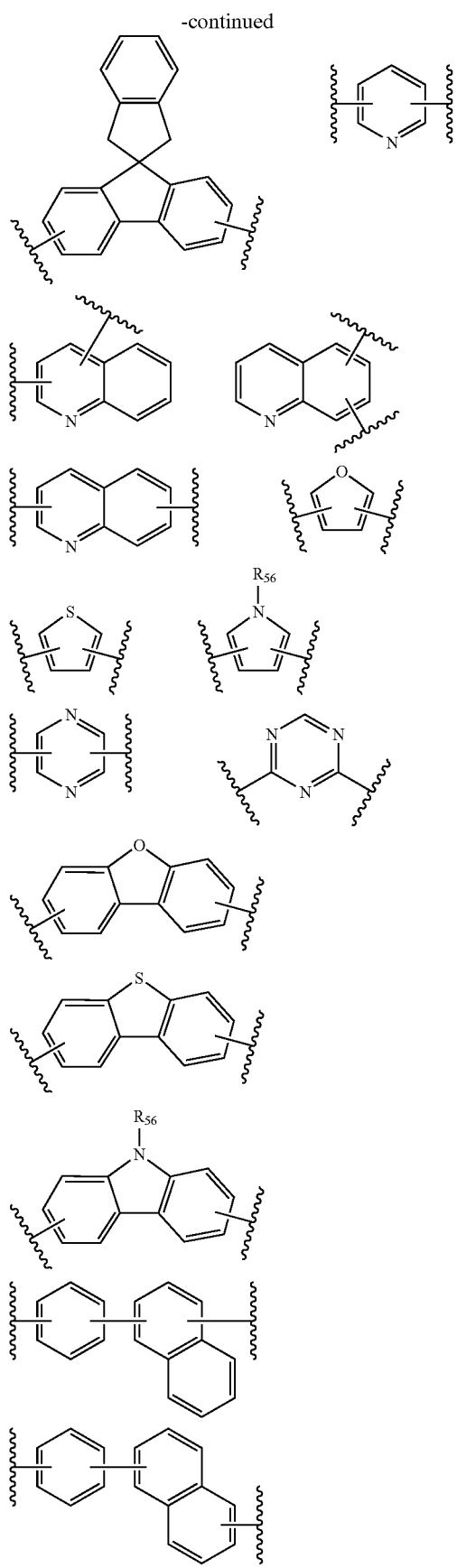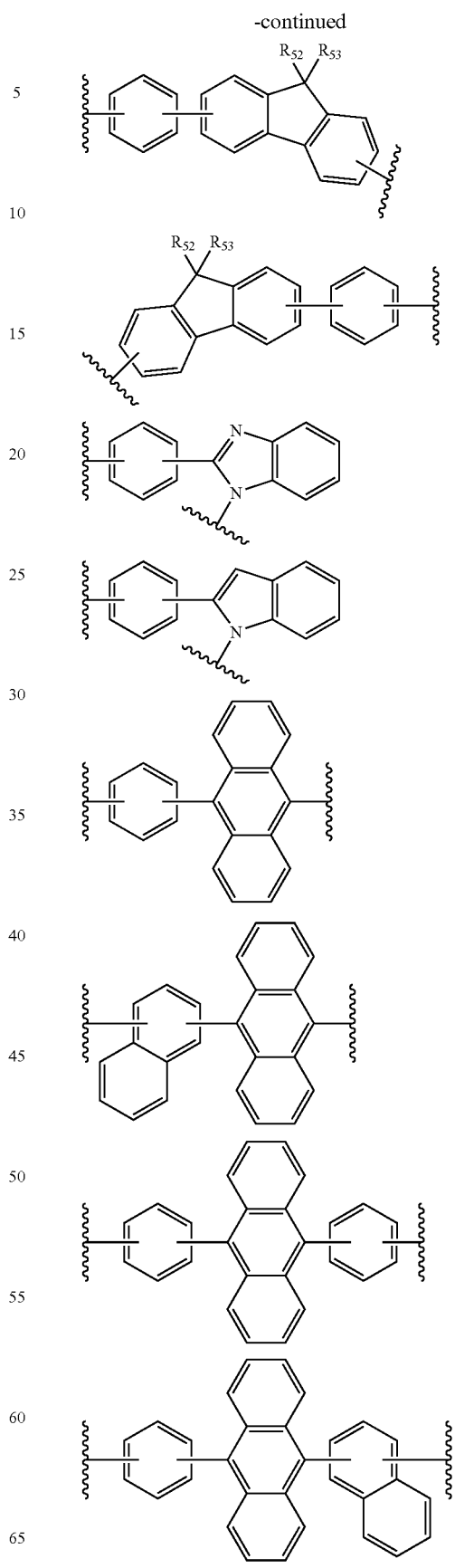

-continued

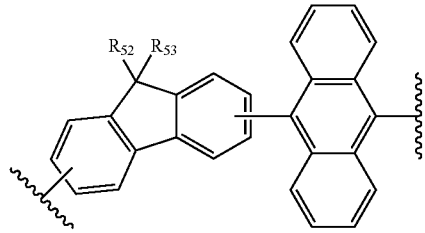

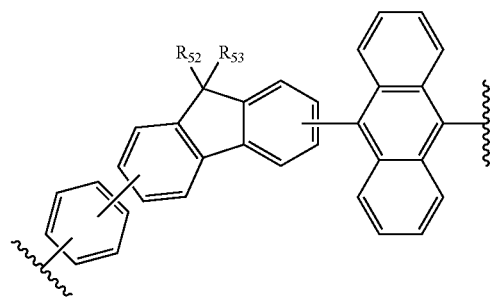

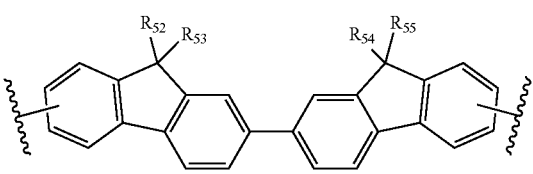

wherein, $R_{51}$ represents halogen, (C1-C60)alkyl, (C6-C60)aryl, (C4-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl;

$R_{52}$ through $R_{56}$ independently represent halogen, (C1-C60)alkyl, (C6-C60)aryl, (C4-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl; or each of $R_{52}$ through $R_{56}$ may be linked to an adjacent substituent via (C3-C60)alkylene or (C3-C60)alkenylene with or without a fused ring to form an alicyclic ring, or a monocyclic or polycyclic aromatic ring.

4. An organic electroluminescent device which is comprised of a first electrode; a second electrode; and at least one organic layer(s) interposed between the first electrode and the second electrode; wherein the organic layer comprises an electroluminescent layer comprising an electronic material represented by Chemical Formula (1):

Chemical Formula 1

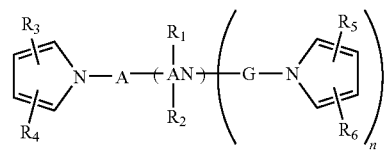

In Chemical Formula (1),

AN is an anthracene ring;

A and G independently represent a chemical bond, or they are selected from (C6-C60)arylene, (C3-C60)heteroarylene, 5- or 6-membered heterocycloalkylene containing one or more heteroatom(s) selected from N, O and S, (C3-C60)cycloalkylene, (C2-C60)alkenylene, (C2-C60)alkynylene, (C1-C60)alkylenoxy, (C6-C60)arylenoxy and (C6-C60)arylenethio;

$R_1$ through $R_6$ independently represent hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; or each of $R_1$ through $R_6$ may be linked to an adjacent substituent via (C3-C60)alkylene or (C3-C60)alkenylene with or without a fused ring to form an alicyclic ring, or a monocyclic or polycyclic aromatic ring;

which may be represented by one of Compounds (A) to (C);

Compound (A)

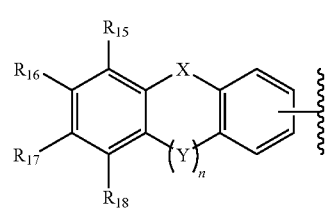

Compound (B)

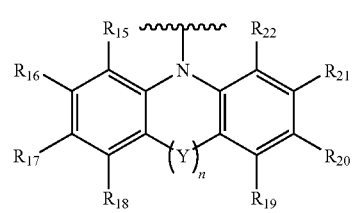

-continued

Compound (C)

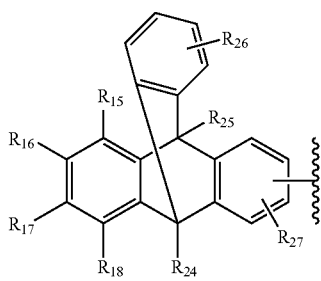

wherein, $R_{15}$ through $R_{27}$ are independently selected from hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl;

X and Y are independently selected from $CR_{28}R_{29}$, $NR_{30}$, S, O, $SiR_{30}R_{31}$, $PR_{32}$, CO, $BR_{33}$, $InR_{34}$, Se, $GeR_{35}R_{36}$, $SnR_{37}R_{38}$, $GaR_{39}$ and $R_{40}C=CR_{41}$; wherein $R_{28}$ through $R_{41}$ represent hydrogen, halogen, (C1-C60) alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60) alkoxy, cyano, (C1-C60)alkylamino, (C6-C60) arylamino, (C6-C60)ar(C1-C60)alkyl, (C6-C60) aryloxy, (C6-C60)arylthio, (C1-C60)alkoxycarbonyl, carboxyl, nitro or hydroxyl, or each of $R_1$ through $R_6$ may be linked to an adjacent substituent via (C3-C60) alkylene or (C3-C60)alkenylene with or without a fused ring to form an alicyclic ring, or a monocyclic or polycyclic aromatic ring; n is an integer from 0 to 4; and the arylene, heteroarylene, heterocycloalkylene, cycloalkylene, alkenylene, alkynylene, alkylenoxy, arylenoxy, arylenethio of A and G; and the alkyl, alkenyl, alkynyl, cycloalkyl, heterocycloalkyl, aryl, heteroaryl, arylsilyl, alkylsilyl, alkylamino and arylamino group of R1 through R6, and R15 through R41 may be further substituted by halogen, (C1-C60)alkyl with or without halogen substituent(s), (C6-C60)aryl, (C3-C60)heteroaryl with or without (C6-C60)aryl substituent, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60) alkoxy, cyano, (C1-C60)alkylamino, (C6-C60) arylamino, (C6-C60)ar(C1-C60)alkyl, (C6-C60) aryloxy, (C6-C60)arylthio, (C1-C60)alkoxycarbonyl, carboxyl, nitro and hydroxyl; or an alicyclic ring, or a monocyclic or polycyclic aromatic ring formed by linkage via (C3-C60)alkylene or (C3-C60)alkenylene with or without a fused ring and one or more host(s) selected from the compounds represented by Chemical Formula (20) to (21):

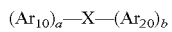 Chemical Formula 20

$(Ar_{30})_c$—Y—$(Ar_{40})_d$ Chemical Formula 21 wherein, X represents (C6-C60)arylene or (C4-C60)heteroarylene;

Y represents anthracenylene;

$Ar_{10}$ through $Ar_{40}$ are independently selected from hydrogen, (C1-C60)alkyl, (C1-C60)alkoxy, halogen, (C4-C60)heteroaryl, (C5-C60)cycloalkyl and (C6-C60)aryl; the cycloalkyl, aryl or heteroaryl of $Ar_{10}$ through $Ar_{40}$ may be further substituted by one or more substituent(s) selected from a group consisting of (C6-C60)aryl or (C4-C60)heteroaryl with or without one or more substituent(s) selected from a group consisting of (C1-C60) alkyl with or without halogen substituent(s), (C1-C60) alkoxy, (C3-C60)cycloalkyl, halogen, cyano, tri(C1-C60)alkylsilyl, di(C1-C60)alkyl(C6-C60)arylsilyl and tri(C6-C60)arylsilyl; (C1-C60)alkyl with or without halogen substituent(s), (C1-C60)alkoxy, (C3-C60)cycloalkyl, halogen, cyano, tri(C1-C60)alkylsilyl, di(C1-C60)alkyl(C6-C60)arylsilyl and tri(C6-C60)arylsilyl; and a, b, c and d independently represent an integer from 0 to 4.

5. The organic electroluminescent device according to claim 4, wherein the organic layer comprises one or more compound(s) selected from a group consisting of arylamine compounds and styrylarylamine compounds.

6. The organic electroluminescent device according to claim 4, wherein the organic layer comprises one or more metal(s) selected from a group consisting of organic metals of Group 1, Group 2, $4^{th}$ period and $5^{th}$ period transition metals, lanthanide metals and d-transition elements from the Periodic Table of Elements.

7. The organic electroluminescent device according to claim 4, wherein the organic layer comprises a charge generating layer as well as the electroluminescent layer.

8. A white electroluminescent device which comprises a compound for electronic material represented by Chemical Formula (1):

Chemical Formula 1

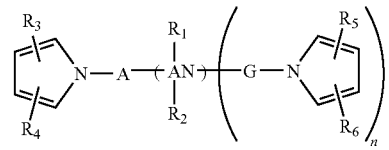

In Chemical Formula (1),

AN is an anthracene ring;

A and G independently represent a chemical bond, or they are selected from (C6-C60)arylene, (C3-C60)heteroarylene, 5- or 6-membered heterocycloalkylene containing one or more heteroatom(s) selected from N, O and S, (C3-C60)cycloalkylene, (C2-C60)alkenylene, (C2-C60)alkynylene, (C1-C60)alkylenoxy, (C6-C60) arylenoxy and (C6-C60)arylenethio;

$R_1$ through $R_6$ independently represent hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-

C60)arylamino, (C6-C60)ar(C1-C60)alkyl, (C6-C60)aryloxy, (C6-C60)arylthio, (C1-C60)alkoxycarbonyl, carboxyl, nitro and hydroxyl; or each of $R_1$ through $R_6$ may be linked to an adjacent substituent via (C3-C60)alkylene or (C3-C60)alkenylene with or without a fused ring to form an alicyclic ring, or a monocyclic or polycyclic aromatic ring; which may be represented by one of Compounds (A) to (C);

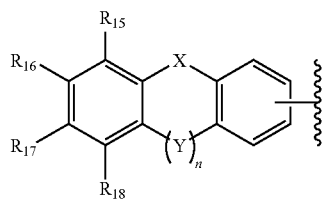

Compound (A)

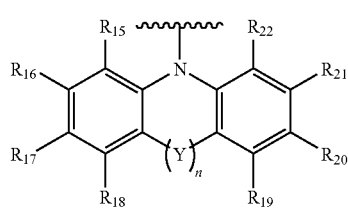

Compound (B)

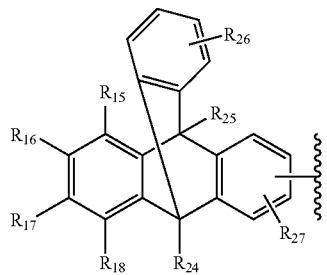

Compound (C)

wherein, $R_{15}$ through $R_{27}$ are independently selected from hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl;

X and Y are independently selected from $CR_{28}R_{29}$, $NR_{30}$, S, O, $SiR_{30}R_{31}$, $PR_{32}$, CO, $BR_{33}$, $InR_{34}$, Se, $GeR_{35}R_{36}$, $SnR_{37}R_{38}$, $GaR_{39}$ and $R_{40}C=CR_{41}$; wherein $R_{28}$ through $R_{41}$ represent hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl, or each of $R_1$ through $R_6$ may be linked to an adjacent substituent via (C3-C60)alkylene or (C3-C60)alkenylene with or without a fused ring to form an alicyclic ring, or a monocyclic or polycyclic aromatic ring; n is an integer from 0 to 4; and the arylene, heteroarylene, heterocycloalkylene, cycloalkylene, alkenylene, alkynylene, alkylenoxy, arylenoxy, arylenethio of A and G; and the alkyl, alkenyl, alkynyl, cycloalkyl, heterocycloalkyl, aryl, heteroaryl, arylsilyl, alkylsilyl, alkylamino and arylamino group of $R_1$ through $R_6$, and $R_{15}$ through $R_{41}$ may be further substituted by halogen, (C1-C60)alkyl with or without halogen substituent(s), (C6-C60)aryl, (C3-C60)heteroaryl with or without (C6-C60)aryl substituent, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; or an alicyclic ring, or a monocyclic or polycyclic aromatic ring formed by linkage via (C3-C60)alkylene or (C3-C60)alkenylene with or without a fused ring.

9. An organic solar cell which comprises a compound for electronic material represented by Chemical Formula (1):

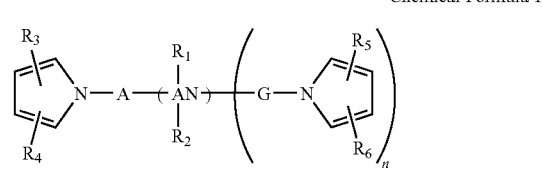

Chemical Formula 1

In Chemical Formula (1),

AN is an anthracene ring;

A and G independently represent a chemical bond, or they are selected from (C6-C60)arylene, (C3-C60)heteroarylene, 5- or 6-membered heterocycloalkylene containing one or more heteroatom(s) selected from N, O and S, (C3-C60)cycloalkylene, (C2-C60)alkenylene, (C2-C60)alkynylene, (C1-C60)alkylenoxy, (C6-C60)arylenoxy and (C6-C60)arylenethio;

$R_1$ through $R_6$ independently represent hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; or each of $R_1$ through $R_6$ may be linked to an adjacent substituent via (C3-C60)alkylene or (C3-C60)alkenylene with or without a fused ring to form an alicyclic ring, or a monocyclic or polycyclic aromatic ring; which may be represented by one of Compounds (A) to (C);

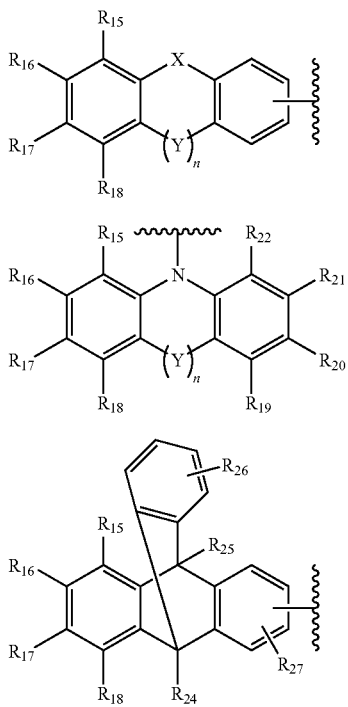

Compound (A)

Compound (B)

Compound (C)

wherein, $R_{15}$ through $R_{27}$ are independently selected from hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl;

X and Y are independently selected from $CR_{28}R_{29}$, $NR_{30}$, S, O, $SiR_{30}R_{31}$, $PR_{32}$, CO, $BR_{33}$, $InR_{34}$, Se, $GeR_{35}R_{36}$, $SnR_{37}R_{38}$, $GaR_{39}$ and $R_{40}C=CR_{41}$; wherein $R_{28}$ through $R_{41}$ represent hydrogen, halogen, (C1-C60)alkyl, (C6-C60)aryl, (C3-C60)heteroaryl, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro or hydroxyl, or each of $R_1$ through $R_6$ may be linked to an adjacent substituent via (C3-C60)alkylene or (C3-C60)alkenylene with or without a fused ring to form an alicyclic ring, or a monocyclic or polycyclic aromatic ring; n is an integer from 0 to 4; and the arylene, heteroarylene, heterocycloalkylene, cycloalkylene, alkenylene, alkynylene, alkylenoxy, arylenoxy, arylenethio of A and G; and the alkyl, alkenyl, alkynyl, cycloalkyl, heterocycloalkyl, aryl, heteroaryl, arylsilyl, alkylsilyl, alkylamino and arylamino group of $R_1$ through $R_6$, and $R_{15}$ through $R_{41}$ may be further substituted by halogen, (C1-C60)alkyl with or without halogen substituent(s), (C6-C60)aryl, (C3-C60)heteroaryl with or without (C6-C60)aryl substituent, 5- or 6-membered heterocycloalkyl containing one or more heteroatom(s) selected from N, O and S, (C3-C60)cycloalkyl, tri(C1-C60)alkylsilyl, di(C1-C60)alkyl(C6-C60)arylsilyl, tri(C6-C60)arylsilyl, adamantyl, (C7-C60)bicycloalkyl, (C2-C60)alkenyl, (C2-C60)alkynyl, (C1-C60)alkoxy, cyano, (C1-C60)alkylamino, (C6-C60)arylamino, (C6-C60)ar(C1-C60)alkyl, (C6-C60)aryloxy, (C6-C60)arylthio, (C1-C60)alkoxycarbonyl, carboxyl, nitro and hydroxyl; or an alicyclic ring, or a monocyclic or polycyclic aromatic ring formed by linkage via (C3-C60)alkylene or (C3-C60)alkenylene with or without a fused ring.

* * * * *